(12) United States Patent
Gresham et al.

(10) Patent No.: US 8,464,924 B2
(45) Date of Patent: Jun. 18, 2013

(54) SURGICAL STAPLING DEVICE FOR PERFORMING CIRCULAR ANASTOMOSES

(75) Inventors: Richard D. Gresham, Monroe, CT (US); Scott E. Manzo, Shelton, CT (US); Ernest Aranyi, Easton, CT (US); Robert J. Geiste, Milford, CT (US); Bruce K. Jankowski, Meriden, CT (US); Keith Milliman, Bethel, CT (US)

(73) Assignee: Covidien LP, Mansfield, MA (US)

( * ) Notice: Subject to any disclaimer, the term of this patent is extended or adjusted under 35 U.S.C. 154(b) by 1060 days.

(21) Appl. No.: 11/803,817

(22) Filed: May 16, 2007

(65) Prior Publication Data
US 2008/0142566 A1  Jun. 19, 2008

Related U.S. Application Data

(60) Continuation of application No. 11/208,667, filed on Aug. 22, 2005, now Pat. No. 7,234,624, which is a division of application No. 10/472,402, filed as application No. PCT/US02/10792 on Apr. 3, 2002, now Pat. No. 6,945,444.

(60) Provisional application No. 60/281,259, filed on Apr. 3, 2001, provisional application No. 60/327,653, filed on Oct. 5, 2001, provisional application No. 60/363,715, filed on Mar. 11, 2002.

(51) Int. Cl.
*A61B 17/06816* (2006.01)

(52) U.S. Cl.
USPC ................................ 227/179.1; 227/178.1

(58) Field of Classification Search
USPC .......... 227/175.1, 175.2, 176.1, 179.1, 180.1, 227/181.1
See application file for complete search history.

(56) References Cited

U.S. PATENT DOCUMENTS

| | | | |
|---|---|---|---|
| 4,198,982 | A | 4/1980 | Fartner et al. |
| 4,207,898 | A | 6/1980 | Becht |
| 4,289,133 | A | 9/1981 | Rothfuss |
| 4,304,236 | A | 12/1981 | Conta et al. |
| 4,319,576 | A | 3/1982 | Rothfuss |
| 4,351,466 | A | 9/1982 | Noiles |
| 4,379,457 | A | 4/1983 | Gravener et al. |
| 4,473,077 | A | 9/1984 | Noiles et al. |
| 4,476,863 | A | 10/1984 | Kanshin et al. |

(Continued)

FOREIGN PATENT DOCUMENTS

| | | |
|---|---|---|
| EP | 0 293 123 A2 | 11/1988 |
| EP | 0 449 394 A2 | 10/1991 |
| EP | 0 623 313 A1 | 11/1994 |
| EP | 0 634 144 A1 | 1/1995 |

*Primary Examiner* — M. Alexandra Elve
*Assistant Examiner* — Nathaniel Chukwurah

(57) ABSTRACT

This application is directed to a surgical stapling device for performing circular anastomoses. The surgical stapling device includes a handle portion, an elongated body portion and a head portion including an anvil assembly and a shell assembly. The handle portion includes a rotatable approximation knob for approximating the anvil and shell assemblies and a firing trigger for actuating a firing mechanism for ejecting staples positioned within the shell assembly. The firing trigger forms one link of a two bar linkage provided to actuate the firing mechanism. The anvil assembly includes a tiltable anvil which will tilt automatically after firing of the device and unapproximating the anvil and shell assemblies. The head portion also includes a retractable trocar assembly which is slidably positioned within an anvil retainer and is automatically advanced and retracted upon attachment and detachment of the anvil assembly onto the anvil retainer, and a lockout tube.

5 Claims, 90 Drawing Sheets

U.S. PATENT DOCUMENTS

| | | |
|---|---|---|
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,754,909 A | 7/1988 | Barker et al. |
| 4,817,847 A | 4/1989 | Redtenbacher et al. |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 5,005,749 A | 4/1991 | Aranyi |
| 5,042,707 A | 8/1991 | Tahesi |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A * | 4/1993 | Brinkerhoff et al. ...... 227/179.1 |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,433,721 A | 7/1995 | Hoover et al. |
| 5,437,684 A | 8/1995 | Calabrese et al. |
| 5,439,156 A | 8/1995 | Grant et al. |
| 5,443,198 A | 8/1995 | Viola et al. |
| 5,445,644 A | 8/1995 | Pietrafitta et al. |
| 5,447,514 A | 9/1995 | Gerry et al. |
| 5,454,825 A | 10/1995 | Van Leeuwen et al. |
| 5,470,006 A | 11/1995 | Rodak |
| 5,474,223 A | 12/1995 | Viola et al. |
| 5,497,934 A | 3/1996 | Brady et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,632,433 A | 5/1997 | Grant et al. |
| 5,639,008 A | 6/1997 | Gallagher et al. |
| 5,658,300 A | 8/1997 | Bito et al. |
| 5,669,918 A | 9/1997 | Balazs et al. |
| 5,685,474 A * | 11/1997 | Seeber ...................... 227/179.1 |
| 5,697,943 A | 12/1997 | Sauer et al. |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,758,814 A | 6/1998 | Gallagher et al. |
| 5,799,857 A | 9/1998 | Robertson et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 * | 2/2001 | Bittner et al. ............... 227/180.1 |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,402,008 B1 | 6/2002 | Lucas |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Hux et al. |
| 6,517,566 B1 | 2/2003 | Hovland et al. |
| 6,520,398 B2 | 2/2003 | Nicolo |
| 6,533,157 B1 | 3/2003 | Whitman |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,595,887 B2 | 7/2003 | Thoma |
| 6,601,749 B2 | 8/2003 | Sullivan et al. |
| 6,605,078 B2 | 8/2003 | Adams |
| 6,623,227 B2 | 9/2003 | Scott et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,659,327 B2 | 12/2003 | Heck et al. |
| 6,676,671 B2 | 1/2004 | Robertson et al. |
| 6,681,979 B2 | 1/2004 | Whitman |

| | | | | | |
|---|---|---|---|---|---|
| 6,685,079 B2 | 2/2004 | Sharma et al. | 6,893,449 B2 | 5/2005 | Vargas et al. |
| 6,695,198 B2 | 2/2004 | Adams et al. | 7,234,624 B2 * | 6/2007 | Gresham et al. ........... 227/179.1 |
| 6,695,199 B2 | 2/2004 | Whitman | | | |
| 6,716,222 B2 | 4/2004 | McAlister et al. | * cited by examiner | | |

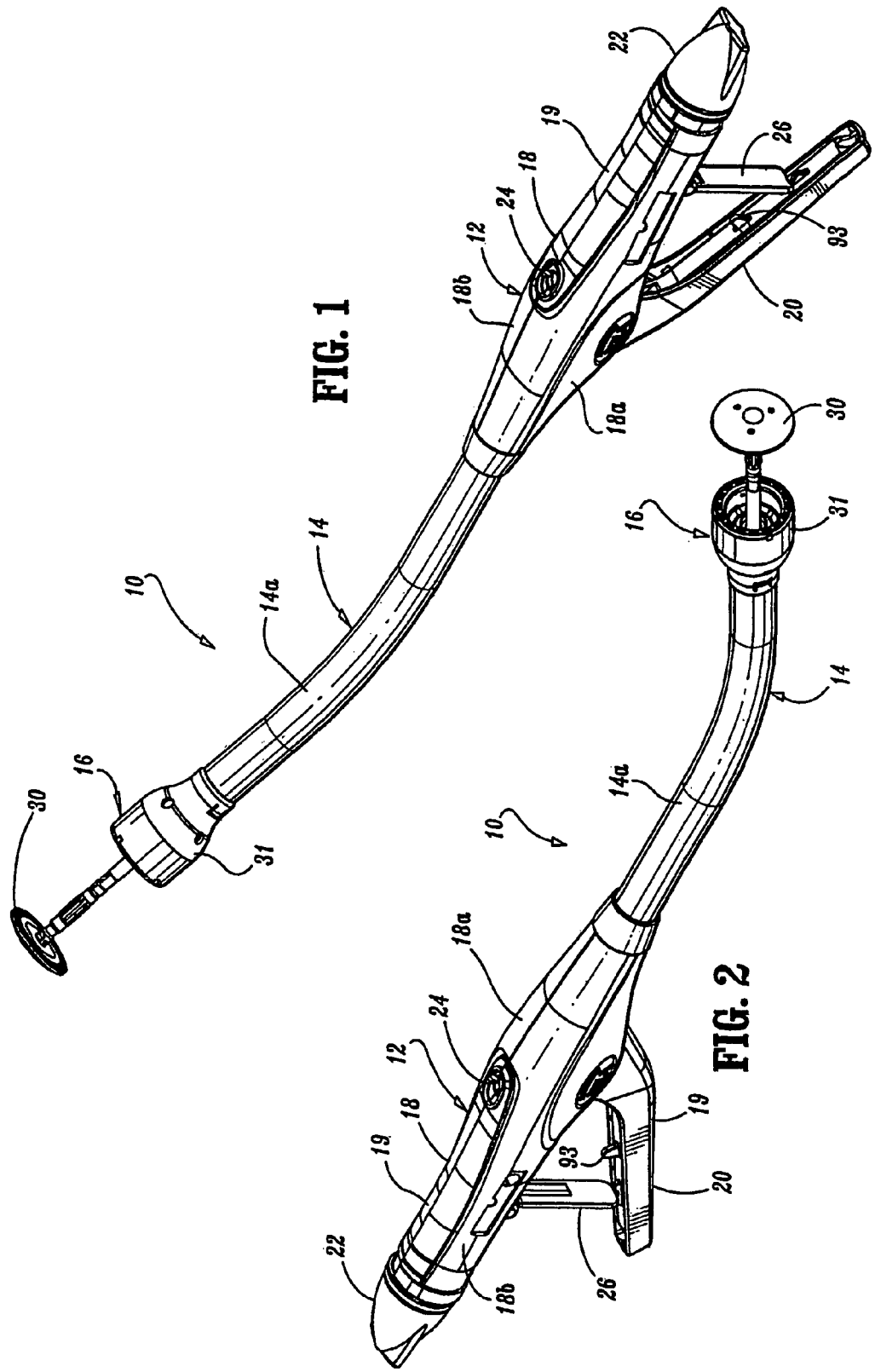

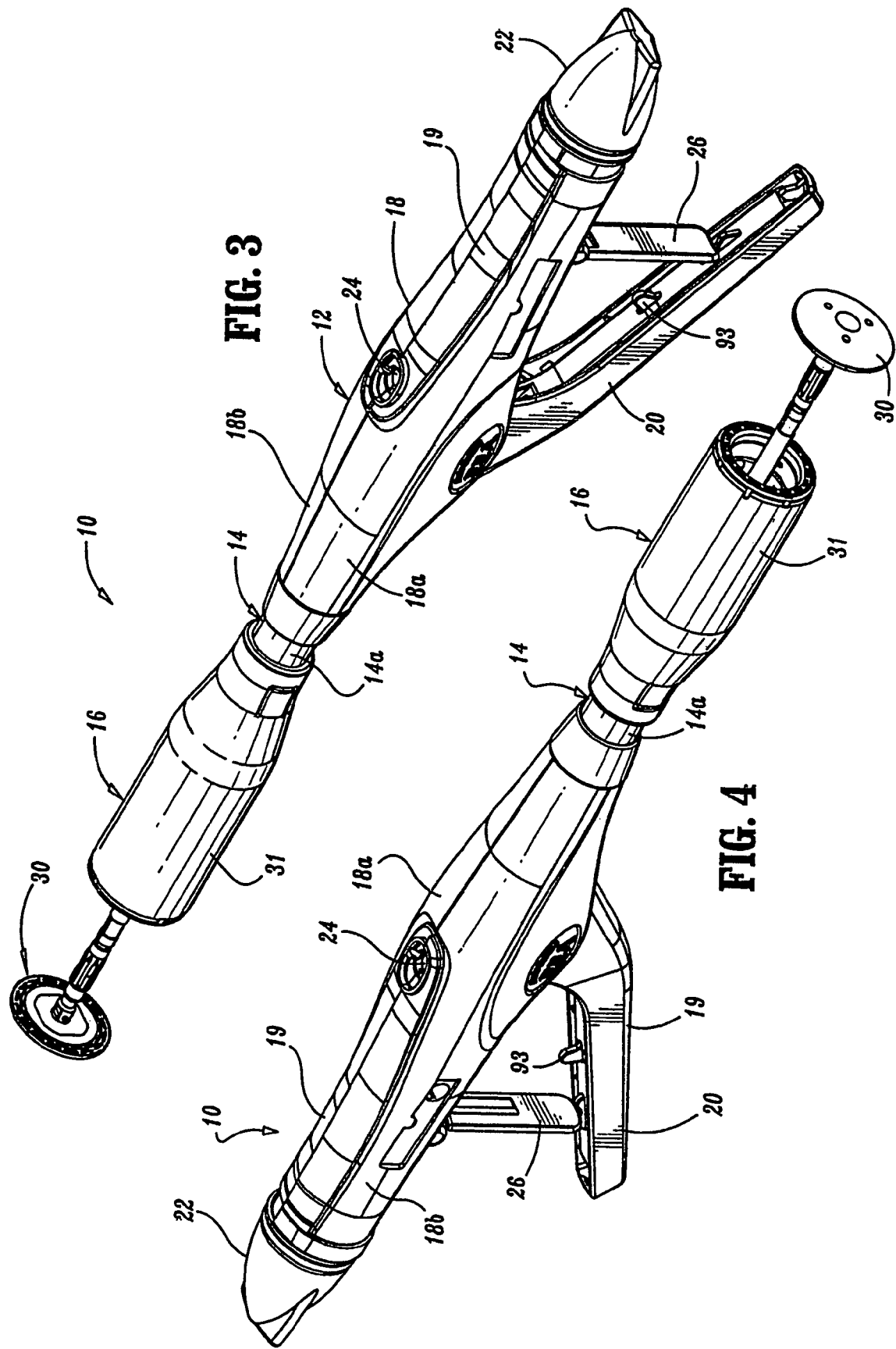

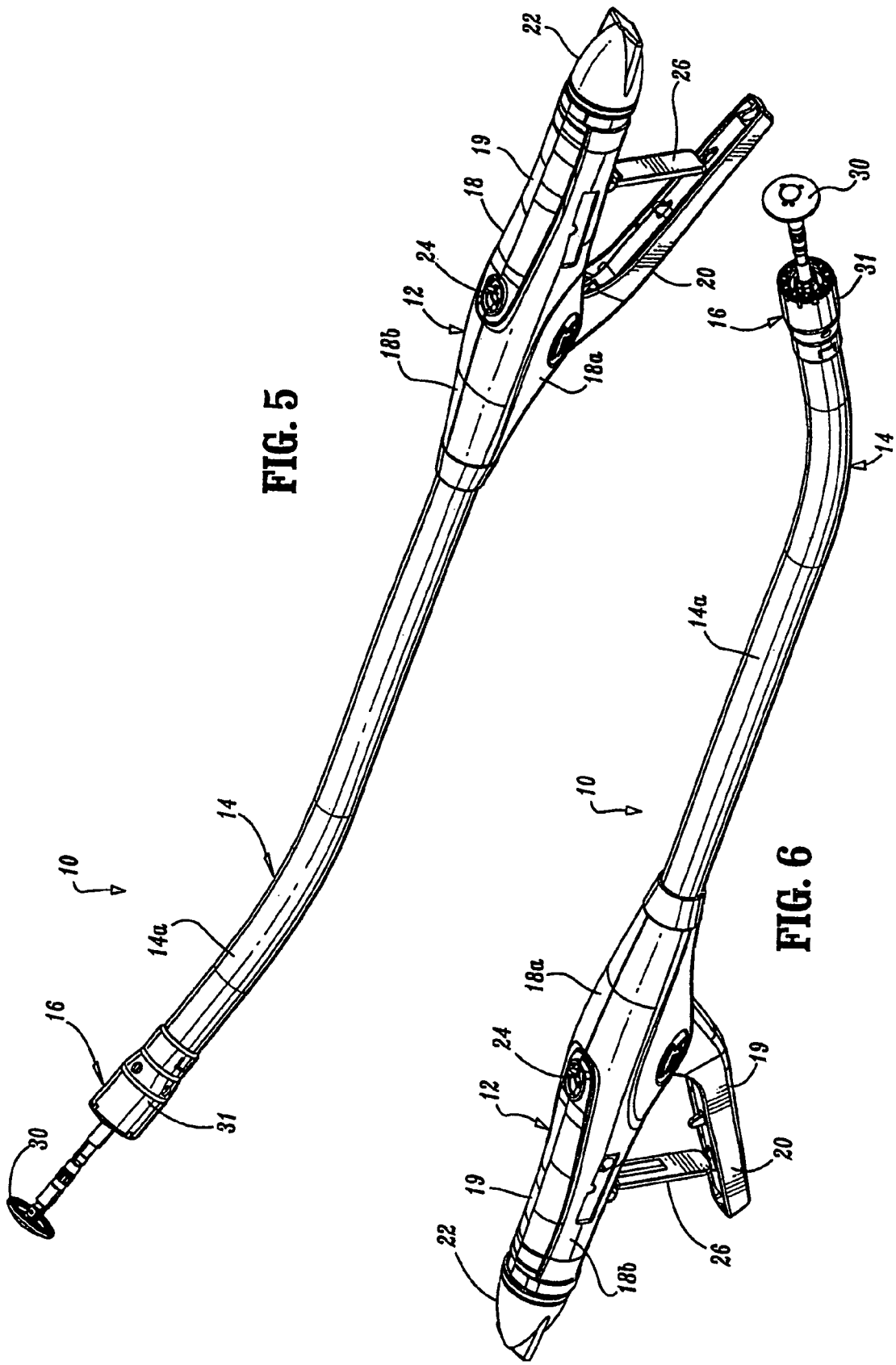

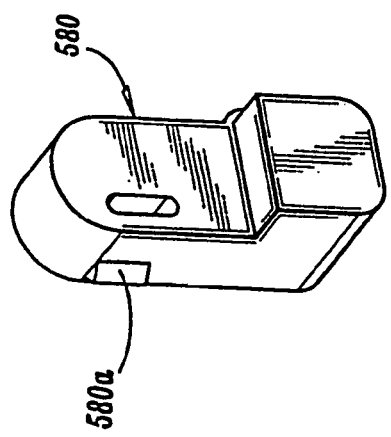
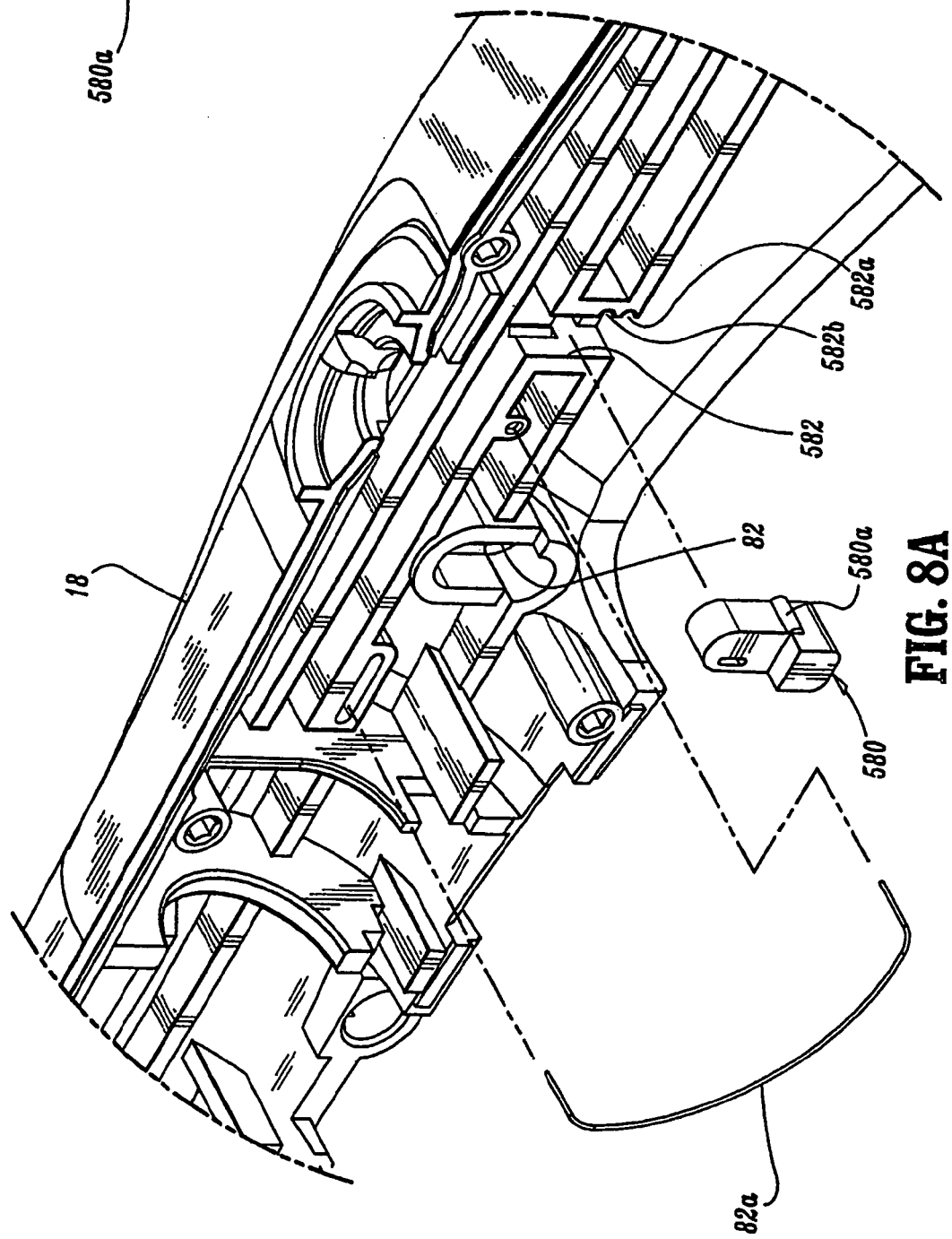

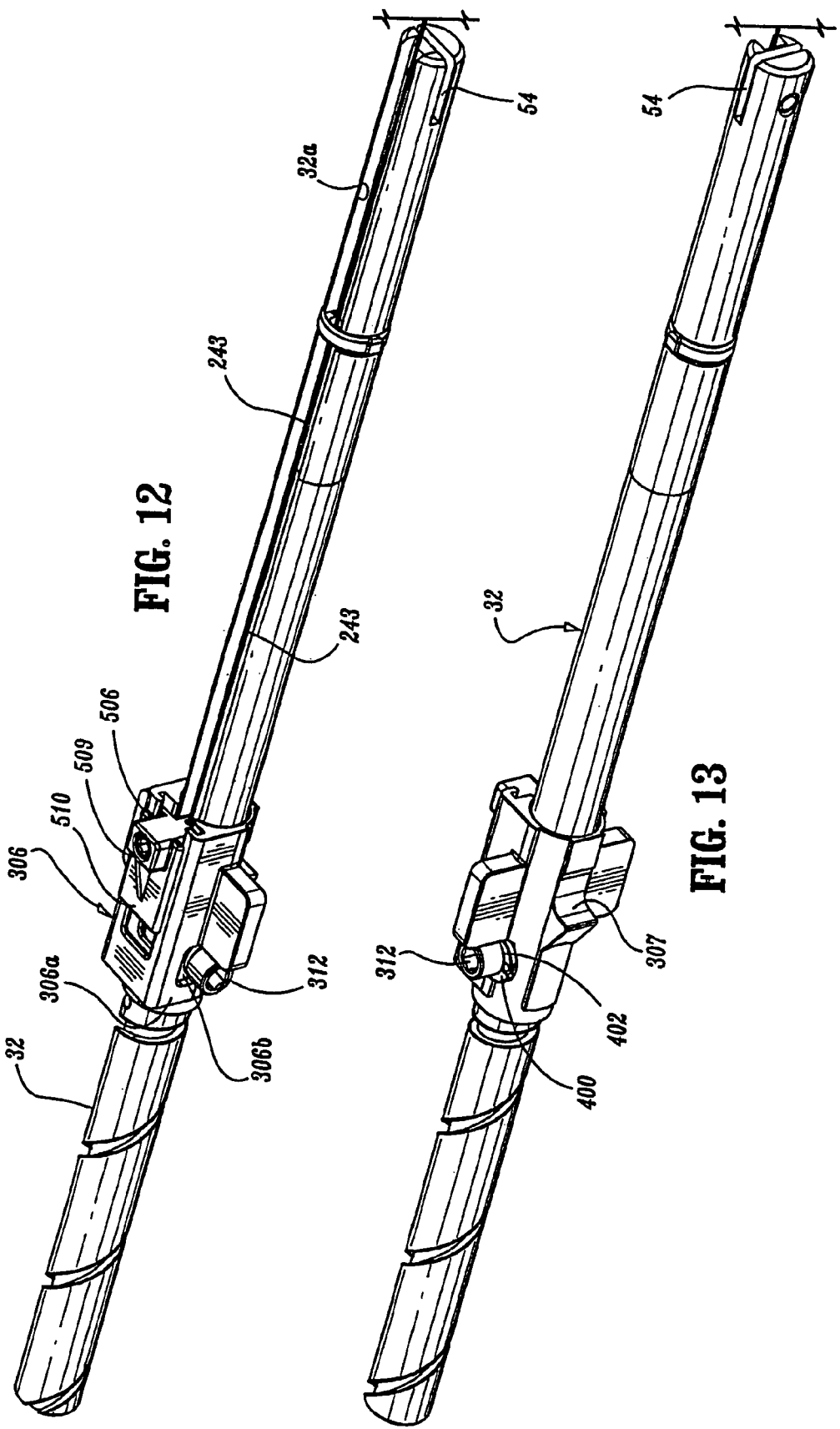

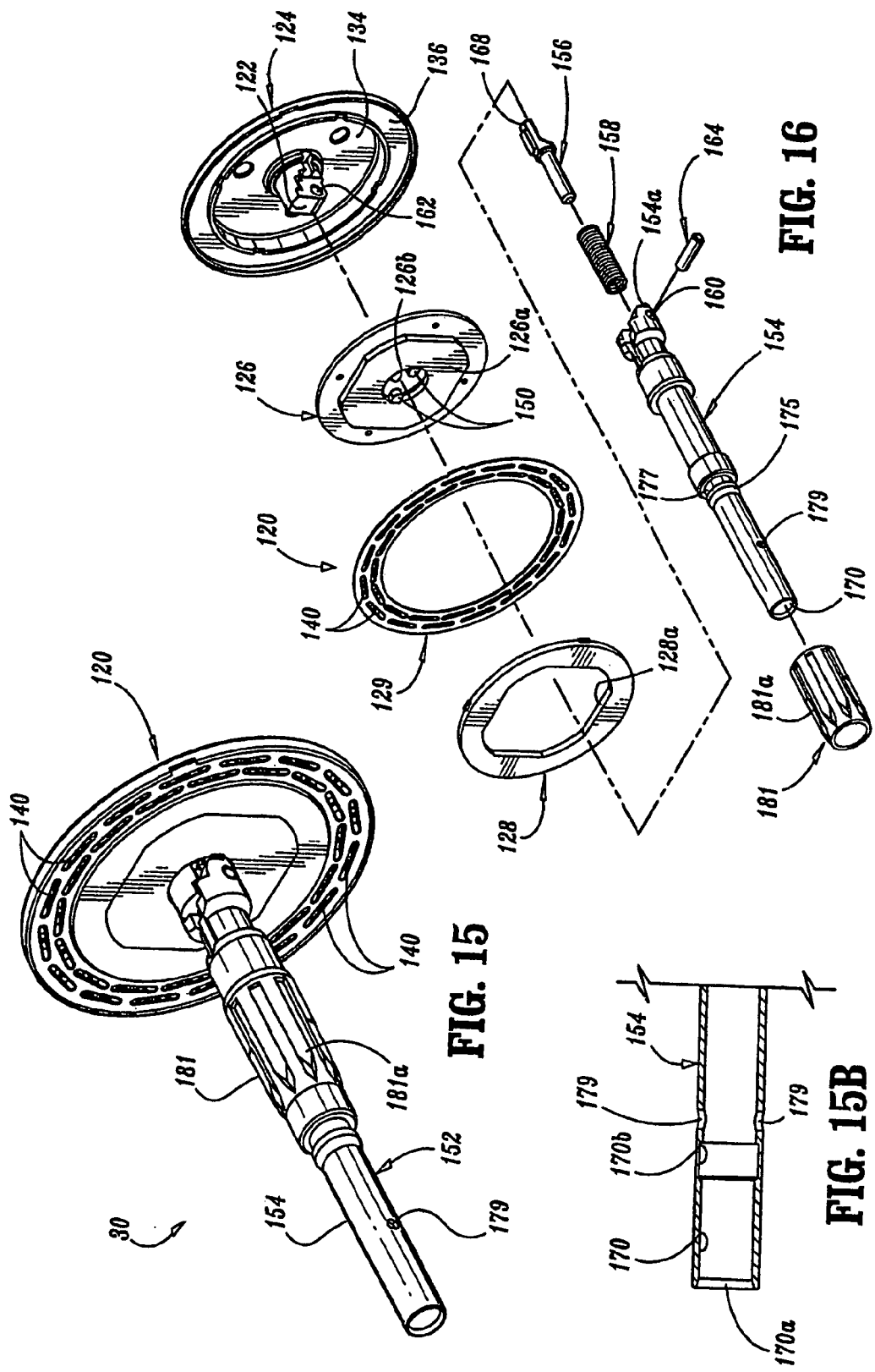

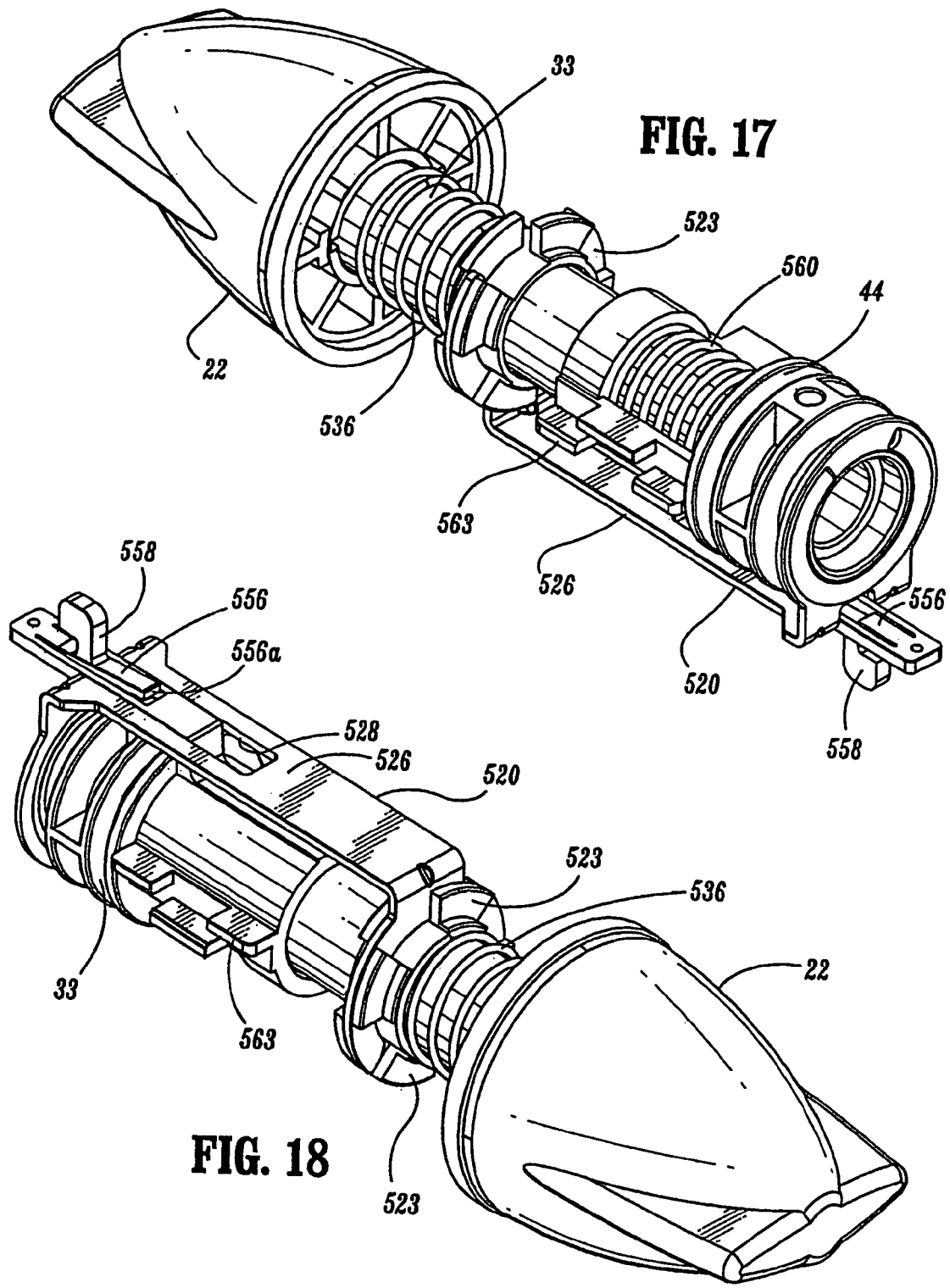

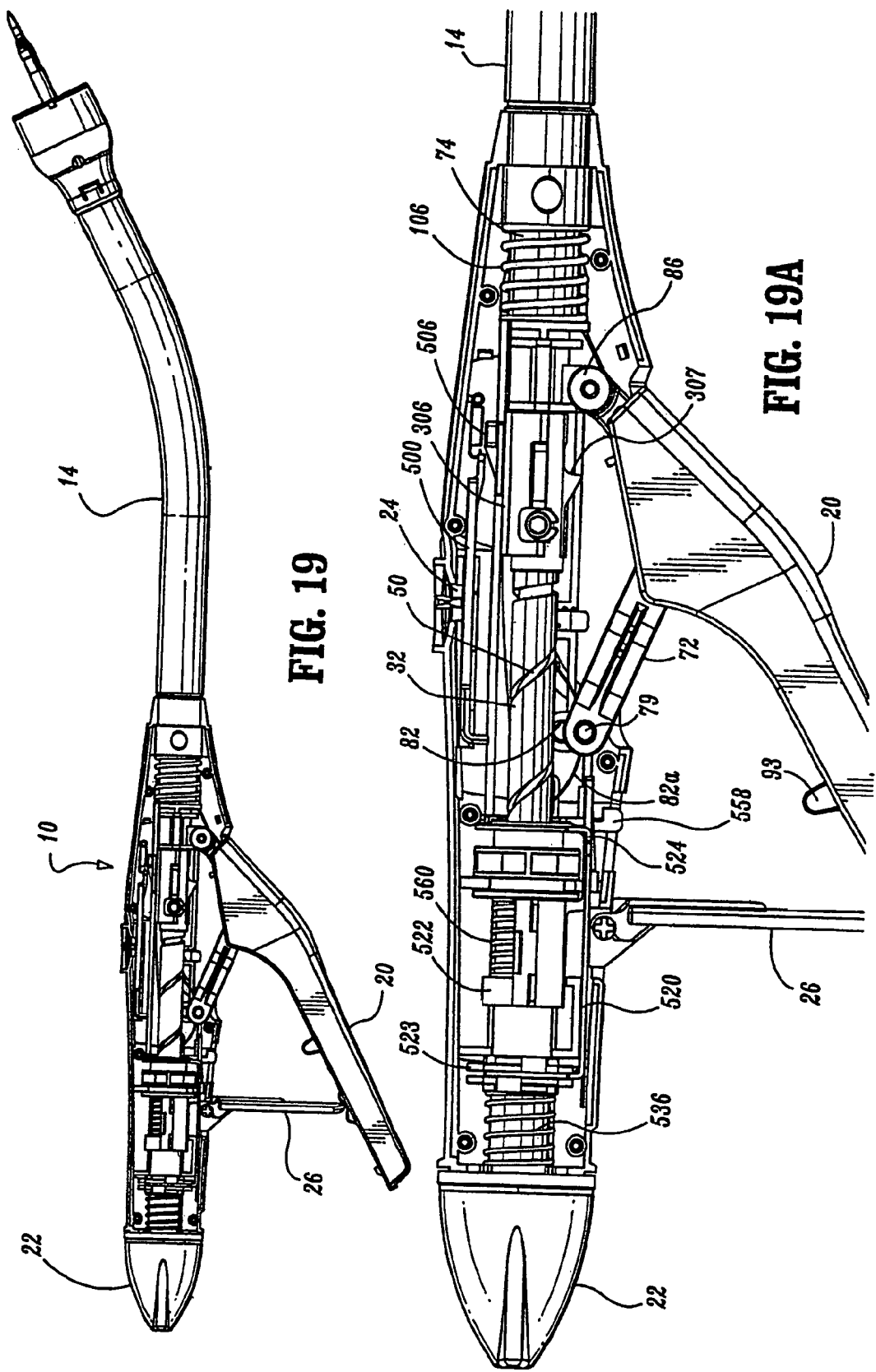

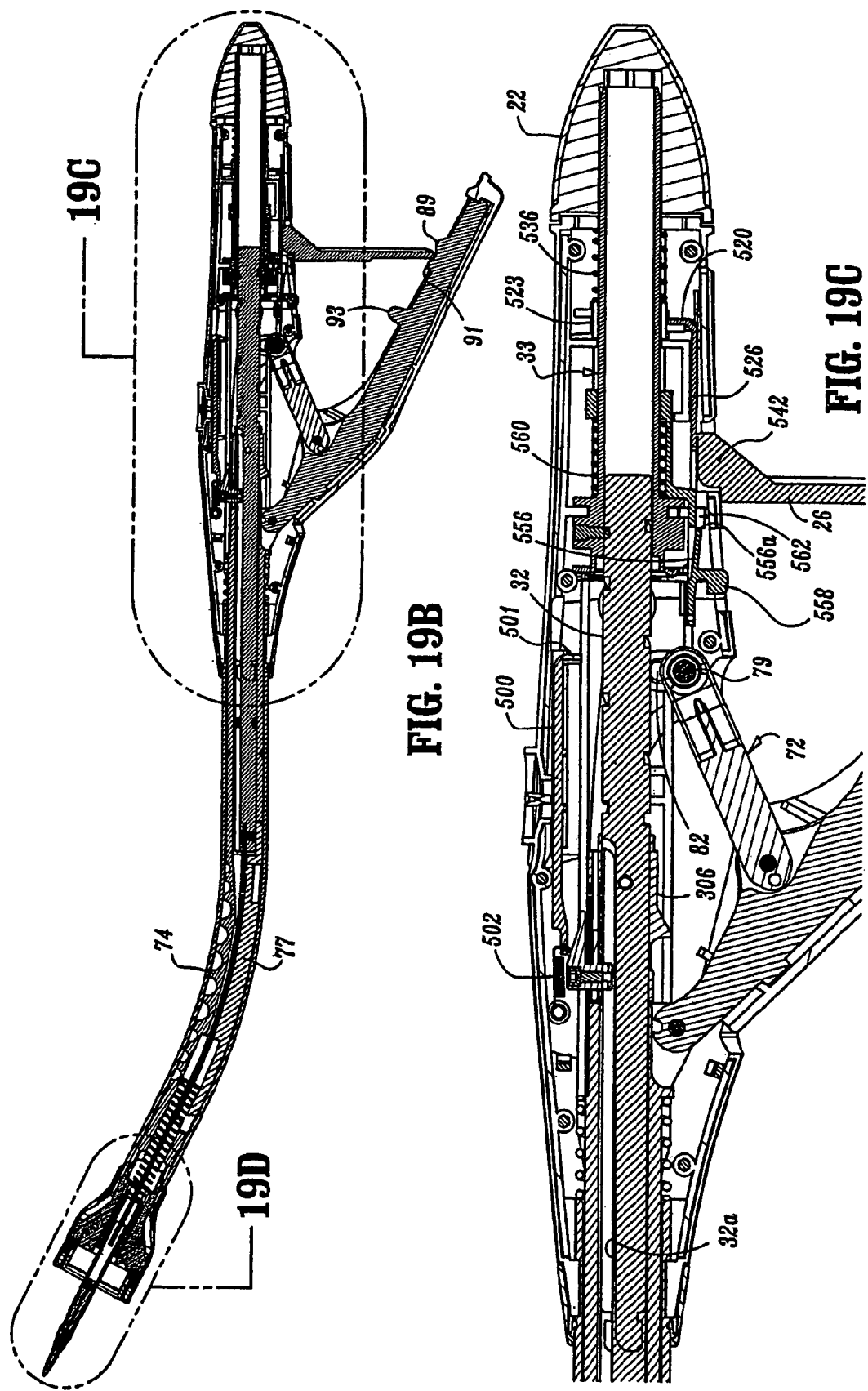

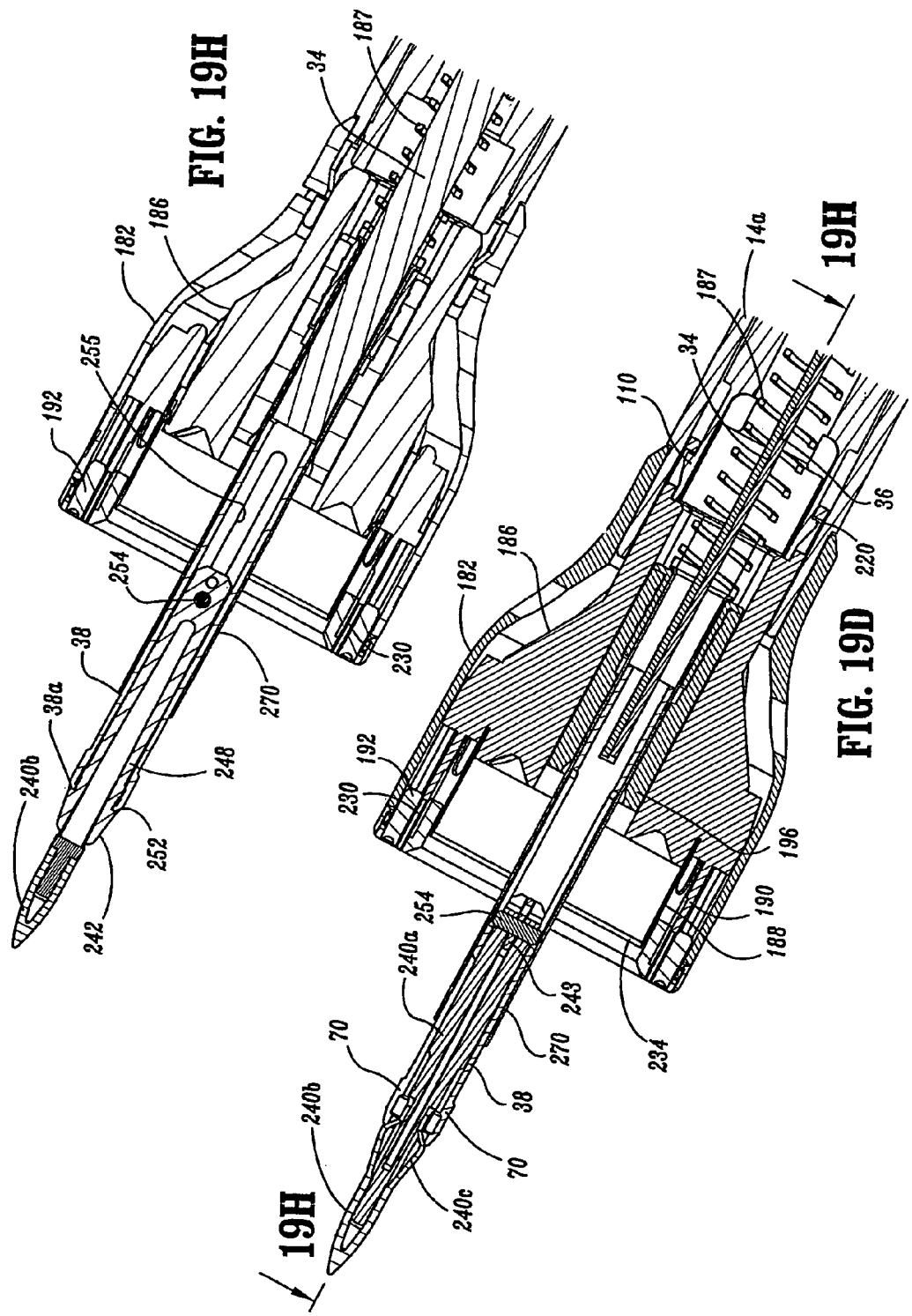

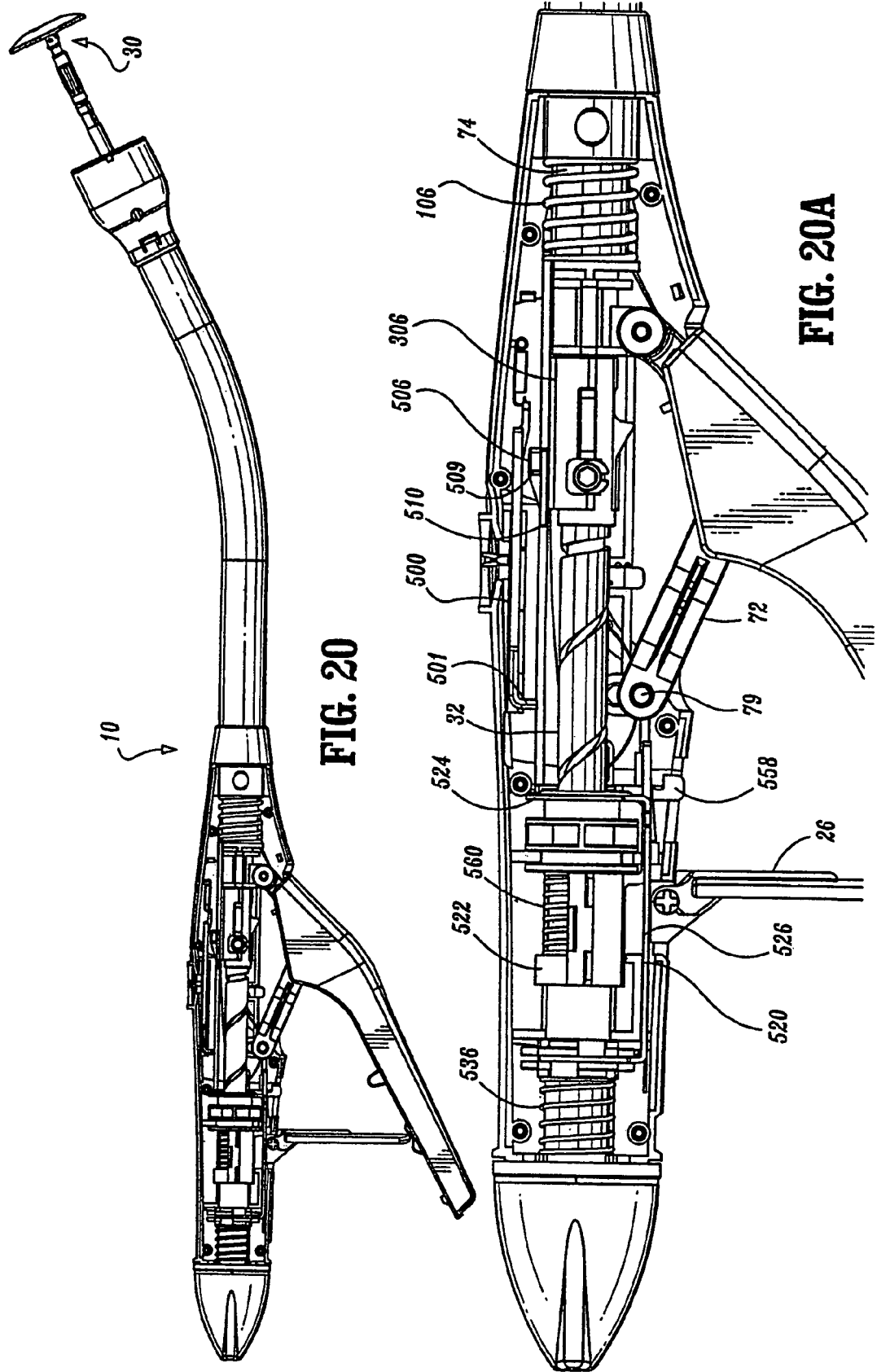

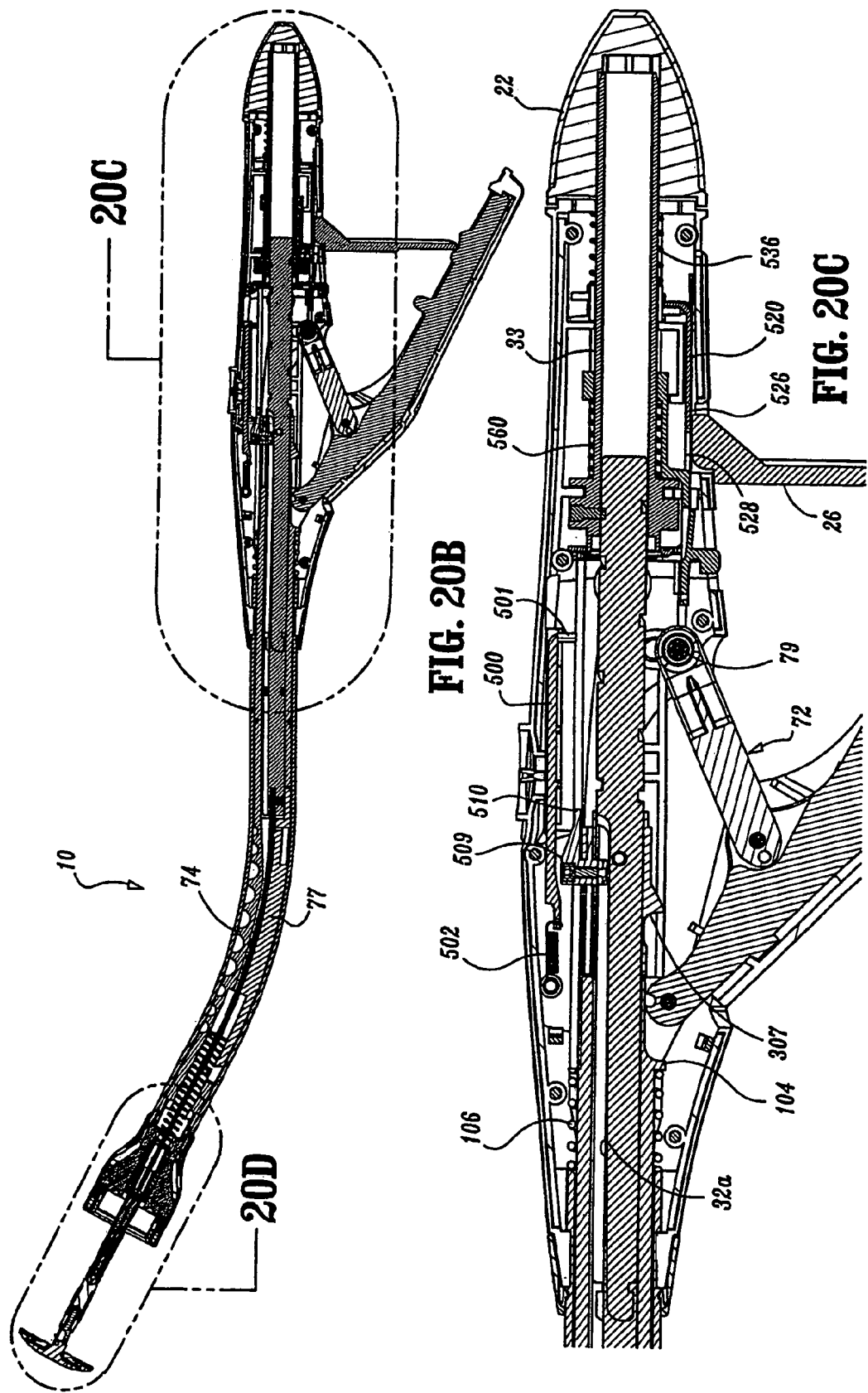

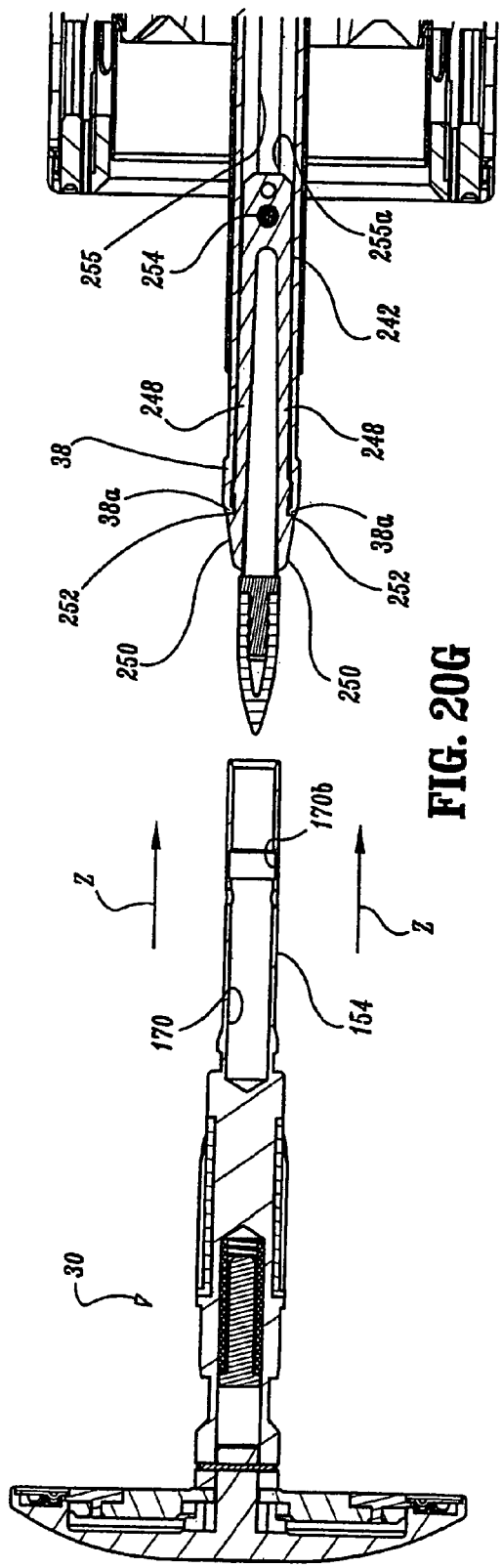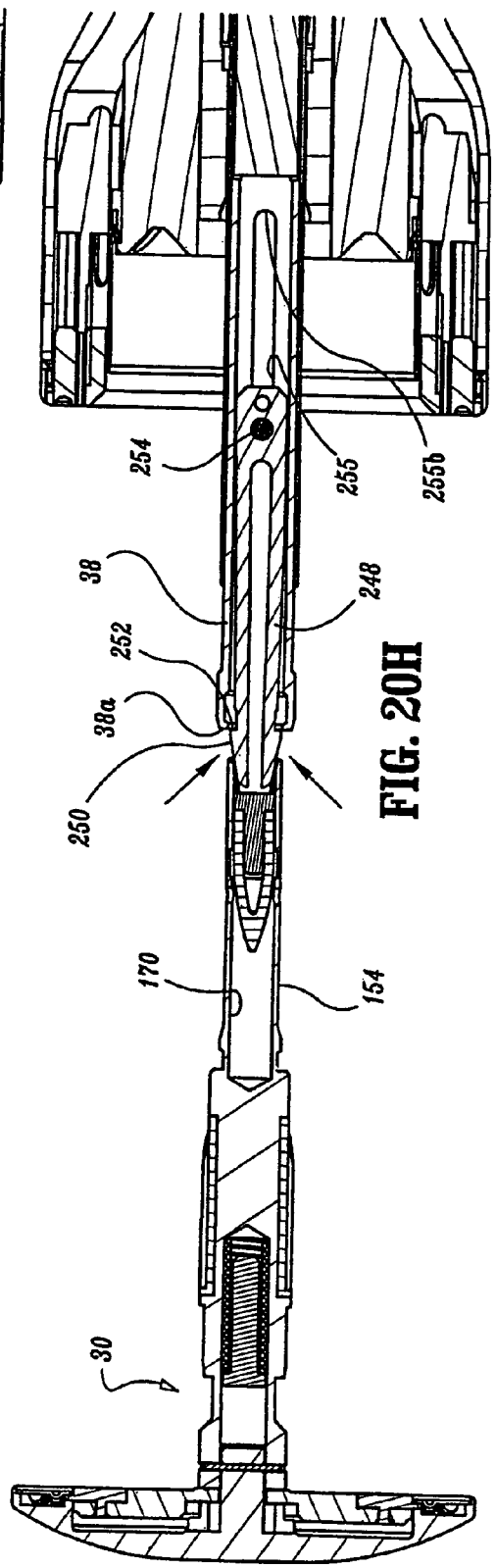

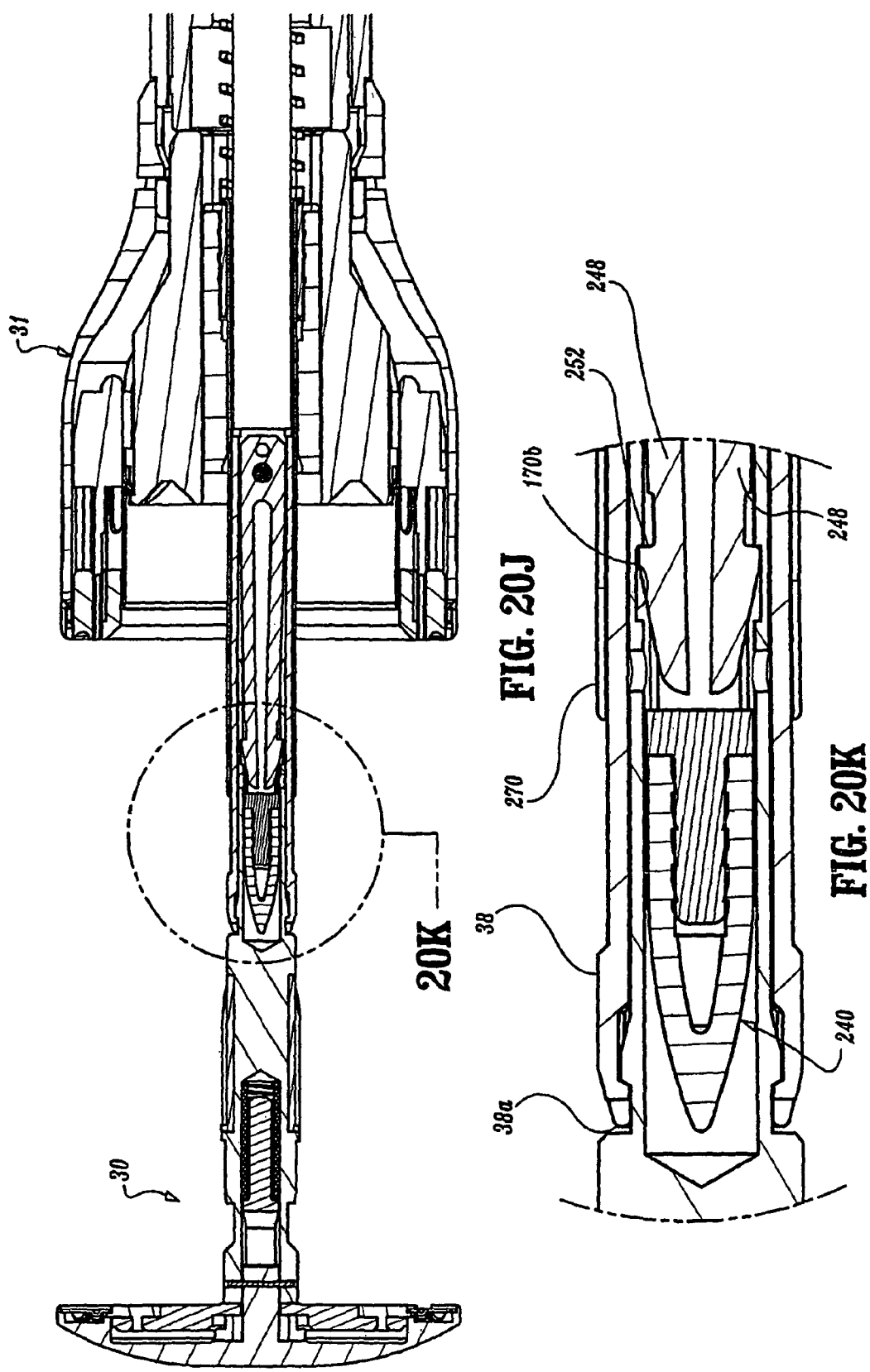

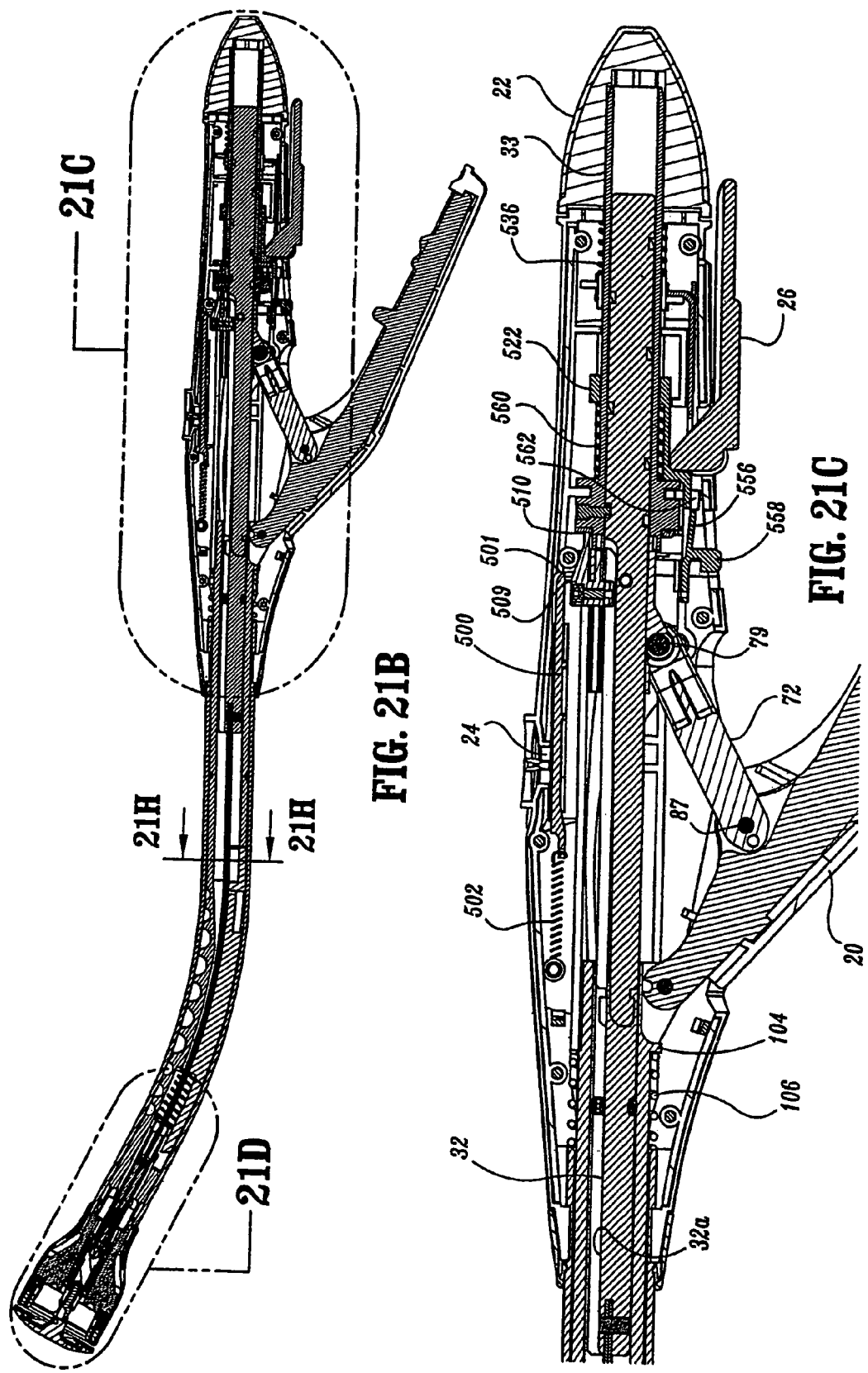

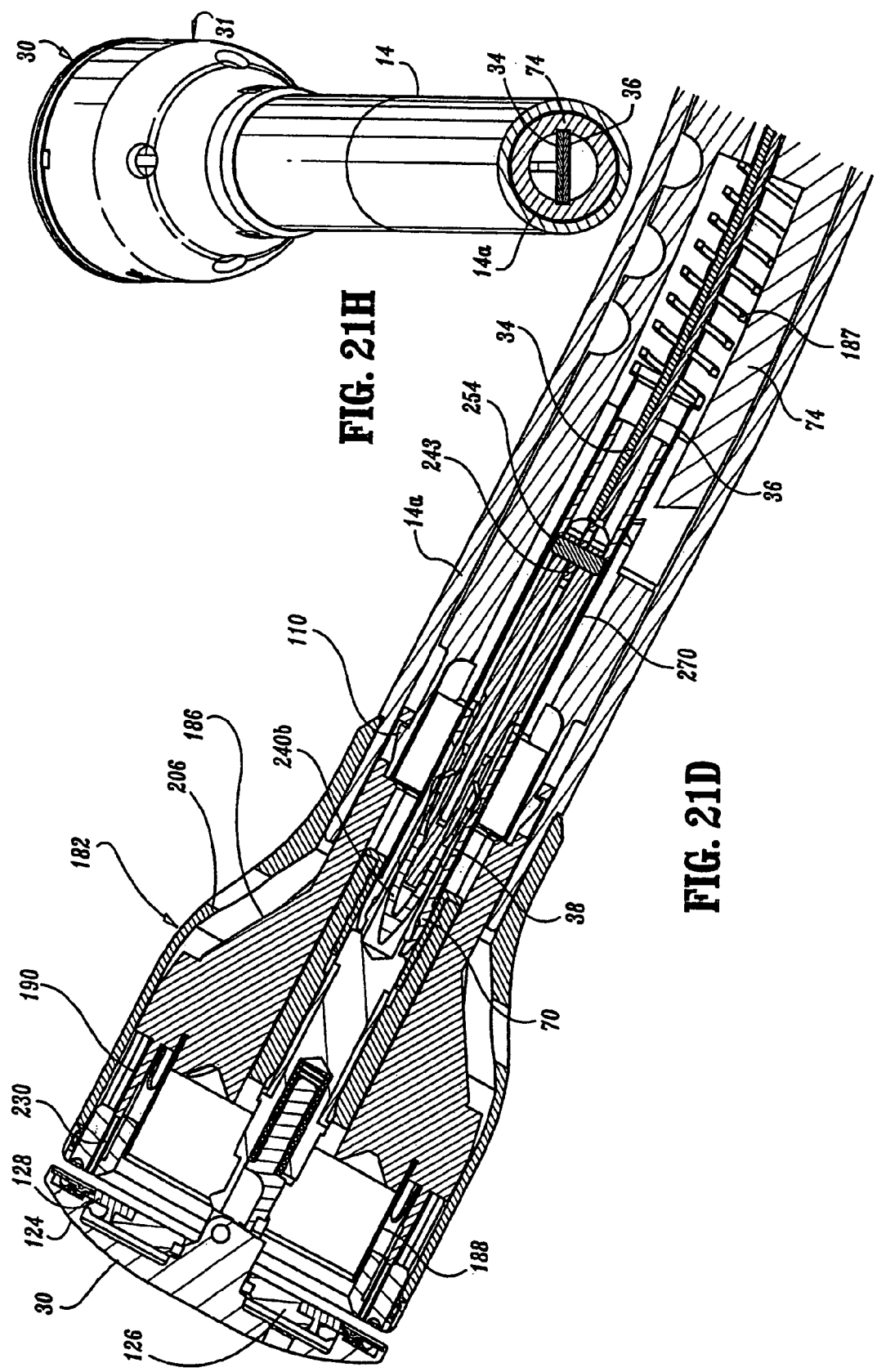

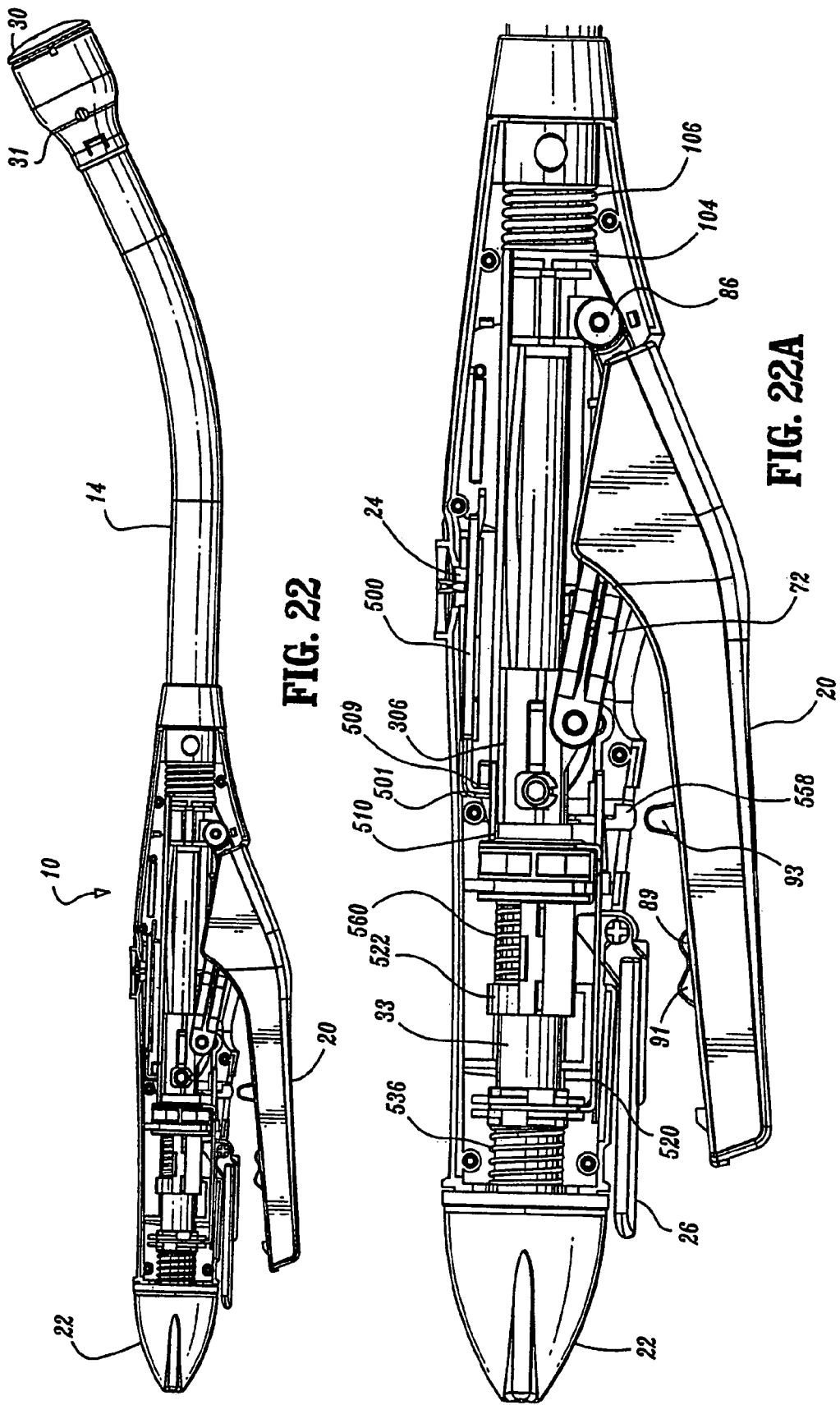

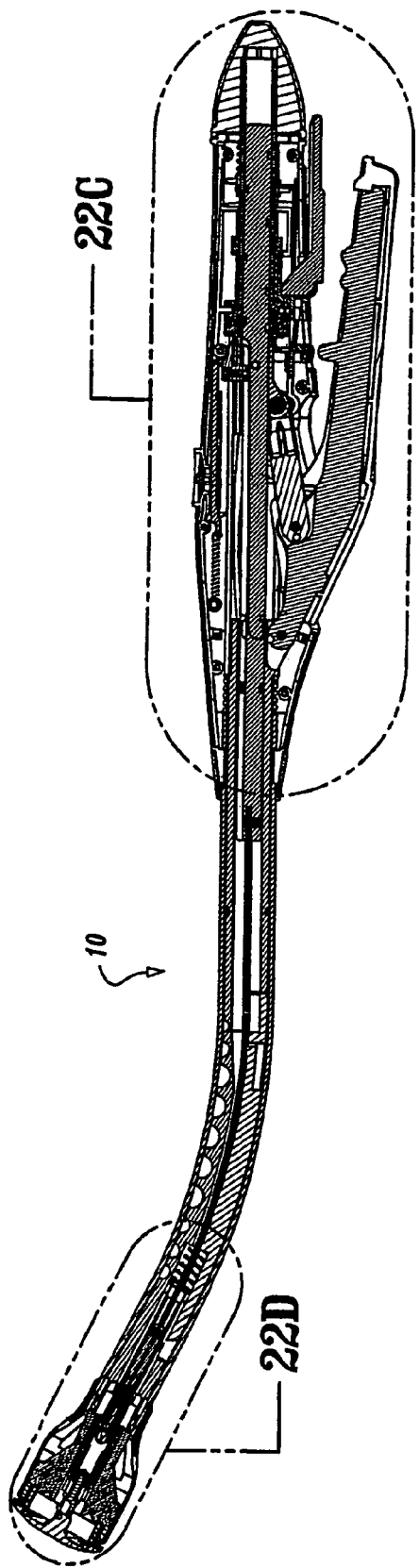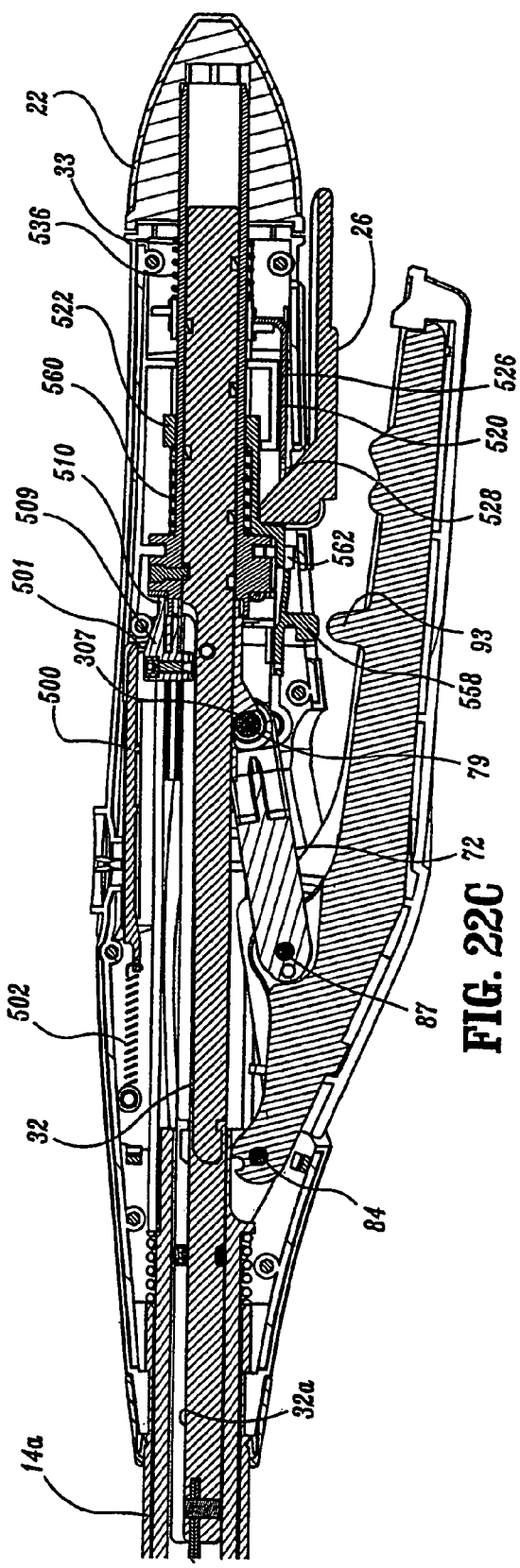
FIG. 22B
FIG. 22C

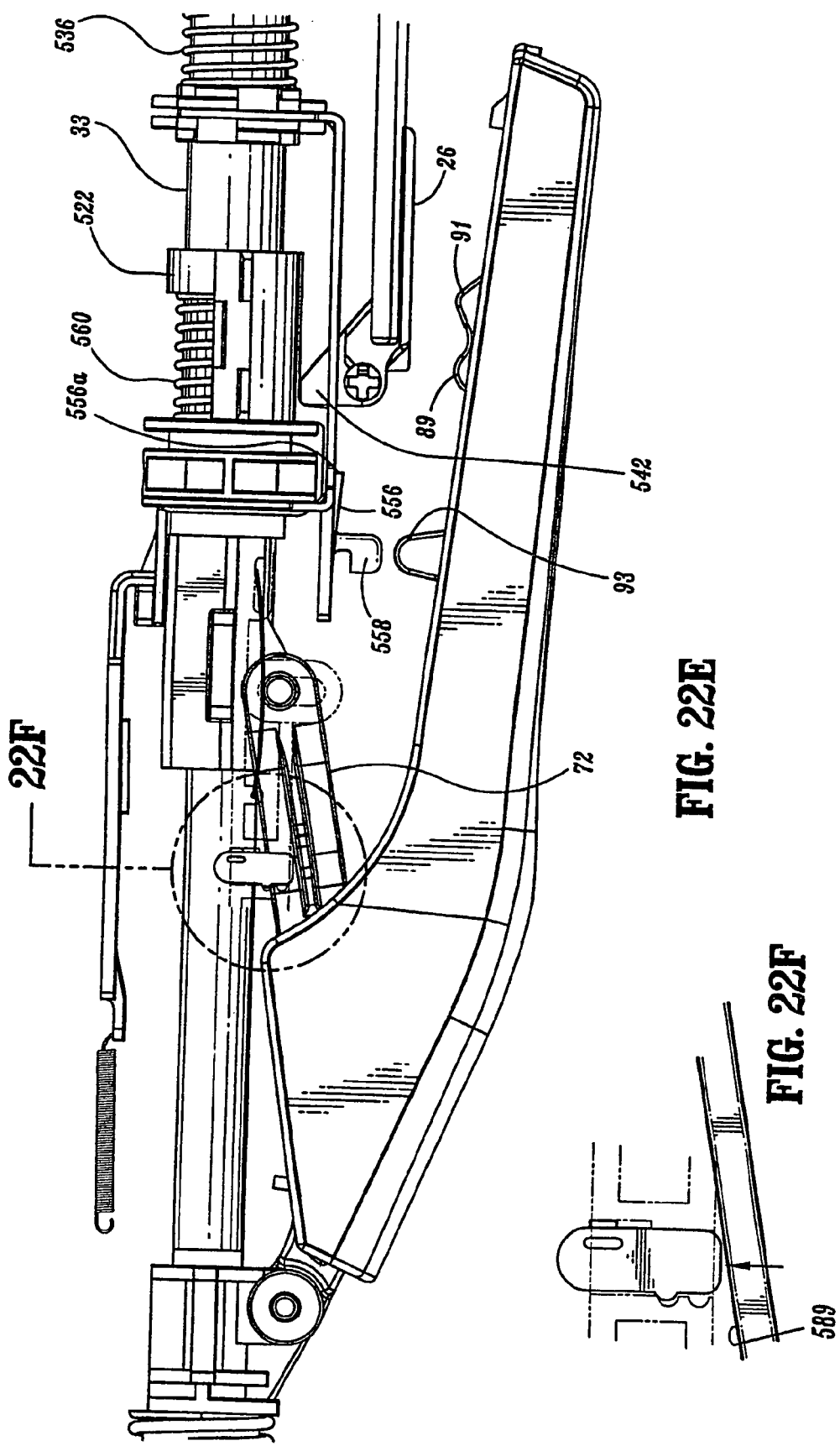

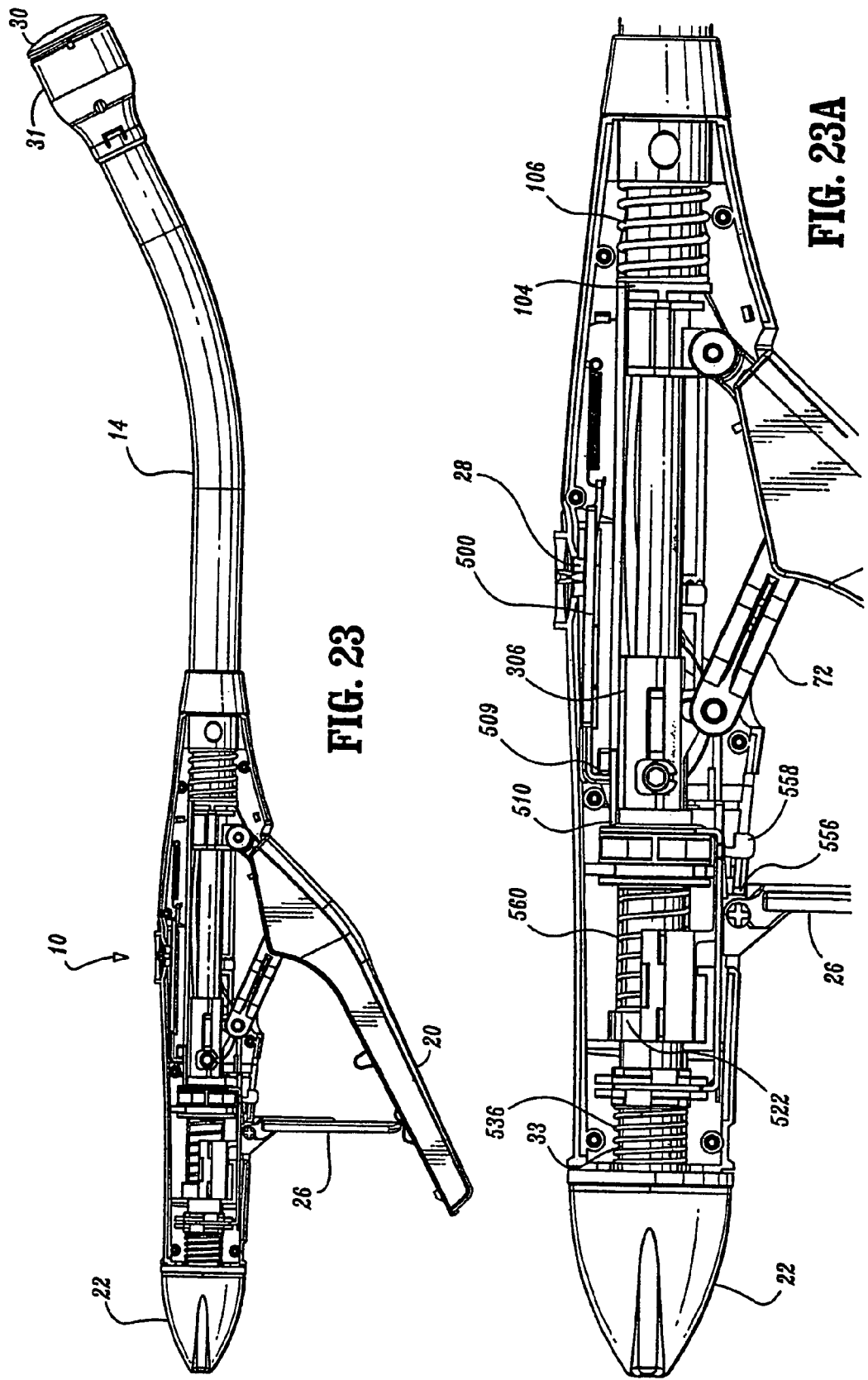

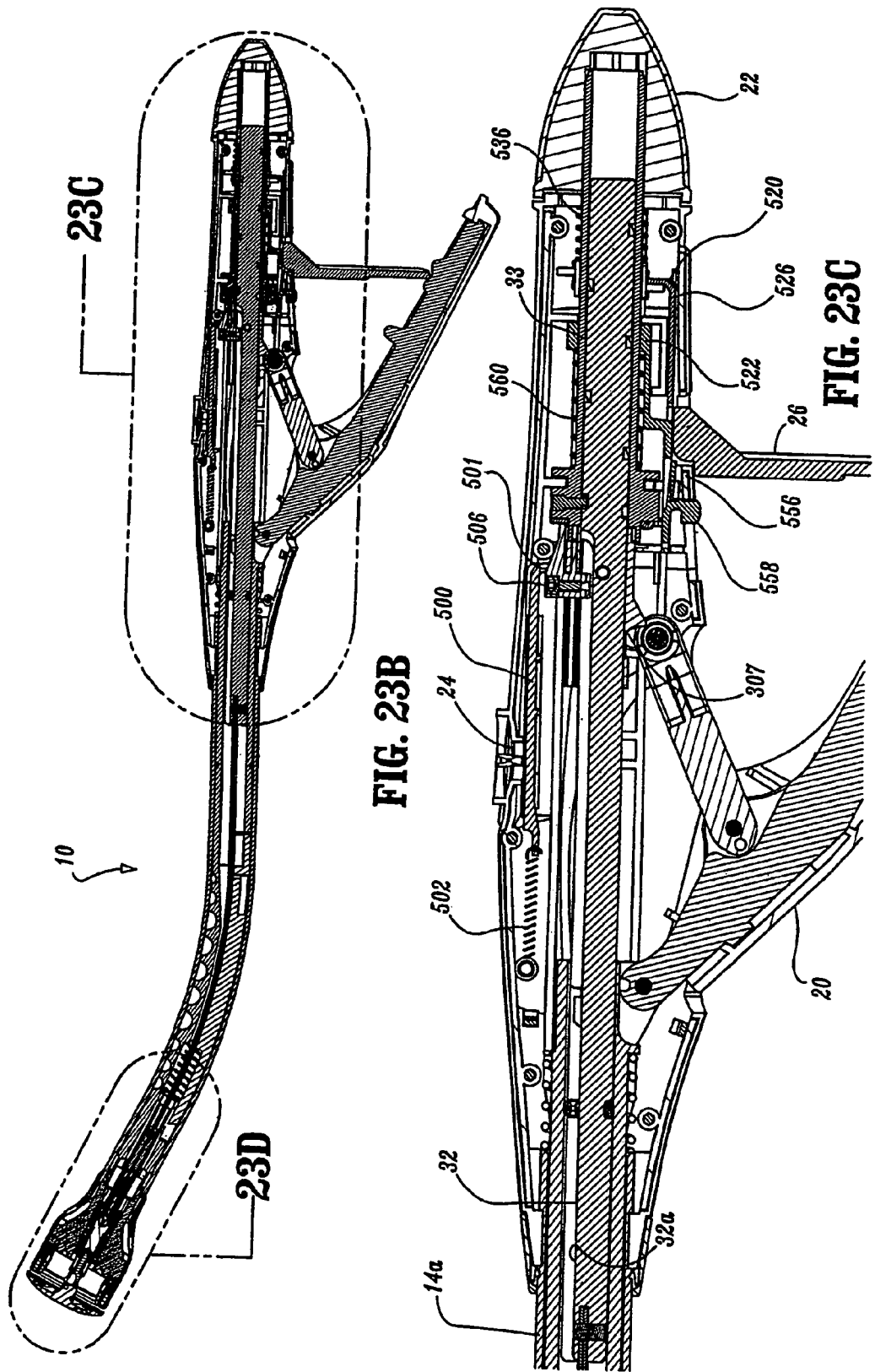

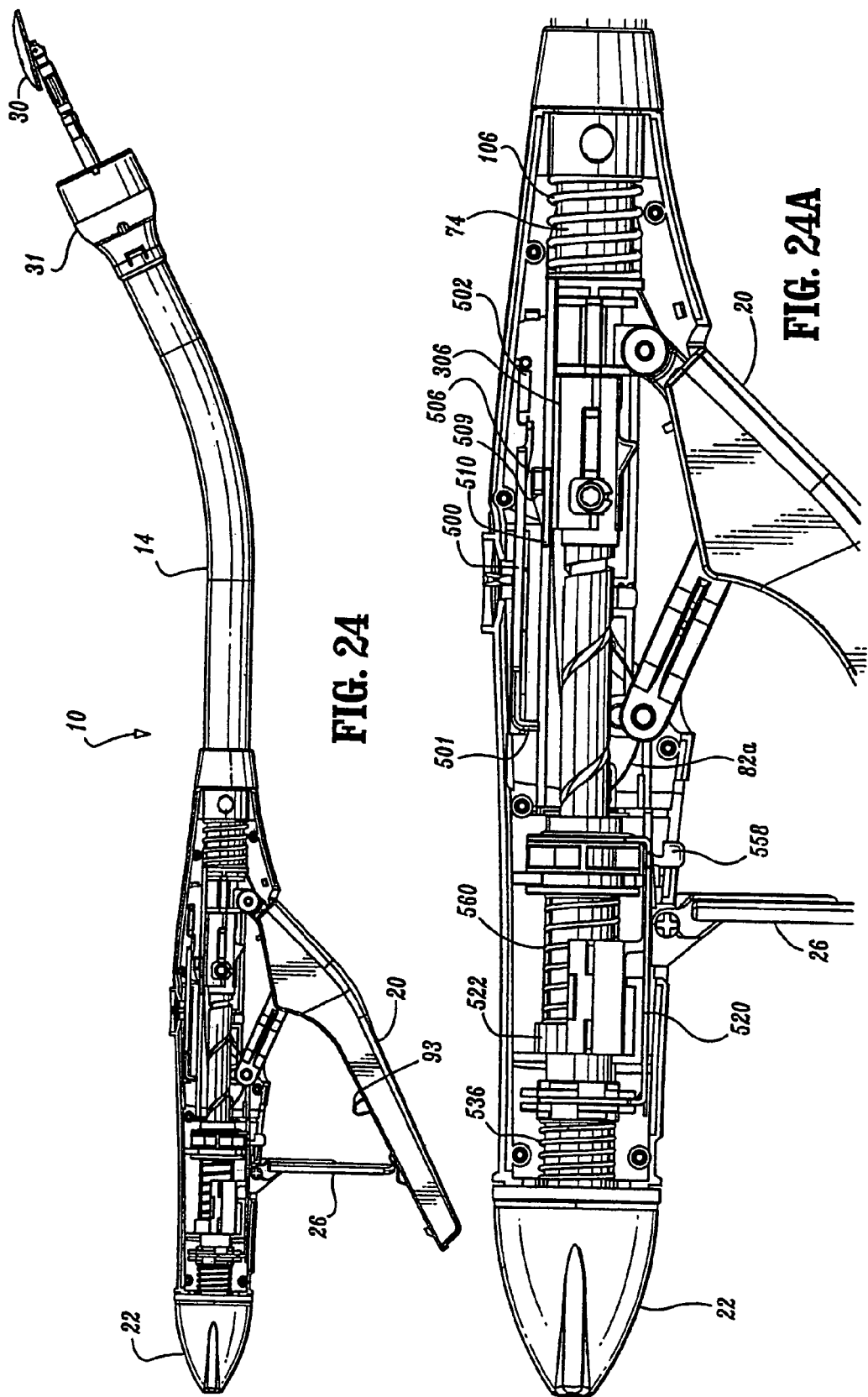

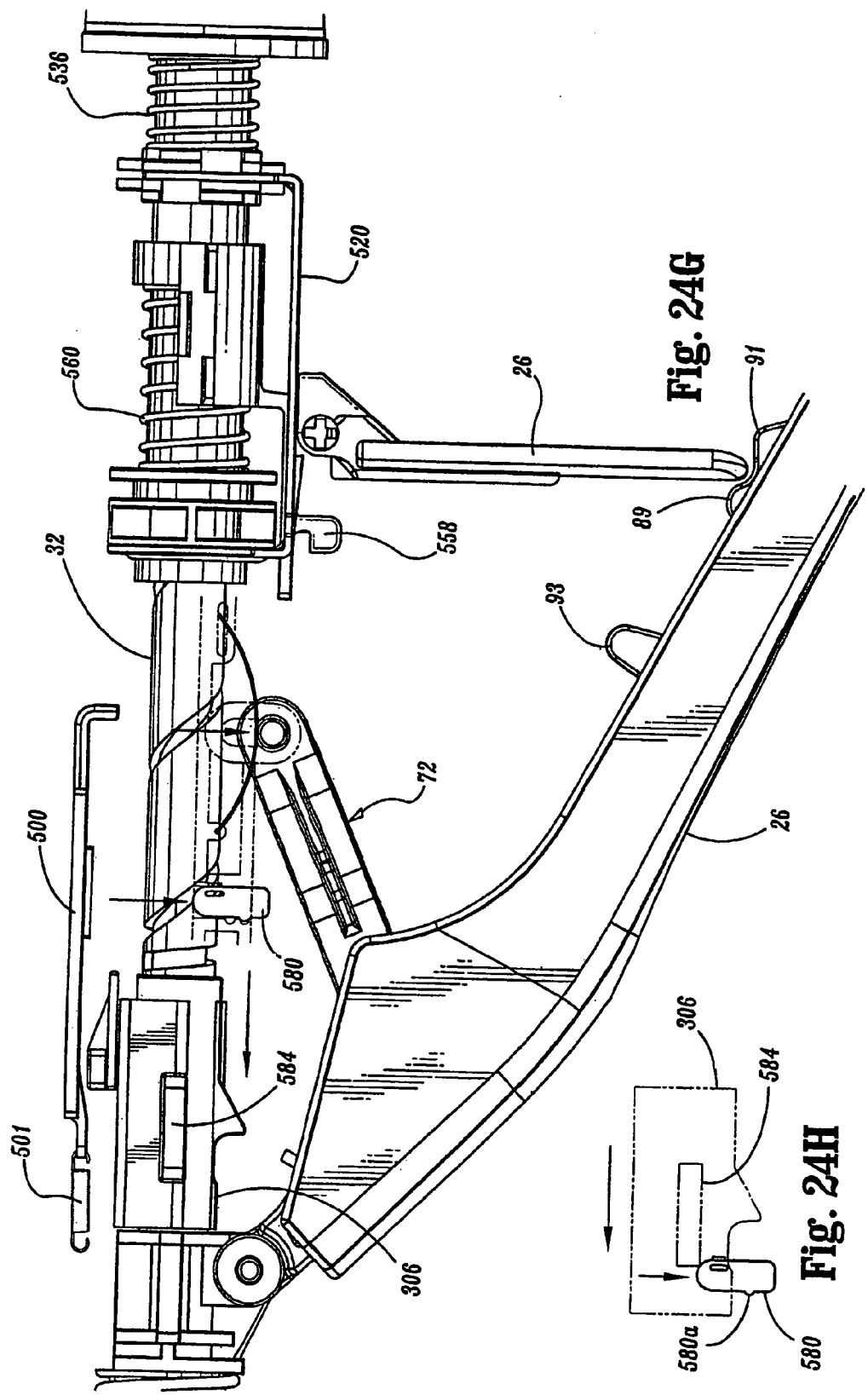

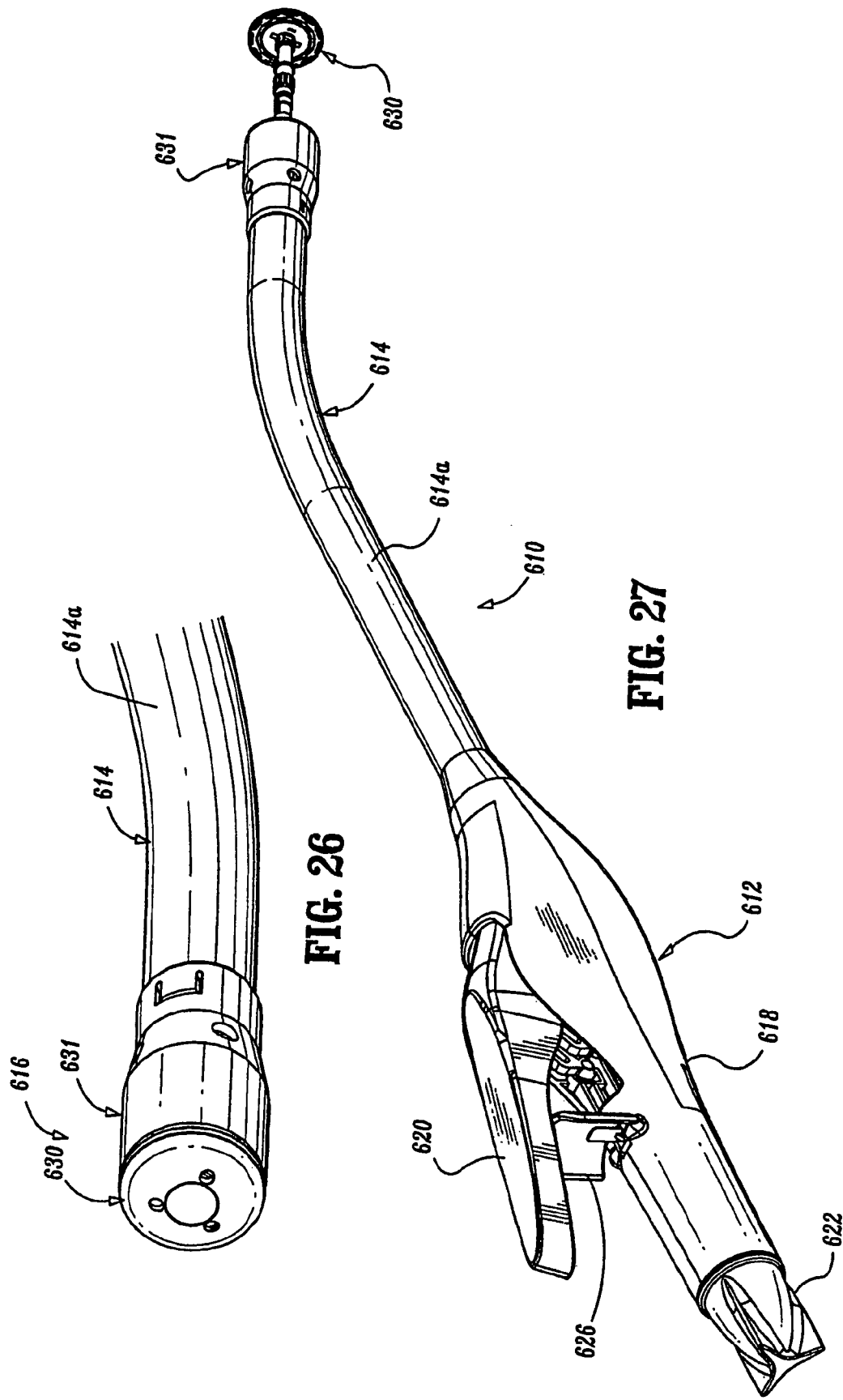

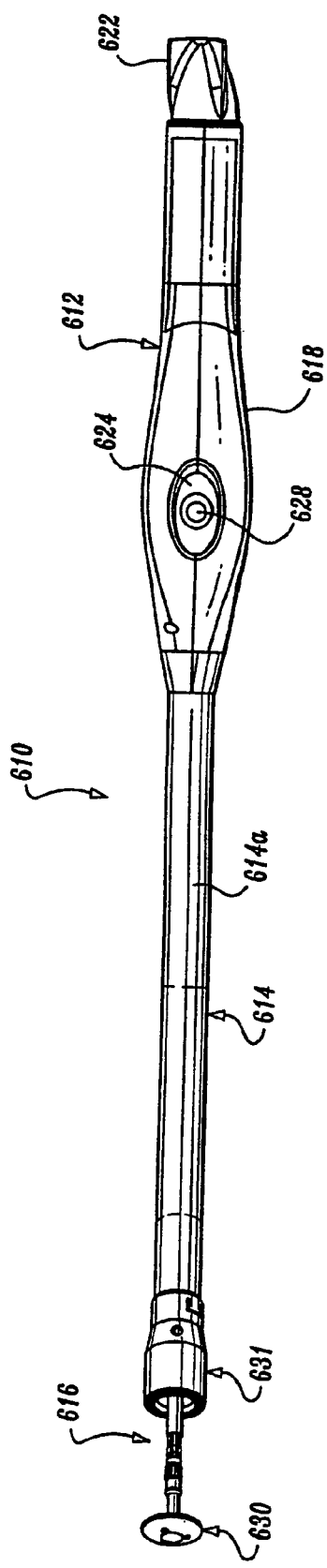
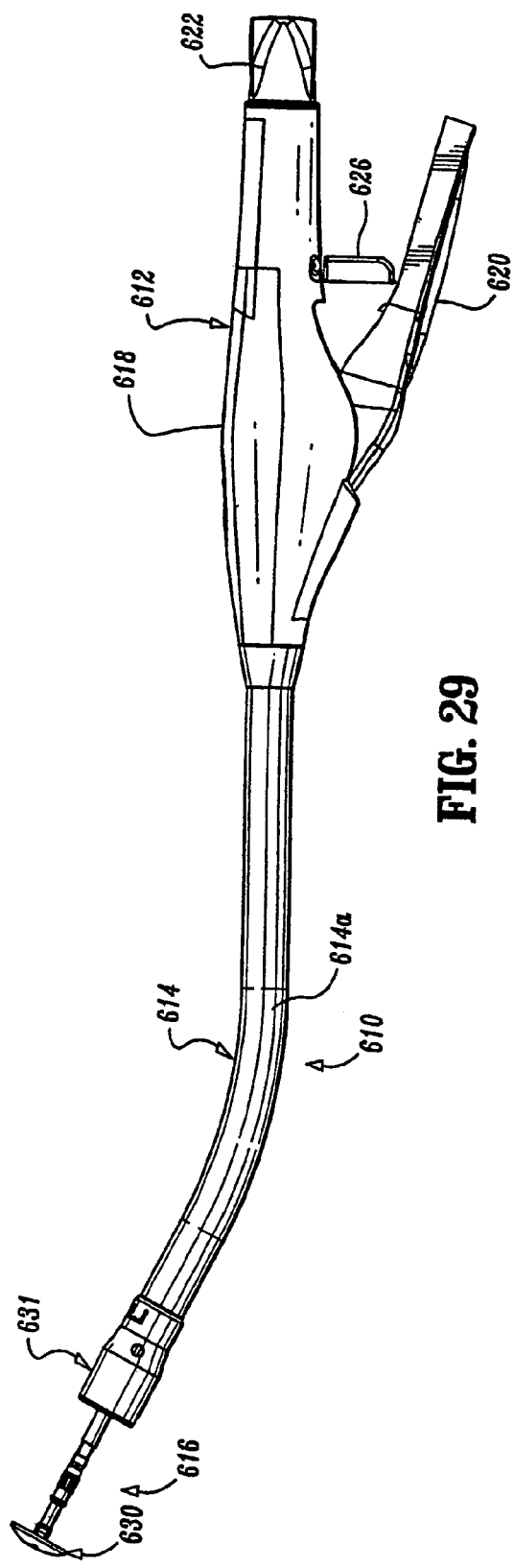
FIG. 28
FIG. 29

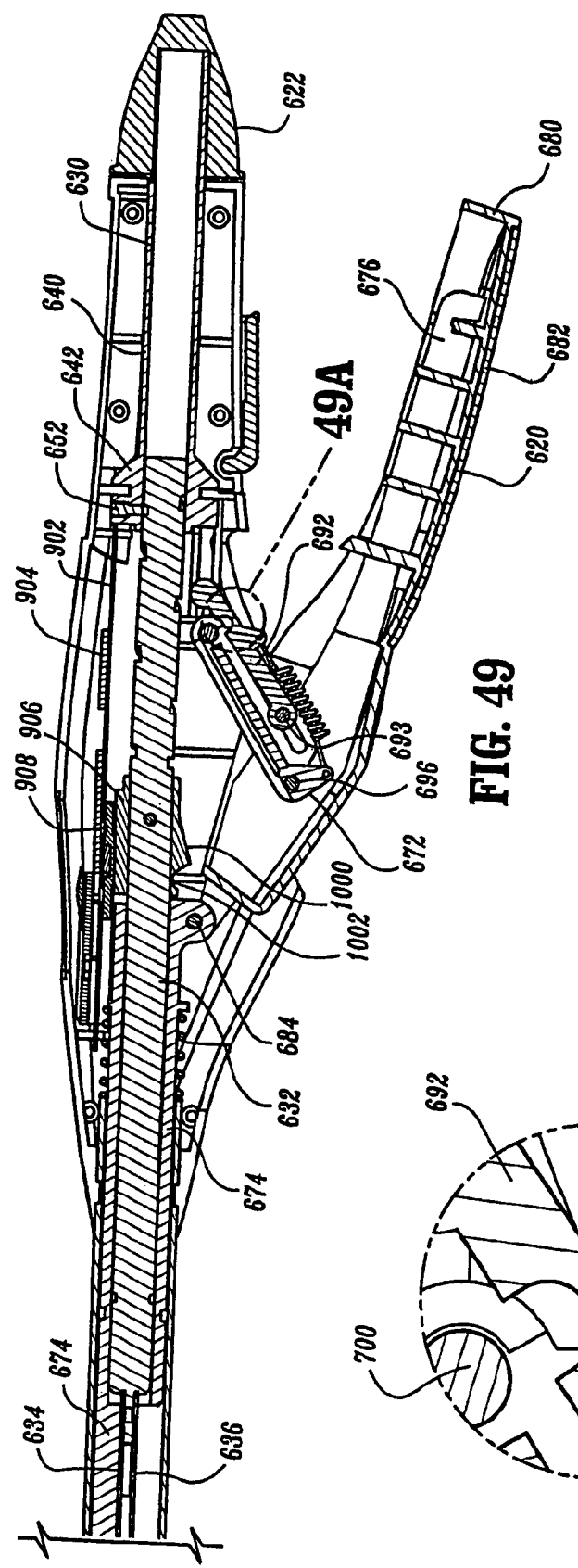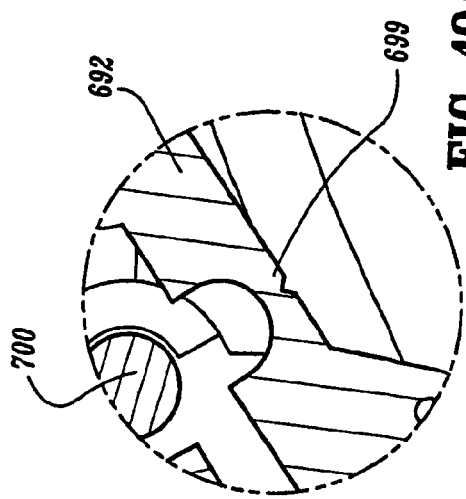

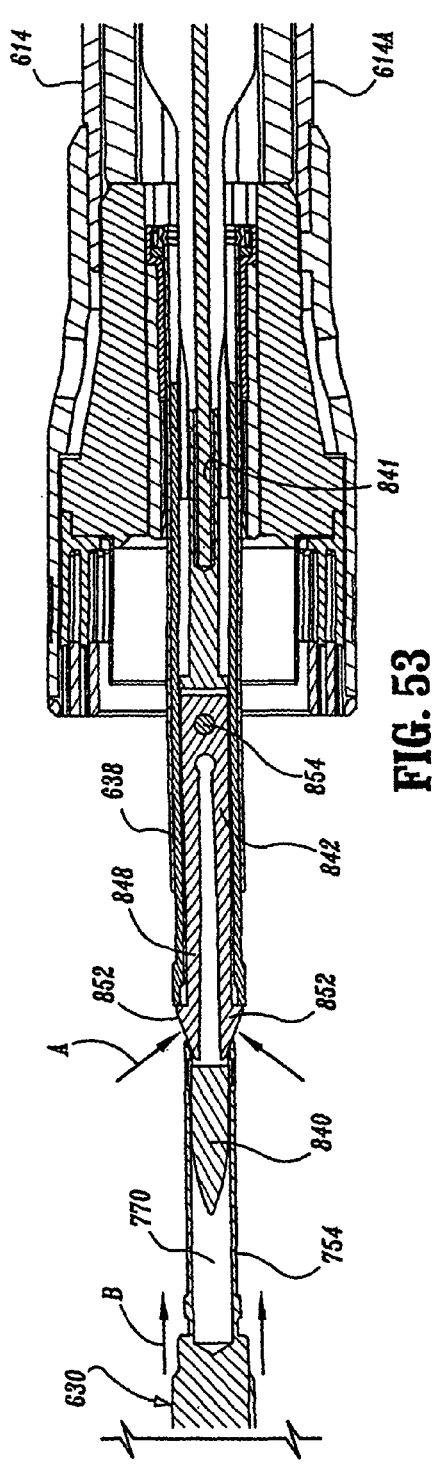
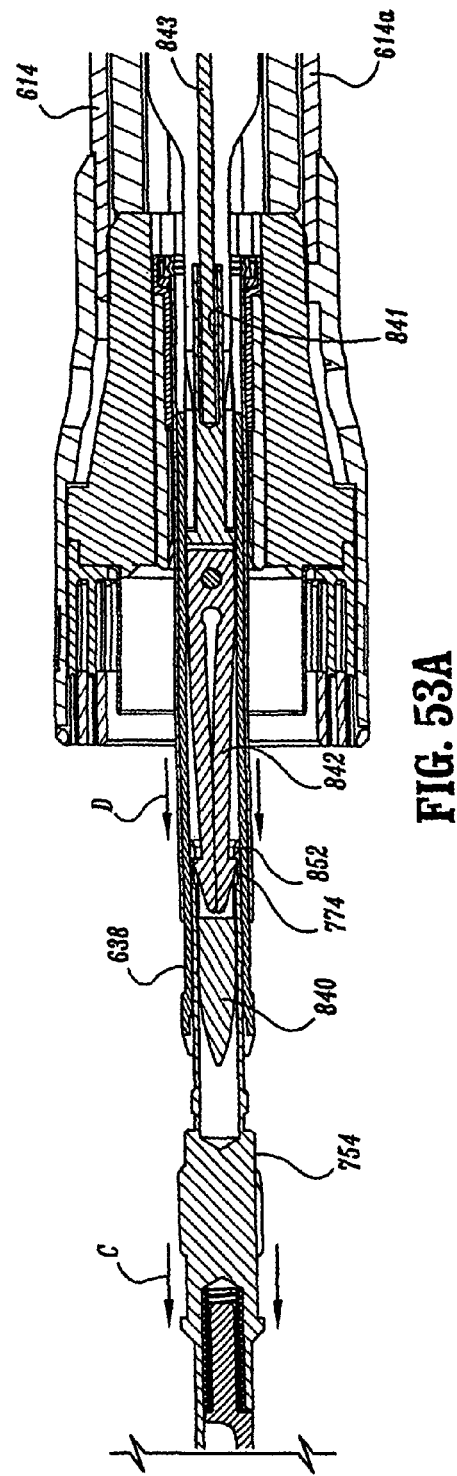

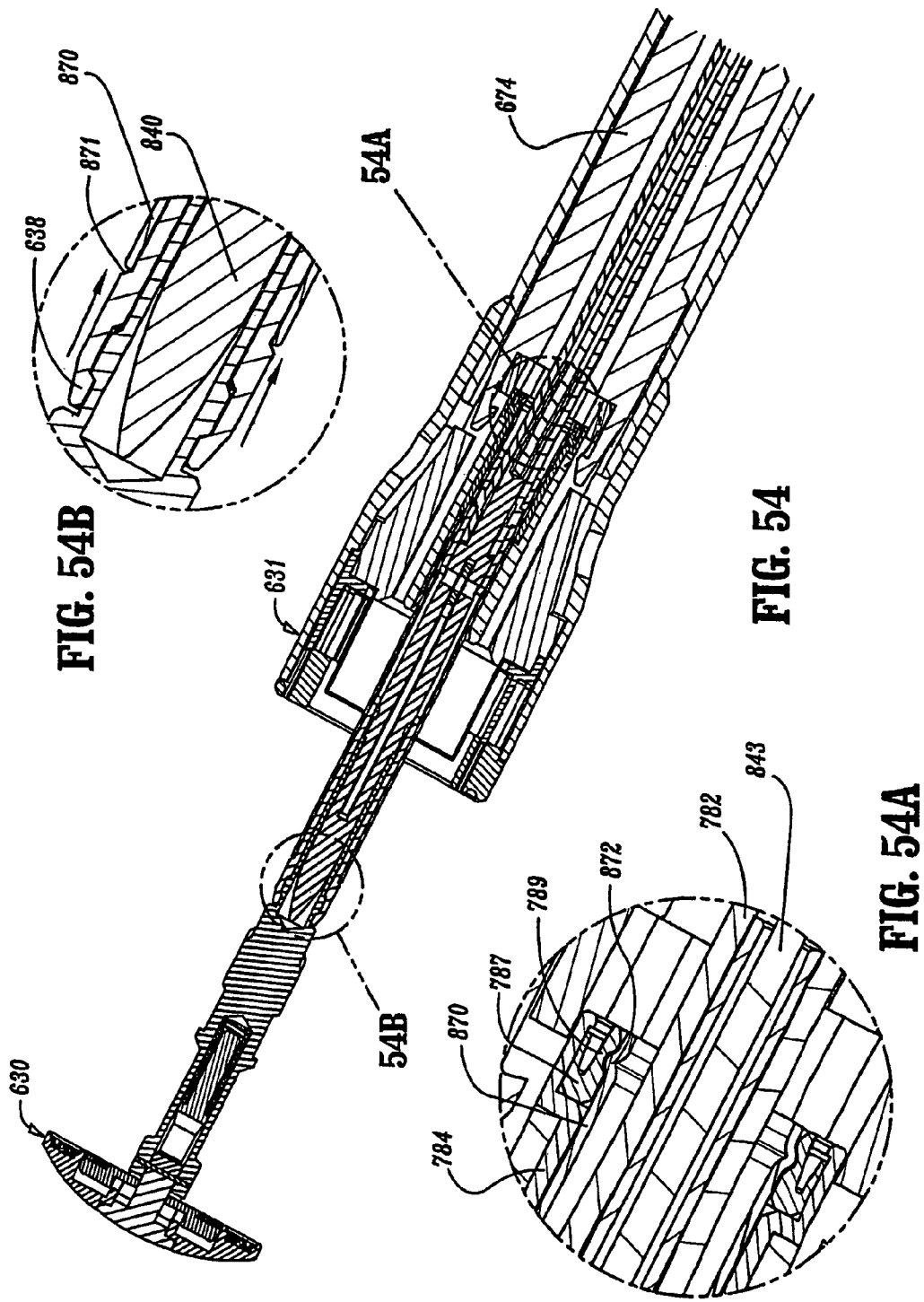

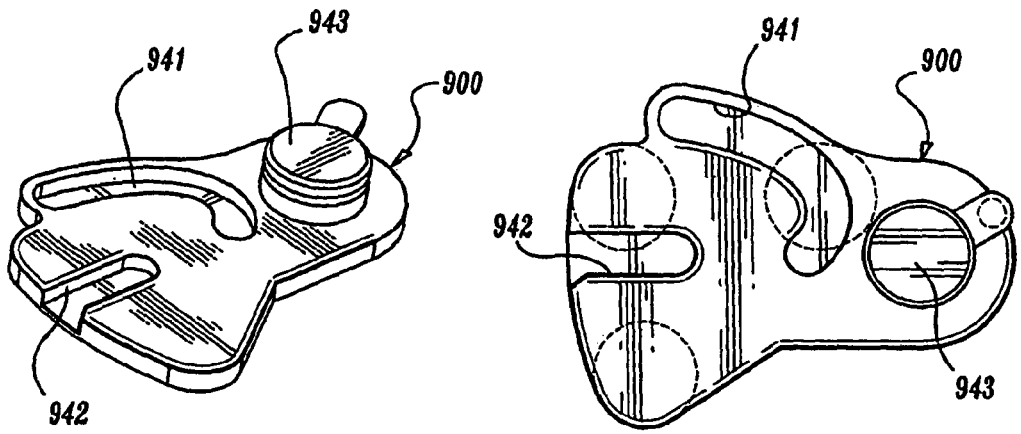
FIG. 69   FIG. 70
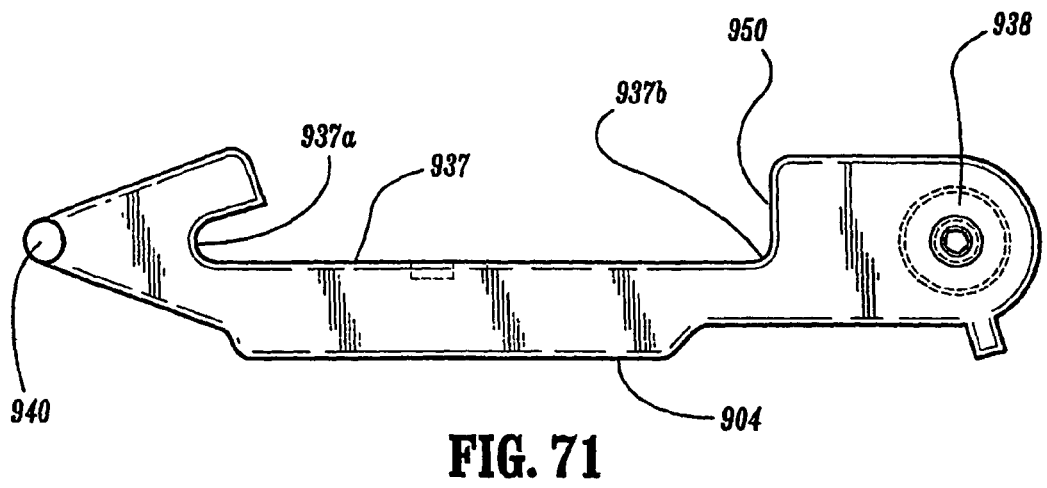
FIG. 71
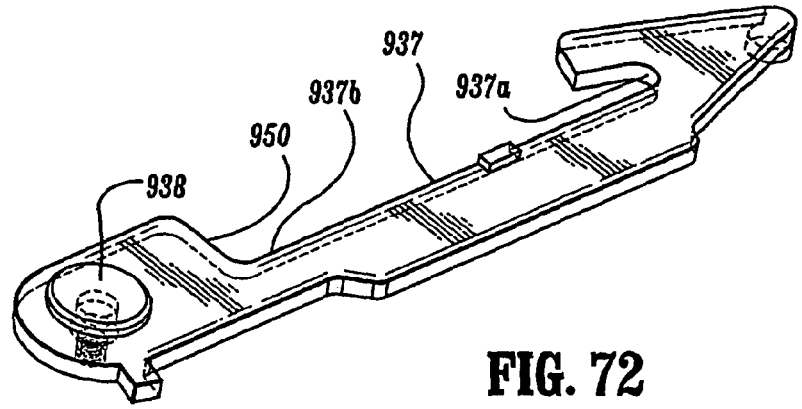
FIG. 72

SURGICAL STAPLING DEVICE FOR PERFORMING CIRCULAR ANASTOMOSES

This application is a continuation of U.S. application Ser. No. 11/208,667, now U.S. Pat. No. 7,234,624, which is a division of U.S. application Ser. No. 10/472,402 filed Sep. 17, 2003. now U.S. Pat. No. 6,945,444, which claims priority from PCT application Ser. No. PCT/US02/10792 filed Apr. 3, 2002, which claims priority from provisional application Ser. Nos. 60/281,259, filed Apr. 3, 2001, 60/327,653, filed Oct. 5, 2001 and 60/363,715, filed Mar. 11, 2002, all of which are incorporated herein by reference in their entirety.

BACKGROUND

1. Technical Field

The present disclosure relates generally to a surgical stapling device for applying surgical staples to body tissue. More particularly, the present disclosure relates to a surgical stapling device for performing circular anastomosis of hollow tissue organs.

2. Background to Related Art

Anastomosis is the surgical joining of separate hollow organ sections so that the sections intercommunicate with each other. Typically, the anastomosis procedure follows surgery in which a diseased or defective section of hollow tissue is removed and the remaining end sections are to be joined. Depending on the desired anastomosis procedure, the end sections may be joined by either circular, end-to-side or side-to-side organ reconstruction methods.

In a circular anastomosis procedure, the two ends of the organ sections are joined by means of a stapling instrument which drives a circular array of staples through the end sections of each organ section and simultaneously cores any overlapping tissue to free the tubular passage. Examples of instruments for performing circular anastomosis of hollow organs are described in U.S. Pat. Nos. 6,053,390, 5,588,579, 5,119,983, 5,005,749, 4,646,745, 4,576,167, and 4,473,077. Typically, these instruments include an elongated shaft having a handle portion at a proximal end to actuate the instrument and a staple holding component disposed at a distal end. An anvil assembly including an anvil rod with attached anvil head is mounted to the distal end. Opposed end portion, of the organs to be stapled are clamped between the anvil head and the staple holding component. The clamped tissue is stapled by driving one or more staples from the staple holding component so that the ends of the staples pass through the tissue and are deformed by the anvil head.

Generally, during an anastomosis procedure, the anvil assembly is separated from the stapling device and positioned within the patient in one of the tissue sections and the stapling device is positioned within the other of the tissue sections. Thereafter, the anvil assembly and the stapling device are reattached to clamp the tissue sections therebetween. Typically, placement requires the use of a detachable trocar for one or both of the anvil assembly and stapling instrument. Because of limitations on visibility and accessibility to the surgical site, it may be difficult and time consuming for a surgeon to attach and detach a trocar to the anvil assembly and/or the stapling device. Moreover, it may be difficult to determine whether the anvil assembly has been properly reattached to the stapling device.

SUMMARY

In accordance with the present disclosure, a surgical stapling device is disclosed for performing circular anastomoses. The surgical stapling device includes a handle portion, an elongated body portion and a head portion including an anvil assembly and a shell assembly. The handle portion includes a rotatable approximation knob for approximating the anvil and shell assemblies and a firing trigger for actuating a firing mechanism for ejecting staples positioned within the shell assembly. The firing trigger forms one link of a two bar linkage provided to actuate the firing mechanism. The two bar linkage provides the device with an improved mechanical advantage to reduce the firing forces required to fire the device.

The head portion includes an anvil assembly including a tiltable anvil which will tilt automatically after firing of the device and unapproximating the anvil and shell assemblies. The tiltable anvil provides a reduced anvil profile to simplify removal of the device after the anastomoses procedure has been performed. The head portion also includes a retractable trocar assembly which is slidably positioned within an anvil retainer and is automatically advanced and retracted upon attachment and detachment of the anvil assembly onto the anvil retainer. The retractable trocar assembly simplifies the anastomoses procedure by eliminating the step of attaching and detaching a trocar to the stapling device. A lockout tube is provided and is positioned about an anvil retainer for releasably engaging an anvil assembly. The lockout tube prevents inadvertent detachment of the anvil assembly from the anvil retainer such as during firing of the stapling device after a predetermined degree of approximation.

The surgical stapling device also includes a firing lockout assembly which prevents actuation of the firing trigger until an anvil has been attached to the device and the anvil has been approximated. In one preferred embodiment, the firing lockout assembly includes a trigger lock and a safety bracket which prevents movement of the trigger lock from a locked to an unlocked position until an anvil has been attached to the device and approximated. The lockout assembly also includes a lockout sleeve for returning the trigger lock to a locked position after the device has been fired. The lockout assembly prevents a surgeon from inadvertently firing the device without an anvil attached and mistakenly firing a device which has already been fired and has no staples.

The surgical stapling device also includes tactile indication mechanism. In one preferred embodiment, the tactile indication mechanism notifies a surgeon that the device has been fired. In another prefered embodiment, the tactile indicator notifies a surgeon that the anvil head has been unapproximated a distance sufficient to permit the anvil head to tilt, and thus, indicating that the device can be removed from the patient.

BRIEF DESCRIPTION OF THE DRAWINGS

Various preferred embodiments of the presently disclosed surgical stapling device are disclosed herein with reference to the drawings, wherein:

FIG. 1 is an elevated side perspective view from the proximal end of one embodiment of the presently disclosed surgical stapling device.

FIG. 2 is an elevated side perspective view from the distal end of the surgical stapling device shown in FIG. 1;

FIG. 3 is an elevated side perspective view from the proximal end of another preferred embodiment of the presently disclosed surgical stapling device;

FIG. 4 is an elevated side perspective view from the distal end of the surgical stapling device shown in FIG. 3;

FIG. 5 is an elevated side perspective view from the proximal end of another preferred embodiment of the presently disclosed surgical stapling device;

FIG. 6 is an elevated side perspective view from the distal end of the surgical stapling device shown in FIG. 5;

FIG. 8A is an enlarged view of the indicated area of detail shown in FIG. 8;

FIG. 8B is an elevated side perspective view of the tactile indicator of the surgical stapling device shown in FIG. 8;

FIG. 12 is a top perspective view of the screw and screw stop assembly and cam adjustment mechanism shown in FIG. 11;

FIG. 13 is a bottom perspective view of the screw and screw stop assembly and cam adjustment shown in FIG. 12;

FIG. 15 is an elevated side perspective view of the anvil assembly of the surgical stapling device shown in FIG. 1;

FIG. 15B is a cross-sectional view of the proximal end of the anvil center rod of the surgical stapling device shown in FIG. 15;

FIG. 16 is an elevated side perspective view with parts separated of the anvil assembly shown in FIG. 15;

FIG. 17 is an elevated side perspective view from the distal end of the rotatable sleeve and firing lookout assembly shown in FIG. 14;

FIG. 18 is an elevated side perspective view from the proximal end of the rotatable sleeve and firing lockout assembly shown in FIG. 14;

FIG. 19 is a side elevational view with a handle section removed of the surgical stapling device shown in FIG. 1 prior to attachment of the anvil assembly;

FIG. 19A is a side view with the handle section removed of the proximal end of the surgical stapling device shown in FIG. 19;

FIG. 19B is a side cross-sectional view of the surgical stapling device shown in FIG. 19;

FIG. 19C is an enlarged view of the indicated area of detail shown in FIG. 19B;

FIG. 19D is an enlarged view of the indicated area of detail shown in FIG. 19B;

FIG. 19H is a cross-sectional view taken along section lines 19H-19H of FIG. 19D;

FIG. 20 is a side elevational view with a handle section removed of the surgical stapling device shown in FIG. 1 with the anvil assembly attached;

FIG. 20A is a side view with a handle section removed of the proximal end of the surgical stapling device shown in FIG. 20;

FIG. 20B is an elevated side cross-sectional view of the surgical stapling device shown in FIG. 20;

FIG. 20C is an enlarged view of the indicated area of detail shown in FIG. 20B;

FIG. 20G is a side cross-sectional view of the distal end of the shell assembly and the anvil assembly as shown in FIG. 1 prior to attachment of the anvil assembly to the anvil retainer;

FIG. 20H is a side cross-sectional view of the distal end of the shell assembly and the anvil assembly shown in FIG. 20G during attachment of the anvil assembly to the anvil retainer;

FIG. 20J is a side cross-sectional view of the distal end of the shell assembly and the anvil assembly shown in FIG. 20G with the anvil assembly attached to the anvil retainer;

FIG. 20K is a enlarged view of the indicated area of detail shown in FIG. 20J;

FIG. 21B is a side cross-sectional view of the surgical stapling device shown in FIG. 21;

FIG. 21C is an enlarged view of the indicated area of detail shown in FIG. 21B;

FIG. 21D is an enlarged view of the indicated area of detail shown in FIG. 21B;

FIG. 21H is a perspective cross-sectional view of the distal end of the surgical stapling device shown in FIG. 21;

FIG. 22 is a side elevational view with a handle section removed of the surgical stapling device shown in FIG. 1 with the anvil assembly attached and the firing trigger actuated;

FIG. 22A is a side view with a handle section removed of the proximal end of the surgical stapling device shown in FIG. 22;

FIG. 22B is a side cross-sectional view of the surgical stapling device shown in FIG. 22;

FIG. 22C is an enlarged view of the indicated area of detail shown in FIG. 22B;

FIG. 22E is a side view of the proximal end of the surgical stapling device shown in FIG. 22 with the handle sections removed;

FIG. 22F is an enlarged view of the indicated are of detail in FIG. 22E;

FIG. 23 is a side elevational view with a handle section removed of the surgical stapling device shown in FIG. 1 with the anvil assembly attached after the device has been fired;

FIG. 23A is a side view with a handle section removed of the proximal end of the surgical stapling device shown in FIG. 23;

FIG. 23B is a side cross-sectional view of the surgical stapling device shown in FIG. 23;

FIG. 23C is an enlarged view of the indicated area of detail shown in FIG. 23B;

FIG. 24 is a side elevational view with a handle section removed of the surgical stapling device shown in FIG. 1 with the anvil assembly unapproximated and the anvil head tilted;

FIG. 24A is a side view with a handle section removed of the proximal end of the surgical stapling device shown in FIG. 24;

FIG. 24G is a side view of the proximal end of the surgical stapling device shown in FIG. 24;

FIG. 24H is an enlarged view of the tactile indicator and screw stop of the surgical stapling device shown in FIG. 1 during unapproximation of the anvil assembly at a location where the anvil head is able to fully tilt;

FIG. 26 is a perspective view of the head portion of the surgical stapling device shown in FIG. 25 in the approximated position;

FIG. 27 is a rear perspective view of the surgical stapling device shown in FIG. 25;

FIG. 28 is a top view of the surgical stapling device shown in FIG. 25;

FIG. 29 is a side view of the surgical stapling device shown in FIG. 25;

FIG. 31A is a perspective view of the rear link of the firing mechanism and the safety link of the surgical stapling device shown in FIG. 25;

FIG. 32A is a rear, perspective view of the proximal portion of FIG. 32;

FIG. 34A is an enlarged view of the indicated area of detail shown in FIG. 34;

FIG. 34B is an enlarged view of the indicated area of detail shown in FIG. 34;

FIG. 43 is a rear, perspective view of the anvil assembly shown in FIG. 41 with a removable trocar attached to the anvil center rod;

FIG. 44 is a perspective view with parts separated of the anvil assembly of the surgical stapling device shown in FIG. 25;

FIG. 45 is a side cross-sectional view of the anvil assembly and removable trocar shown in FIG. 43 prior to attachment;

FIG. 46 is a side cross-sectional view of the anvil assembly and removable trocar in the attached configuration;

FIG. 47 is a side view of the handle portion of the surgical stapling device shown in FIG. 25 prior to approximation and firing of the device with a section of the stationary handle removed;

FIG. 48 is a side cross-sectional view of the surgical stapling device shown in FIG. 25;

FIG. 49 is an enlarged view of the indicated area of detail shown in FIG. 48;

FIG. 49A is an enlarged view of the indicated area of detail shown in FIG. 49;

FIG. 50 is an enlarged view of the indicated area of detail shown in FIG. 48;

FIG. 51 is a side cross-sectional view of the head portion of the surgical stapling device excluding the anvil assembly, with the trocar assembly in an extended position;

FIG. 52 is a side cross-sectional view taken along section lines 52-52 in FIG. 50;

FIG. 53 is a side cross-sectional view of the distal end of the surgical stapling device shown in FIG. 25 immediately prior to attachment of the anvil assembly to the anvil retainer;

Figure 25:
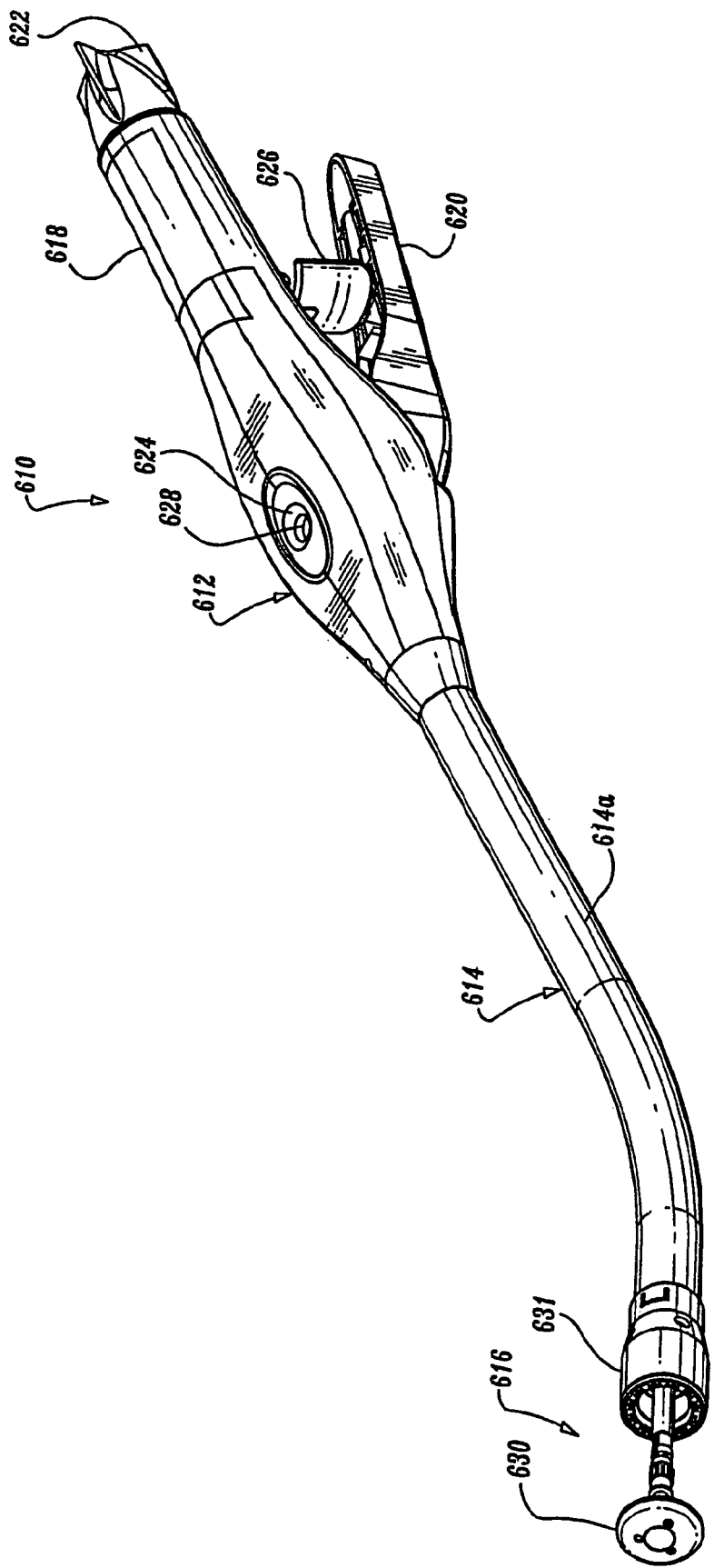
FIG. 25 is a front perspective view of one embodiment of the presently disclosed surgical stapling device in the unapproximated position.
Figure 55:
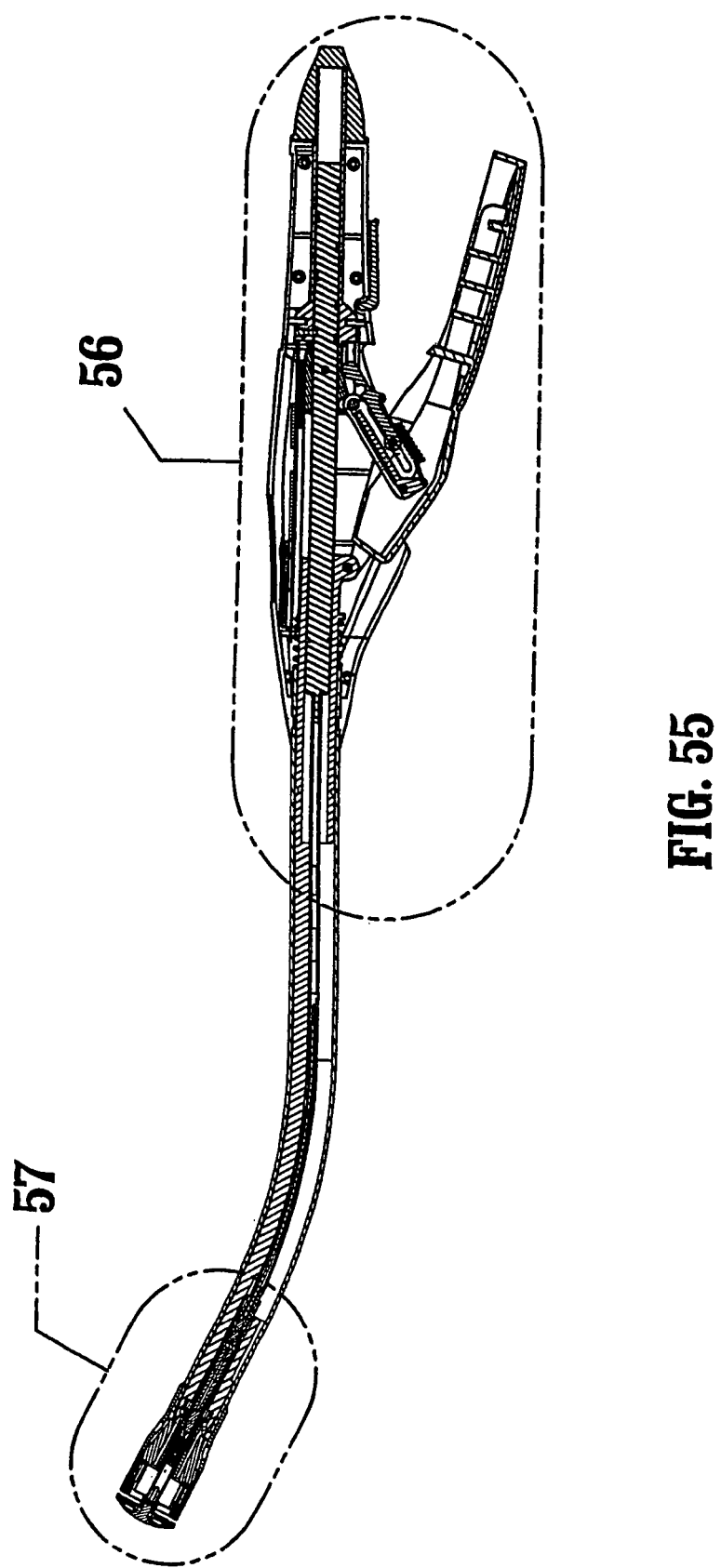
Figure 56:
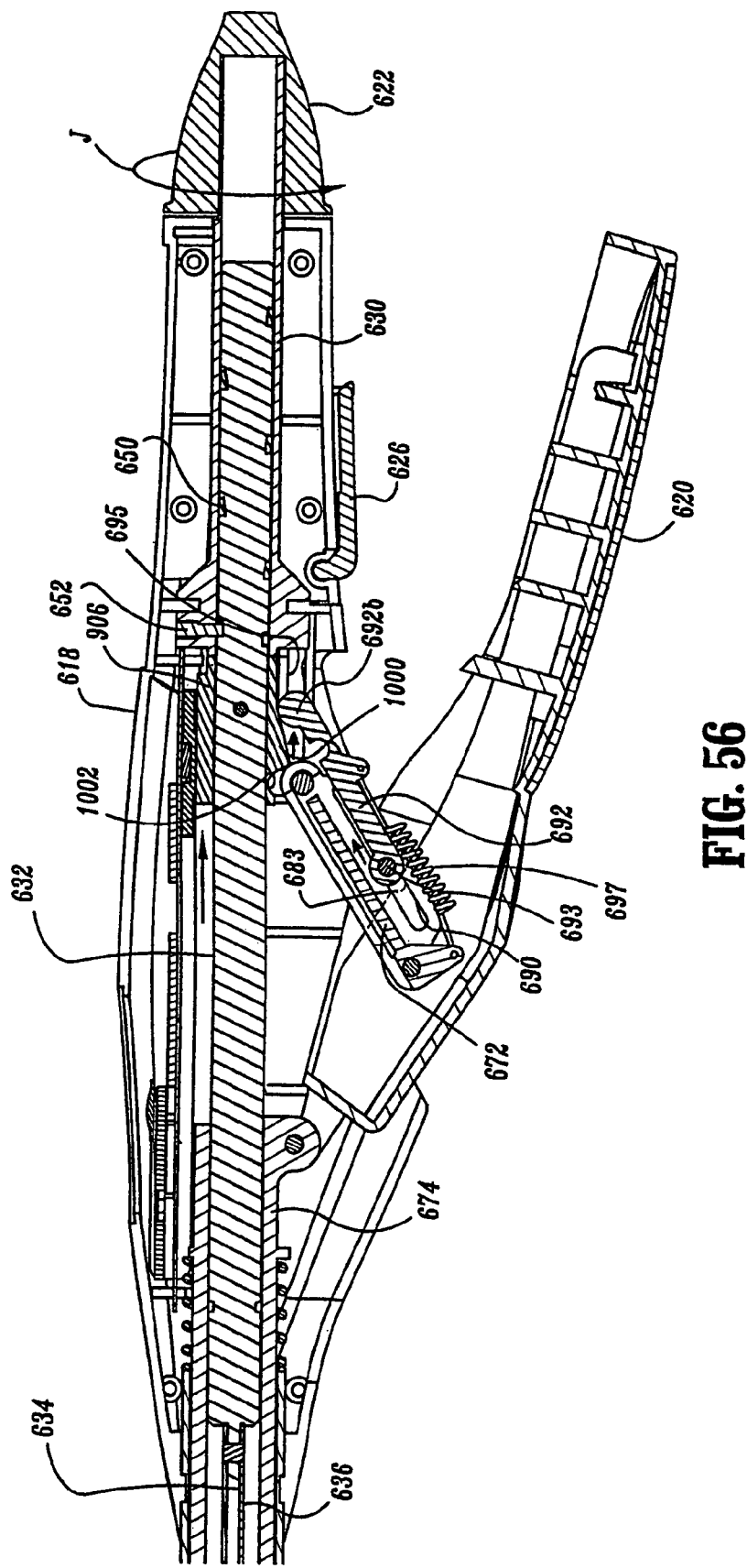
Figure 57:
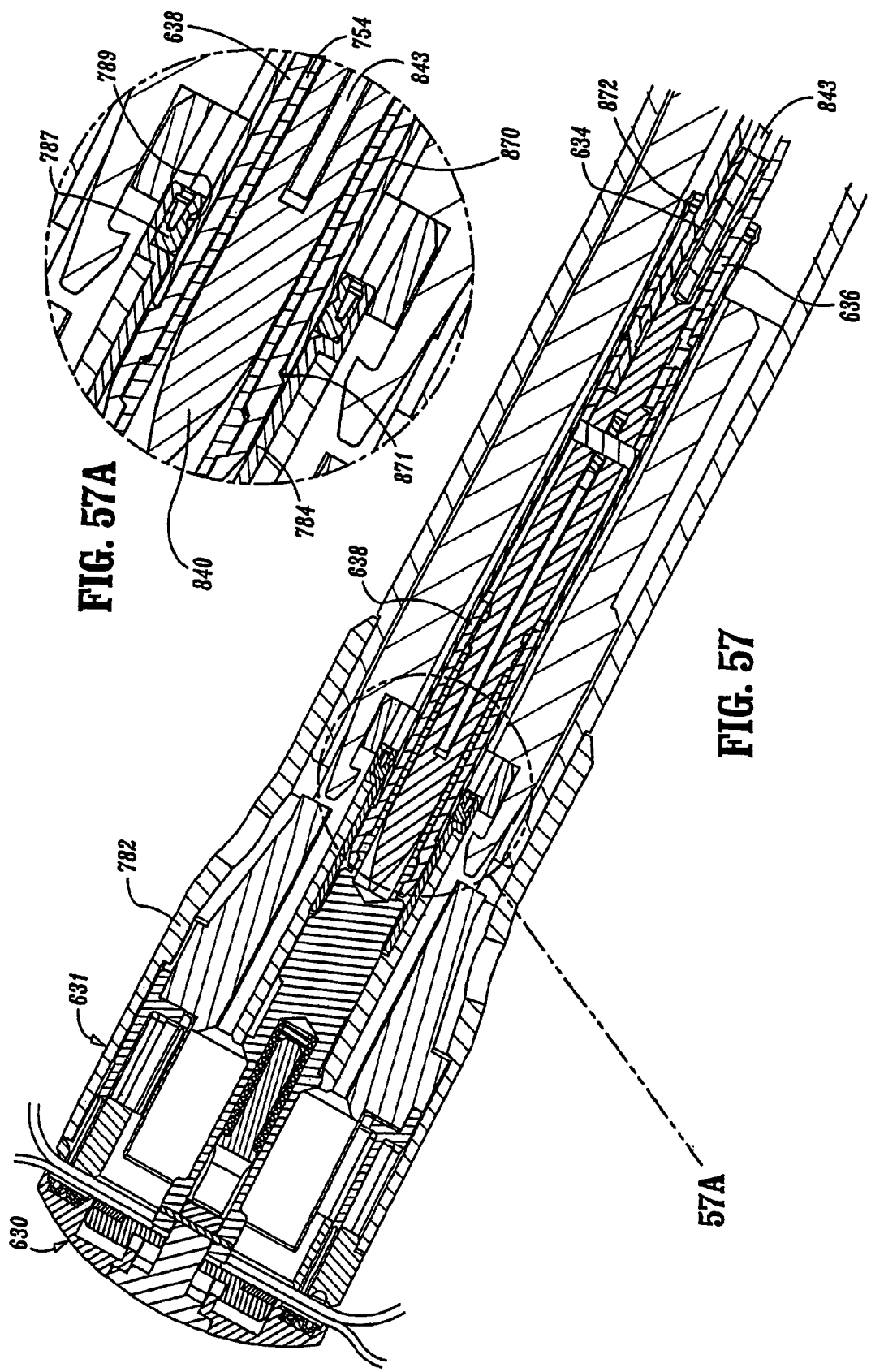
Figure 58:
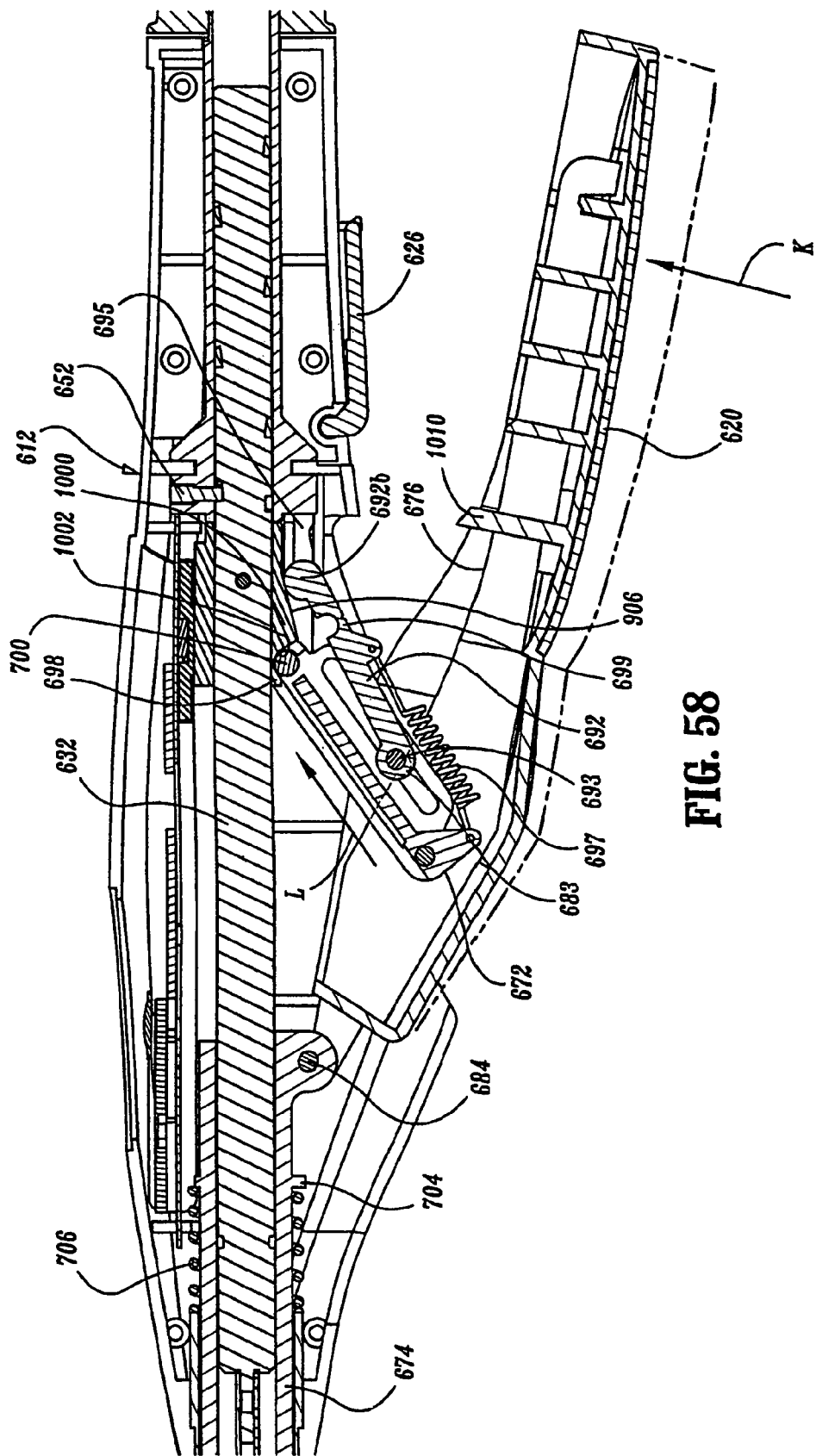
Figure 59:
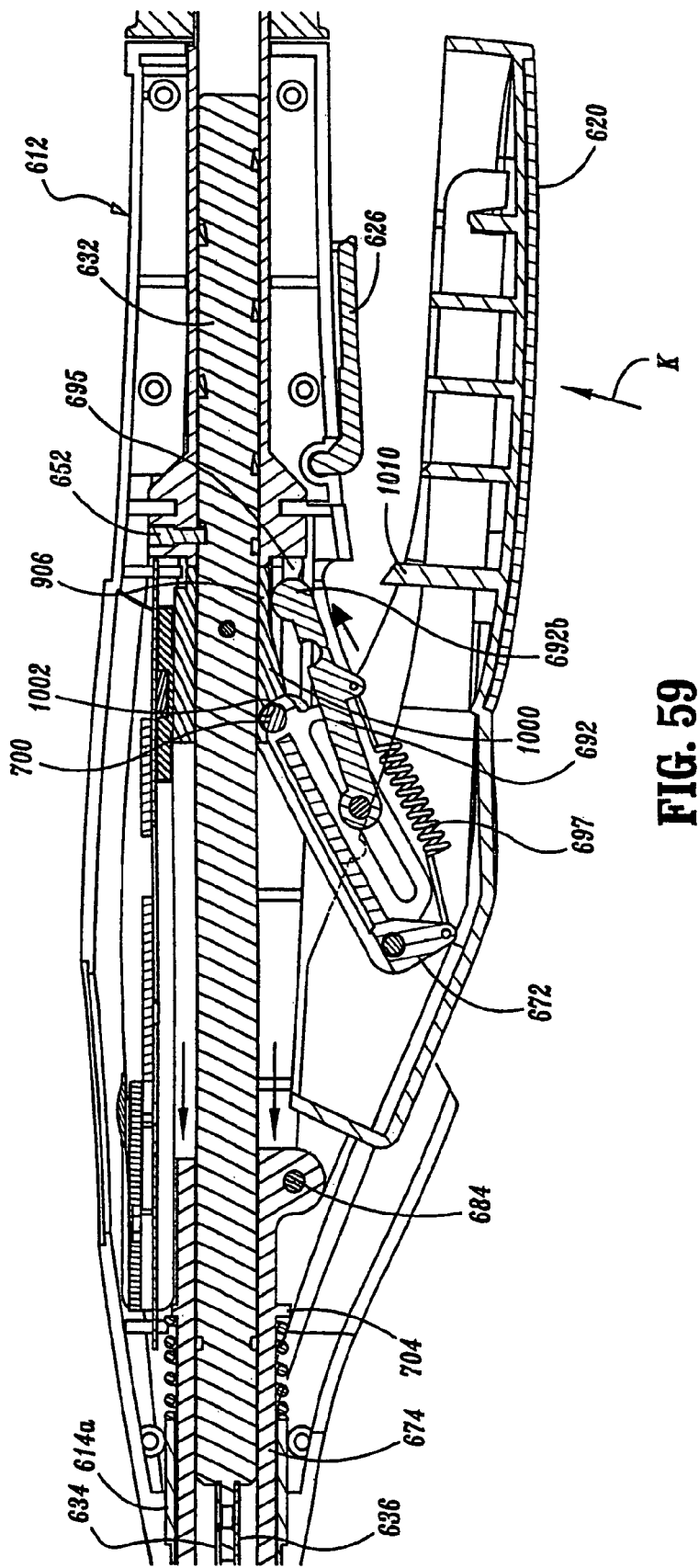
Figure 60:
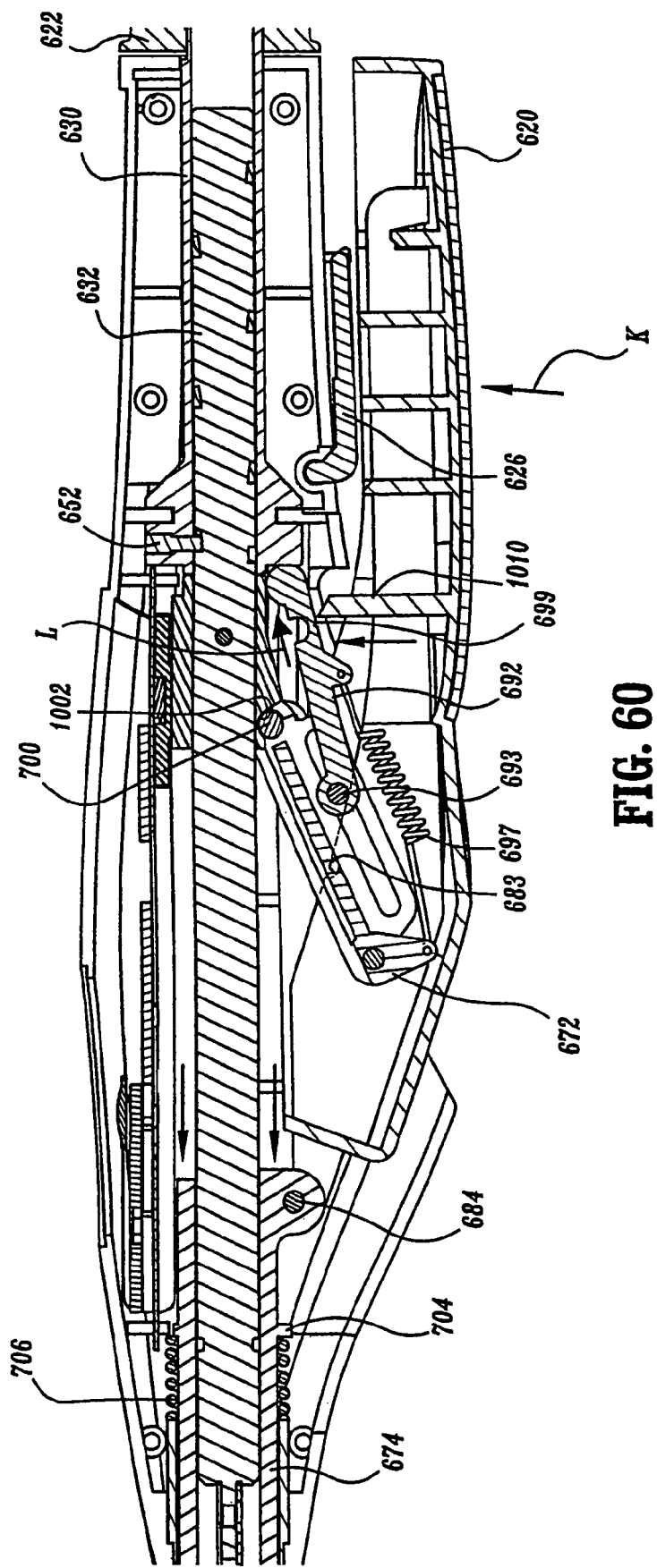
Figure 61:
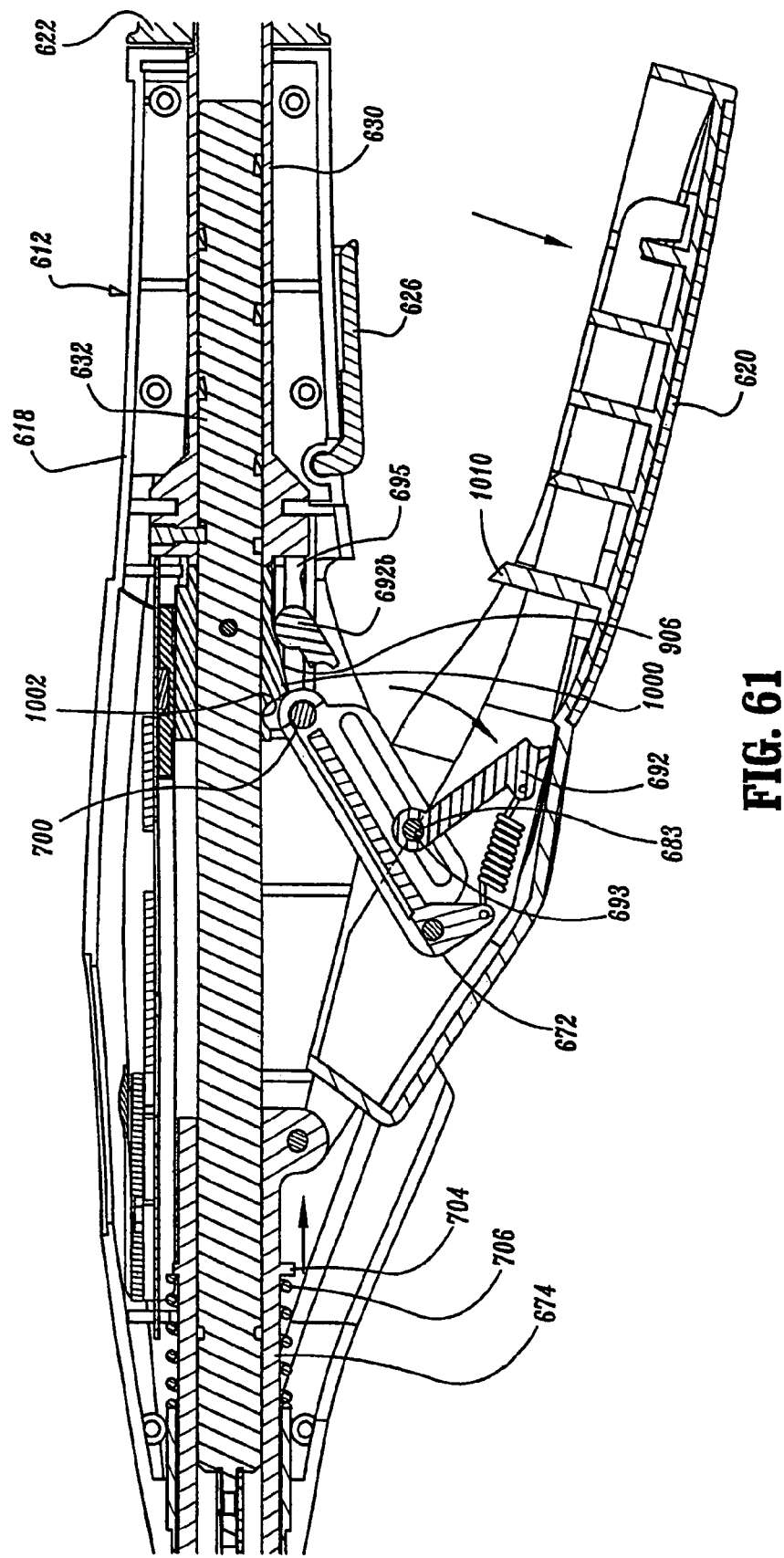
Figure 62:
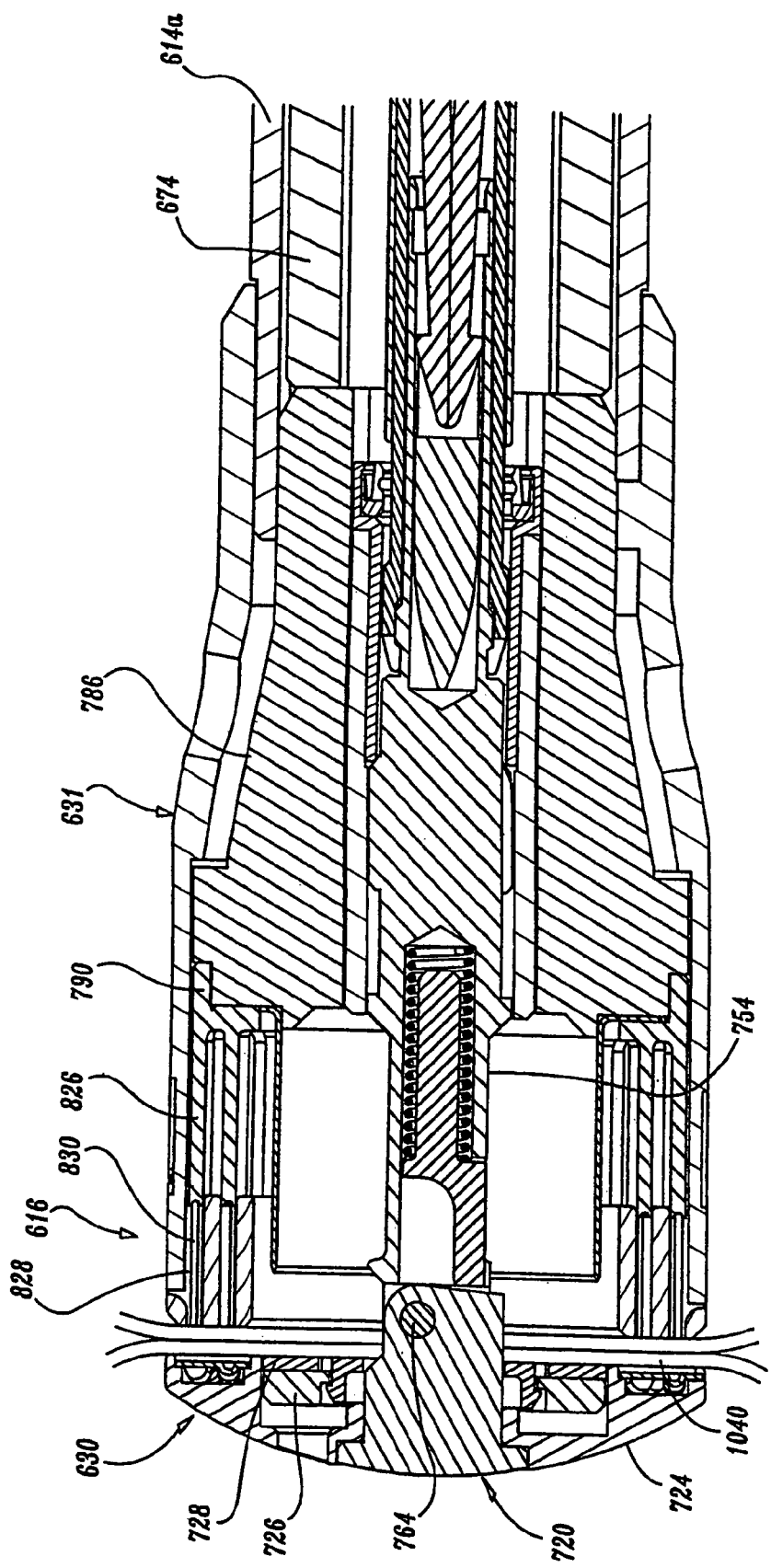
Figure 63:
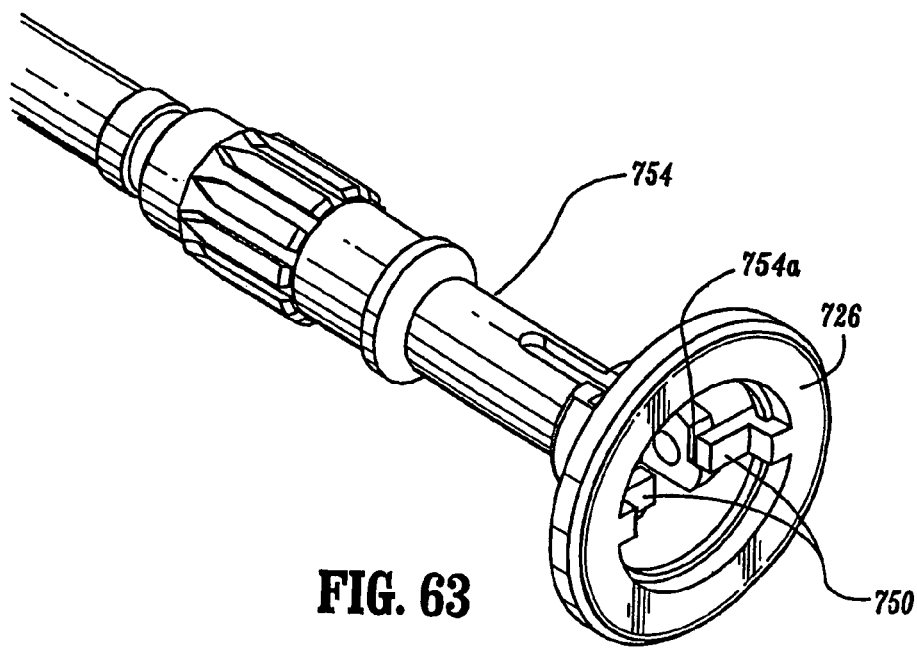
Figure 64:
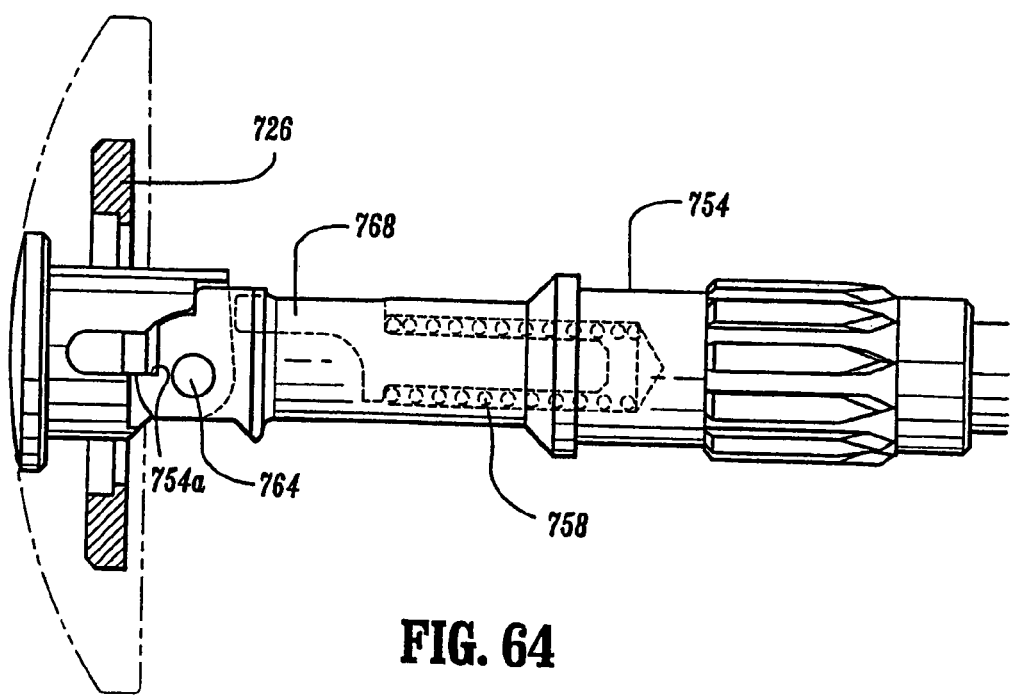
Figure 65:
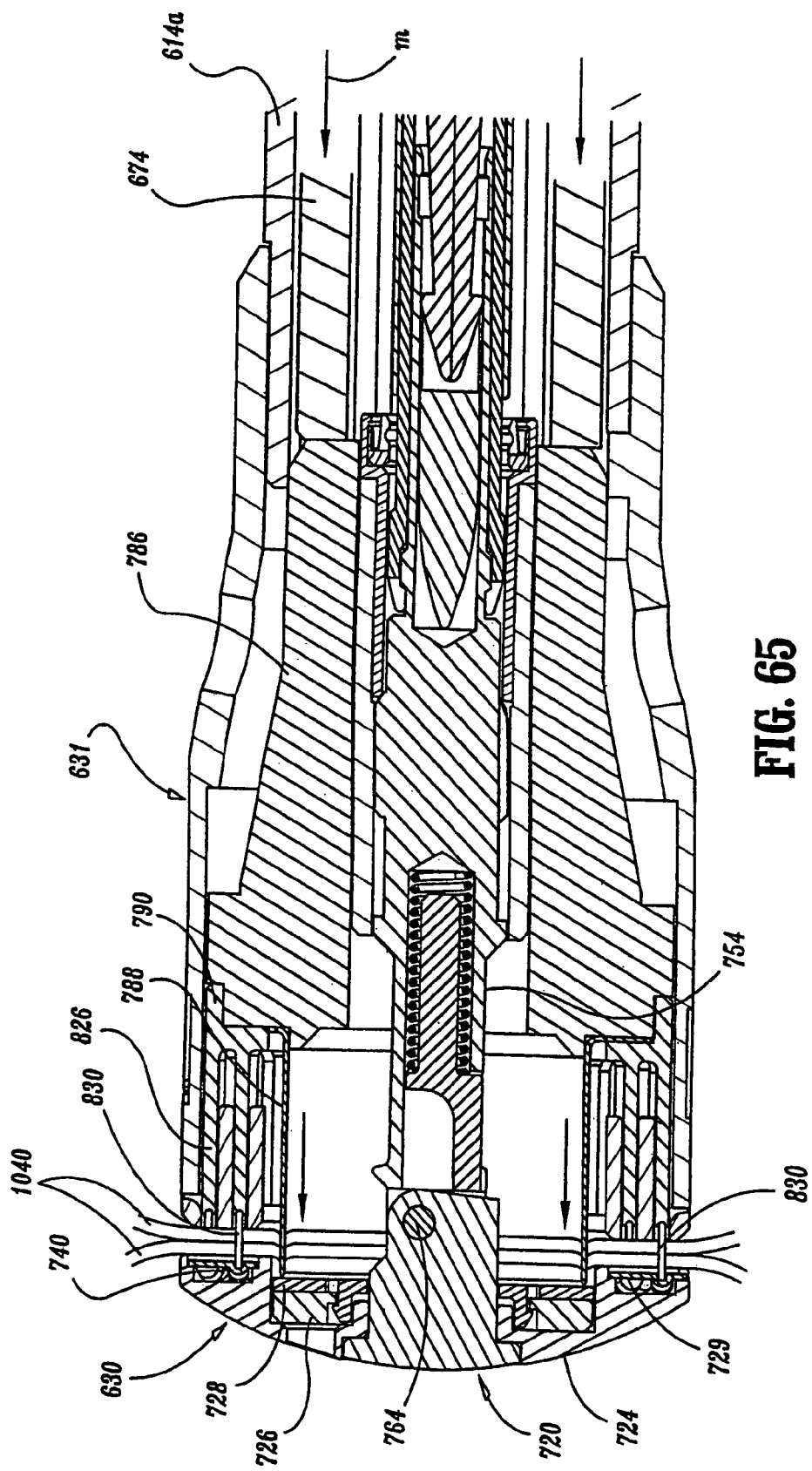
Figure 66:
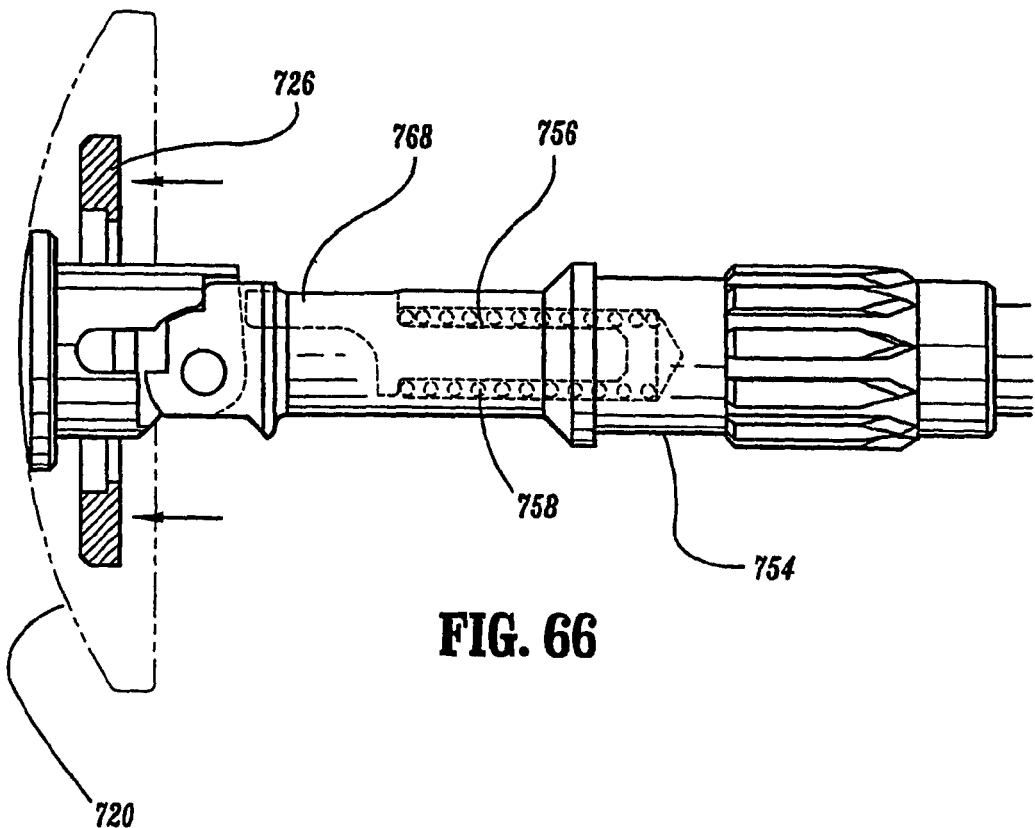
Figure 67:
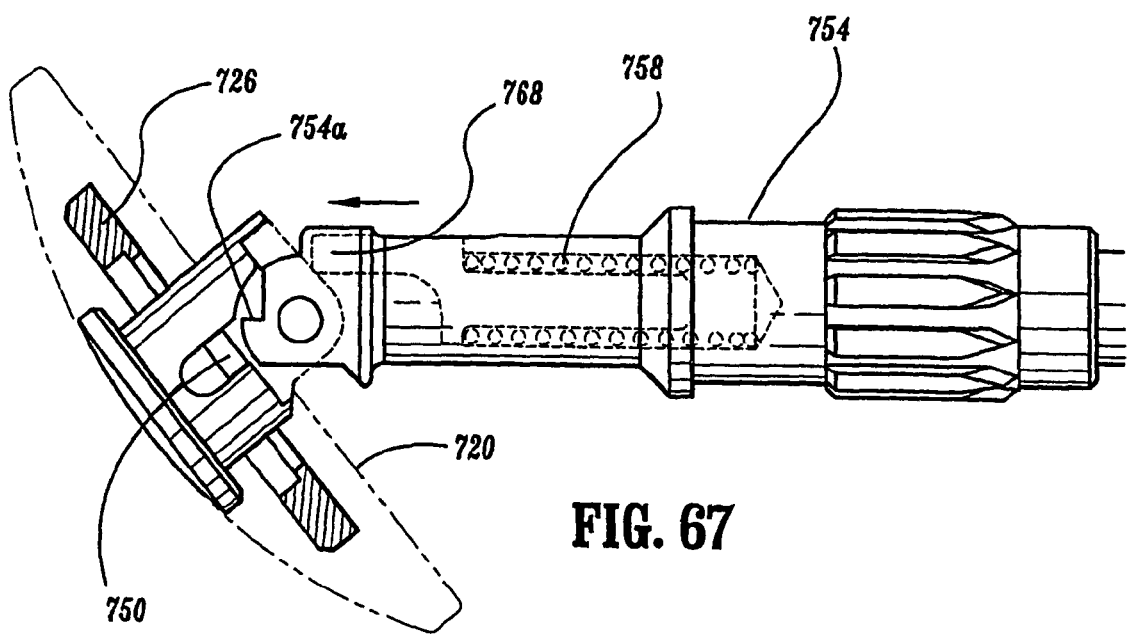
Figure 68:
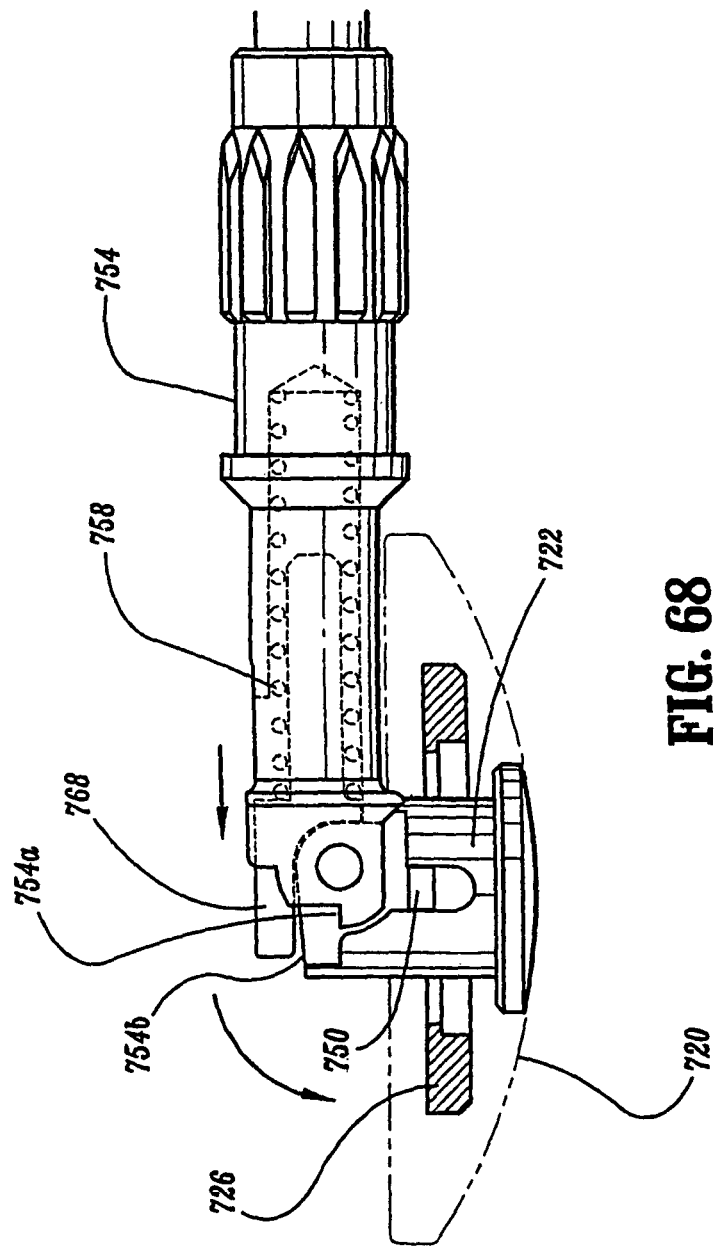
Figure 73:
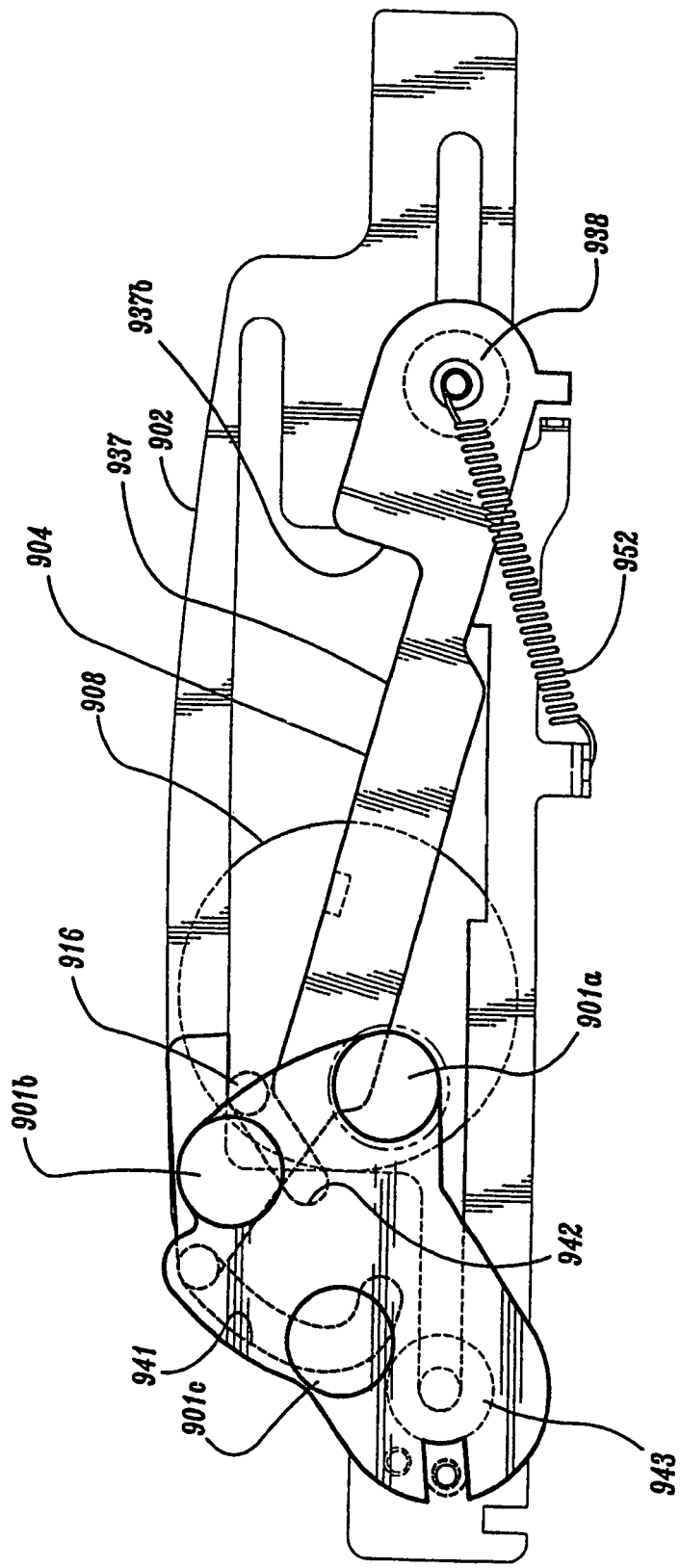
Figure 74:
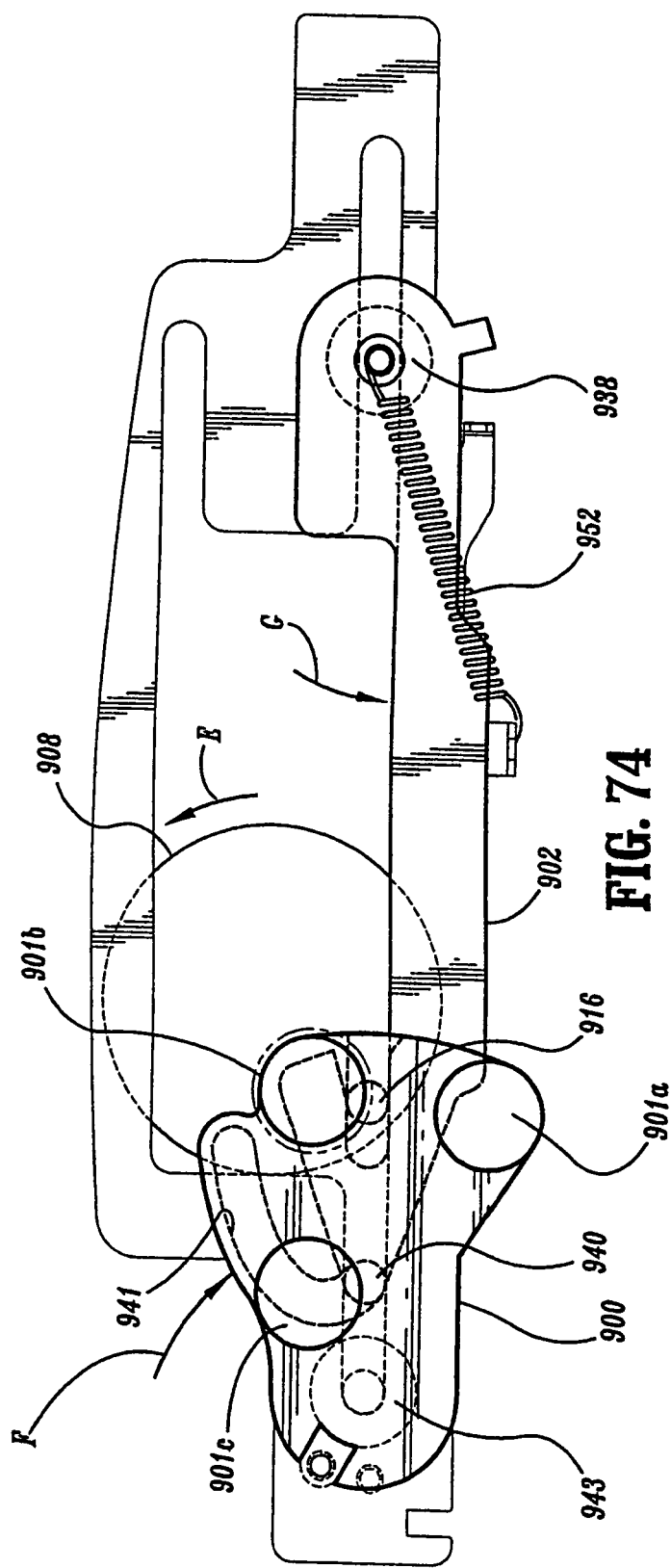
Figure 75:
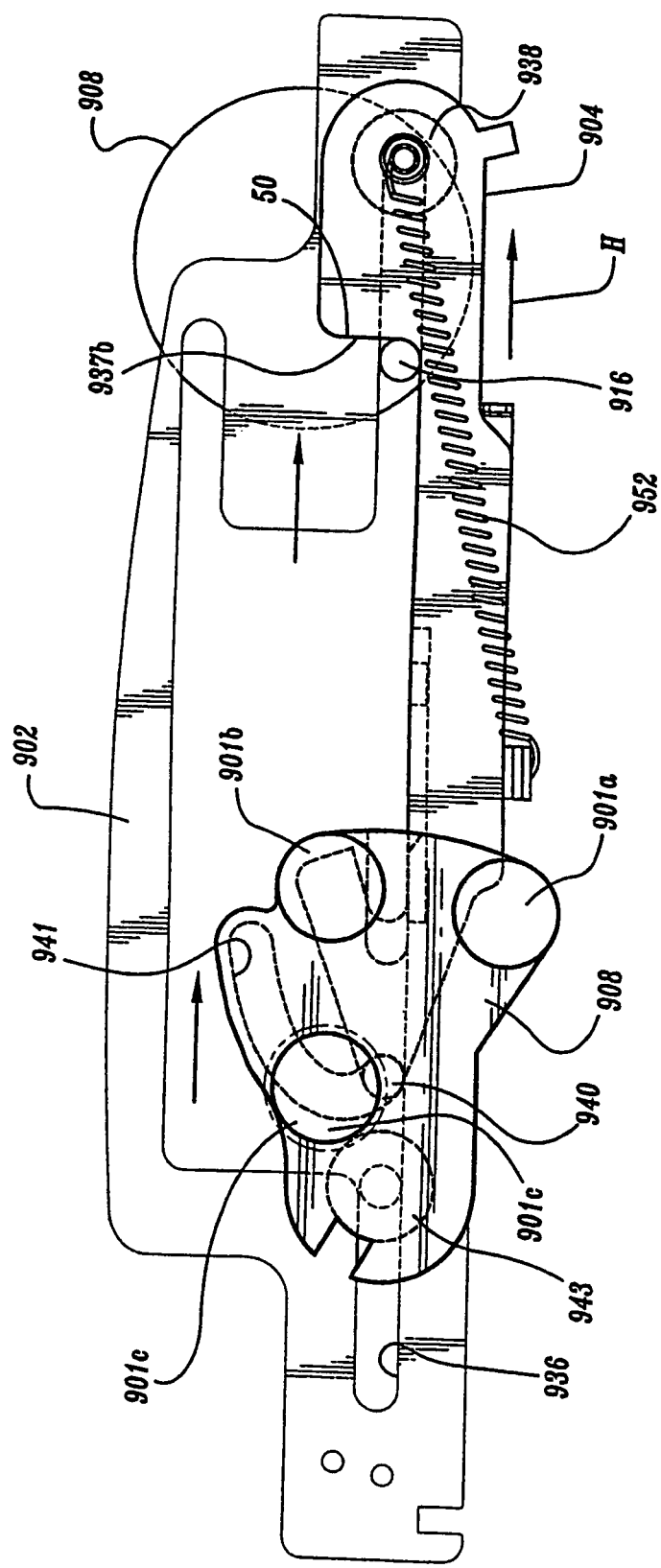

FIG. 53A is a side cross-sectional view of the distal end of the surgical stapling device shown in FIG. 25 during attachment of the anvil assembly to the anvil retainer;

FIG. 54 is a side cross-sectional view of the distal end of the surgical stapling device shown in FIG. 25 with the anvil assembly spaced from the shell assembly;

FIG. 54A is an enlarged view of the indicated area of detail shown in FIG. 54;

FIG. 54B is an enlarged view of the indicated area of detail shown in FIG. 54;

FIG. 55 is a side cross-sectional view of the surgical stapling device shown in FIG. 25 with the anvil assembly and the shell assembly in the approximated position;

FIG. 56 is an enlarged view of the indicated area of detail shown in FIG. 55;

FIG. 57 is an enlarged view of the indicated area of detail shown in FIG. 55;

FIG. 57A is an enlarged view of the indicated area of detail shown in FIG. 57;

FIG. 58 is a side cross-sectional view of the handle portion of the surgical stapling device shown in FIG. 25, after the device has been approximated and during the beginning of the firing stroke of the firing trigger;

FIG. 59 is a side cross-sectional view of the handle portion of the surgical stapling device shown in FIG. 25 after the device has been approximated and during the end of the firing stroke of the firing trigger;

FIG. 60 is a side cross-sectional view of the handle portion of the surgical stapling device shown in FIG. 25 after the firing stroke of the firing trigger;

FIG. 61 is a side cross-sectional view of the handle portion of the surgical stapling device shown in FIG. 25 after the firing stroke of the firing trigger with the trigger released;

FIG. 62 is a side cross-sectional view of the head portion of the surgical stapling device shown in FIG. 25 in the approximated position;

FIG. 63 is a perspective view of the anvil assembly of the stapling device shown in FIG. 25 with the anvil head and anvil removed;

FIG. 64 is a side view of the anvil assembly of the stapling device shown in FIG. 25 with portions of the anvil head assembly in phantom;

FIG. 65 is a side cross-sectional view of the head portion of the surgical stapling device shown in FIG. 25 during the firing stroke of the device;

FIG. 66 is a side view with parts in phantom of the anvil assembly during the firing stroke of the stapling device;

FIG. 67 is a side view of the anvil assembly shown in FIG. 66 with the anvil head assembly in a partially tilted position;

FIG. 68 is a side view of the anvil assembly shown in FIG. 66 in a fully tilted position;

FIG. 69 is a bottom perspective view of the indicator of the indicator assembly of the surgical stapling device shown in FIG. 25;

FIG. 70 is a bottom view of the indicator of the indicator assembly of the surgical stapling device shown in FIG. 25;

FIG. 71 is a top view of the indicator arm of the indicator assembly of the surgical stapling device shown in FIG. 25;

FIG. 72 is a bottom view of the indicator plate of the indicator assembly of the surgical stapling device shown in FIG. 25;

FIG. 73 is a top view of the indicator assembly of the surgical stapling device shown in FIG. 25 prior to anvil attachment and approximation of the device;

FIG. 74 is a top view of the indicator assembly of the surgical stapling device shown in FIG. 25 after the anvil assembly has been attached but prior to approximation of the device; and FIG. 75 is a top view of the indicator assembly of the surgical stapling device shown in FIG. 25 after the anvil assembly has been attached and the device has been approximated.

DETAILED DESCRIPTION OF PREFERRED EMBODIMENTS

Preferred embodiments of the presently disclosed surgical stapling device will now be described in detail with reference to the drawings in which like reference numerals designate identical or corresponding elements in each of the several views.

FIGS. 1-6 illustrate one preferred embodiment of the presently disclosed surgical stapling device shown generally as 10. Briefly, surgical stapling device 10 includes a proximal handle portion 12, an elongated central body portion 14 including a curved elongated outer tube 14a, and a distal head portion 16. Alternately, in some surgical procedures e.g., the treatment of hemorrhoids, it is desirable to have a substantially straight central body portion. See FIGS. 3 and 4. Moreover, the length and or the diameter of body portion 14 and head portion 16 may be varied to suit a particular surgical procedure. See FIGS. 5 and 6. Throughout this description, the term "proximal" will refer to the portion of the instrument closest to the operator and the term "distal" will refer to the portion of the instrument furthest from the operator.

Handle portion 12 includes a stationary handle 18, a firing trigger 20, a rotatable approximation knob 22 and an indicator opening 24. Stationary handle 18 is preferably formed from thermoplastic handle sections 18a and 18b, e.g., polycarbonate, which together define a housing for the internal components of handle portion 12. Handle sections 18a and 18b are preferably secured together by sonic welding. Alternately, other known securement techniques may be employed including screws, adhesives, snap-fit connectors, etc. The internal components of handle portion 12 will be discussed in detail below. A cushioned and/or resilient slip resistant grip 19 is fastened to or included as part of handle sections 18a and 18b and firing trigger 20, preferably using an overmolding procedure. Grip 19 may be formed from neoprene or rubber. Alternately, other suitable materials and joining techniques may be employed. A pivotally mounted trigger lock 26 is fastened to handle portion 12 and is manually positioned to prevent inadvertent firing of stapling device 10. Indicator opening 24 defines an opening or translucent surface which facilitates viewing of an internally positioned indicator which identifies whether stapling device 10 is in a fire ready position or not.

Head portion 16 includes an anvil assembly 30 and a shell assembly 31. Each of these assemblies will be discussed in detail below. Except where otherwise noted, the components of surgical device 10 are formed from thermoplastics including polycarbonates and metals including stainless steel and aluminum. The particular material selected to form a particular component will depend upon the strength requirements of the particular component. For example, the anvil will be formed from a metal, such as stainless steel, and the stationary handle will be formed from a thermoplastic such as polycarbonate. Alternately, other materials not listed above, which preferably can withstand sterilization procedures, may be used to form components of stapling device 10 provided the materials are suitable for surgical use and meet the strength requirements of the particular component.

Figure 7:
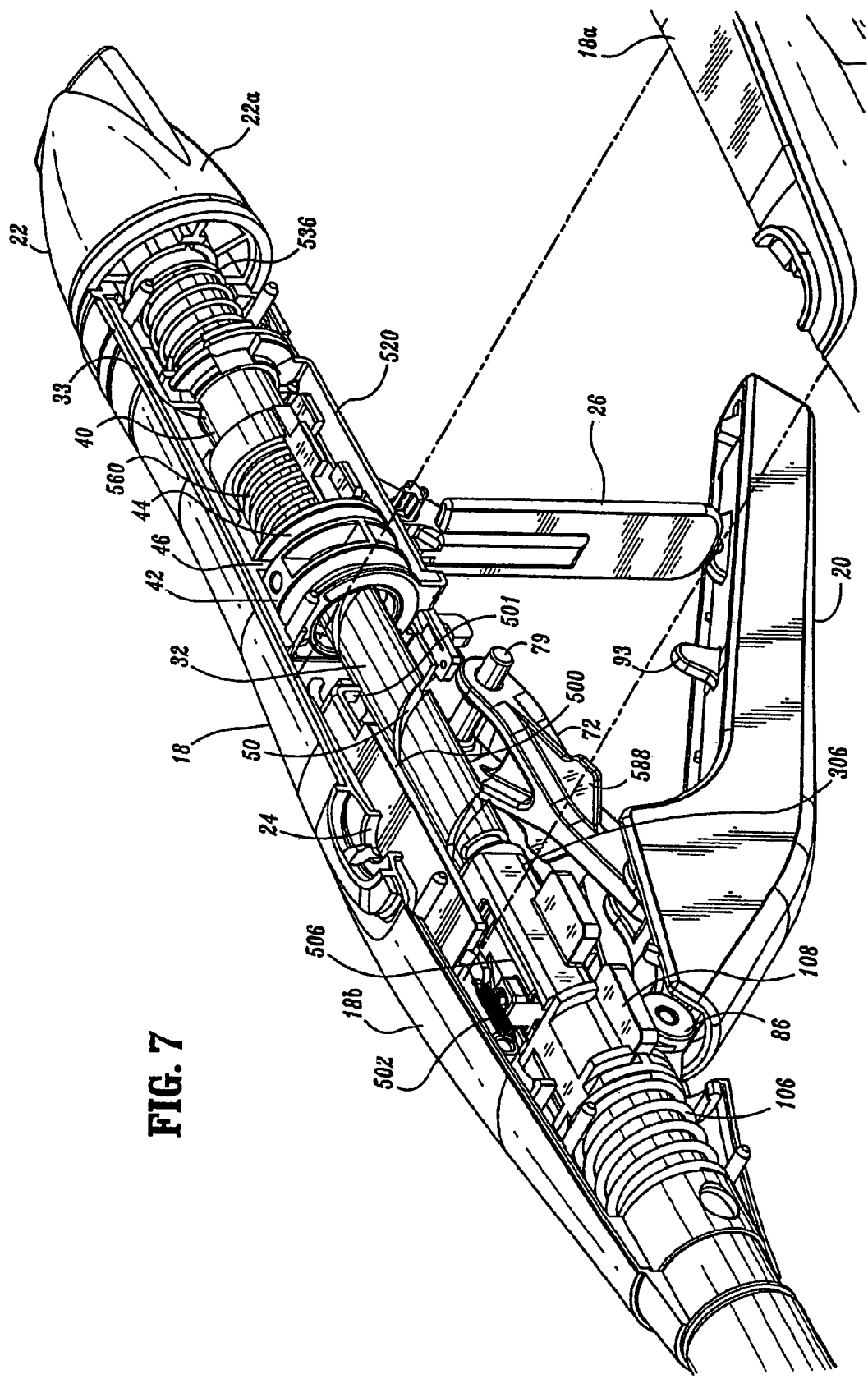
FIG. 7 is an elevated side perspective view of the proximal end of the surgical stapling device shown in FIG. 1 with a handle section removed.
Figure 8:
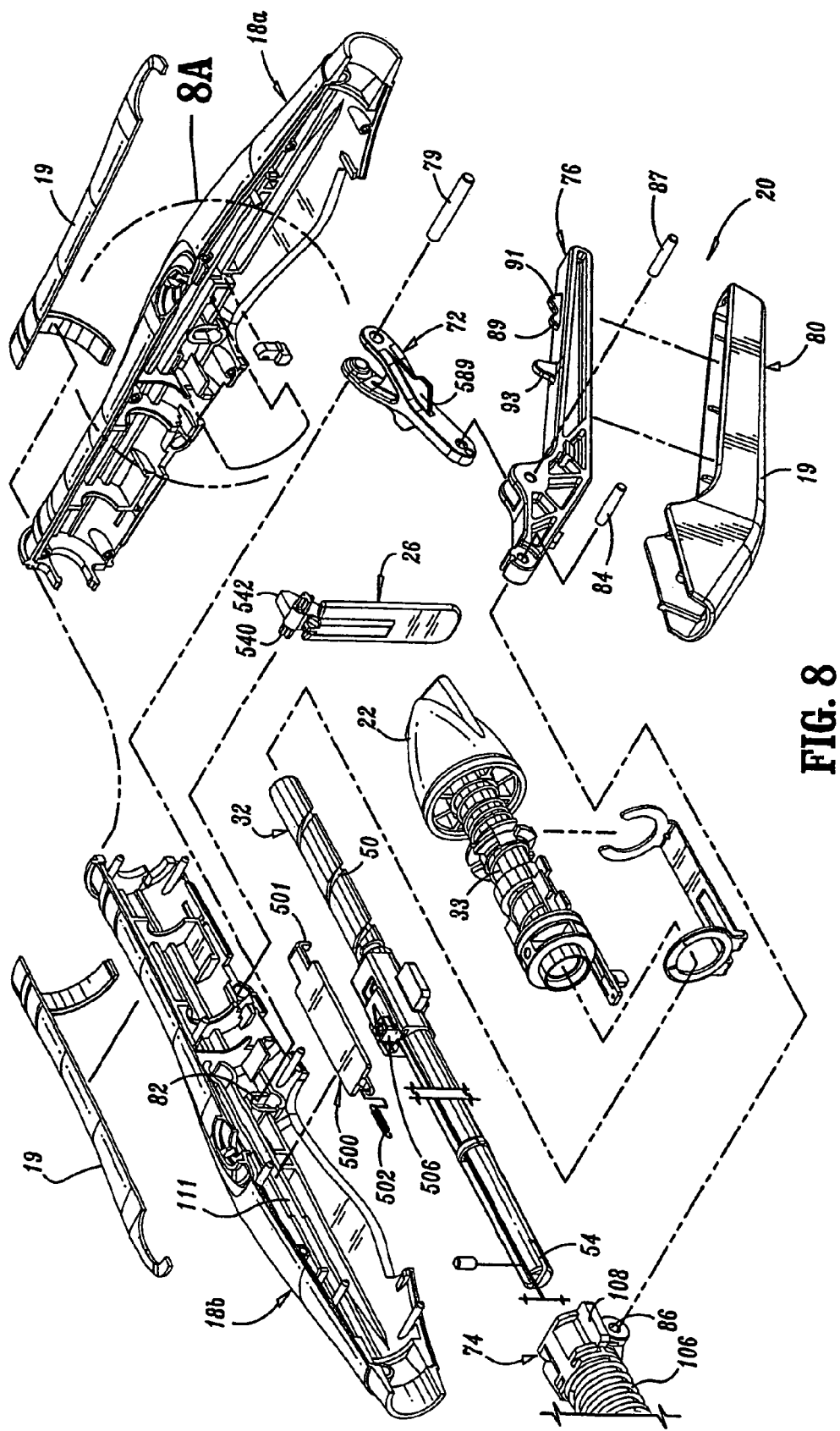
FIG. 8 is an elevated side perspective view of the proximal end of the surgical stapling device shown in FIG. 7 with parts separated.

FIGS. 7 and 8 illustrate the internal components of handle portion 12 of surgical stapling device 10. Handle portion 12 houses an indicator mechanism, a lockout mechanism, the proximal components of an approximation mechanism and a firing mechanism and other mechanisms for obtaining safe and effective operation of the surgical stapling device. Each of these mechanisms will be described in detail hereinbelow.

Approximation Mechanism

Figure 9:
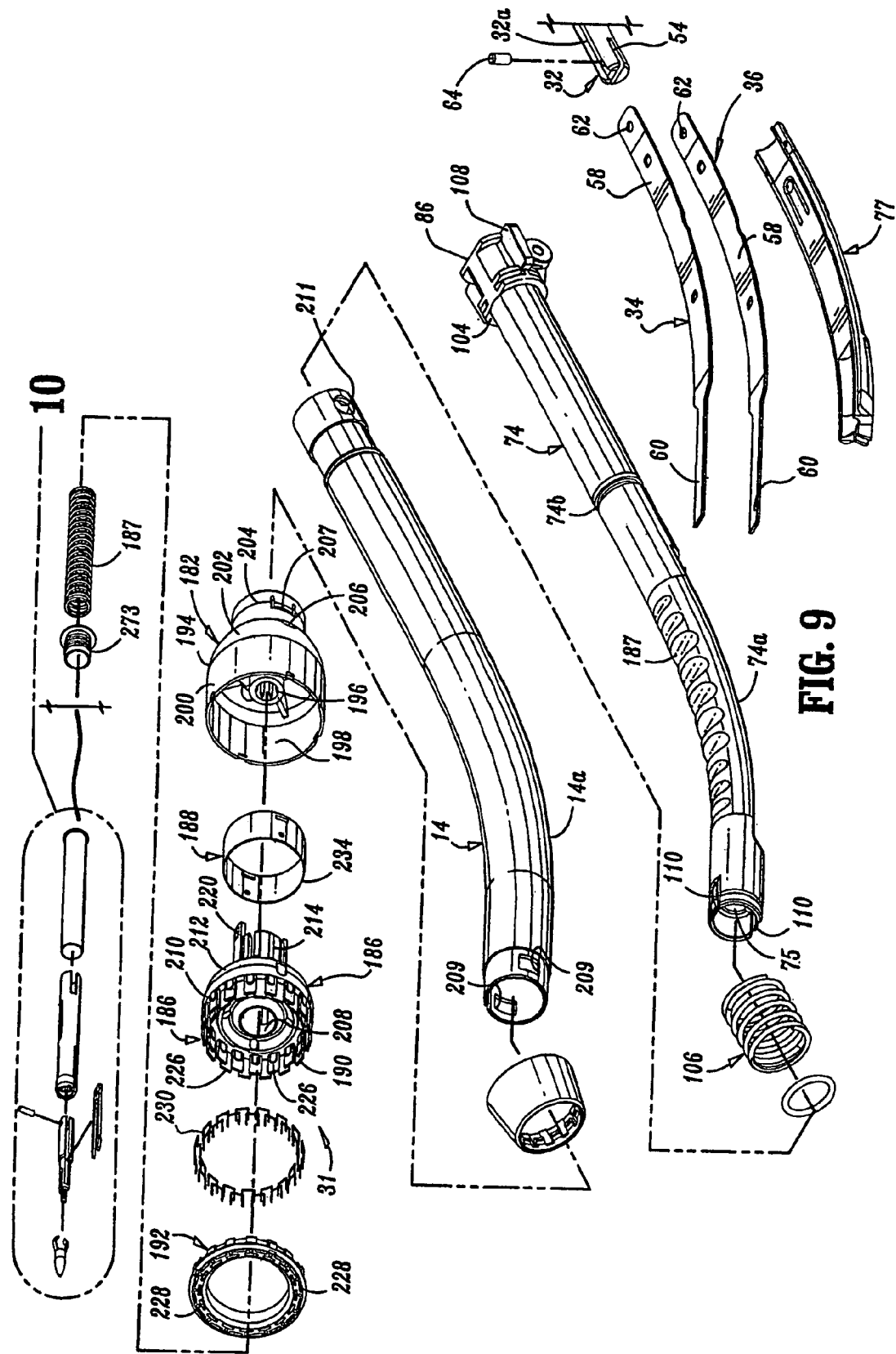
FIG. 9 is an elevated side perspective view of the central and distal portions of the surgical stapling device shown in FIG. 1 with parts separated.
Figure 10:
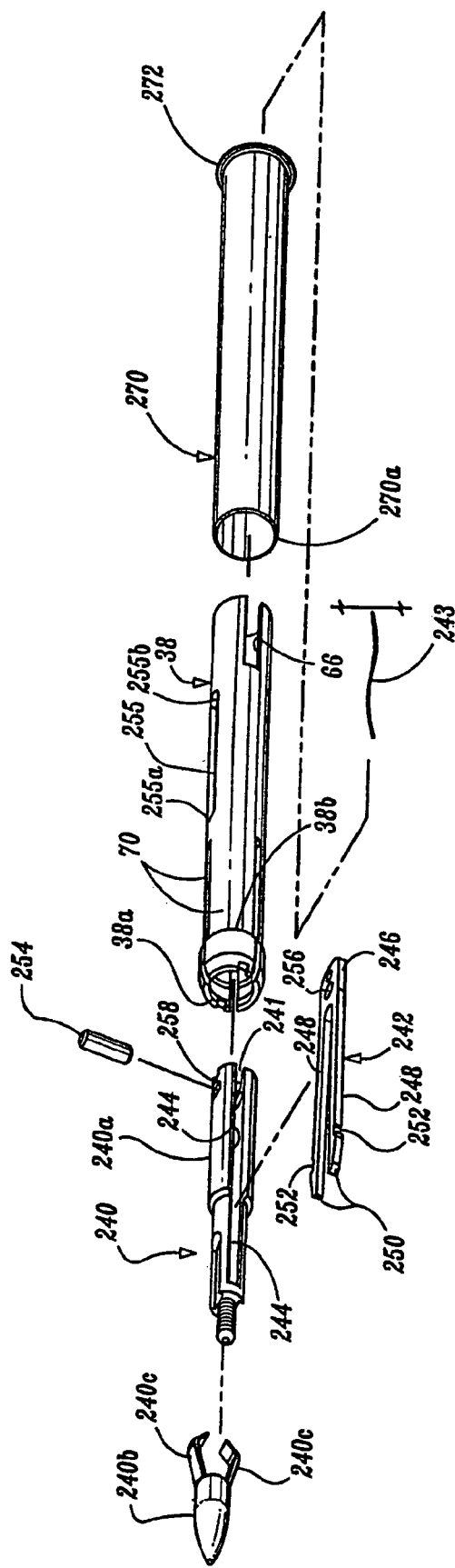
FIG. 10 is an enlarged view of the indicated area of detail shown in FIG. 9.

Referring to FIGS. 7-14, the approximation mechanism includes approximation knob 22, a rotatable sleeve 33 (FIG. 14), a screw 32, first and second screw extensions 34 and 36 (FIG. 9), respectively, and anvil retainer assembly 38 (FIG. 10). Rotatable sleeve 33 includes a small diameter cylindrical hollow body portion 40 and a large diameter hollow body portion 42. Body portions 40 and 42 define a central bore 33a. Body portion 42 includes an annular groove 44 dimensioned to receive an inwardly extending annular flange 46 (FIG. 7) formed on an internal wall of stationary handle 18. Engagement between groove 44 and flange 46 axially fixes sleeve 30 within stationary handle 18 while permitting relative rotation. The proximal end of hollow body portion 40 of rotatable sleeve 33 extends through an opening formed in the proximal end of stationary handle 18 and includes diametrically opposed elongated ribs 48. Approximation knob 22 includes a cap 22a and a body 22b defining a bore 49 having diametrically opposed elongated slots 49a configured to receive ribs 48 of sleeve 30 such that rotation of knob 22 effects concurrent rotation of sleeve 30.

The proximal end of screw 32 includes a helical channel 50 and is dimensioned to be slidably positioned within central bore 33a of rotatable sleeve 33. A pin 52 (FIG. 14) extends radially through body portion 42 of sleeve 33 into helical channel 50. Since sleeve 33 is axially fixed with respect to stationary handle 18, rotation of sleeve 33 about screw 32 causes pin 52 to move along channel 50 of screw 32 to effect axial movement of screw 32 within stationary handle 18. An axially extending groove 32a is formed along the distal portion of screw 32. Groove 32a is dimensioned to receive an indicator link or wire as will be described below.

The distal end of screw 32 includes a transverse slot 54. Top and bottom screw extensions 34 and 36 (FIG. 9) each include a proximally located flexible flat band portion 58 and a distally located flat band portion 60. The flexibility of top and bottom screw extensions 34 and 36 permits movement of screw extensions 34 and 36 through curved elongated body portion 14. The proximal end of each band portion 58 includes a hole 62 dimensioned to receive a pin 64 for securing the proximal end of screw extensions 34 and 36 within transverse slot 54 of screw 32. Alternately, other fastening techniques may be used to secure each band portion 58 to screw 32, e.g., welding, crimping, etc. Distally located band portion 60 of each screw extension 34 and 36 is dimensioned to be received within a transverse slot 66 formed in a proximal end of anvil retainer 38 (FIG. 10) to fasten anvil retainer 38 to the distal end of screw extensions 34 and 36. Preferably, band portion 60 is brazed or welded within slot 66. Alternately, other fastening techniques may be used including screws, crimping, etc. The distal end of anvil retainer 38 includes a plurality of flexible legs 70 which are configured to flex outwardly to receive and engage the anvil assembly as will be discussed in further detail below.

In operation, when approximation knob 22 is manually rotated, rotatable sleeve 33 is rotated about the proximal end of screw 32 to move pin 52 along helical channel 50 of screw 32. Since sleeve 33 is axially fixed to stationary handle 18, as pin 52 is moved through channel 50, screw 32 is advanced or retracted within stationary handle 18. As a result, top and bottom screw extensions 34 and 36, which are fastened to the distal end of screw 32, and anvil retainer 38, which is fastened to the distal end of screw extensions 34 and 36, are moved axially within elongated body portion 14. Since anvil assembly 30 is secured to the distal end of anvil retainer 38, rotation of approximation knob 22 will effect movement of anvil assembly 30 in relation to shell assembly 31 between spaced and approximated positions.

Firing Mechanism

Referring to FIGS. 7-9, the firing mechanism includes firing trigger 20, a firing link 72 and an elongated pusher link 74. Firing trigger 20 includes a body portion 76 and a trigger cover 80. A cushioned gripping surface 82 preferably formed of neoprene or rubber is provided on trigger cover 80. Cushioned gripping surface 19 provides a non-slip cushioned surface to make actuation of device 10 more comfortable to a surgeon. Body portion 76 of trigger 20 is pivotally connected to a coupling member 86 secured to the proximal end of pusher link 74 by a pivot member 84. Coupling member 86 may be formed integrally with pusher link 74 or as a separate element fastened thereto. Firing link 72 has a first end pivotally secured to body portion 76 of trigger 20 by a pivot member 87 and a second end pivotally secured within a vertical slot 82 formed between stationary handle half-sections 18a and 18b of stationary handle 18 by pivot member 79. Pivot member 79 is free to move vertically within slot 82. A spring 82a is supported within handle 18 to urge pivot member 79 downwardly towards the bottom of slot 82. Body portion 76 further includes a pair of abutments including an abutment 89 and an abutment 91 which are positioned to engage the distal end of trigger lock 26 in a manner to be described in greater detail below to prevent actuation of trigger 20 prior to approximation of device 10 and after device 10 has been fired. A projection 93 is also formed on body portion 76 of firing trigger 20 and is configured to activate a trigger lock return mechanism of a firing lockout mechanism of surgical stapling device 10 as will be described below.

Coupling member 86 which is supported on the proximal end of elongated pusher link 74 includes a flange 104 (FIG. 9). A spring 106, positioned between an inner wall or abutment within stationary handle 18 and flange 104, biases pusher link 74 proximally to a retracted, non-fired position. A pair of wings 108 extend radially outwardly from coupling member 86. Wings 108 are dimensioned to slide along slots 111 (FIG. 8) formed along the internal walls of stationary handle 18 to maintain proper alignment of pusher link 74 within stationary handle 18 during firing of device 10.

The distal end of pusher link 74 includes a pair of engagement fingers 110 which are dimensioned to lockingly engage with members 220 formed in the proximal end of pusher back 186. Pusher back 186 forms part of shell assembly 31 and will be discussed in greater detail below. Pusher link 74 is preferably formed from a flexible plastic material and can include a plurality of notches 187 which allow the pusher link to bend more easily as it moves through body 14. Pusher link 74 defines a hollow channel 75 for slidably receiving the approximation mechanism. A flat surface or cutout 74a slidably supports screw extensions 34 and 36. A spacer 77 is positioned within outer tube 14a adjacent cutout 74a to provide additional support for screw extensions 34 and 36 and pusher link 74 to prevent each component from buckling during actuation. An annular channel 74b is formed about pusher link 74 to receive an O-ring seal 74c. Pusher link 74 is slidably positioned within body portion 14 such that O-ring 74c seals the space between pusher link 74 and an internal wall of body portion 14. Operation of the firing mechanism of the device will be described in detail below.

Figure 9A:
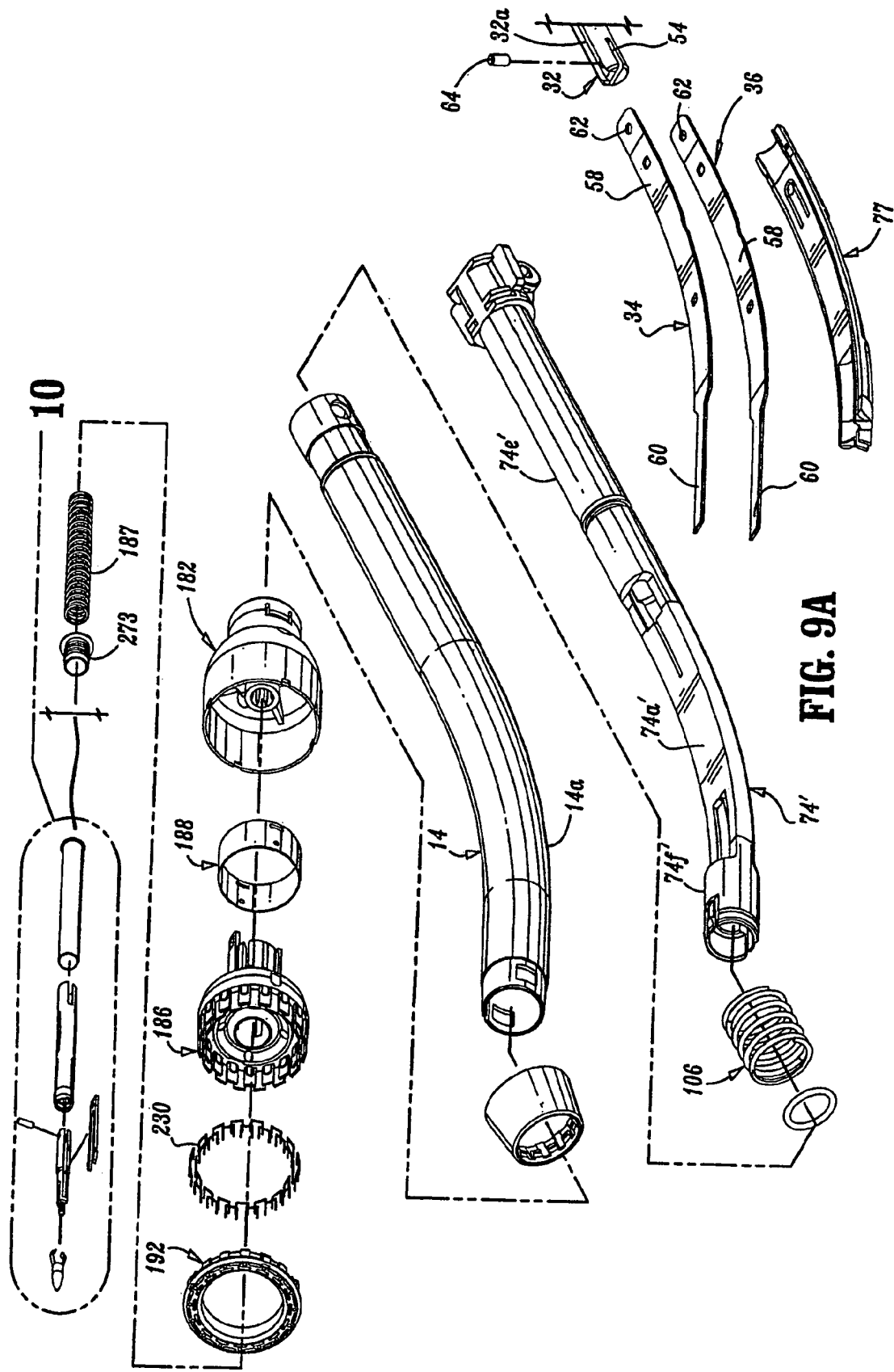
FIG. 9A is an elevated side perspective view of another preferred embodiment of the central and distal portions of the surgical stapling device shown in FIG. 1 with parts separated.
Figures 9B, 9C, 9D:
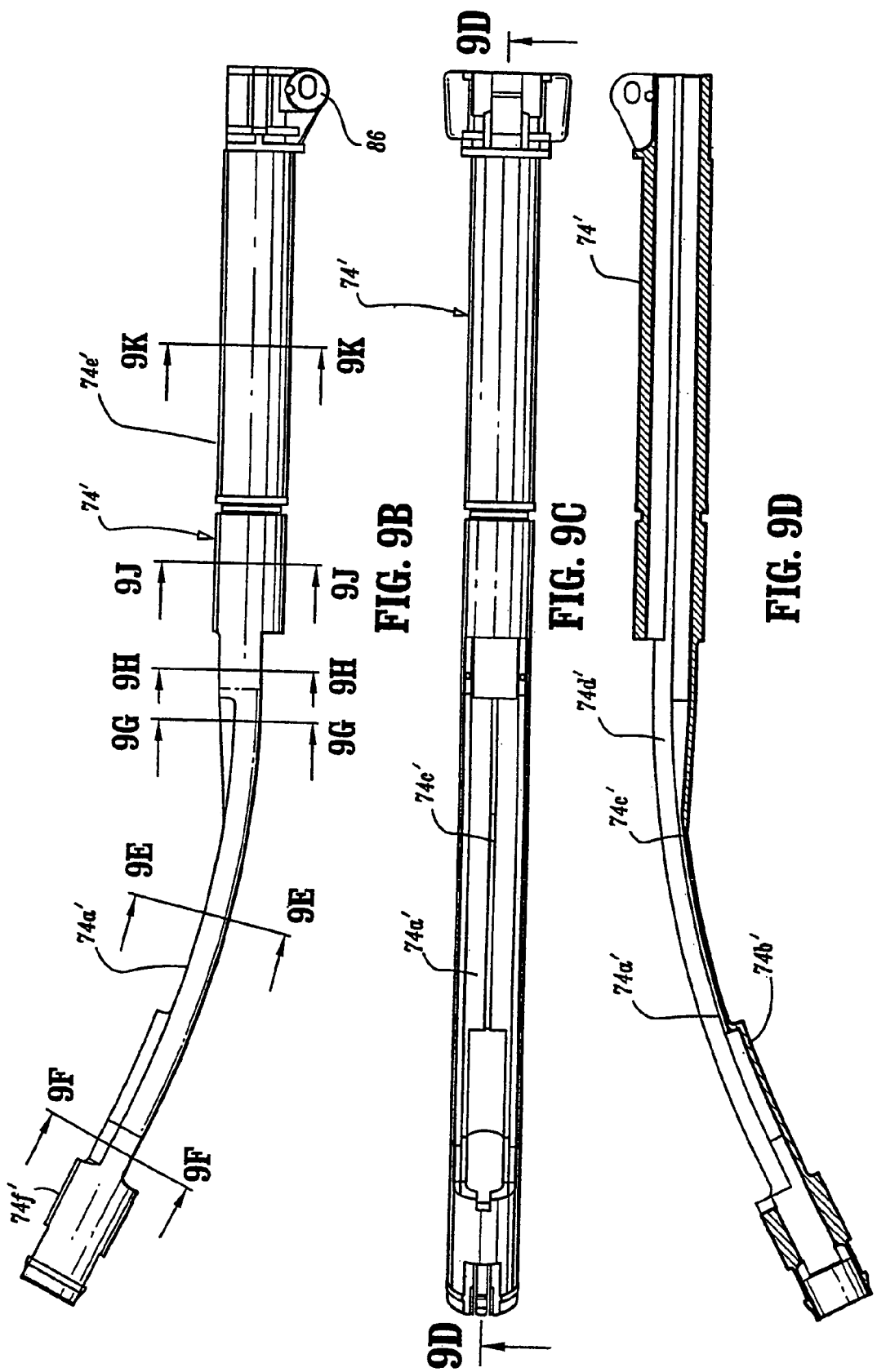
FIG. 9B is a side elevational view of the pusher link shown in FIG. 9A.
FIG. 9C is a top view of the pusher link shown in FIG. 9A.
FIG. 9D is a cross-sectional view of taken along section line 9D-9D of FIG. 9C.
Figure 9G:
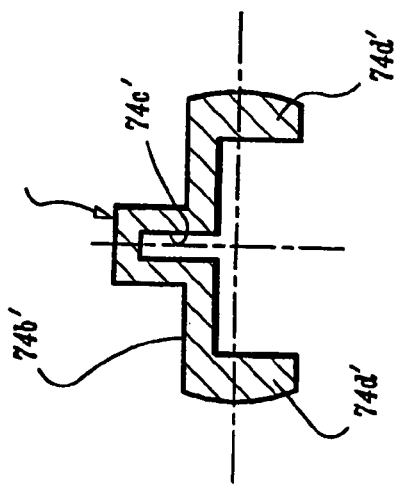
FIG. 9G is a cross-sectional view taken along section lines 9G-9G of FIG. 9B.
Figure 9K:
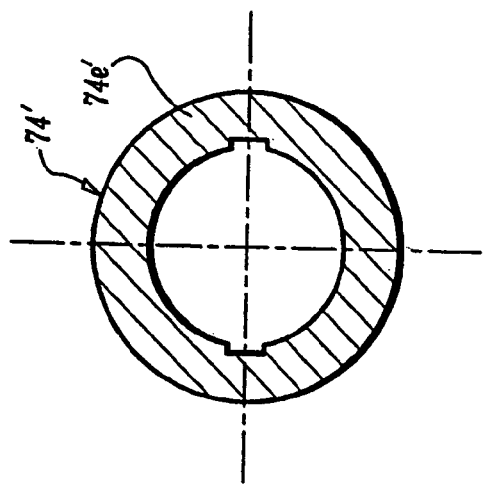
FIG. 9K is a cross-sectional view taken along section lines 9K-9K of FIG. 9B.
Figure 9E:
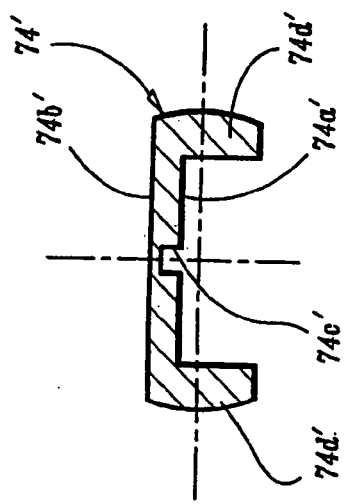
FIG. 9E is a cross-sectional view taken along section line 9E-9E of FIG. 9B.
Figure 9J:
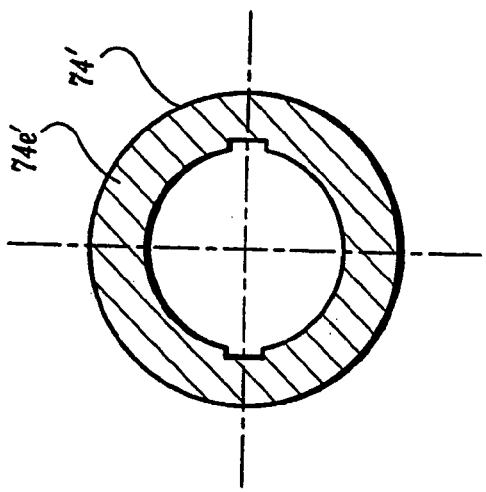
FIG. 9J is a cross-sectional view taken along section lines 9J-9J of FIG. 9B.
Figure 9F:
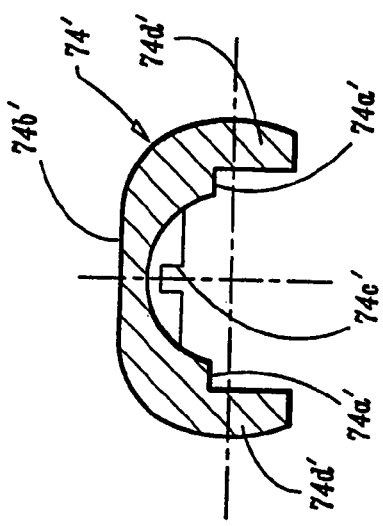
FIG. 9F is a cross-sectional view taken along section lines 9F-9F of FIG. 9B.
Figure 9H:
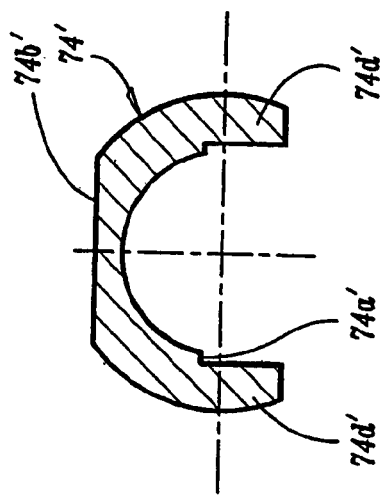
FIG. 9H is a cross-sectional view taken along section lines 9H-9H of FIG. 9B.
Figure 9M:
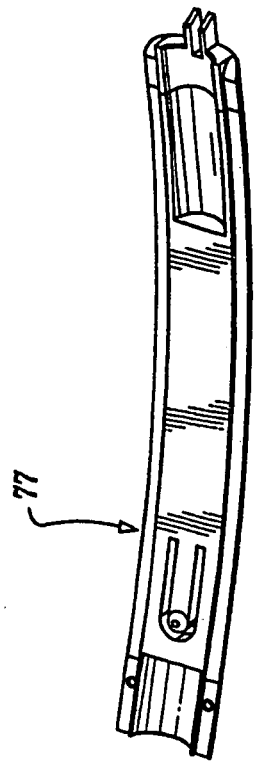
FIG. 9M is a top perspective view of the spacer of the surgical stapling device shown in FIG. 1.
Figure 9N:
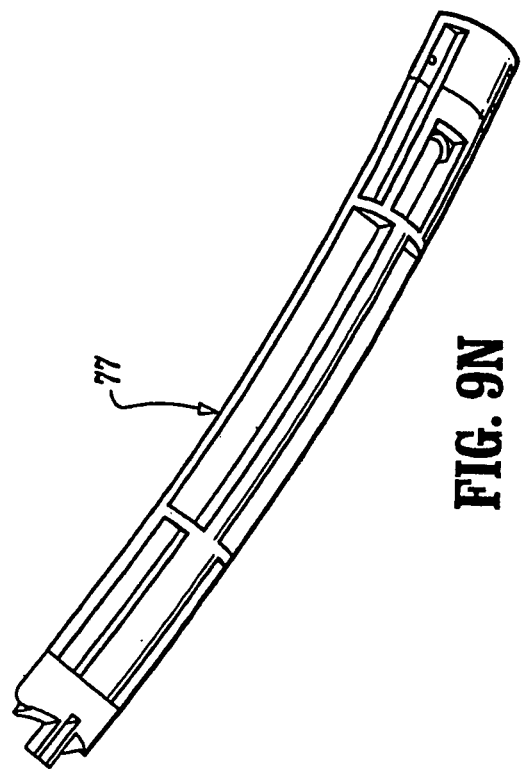
FIG. 9N is a bottom perspective view of the spacer shown in FIG. 9M.
Figure 9L:
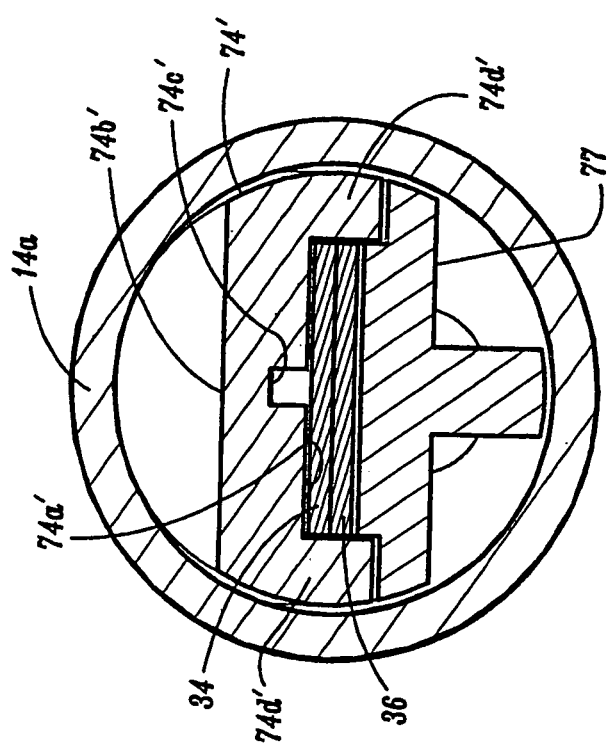
FIG. 9L is a cross-sectional view of the elongated body of the surgical stapling device shown in FIG. 1.

FIG. 9A illustrates a preferred embodiment of the firing mechanism of the presently disclosed surgical stapling device. In FIG. 9A, pusher link 74' is modified to reduce the amount of material from which the pusher link is made and yet reduce the bending moment of the pusher link and, accordingly the force required to actuate the firing mechanism. Referring also to FIGS. 9B-9E, pusher link 74' includes a curved body portion having upper and lower flats 74a' and 74b' and distal and proximal annular end sections 74f and 74e'. A slot 74c' is formed in upper flat 74a' and is dimensioned to receive an indicator link or wire as will be described in further detail below. Upper flat 74a' is dimensioned to slidably support screw extensions 34 and 36. Spacer 77, as discussed above, is positioned adjacent upper flat 74a' to abut screw extensions 34 and 36 (FIG. 9L). Pusher link 74' includes a pair of sidewalls 74d' which confine screw extensions 34 and 36. As shown in FIG. 9D, preferably sidewalls 74d' extend the length of upper flat 74a' and communicates with annular end sections 74e' and 74f' of pusher link 74'. Sidewalls 74d' convey compressive force in order to balance or equalize the compressive force exerted along pusher link 74' in the portions of the pusher link relative to the portions thereof above and below the centerline of outer tube 14a.

When firing trigger 20 is actuated, i.e., pivoted about pivot member 84, firing link 72 is moved proximally until pivot member 79 engages an abutment surface 307 (FIG. 11A-D) formed on screw stop 306. Thereafter, firing trigger 20 is pushed distally to advance pusher link 74 or 74' distally against the bias of spring 106. Since the distal end of pusher link 74 or 74' is connected to pusher back 186, actuation of firing trigger 20 effects advancement of pusher back 186 within shell assembly 31 to eject staples from shell assembly 31 in a manner to be described below.

Anvil Assembly

Figure 15A:
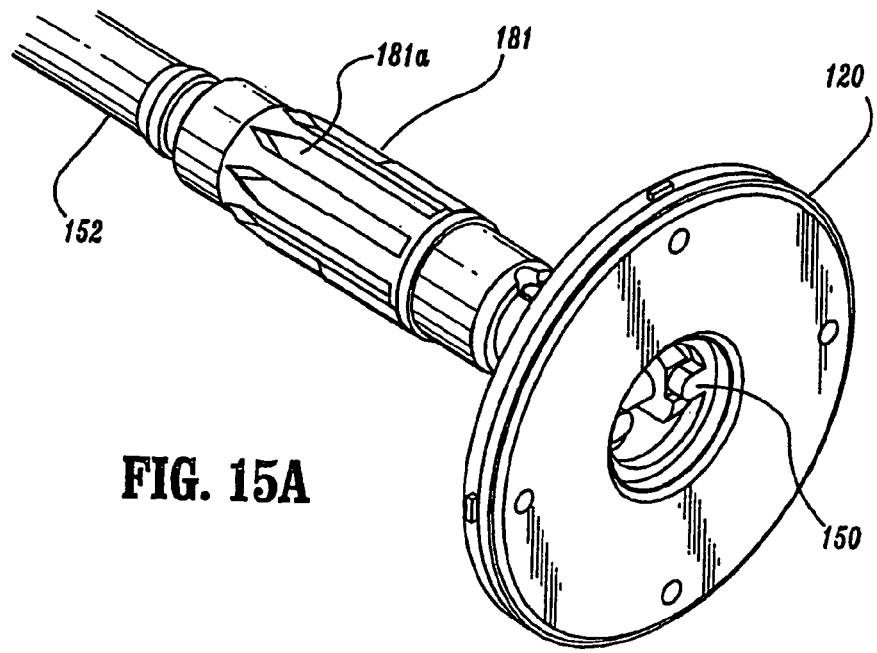
FIG. 15A is an elevated perspective view from the distal end of the anvil assembly of the surgical stapling device shown in FIG. 1.
Figure 16A:
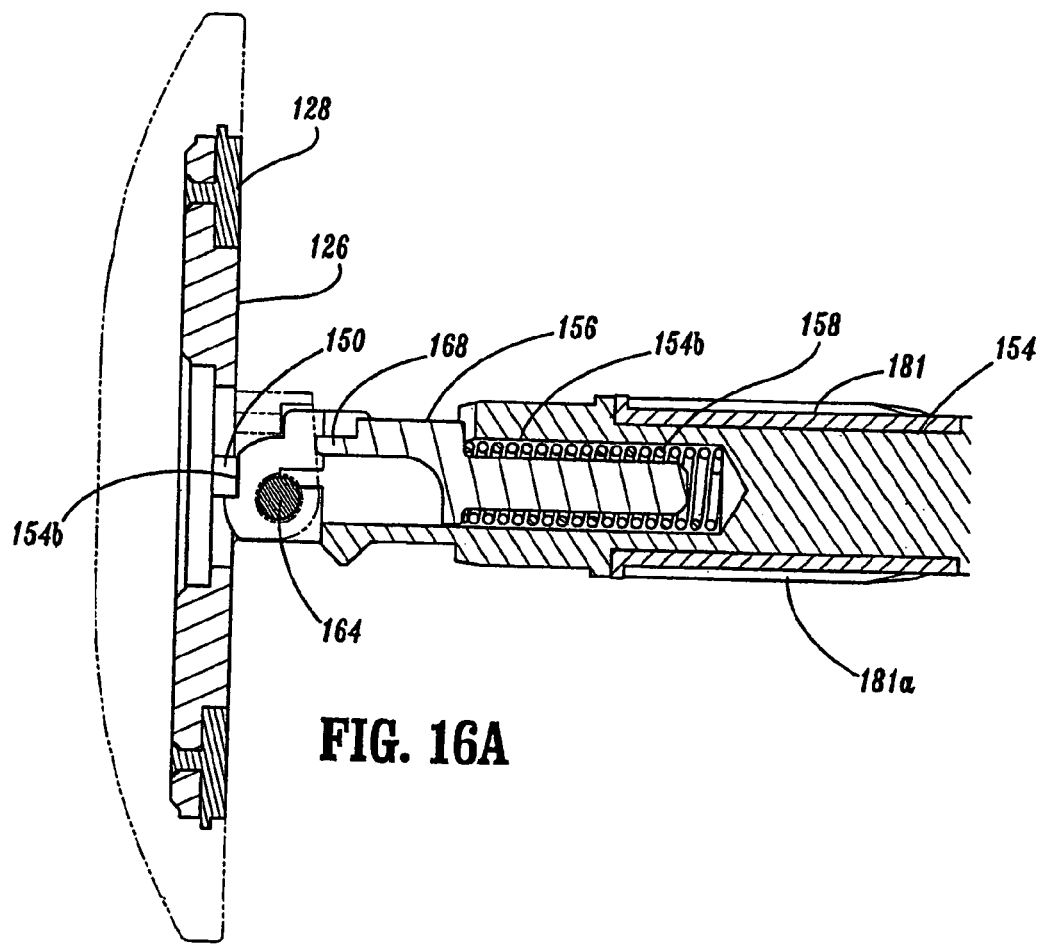
FIG. 16A is a side cross-sectional view of the anvil assembly shown in FIG. 15.

Referring to FIGS. 15-16A, anvil assembly 30 includes an anvil head assembly 120 and an anvil center rod assembly 152. Anvil head assembly 120 includes a post 122, an anvil head 124, a backup plate 126, a cutting ring 128 and an anvil 129. Anvil head 124 includes an inner annular recess 134 and an outer annular recess 136. Post 122 is centrally located within inner annular recess 134 of anvil head 124. Anvil 129 is supported on anvil head 124 in annular recess 136 and includes a plurality of pockets 140 for receiving and deforming staples. Backup plate 126 includes a central opening 126b which is positioned about post 122 within recess 134 defined between post 122 and annular recess 136. Backup ring 126 includes a raised platform 126a. Cutting ring 128 includes an opening 128a having a configuration substantially the same as platform 126a. Opening 128a is positioned about platform to rotatably fix cutting ring 128a on backup ring 126. Preferably, cutting ring 128 is formed from polyethylene and is fixedly secured to backup plate 126 using, for example, an adhesive. Backup ring 126 is preferably formed from metal. Alternately other materials of construction may be used to construct plate 126 and ring 128. Cutting ring 126 and backup plate 148 are slidably mounted about post 122. Backup plate 126 includes a pair of inwardly extending tabs 150 which will be described in further detail below.

Anvil center rod assembly 152 includes anvil center rod 154, a plunger 156 and plunger spring 158. A first end of center rod 154 includes a transverse throughbore 160 which is spaced radially of a central longitudinal axis of center rod 154. Post 122 of anvil head assembly 120 also includes a transverse throughbore 162. A pivot member 164 pivotably secures post 122 to center rod 154 such that anvil head assembly 120 is pivotably mounted to anvil center rod assembly 152. Plunger 156 is slidably positioned in a bore 154b (FIG. 16A) formed in the first end of center rod 154. Plunger 156 includes an engagement finger 168 which is offset from the pivot axis of anvil head assembly 120 and biased into engagement with the base 122a of post 122 by plunger spring 158 to urge anvil head assembly 120 to a pivoted position. In a prefired position, tabs 150 formed on backup plate 126 engage a top surface 154a (FIG. 16B) of center rod 154 to prevent anvil head assembly 120 from pivoting about pivot member 164. As device 10 is being fired, backup plate 126 and cutting ring 128 are moved deeper into anvil recess 134 of anvil head 124 about post 122 (FIG. 16B) by knife 188 (FIG. 9) in a manner to be described in further detail below to move tabs 150 out of engagement with top surface 154a of center rod 154 to permit plunger 156 to pivot anvil head assembly 120 about pivot member 164.

Figure 15C:
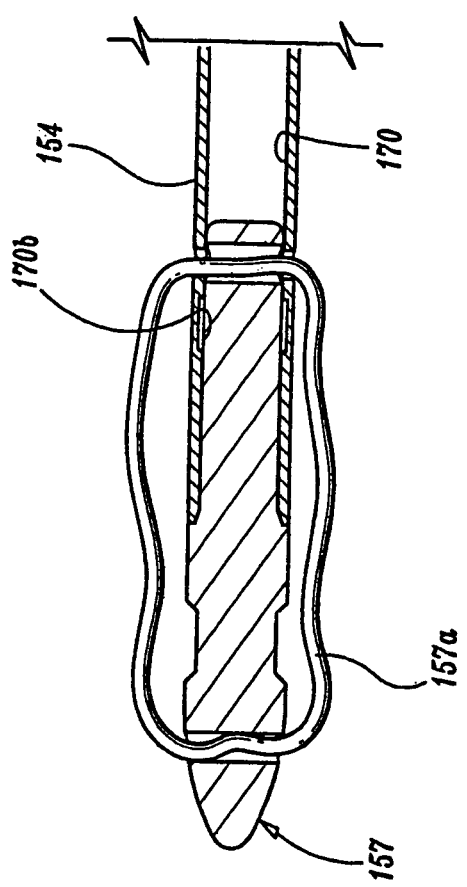
FIG. 15C is a side cross-sectional view of a trocar positioned in the distal end of the anvil center rod of the anvil assembly shown in FIG. 15.

A second end of center rod 154 includes a blind bore 170 (FIG. 15B) which includes an inwardly tapering opening 170a and a spaced annular recess 170b. Blind bore 170 is dimensioned to receive a removable trocar 157 (FIG. 15C). The annular recess is positioned within blind bore 170 and dimensioned to receive an annular rib formed on the trocar (not shown) to secure center rod 154 in engagement with the trocar. Alternately, trocar 157 may be retained within center rod 154 using only a suture 157a, i.e., no frictional contact is provided between trocar 157 and center rod 154. This allows for easy removal of trocar 157 from center rod 154 (FIG. 15C). The outer surface of center rod 154 includes an annular abutment 175 which defines an annular recess 177. Annular recess 177 is dimensioned to engage legs 70 of anvil retainer 38 to releasably secure anvil assembly 30 to anvil retainer 38. A bore 179 extends transversely through center rod 154 and is dimensioned to receive a suture for securing a trocar to the center rod. A collar 181 including a plurality of splines 181a is secured about center rod 154. Splines 181a function to align anvil assembly 30 with shell assembly 31 during approximation of the anvil and shell assemblies.

Shell Assembly

Referring to FIG. 9, shell assembly 31 includes a shell 182, a pusher back 186, a cylindrical knife 188, and a staple guide 192. Shell 182 includes an outer housing portion 194 and an inner guide portion 196. Outer housing portion 194 defines a throughbore 198 having a distal cylindrical section 200, a central conical section 202 and a proximal smaller diameter cylindrical section 204. A plurality of openings 206 are formed in conical section 202. Openings 206 are dimensioned to permit fluid and tissue passage during operation of the device. A pair of diametrically opposed flexible engagement members 207 are formed on proximal cylindrical section 204 of shell 182. Engagement members 207 are positioned to be received in openings 209 formed on the distal end of elongated body 14 to secure shell 182 to elongated body 14. A pair of openings 211 are formed in the proximal end of outer tube 14a. Openings 211 are dimensioned to receive protrusions (not shown) formed on the internal wall of stationary handle 18 to facilitate attachment of tube 14a to handle portion 12.

Pusher back 186 includes a central throughbore 208 which is slidably positioned about inner guide portion 196 of shell 182. Pusher back 186 includes a distal cylindrical section 210 which is slidably positioned within distal cylindrical section 200 of shell 182, a central conical section 212 and a proximal smaller diameter cylindrical section 214. The proximal end of pusher back 186 includes members 220 which are configured to lockingly engage with resilient fingers 110 of pusher link 74 to fasten pusher link 74 to pusher back 186 such that a distal face of pusher link 74 abuts a proximal face of pusher back 186.

The distal end of pusher back 186 defines a pusher 190. Pusher 190 includes a multiplicity of distally extending fingers 226 dimensioned to be slidably received within slots 228 formed in staple guide 192 to eject staples 230 therefrom. Cylindrical knife 188 is frictionally retained within the central throughbore of pusher back 186 to fixedly secure knife 188 in relation to pusher 190. Alternately, knife 188 may be retained within pusher back 186 using adhesives, crimping, pins, etc. The distal end of knife 188 includes a circular cutting edge 234.

In operation, when pusher link 74 is advanced distally in response to actuation of firing trigger 20, as will be described below, pusher back 186 is advanced distally within shell 182. Advancement of pusher back 186 advances fingers 226 through slots 228 of staple guide 192 to advance staples 230 positioned within slots 228 and eject staples 230 from staple guide 192. Since knife 188 is secured to pusher back 186, knife 188 is also advanced distally to core tissue as will be described in more detail below.

Cam Adjustment Mechanism

Figure 11:
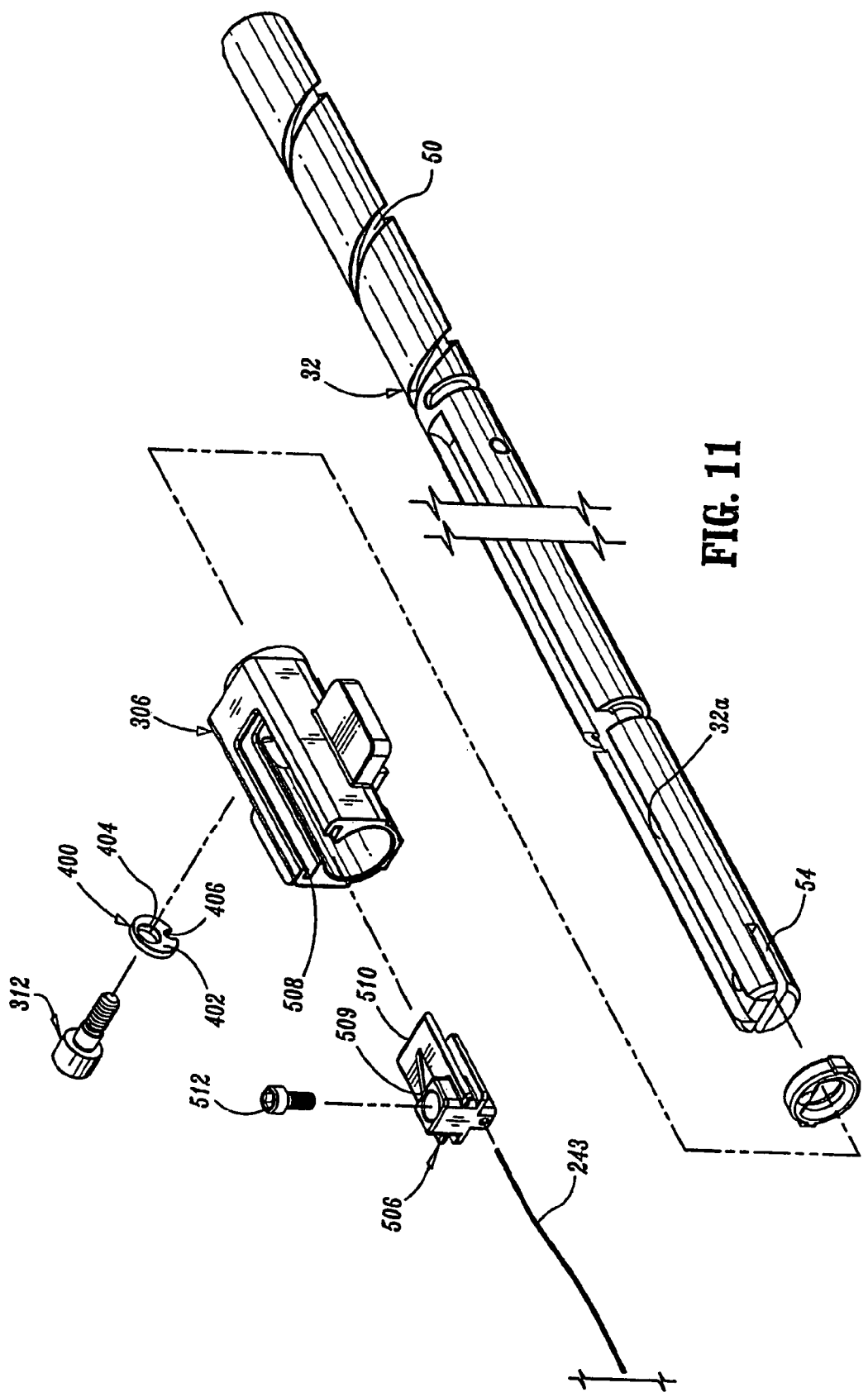
FIG. 11 is an elevated side perspective view of the screw and screw stop assembly and cam adjustment mechanism with parts separated of the surgical stapling device shown in FIG. 1.
Figure 11A:
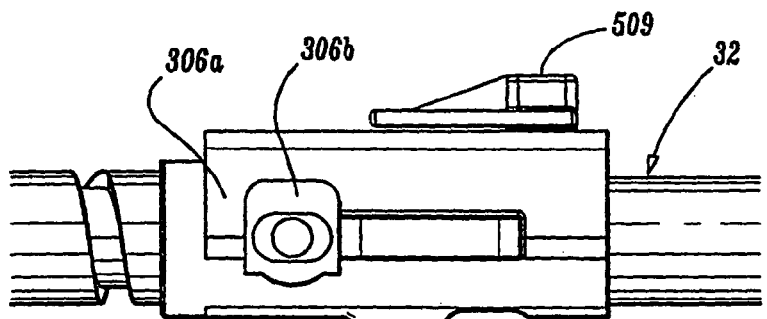
FIG. 11A is a side elevational partial cutaway view of the screw and screw stop assembly of the surgical stapling device shown in FIG. 11.
Figure 11B:
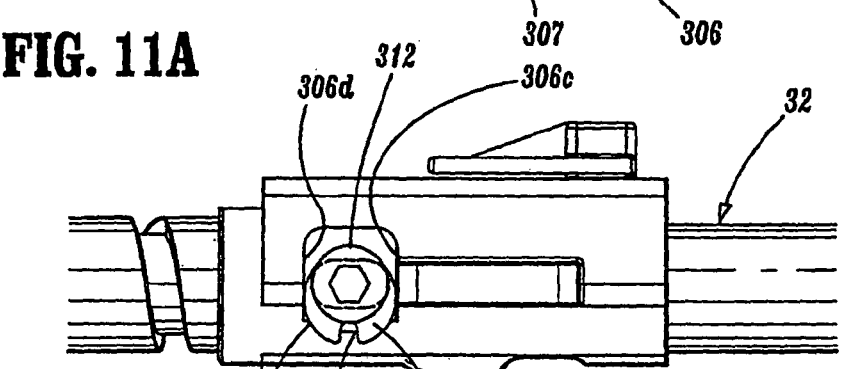
FIG. 11B is a side elevational partial cutaway view of the screw and screw stop assembly and cam adjustment mechanism shown in FIG. 11.
Figure 11C:
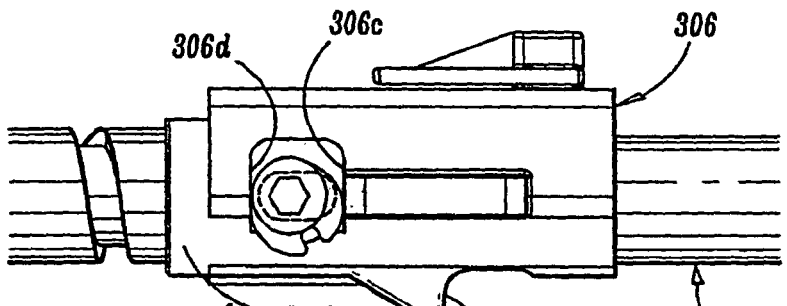
FIG. 11C is a side elevational partial cutaway view of the screw and screw stop assembly and cam adjustment mechanism shown in FIG. 11 with the cam adjustment mechanism being rotated in a counter-clockwise direction.
Figure 11D:
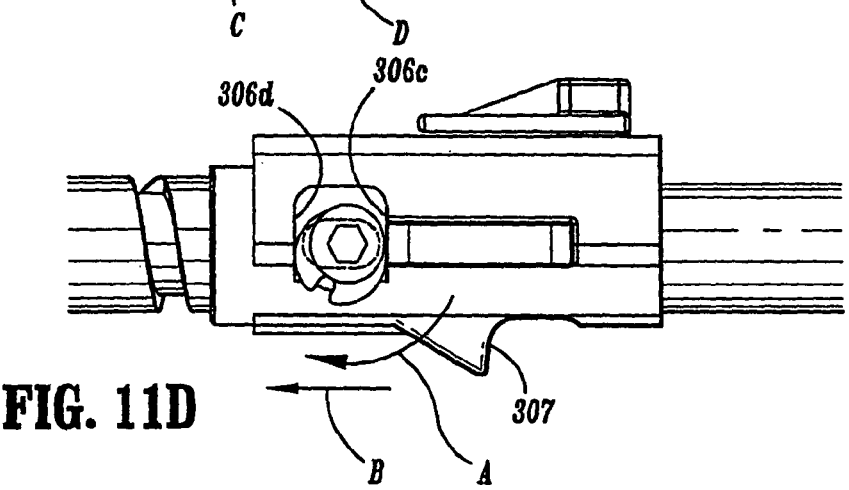
FIG. 11D is a side elevational partial cutaway view of the screw and screw stop assembly and cam adjustment mechanism shown in FIG. 11 with the cam adjustment mechanism being rotated in a clockwise direction.
Figure 14:
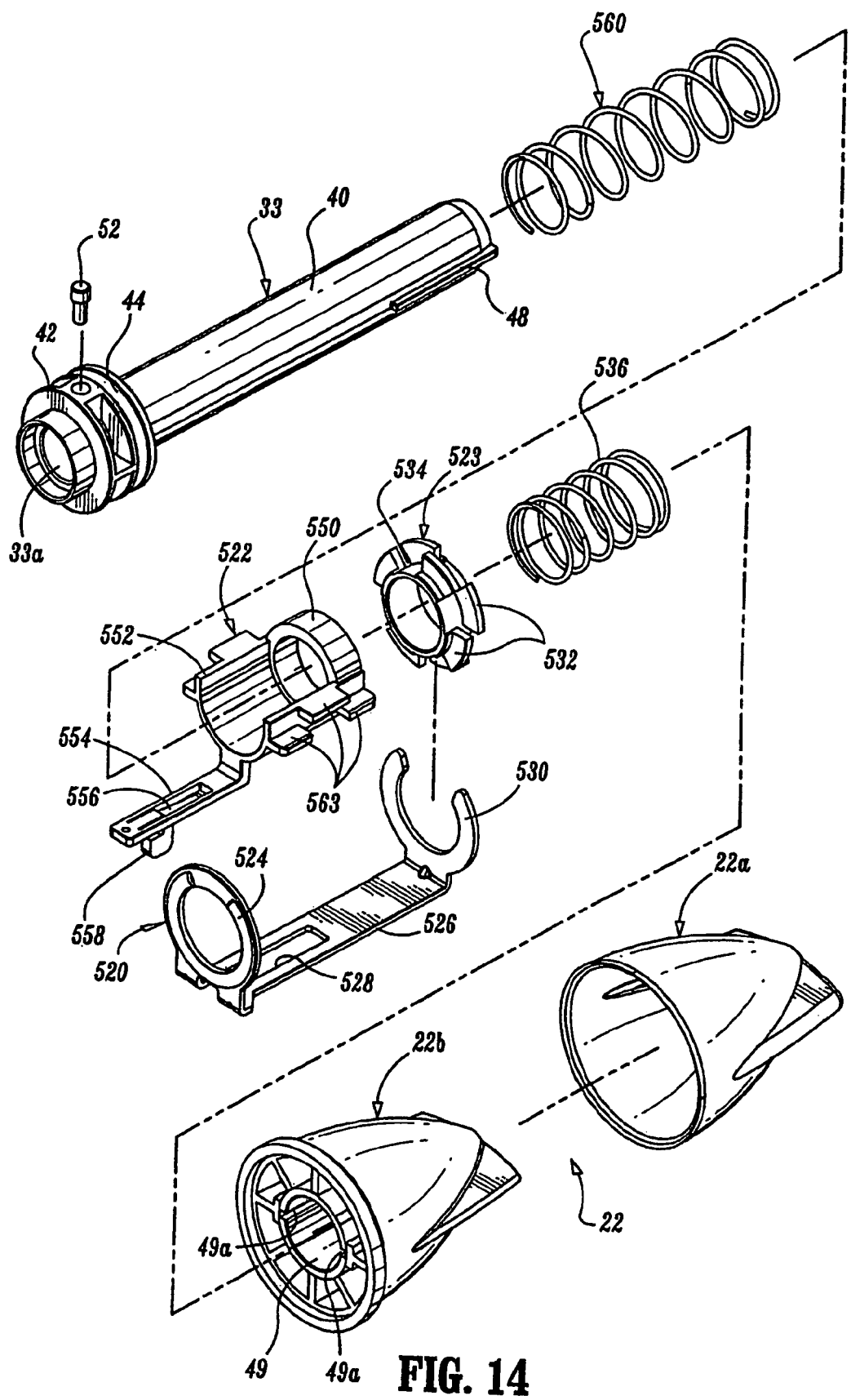
FIG. 14 is an elevated side perspective view with parts separated of the rotatable sleeve and firing lockout assembly of the surgical stapling device shown in FIG. 1.

Referring to FIGS. 11-13, a cam adjustment member 400 is secured by set screw 312 onto a sidewall 306a of screw stop 306, within a recess 306b formed in sidewall 306a. Cam adjustment member 400 includes a circular disc 402 having a throughbore 404. Throughbore 404 is eccentrically formed through disc 402 and is dimensioned to receive set screw 312. A smaller notch or hole 406 is also formed in disc 402. Notch 406 is dimensioned to receive the tip of an adjustment tool (not shown). Recess 306b (FIG. 11A) includes a forward and a rear shoulder or abutment surface 306c and 306d, respectively, and is dimensioned to receive disc 402 such that the outer edge of disc 402 abuts forward and rear shoulders 306c and 306d.

As discussed above, set screw 312 extends through disc 402 and screw stop 306 and engages screw 32 to secure screw stop 306 in an axially fixed position on screw 32. Cam adjustment member 400 functions to adjust the axial position of screw stop 306 on screw 32. More specifically, set screw 312 can be loosened to allow disc 402 to rotate within recess 306b of screw stop 306 while still remaining axially fixed to screw 32. Since disc 402 is eccentrically mounted about screw 32 and engages forward and rear shoulders 306c and 306d of recess 306b, rotation of disc 402 about fixed set screw 312 will urge screw stop 306 axially along screw 32 to adjust the axial position of screw stop 306 on screw 32. For example, when disc 402 is rotated in a clockwise direction (as viewed in FIG. 11D) identified by arrow "A", screw stop 306 will be moved axially in relation to screw 32 in the direction indicated by arrow "B" in response to engagement between the outer edge of disc 402 and rear shoulder 306d of recess 306b. Conversely, when disc 402 is rotated in a counter-clockwise direction (as viewed in FIG. 11C), identified by arrow "C", screw stop 306 will be moved axially in relation to screw 32 in the direction indicated by arrow "D" in response to engagement between the outer edge of disc 402 and forward shoulder 306c of recess 306b.

When stapling device 10 is in a fully approximated position, i.e., anvil assembly 30 and shell assembly 31 are brought into juxtaposed alignment to define a tissue receiving clearance, screw stop 306 abuts against body portion 42 of the rotatable sleeve 33. In this position, anvil assembly 30 and shell assembly 31 will be spaced slightly to define the tissue receiving clearance. By providing cam adjustment member 400, the tissue receiving clearance can be selectively adjusted by adjusting the position of screw stop 306 on screw 32 to be within a desired range. Preferably, cam adjustment member 400 permits adjustment of the tissue receiving clearance of ±0.045 inches, although greater or lesser adjustment capabilities are also envisioned. Typically, adjustments to the tissue receiving clearance will be made by the device manufacturer.

A hole or opening (not shown) may be provided in handle portion 12 (FIG. 1) to provide access to cam adjustment member 400.

Retractable Trocar Assembly

Referring to FIGS. 9 and 10, stapling device 10 includes a retractable trocar assembly slidably positioned within anvil retainer 38. The retractable trocar assembly includes a trocar assembly 240 and an engagement member 242. Engagement member 242 may be in the form of a spring clip, as shown. Alternately, other engagement members are envisioned, e.g., spring loaded protrusions, etc. Trocar assembly 240 includes a trocar body 240a and trocar tip 240b. Trocar body 240a has a slot 244 which extends through trocar body 240a along a portion of its length. Slot 244 is dimensioned to receive engagement member 242. Trocar tip 240b is secured to trocar body 240a using, for example screw threads. Alternately, other fastening techniques can be used to secure trocar tip 240b to trocar body 240a. While trocar tip 240a is shown rounded or blunt, other tip configurations are envisioned. Trocar tip 240b includes a pair of resilient legs 240c which deform, i.e., straighten out, as the trocar is pushed through tissue to ramp tissue over anvil retainer 38. By providing legs 240c, tissue is less likely to become caught on anvil retainer 38 during use.

As shown in FIG. 10, engagement member 242 includes a proximal body portion 246 and a pair of distally extending resilient legs 248. Each leg 248 includes a tapered tip 250 and a proximally facing shoulder 252. A pin 254 is positioned through openings 256 and 258 formed in body portion 246 of member 242 and trocar 240, respectively, to secure engagement member 242 within slot 244 of trocar 240. Pin 254 also extends through an elongated slot 255 formed in anvil retainer 38, such that the distal and proximal surfaces of slot 255 function as stops to define the fully advanced and fully retracted positions of the retractable trocar assembly. Legs 248 are formed of a resilient material such as spring steel. Alternately, other materials including plastics may be used to form engagement member 242. In an unbiased position, legs 248 of member 242 extend outwardly of slot 244 of trocar 240 and beyond the outer diameter of anvil retainer 38 such that in the fully advanced position of trocar 240, shoulders 252 of legs 248 engage a distal end 38a of anvil retainer 38 to retain the trocar 240 in the advanced position. See FIGS. 19H and 20G.

Referring to FIGS. 20G-20K, when the anvil assembly 30 is attached to anvil retainer 38, anvil center rod 154 of anvil assembly 30 is slid in the direction indicated by arrow "Z" in FIG. 20G over tapered tips 250 of legs 248 of engagement member 242 to compress legs 248 inwardly (FIG. 20H) into the confines of slot 244 (FIG. 10) such that trocar 240 and member 242 move inside blind bore 170 of center rod 154. As anvil assembly 30 is forced about trocar 240, trocar 240 is moved from its extended to its retracted position within anvil retainer 38. As illustrated, pin 254 moves from a first end 255a of slot 255 to a second end 255b of slot 255.

When the anvil assembly is disengaged from anvil retainer 38 by pulling the anvil assembly in a direction away from anvil retainer 38, legs 248 of member 242 flex outwardly to move shoulders 252 of legs 248 of member 242 into annular recess 170b of center rod 154 (See FIG. 20K). As a result, as anvil assembly 30 is disengaged from anvil retainer 38, engagement member 242 and thus trocar 240 are pulled distally to move trocar 240 to the advanced position. As discussed above, in the advanced position shoulders 252 of engagement member 242 engage the distal face 38a of anvil retainer 38.

The proximal end of trocar 240 includes a transverse slot 241 (FIG. 10). A rigid flexible indicator link or wire 243 has a distal end which is secured within slot 241 of trocar 240 and extends rearwardly through elongated body portion 14 within slot 74c (FIG. 9) of pusher link 74 and along slot 32a (FIG. 12) in screw 32 into handle portion 12 of stapling device 10. Wire 243 has a proximal end which is secured to an indicator assembly in handle portion 12 which will be discussed in detail below.

Lockout Tube Assembly

Figure 20D:
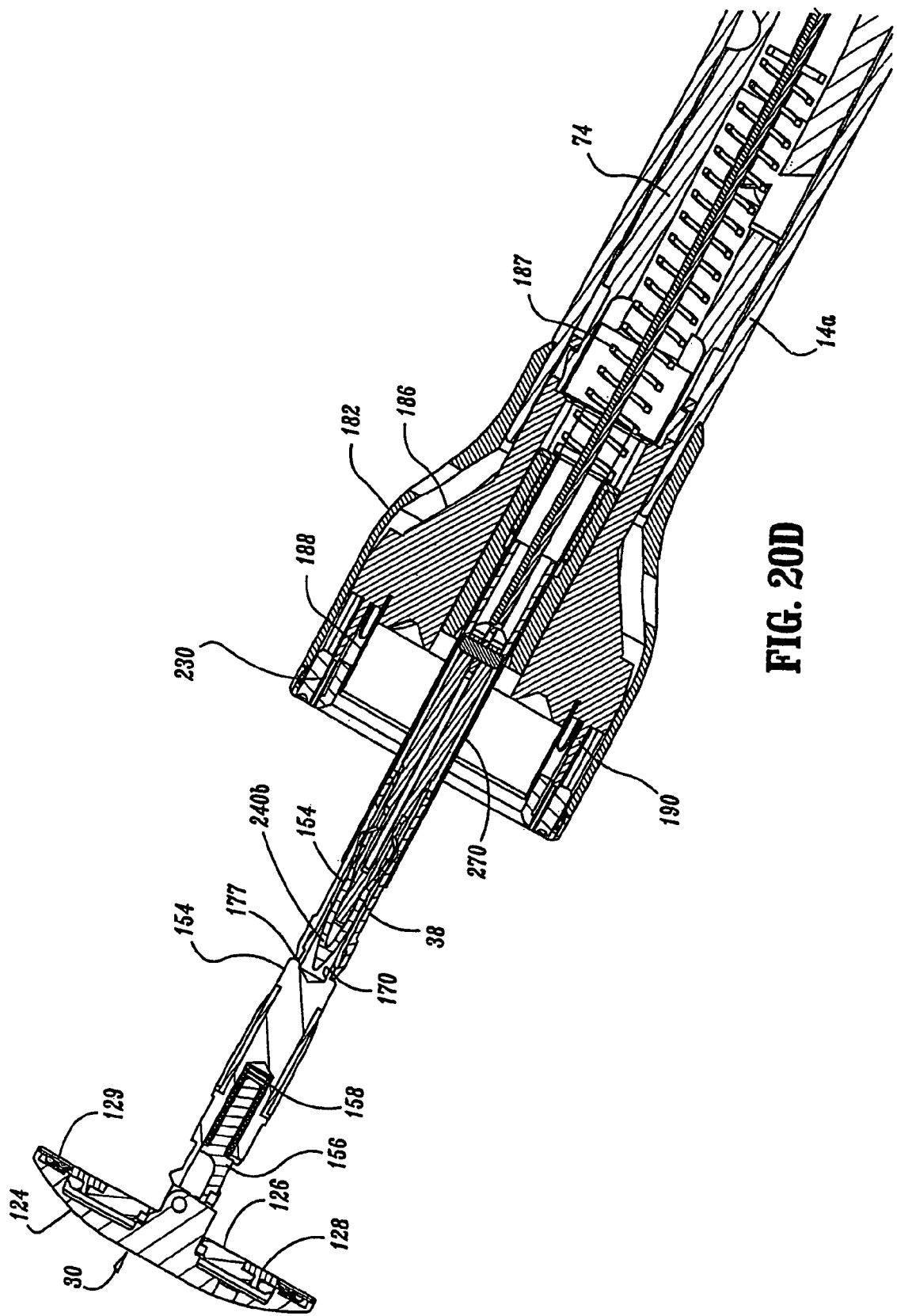
FIG. 20D is an enlarged view of the indicted area of detail shown in FIG. 20B.

Referring again to FIGS. 9 and 10, a cylindrical lockout tube 270 is slidably positioned about the outer surface of anvil retainer 38 and positioned to extend through inner guide portion 196 of shell 182 and central bore 208 of pusher back 186. The proximal end of lockout tube 270 includes an annular flange 272. A cylindrical fitting 273 is secured about the proximal end of lockout tube 270 in the proximal end of bore 208 of pusher back 186. A biasing member 187 engages flange 272 and urges lockout tube 270 distally to a position in which flange 272 engages fitting 273 (FIG. 20D). Biasing member 187 is preferably a torsion spring which is positioned in compression between flange 272 of lockout tube 270 and an abutment formed within pusher link 74.

Lockout tube 270 is positioned about flexible legs 70 of anvil retainer 38 to provide rigidity to legs 70 during approximation of the anvil and cartridge assemblies. Initially, prior to approximation, legs 70 of anvil retainer 38 project from lockout tube 270. Accordingly, legs 70 are free to flex outwardly to allow attachment and detachment of anvil assembly 30 to anvil retainer 38. During approximation, legs 70 are withdrawn into lockout tube 270 to clamp legs 70 about center rod 154 of the anvil and prevent removal of the anvil assembly from the anvil retainer. Anvil retainer 38 is withdrawn into lockout tube 270 during approximation until shoulder 38b of anvil retainer 38 engages distal face 270a of lockout tube 270. Thereafter, both anvil retainer 38 and lockout tube 270 are retracted against the bias of spring 187 into bore 208 of pusher back 186.

Indicator Assembly

Referring to FIGS. 7, 8 and 11-13, an indicator assembly is mounted within stationary handle 18 and includes an indicator plate 500 having an engagement member 501 and indicia (not shown) formed thereon. The indicia is preferably in the form of colored dots which identify whether the device 10 is in a fire-ready condition or not. For example, a green dot may indicate a fire-ready position and a red dot may indicate a fire not ready position. Alternately, other forms of indicia may be used including graphic, written or numeric indicia. Indicator plate 500 is slidably positioned within stationary handle 18 such that the indicia is visible through indicator opening 24. A biasing member 502, preferably a coil spring, is secured at one end to an inner wall of stationary handle 18 and at the other end to indicator plate 500. Biasing member 502 is positioned in tension to urge indicator plate 500 to its forward-most position within stationary handle 18.

A retainer slide 506 is slidably positioned within a pair of grooves 508 formed in screw stop 306 and includes a first abutment surface 509 and a second abutment surface 510. A substantially rigid indicator link or wire 243 extends from the proximal end of trocar body 240a (FIG. 10) and is connected to retainer slide 506 by a set screw 512. Alternately, other fastening techniques may be employed. Wire 243 translates linear movement of trocar assembly 240 into linear movement of retainer slide 506 when an anvil assembly is being attached to anvil retainer 38. Accordingly, when anvil assembly 30 is attached to anvil retainer 38 to move trocar 240 from its advanced position to its retracted position, wire 243 effects movement of retainer slide 506 from its forward-most position on screw stop 306 (FIG. 12) to its rearward-most position.

As discussed above, screw stop 306 is secured to screw 32 by set screw 312. When approximation knob 22 is rotated to retract screw 32 into sleeve 30, screw stop 306 is retracted towards sleeve 30. After anvil assembly 30 has been attached to anvil retainer 38 and screw 32 has been retracted a predetermined distance, first abutment surface 509 abuts engagement member 501 of indicator plate 500 such that further approximation moves indicator plate 500 against the urging of biasing member 502 to its rearward-most position. In its rearward-most position, the indicia on plate 500 is visible through opening 24 and identifies that device 10 is in a fire-ready condition.

It is noted that if device 10 is approximated without an anvil assembly 30 attached to the anvil retainer 38, retainer slide 506 will remain in its forward-most position on screw stop 306, abutment surface 509 of retainer slide 506 will not be in position to contact engagement member 501 of indicator plate 500 during approximation of the device and the indicator assembly will remain in a fire-not ready position and indicated as such through opening 24.

Fire Lockout Assembly

Referring to FIGS. 8, 14, 17, and 18, a firing lockout assembly is provided which includes trigger lock 26 (FIGS. 1 and 8), safety bracket 520, a lockout sleeve 522 and a compression member 523. Safety bracket 520 includes a forward collar portion 524, a body portion 526 having an elongated slot 528 and a rear C-shaped portion 530. Forward collar portion 524 is positioned about the proximal end of screw 32 adjacent and forward of body portion 42 of rotatable sleeve 30. Compression member 523 includes a plurality of fins 532 which partially define an annular channel 534, C-shaped portion 530 is positioned within annular channel 534 of compression member 523. A biasing member 536, preferably a coil spring, is positioned in stationary handle 18 behind compression member 523 to urge compression member 523 and safety bracket 520 forwardly within stationary handle 18.

Trigger lock 26 (FIG. 8) is pivotally supported between handle sections 18a and 18b about pivot member 540 and includes an integrally formed locking portion 542 positioned adjacent pivot member 540. When device 10 is in the unapproximated position, body portion 526 of safety bracket 520 is positioned adjacent or juxtaposed locking portion 542 of trigger lock 26 to prevent trigger lock 26 from pivoting about pivot member 540 from its locking position (FIG. 1).

When device 10 is approximated, retainer slide 506 (FIG. 11) moves with screw stop 306 to a position in which second abutment surface 510 engages forward collar portion 524 of safety bracket 520 to move safety bracket 520 rearwardly. In the rearward position of safety bracket 520, elongated slot 528 is aligned with locking portion 542 of trigger lock 26 to allow trigger lock 26 to be pivoted away from trigger 20 towards stationary handle 18 and permit actuation of firing trigger 20.

It is noted that if an anvil has not been attached to device 10 and retainer slide 506 is in its forward-most position on screw stop 306, second abutment surface 510 will not be in position to engage forward collar portion 524 of safety bracket 520, locking portion 542 will abut body portion 526 of safety bracket 520, and trigger lock 26 will not be pivotable to an unlocked position.

Lockout sleeve 522 includes a cylindrical portion 550, a semi-cylindrical body portion 552 and a forwardly extending arm 554. A flexible tab 556 extends downwardly from arm 554 and includes a retaining surface 556a. A drive member 558 extends downwardly from one end of tab 556. Lockout sleeve 522 is positioned about rotatable sleeve 33. A biasing member 560 which is preferably a torsion spring is positioned to urge lockout sleeve 522 rearwardly within stationary handle 18. Lockout sleeve 522 also includes side fins 563 which are received within grooves within stationary handle 18 to confine lockout sleeve 522 to linear movement.

When lockout sleeve 522 is positioned within stationary handle 18, biasing member 560 is compressed between body portion 42 of rotatable sleeve 33 and cylindrical portion 550 of lockout sleeve 522. Retaining surface 556a of flexible tab 556 is positioned to engage a surface 562 (FIG. 19C) within stationary handle 18 such that biasing member 560 is maintained in compression.

In operation, when firing trigger 20 is actuated, a projection 93 (FIG. 1) formed on trigger actuator 20 moves into engagement with drive member 558 to disengage retaining surface 556a of tab 556 from surface 562 within stationary handle 18. When this occurs, spring 560 moves lockout sleeve 522 rearwardly such that a portion of sleeve 522 engages locking portion 542 of trigger lock 26 to pivot trigger lock 26 from an unlocked position to a locked position. In this post fire locked position, the distal end of trigger lock 26 returns to a position between abutments 89 and 91 to again prevent the inadvertent firing of device 10.

Tactile Indication

Referring to FIGS. 8, 8A, 8B, and 11, a tactile indicator 580 is positioned within stationary handle 18 and is movable within a vertical slot 582 between retracted and extended positions. Tactile indicator 580 includes a protrusion 580a which is configured to be received within one of two recesses 582a and 582b formed in slot 582. In the extended position, tactile indicator 580 is positioned to engage a wing 584 formed on screw stop 306 at a position of unapproximation sufficient to permit the tilt anvil assembly to have tilted. Prior to firing device 10, tactile indicator 580 is in the retracted position with protrusion 580a positioned within recess 582a. When device 10 is fired, an abutment surface 588 formed on firing link 72 (FIG. 8) engages indicator 580 to move indicator 580 to the extended position such that protrusion 580a is positioned in recess 582a. When device 10 is unapproximated a distance sufficient to allow the anvil head to pivot, wing 584 of screw stop 306 engages indicator 580 to provide an audible and/or tactile indication that such a point of unapproximation has been reached. Thereafter, a surgeon can remove the device from the patient in order to remove the anvil assembly from the anvil retainer, after it has been removed from the patient the surgeon needs to further unapproximate the device further by providing a force to approximation knob 22 sufficient to urge tactile indicator 580 from the extended to the retracted position.

Operation of surgical stapling device 10 will now be described in detail with reference to FIGS. 19-24F.

Figure 19E:
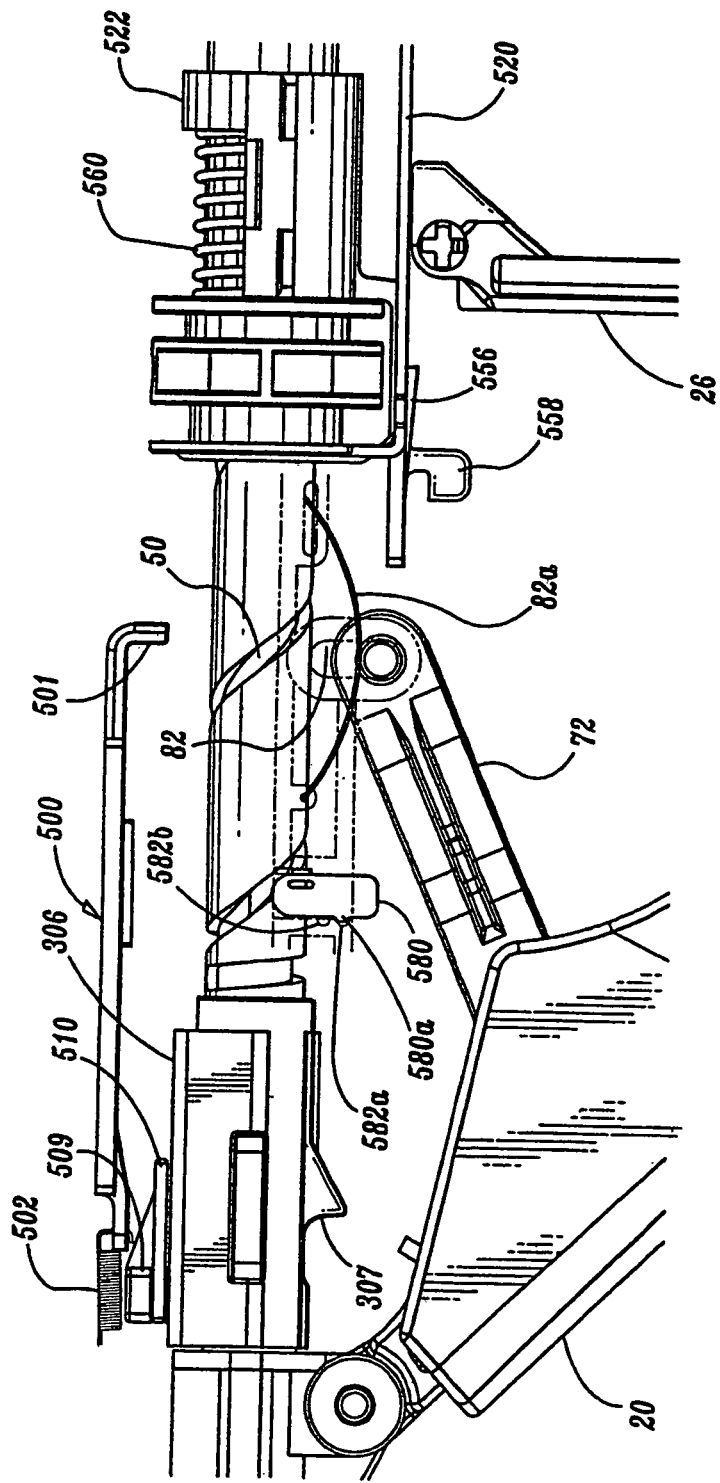
FIG. 19E is a side view of the proximal end of the surgical stapling device shown in FIG. 19 with the handle sections removed.
Figure 19F:
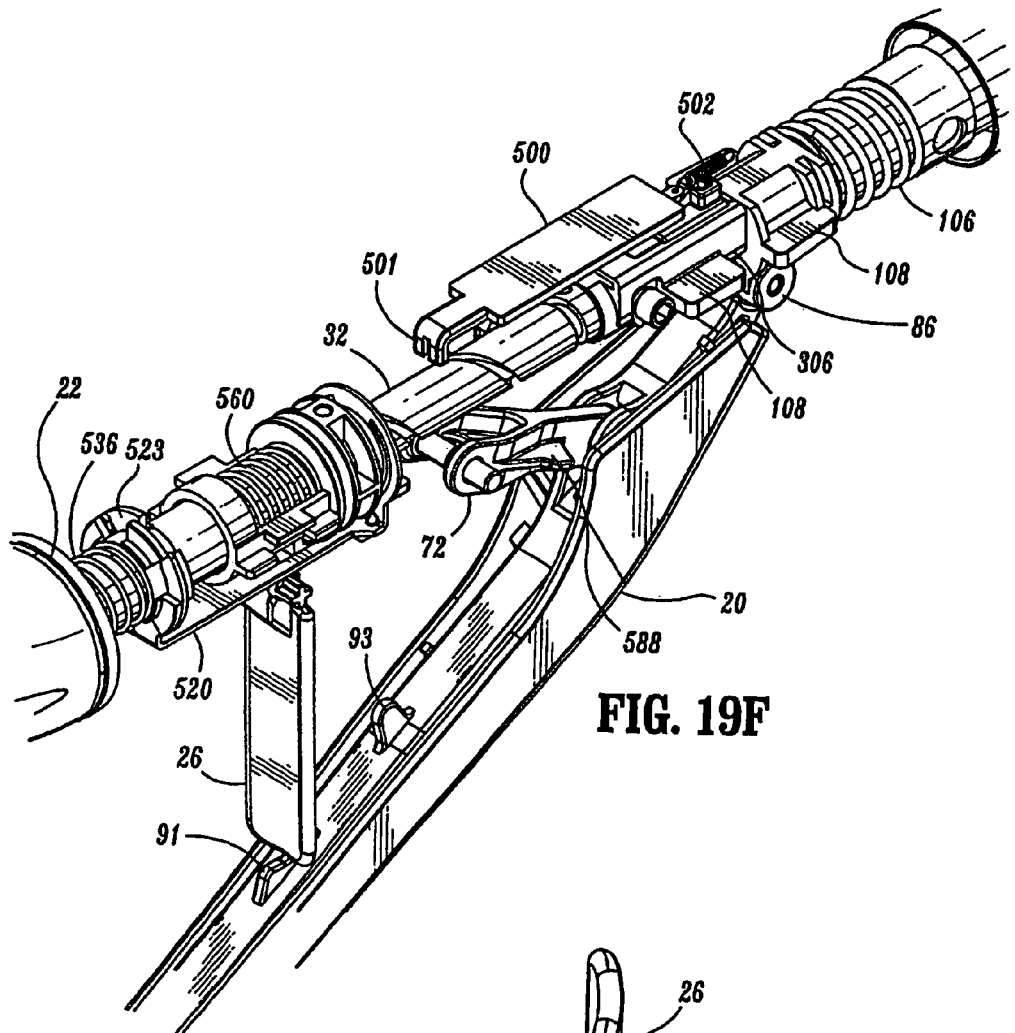
FIG. 19F is a top perspective view of the proximal end of the surgical stapling device shown in FIG. 19 with the handle sections removed.
Figure 19G:
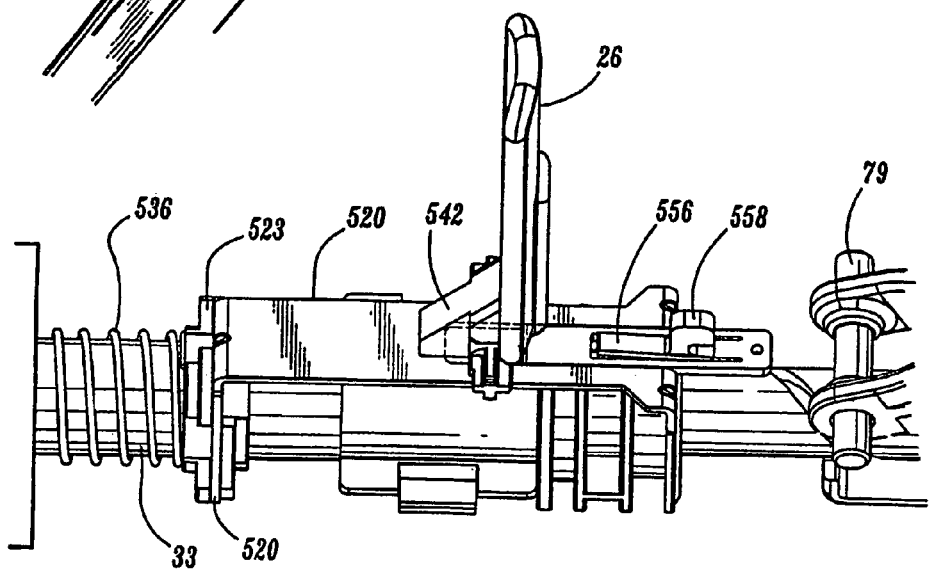
FIG. 19G is a bottom perspective view of a portion of the proximal end of the surgical stapling device shown in FIG. 19 with the handle sections removed.

FIGS. 19-19H illustrate surgical stapling device 10 in the unapproximated or open position prior to attachment of anvil assembly 30 (FIG. 1) to anvil retainer 38. In this position, screw stop 306 is positioned adjacent coupling 86 which is secured to the proximal end of pusher link 74 and retainer slide 506 is located in its forward-most position on screw stop 306. Pusher link 74 is urged by spring 106 to its retracted position. Body portion 526 of safety bracket 520 of the fire lockout assembly is urged by spring 560 to a position to prevent trigger lock 26 from pivoting. See FIG. 19C. Pivot member 79 secured to firing link 72 is positioned in the base of vertical slot 82 by biasing member 82*a* (FIG. 19E). Tactile indicator 580 is in its retracted position with protrusion 580*a* positioned within detent 582*a*.

Referring to FIGS. 19D and 19H, as discussed above, prior to attachment of anvil assembly 30 to anvil retainer 38, trocar assembly 240 is in it extended position with trocar tip 240*b* extending outwardly from anvil retainer 38. Shoulders 252 of engagement member legs 248 abut against distal face 38*a* of anvil retainer 38 to prevent trocar assembly 240 from being forced to its retracted position.

Figure 20E:
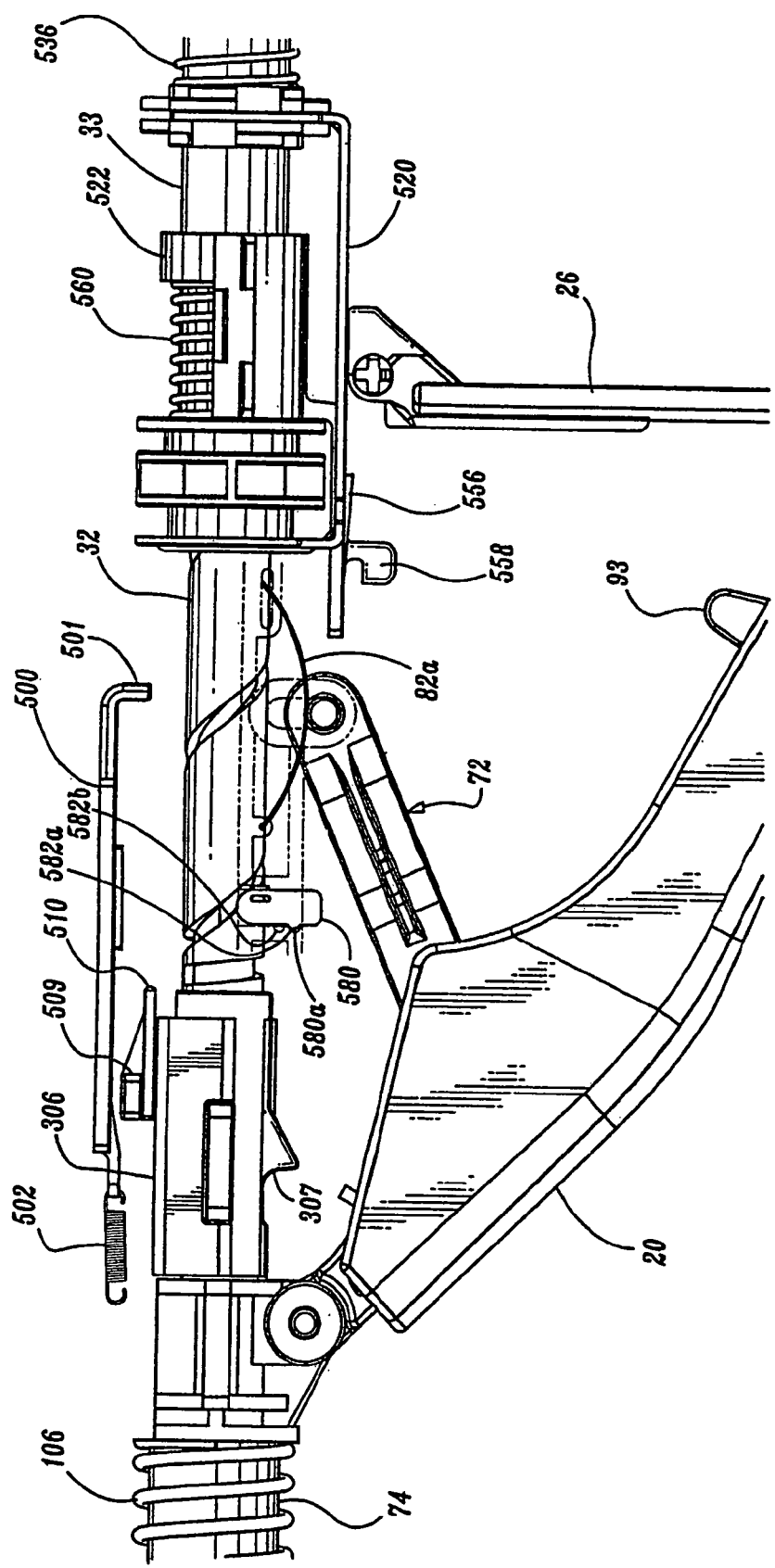
FIG. 20E is a side view of the proximal end of the surgical stapling device shown in FIG. 20 with the handle sections removed.
Figure 20F:
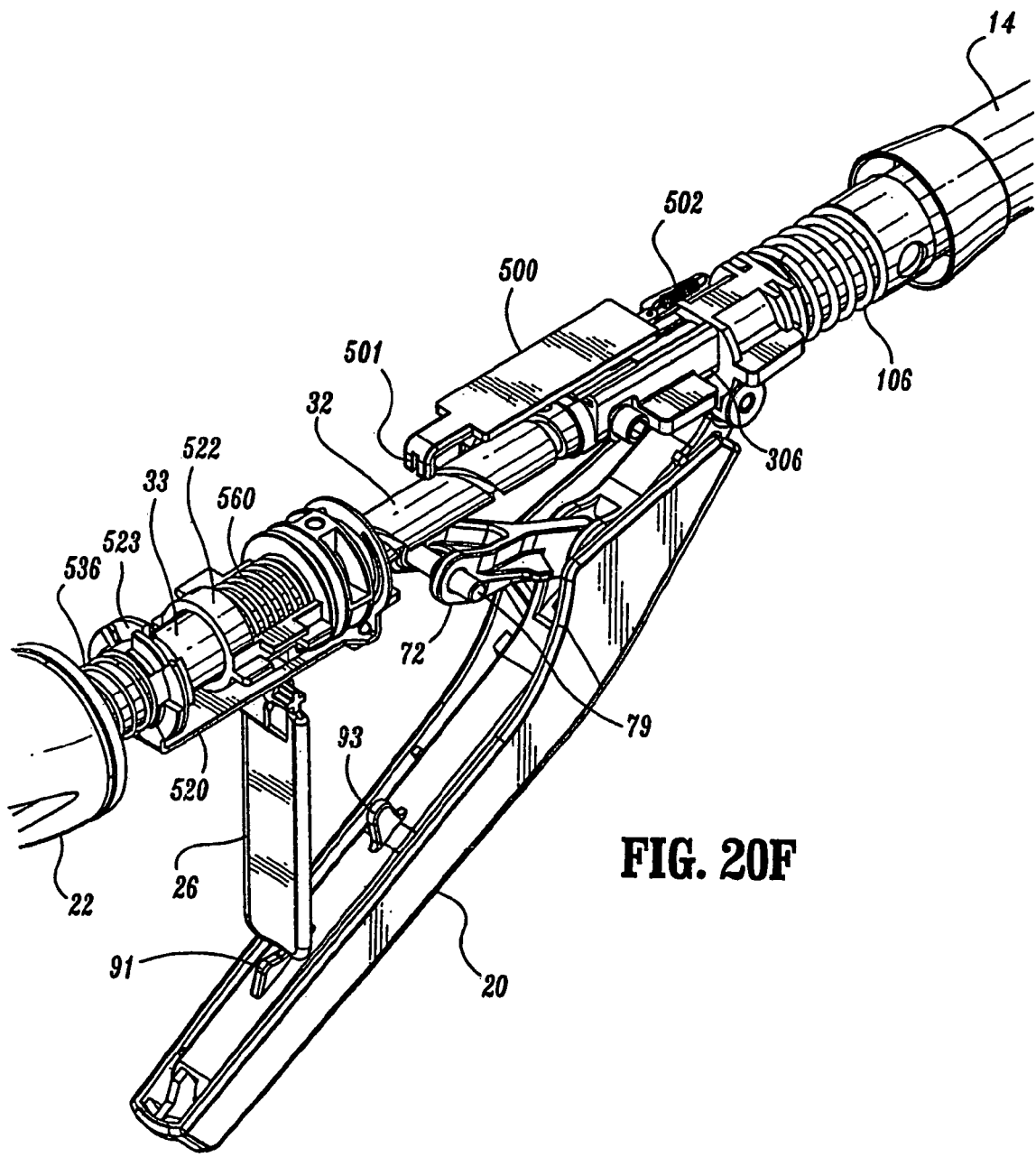
FIG. 20F is a top perspective view of the proximal end of the surgical stapling device shown in FIG. 20 with the handle sections removed.

FIGS. 20-20F illustrate surgical stapling device 10 having anvil assembly 30 secured to anvil retainer 38 and in the unapproximated or open position. Referring to FIG. 20D, when anvil assembly 30 is attached to anvil retainer 38, anvil center rod 154 is positioned over trocar tip 240*b* and pushed into anvil retainer 38. When this occurs, legs 248 of engagement member 242 are compressed inwardly to disengage shoulder 252 of legs 248 from engagement with distal face 38*a* of anvil retainer. This allows center rod 154 to be inserted into anvil retainer 38 until the distal ends of flexible legs 70 of anvil retainer 38 are received within annular recess 177 of anvil center rod 154. As this happens, trocar assembly 240 is moved to its retracted position with pin 254 positioned at the proximal end of slot 255 in anvil retainer 38.

As the trocar assembly is moved to the retracted position, indicator link or wire 243 (FIGS. 11 and 12) moves retainer 506 from its forward-most position on screw stop 306 to its rearward-most position. In the rearward-most position, upon approximation of device 10, first abutment surface 509 of retainer slide 506 will engage member 501 of indicator plate 500 and abutment surface 510 will engage forward collar position 524 of safety bracket 520. The remaining components of device 10 are not affected by attachment of anvil assembly 30 to anvil retainer 38.

Figures 21, 21A:
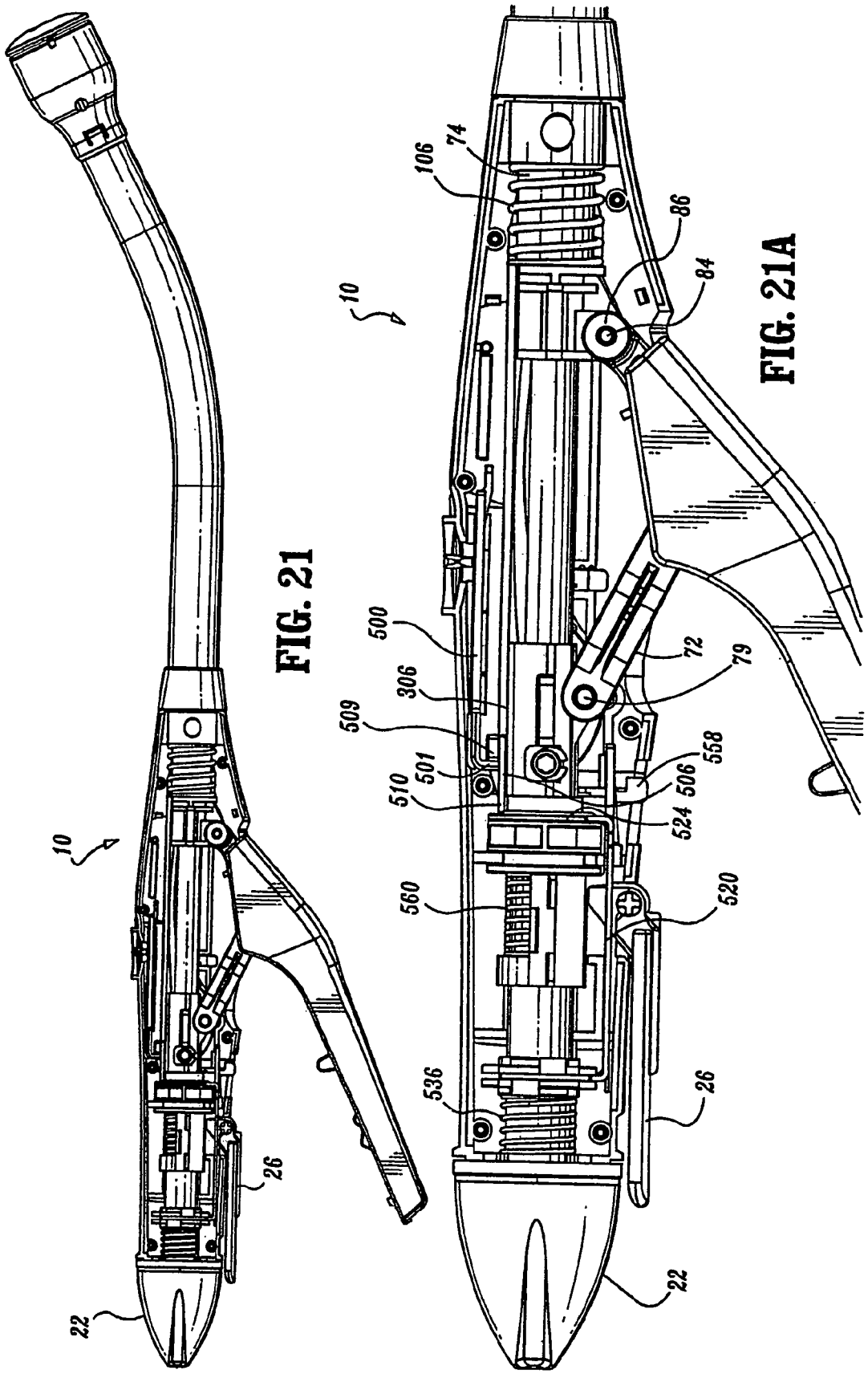
FIG. 21 is a side elevational view with a handle section removed of the surgical stapling device shown in FIG. 1 with the anvil assembly in the approximated position.
FIG. 21A is a side view with a handle section removed of the proximal end of the surgical stapling device shown in FIG. 21.
Figure 21E:
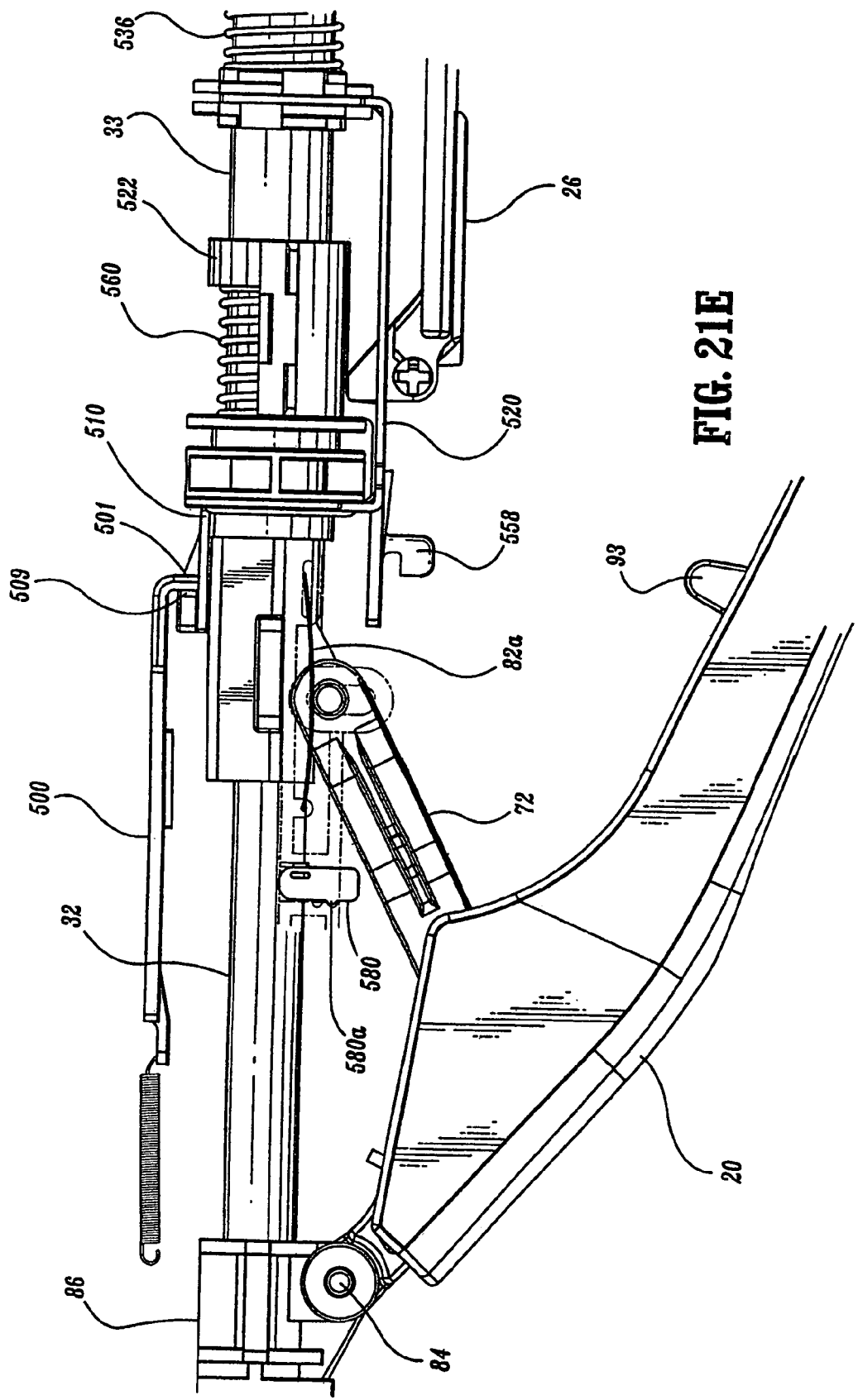
FIG. 21E is a side view of the proximal end of the surgical stapling device shown in FIG. 20 with the handle sections removed.
Figure 21F:
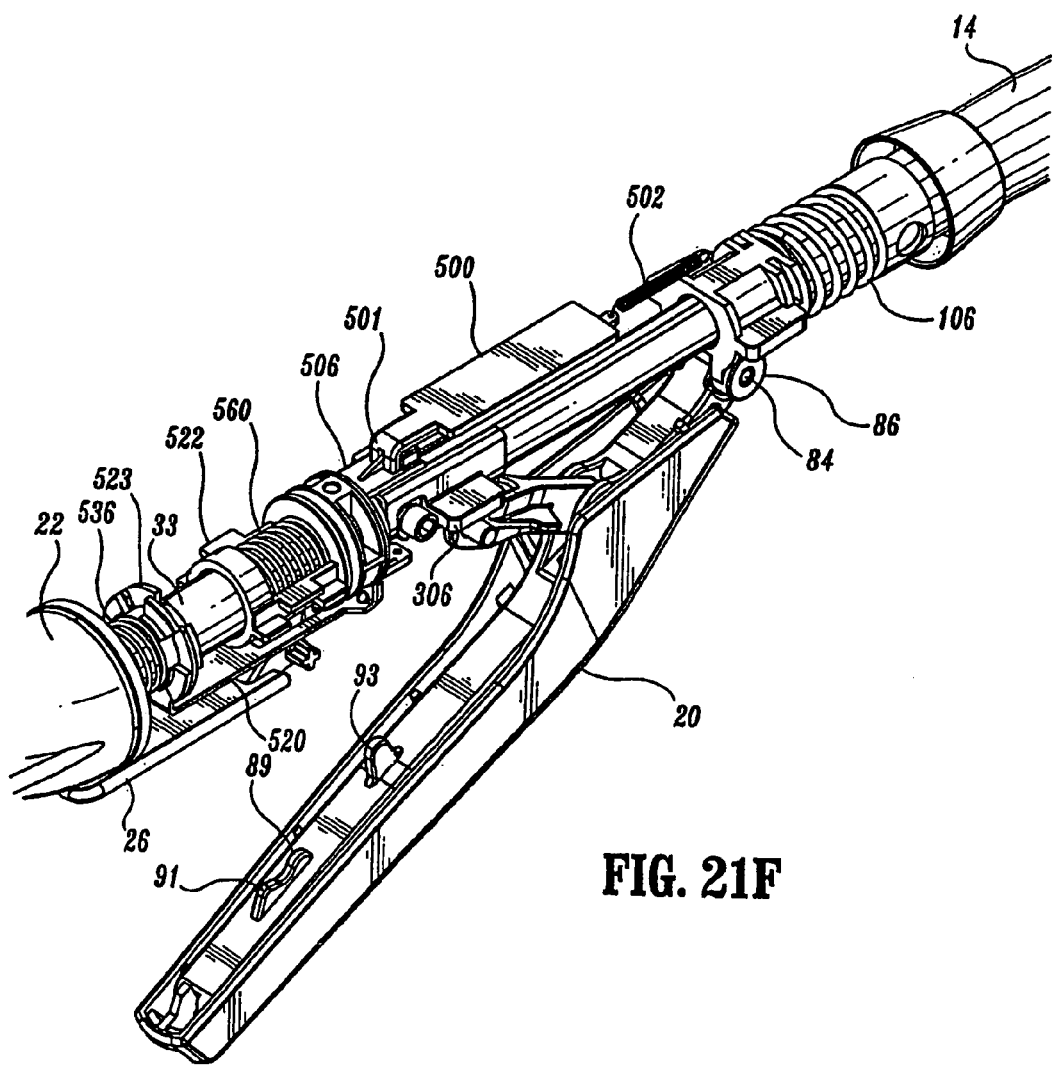
FIG. 21F is a top perspective view of the proximal end of the surgical stapling device shown in FIG. 21 with the handle sections removed.
Figure 21G:
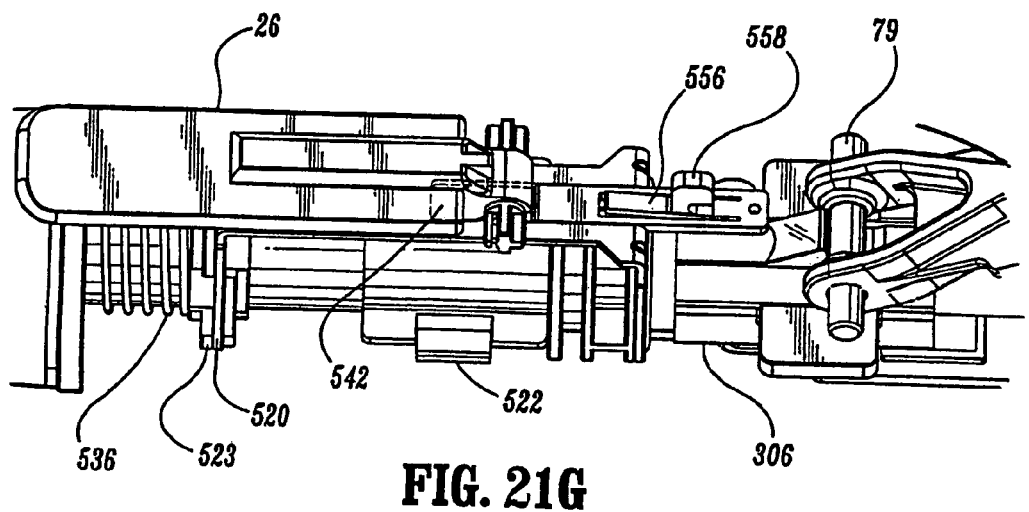
FIG. 21G is a bottom perspective view of a portion of the proximal end of the surgical stapling device shown in FIG. 21 with the handle sections removed.

FIGS. 21-21G illustrate surgical stapling device 10 with an anvil assembly 30 attached to anvil retainer 38 in the approximated position. As discussed above, anvil assembly 30 is moved to the approximated position from the unapproximated position shown in FIG. 20 by rotating rotation knob 22. Rotation of knob 22 causes rotation of cylindrical sleeve 33 which rotates pin 52 within helical channel 50 of screw 32. Since sleeve 33 is axially fixed, movement of pin 52 within helical channel 50 effects linear retraction of screw 32 into hollow sleeve 33. The distal end of screw 32 is connected to screw extensions 34 and 36 which are fastened at their distal ends to anvil retainer 38 such linear movement of screw 32 is translated into linear movement of anvil retainer 38 and anvil assembly 30.

Screw stop 306 is secured to screw 32 by set screw 312. Thus, during approximation of device 10, screw stop 306 is moved from a forward position within handle 18 (FIG. 20) to a rearward position within handle 18 (FIG. 21). As screw stop 306 is moved from its forward-most position to its rearward-most position, first abutment member 509 on retainer slide 506 engages member 501 of indicator plate 500 and abutment member 510 on retainer slide 506 engages collar portion 524 of safety bracket 520 to move indicator plate 500, against the bias of spring 502, and safety bracket 520, against the bias of spring 536, rearwardly within handle 18. Movement of indicator plate 500 rearwardly positions the fire-ready indicia beneath indicator opening 24. Movement of safety bracket 520 rearwardly aligns elongated slot 528 in body 526 of safety bracket 520 with locking portion 542 of trigger lock 26 such that trigger lock 26 is free to pivot to the unlocked position.

It is also noted that in the rearward-most position of screw stop 306, abutment surface 307 which is formed on the base of screw stop 306 (FIG. 11A) and comprises a substantially concave surface is positioned to receive and engage pivot member 79 of firing link 72.

Figure 22D:
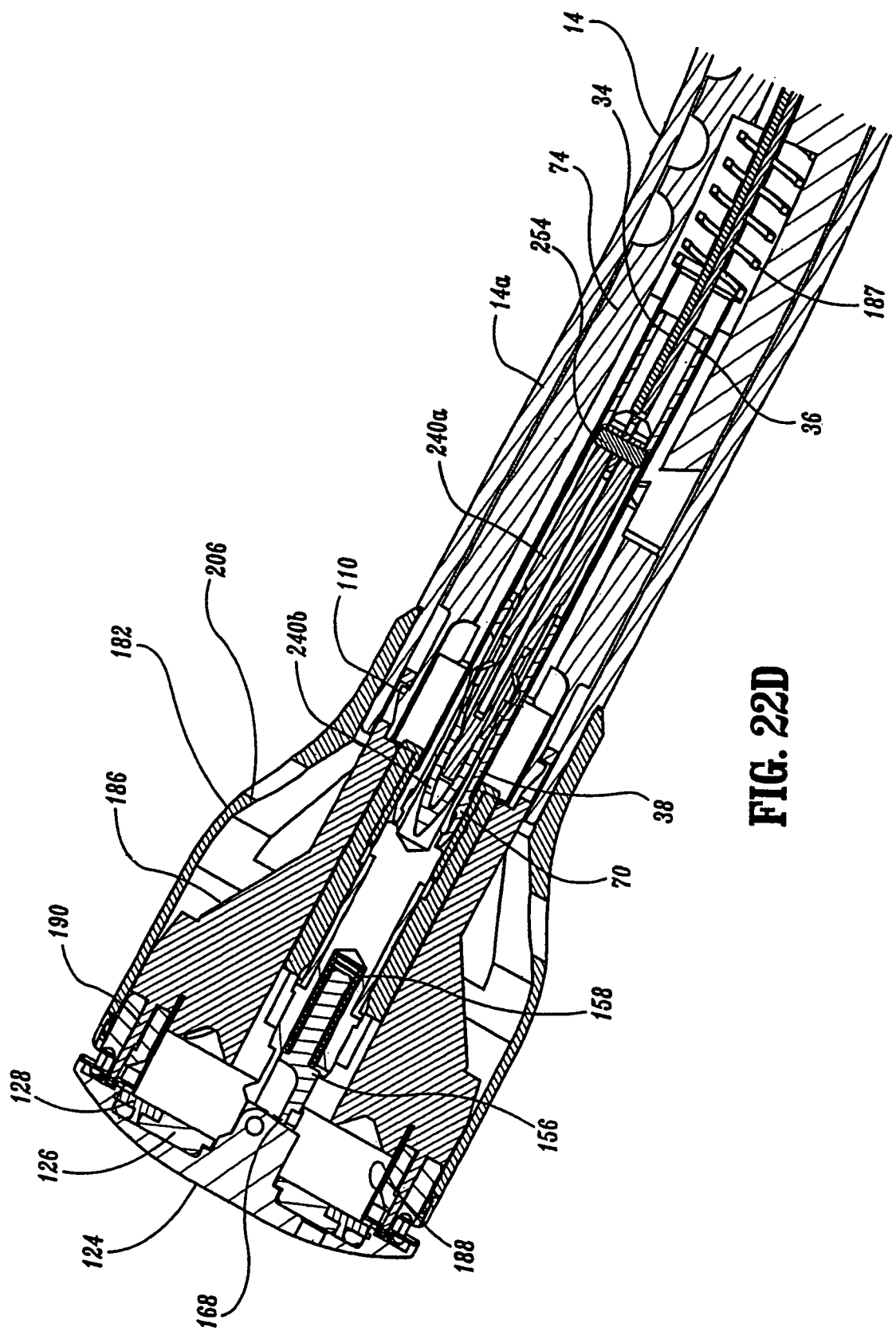
FIG. 22D is an enlarged view of the indicated are of detail shown in FIG. 22B.

FIGS. 22-22D illustrate surgical stapling device 10 during the firing stroke of firing trigger 20. As trigger 20 is compressed towards stationary handle 18, pivot member 79 engages abutment surface 307 on screw stop 306 and firing trigger 20 is pushed distally. As discussed above, the distal end of firing trigger 22 is connected through coupling member 86 to the proximal end of pusher link 74. Accordingly, as firing trigger 20 is moved distally, pusher link 74 is moved distally to effect advancement of pusher back 186 within shell assembly 31. Fingers 190 of pusher back 186 engage and eject staples 230 from staple guide 192.

Figure 16B:
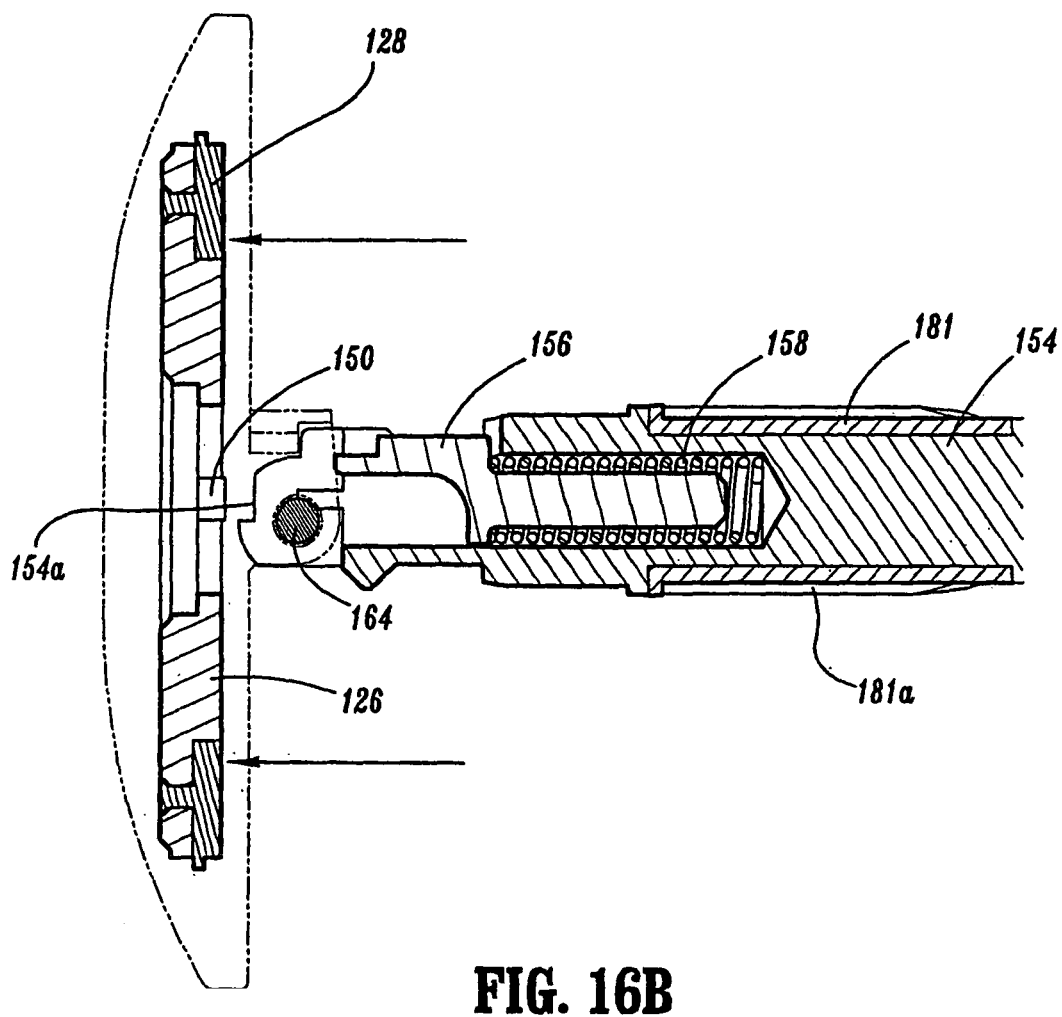
FIG. 16B is a side cross-sectional view of the anvil assembly shown in FIG. 15 with the backup plate and cutting ring advanced distally.

Cylindrical knife 188 is moved concurrently with pusher back 186 such that knife 188 moves into engagement with cutting ring 128 and backup plate 126. As discussed above, cutting ring 128 is preferably formed from polyethylene and backup plate 126 is preferably formed from metal. When knife 188 engages cutting ring 128, it cuts through cutting ring 128 and pushes backup plate 126 deeper into anvil head 124 to move tabs 150 from engagement with top surface 154*a* of center rod 154 (FIG. 16B). Anvil head 124 is now free to pivot about member 164 and is urged to do so by plunger 156 (FIG. 24F). It is noted that because the anvil assembly is in juxtaposed alignment with shell assembly 31, the anvil head 14 will not pivot fully until the anvil and shell assemblies have been unapproximated a distance sufficient to allow the anvil head to fully pivot.

As illustrated in FIG. 22C, projection 93 on firing trigger 20 is aligned with drive member 558 of lockout sleeve 522. When firing trigger 20 is fully actuated, projection 93 engages drive member 588 to deflect tab 556 upwardly to disengage retaining surface 556*a* from surface 562 of inner wall of stationary handle 18. When this occurs, spring 560 which is in compression drives lockout sleeve 522 rearwardly within handle 18 such that a portion of sleeve 522 engages locking portion 542 of trigger lock 26 to pivot trigger lock 26 from the unlocked position (FIG. 22C) to the locked position (FIG. 23). In the locked position the distal end of trigger lock 26 is positioned between abutments 89 and 91.

During actuation of firing trigger 20, an extension 589 on firing link 72 engages tactile indicator 580 and moves tactile indicator 580 from a retracted to an extended position. In the extended position, indicator 580 is positioned to engage wing 584 of screw stop 306 during unapproximation of the anvil and shell assemblies (FIG. 22F).

Figure 23D:
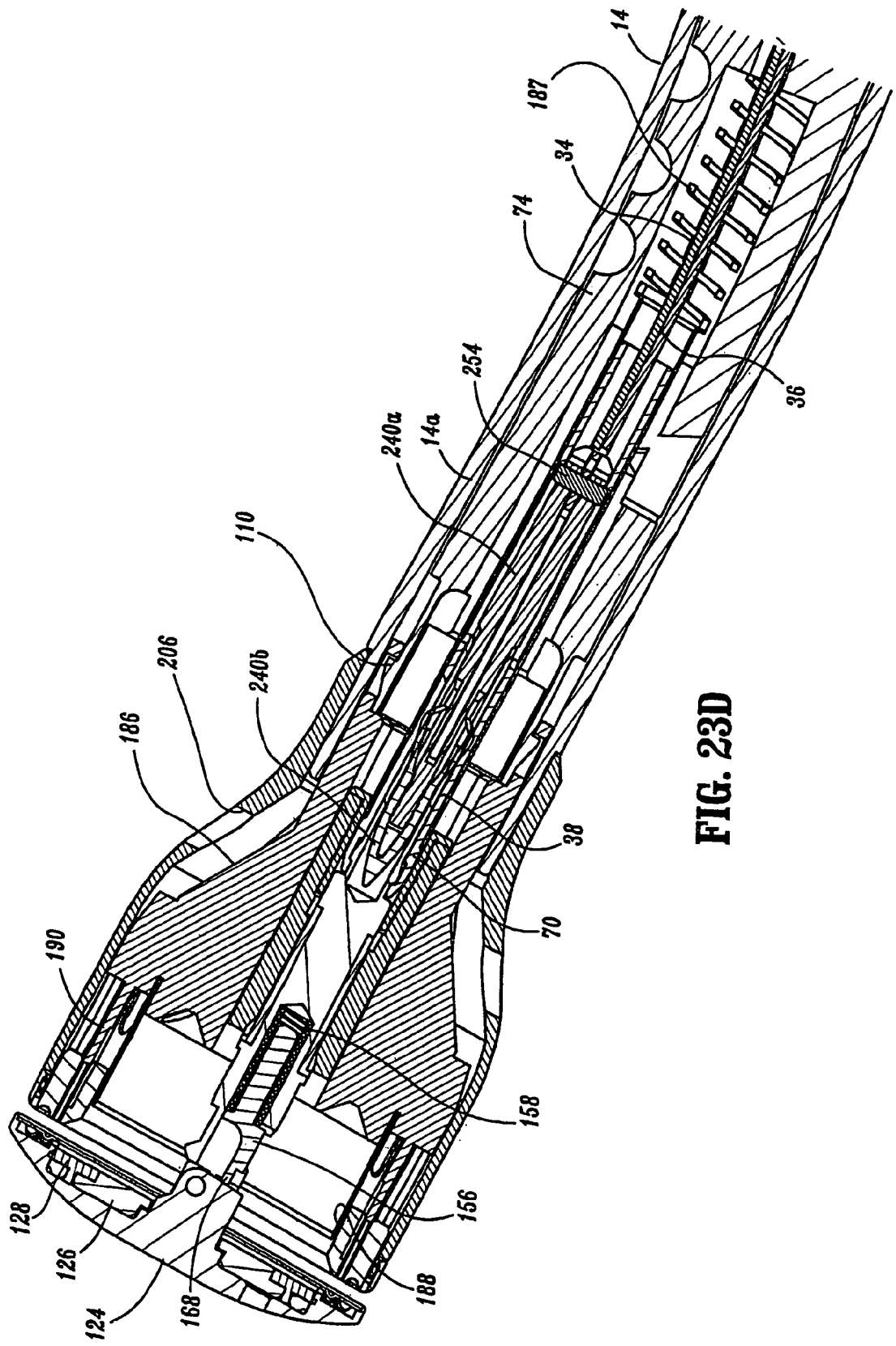
FIG. 23D is an enlarged view of the indicated area of detail shown in FIG. 23B.
Figure 23E:
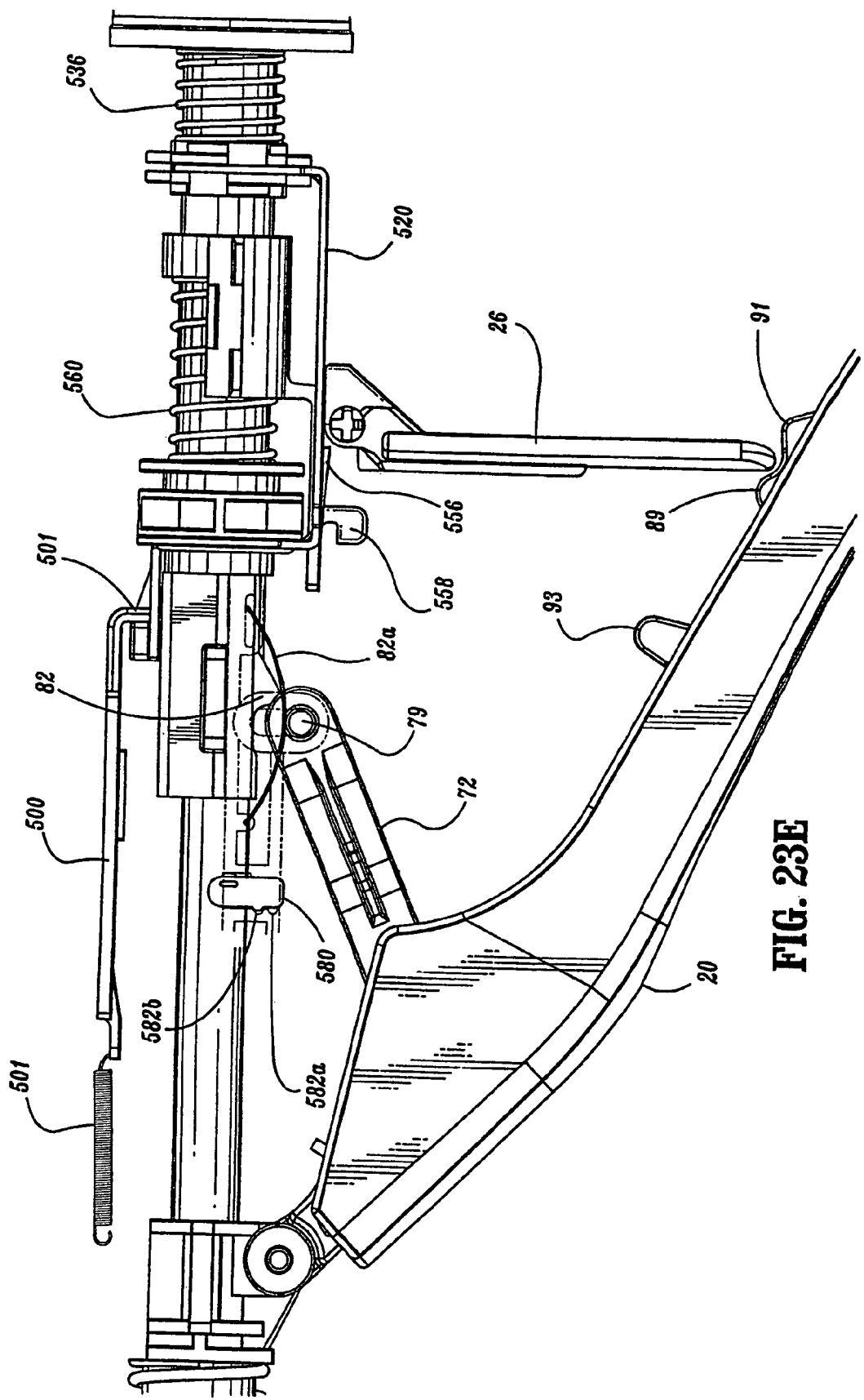
FIG. 23E is a side view of the proximal end of the surgical stapling device shown in FIG. 23E with the handle sections removed.
Figure 23F:
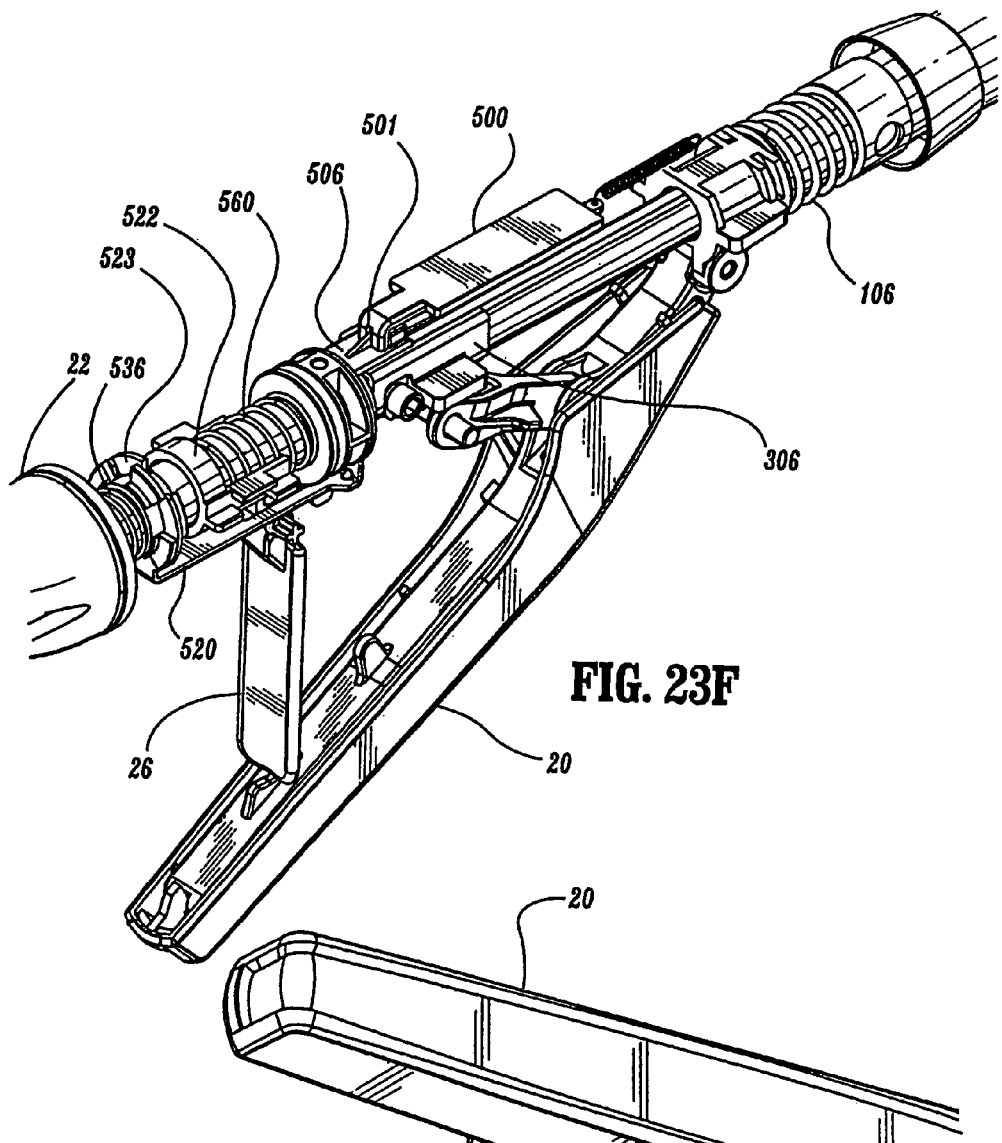
FIG. 23F is a top perspective view of the proximal end of the surgical stapling device shown in FIG. 23 with the handle sections removed.
Figure 23G:
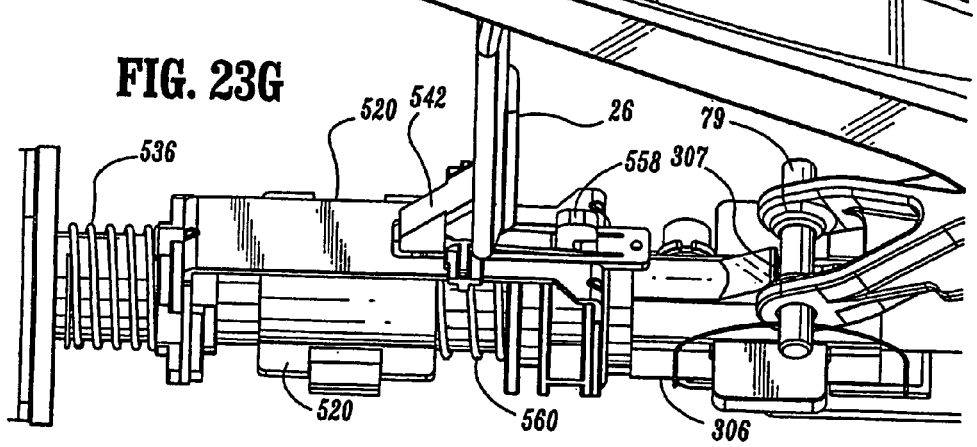
FIG. 23G is a bottom perspective view of a portion of the proximal end of the surgical stapling device shown in FIG. 23 with the handle sections removed.

FIGS. 23-23G illustrate surgical stapling device 10 after firing trigger 20 has been released. As illustrated, biasing member 106 has urged pusher link 74 proximally to its retracted position and trigger lock 26 has been moved to the locked position in the manner discussed above by lockout sleeve 522. As shown in FIG. 23D, pusher back 186 has moved, in response to movement of pusher link 74, proximally to its retracted position. Anvil head 124 has begun to pivot but is prevented from further pivoting by shell assembly 31.

Figures 24B, 24C:
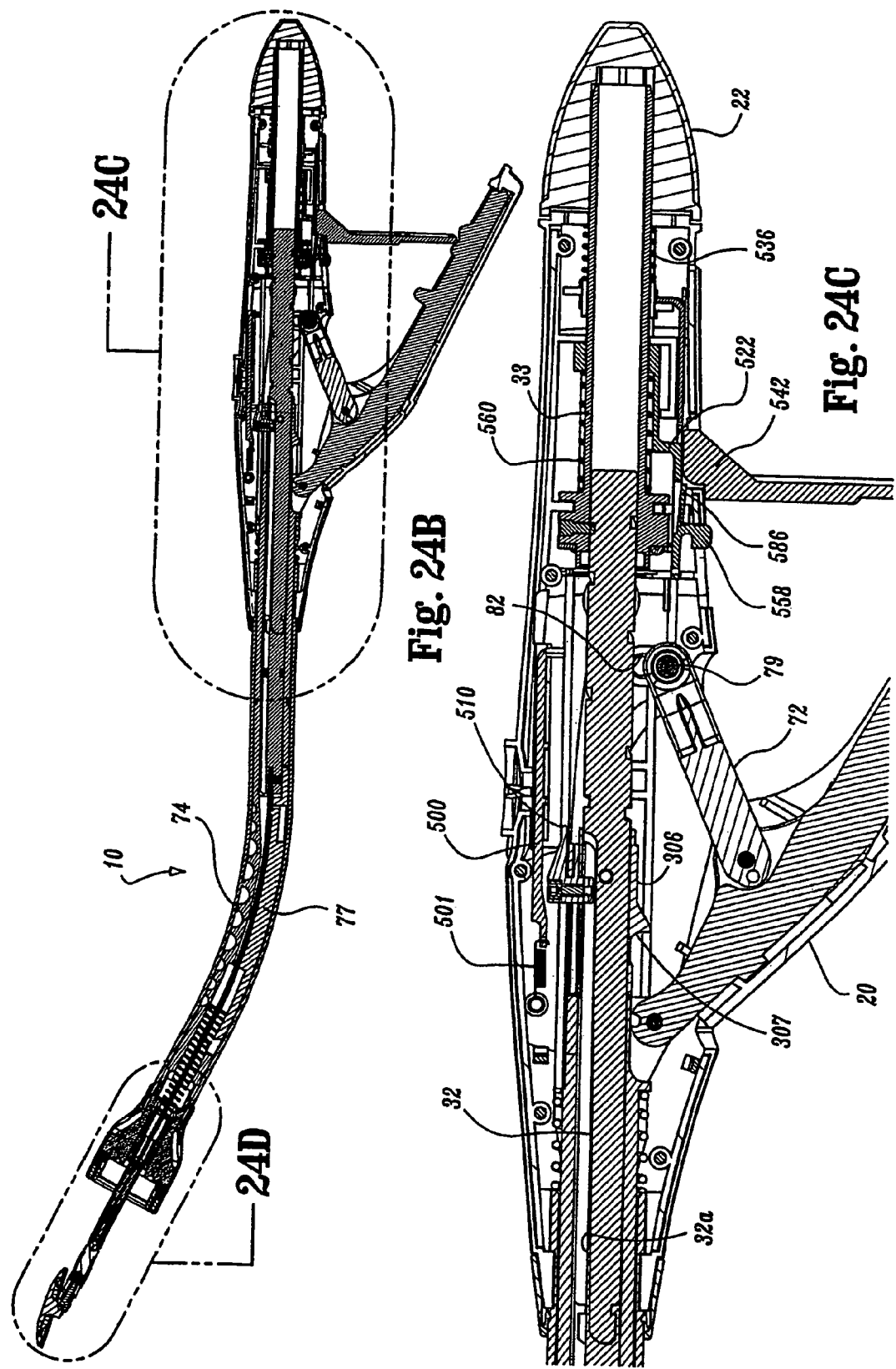
FIG. 24B is a side cross-sectional view of the surgical stapling device shown in FIG. 24.
FIG. 24C is an enlarged view of the indicated area of detail shown in FIG. 24B.
Figure 24D:
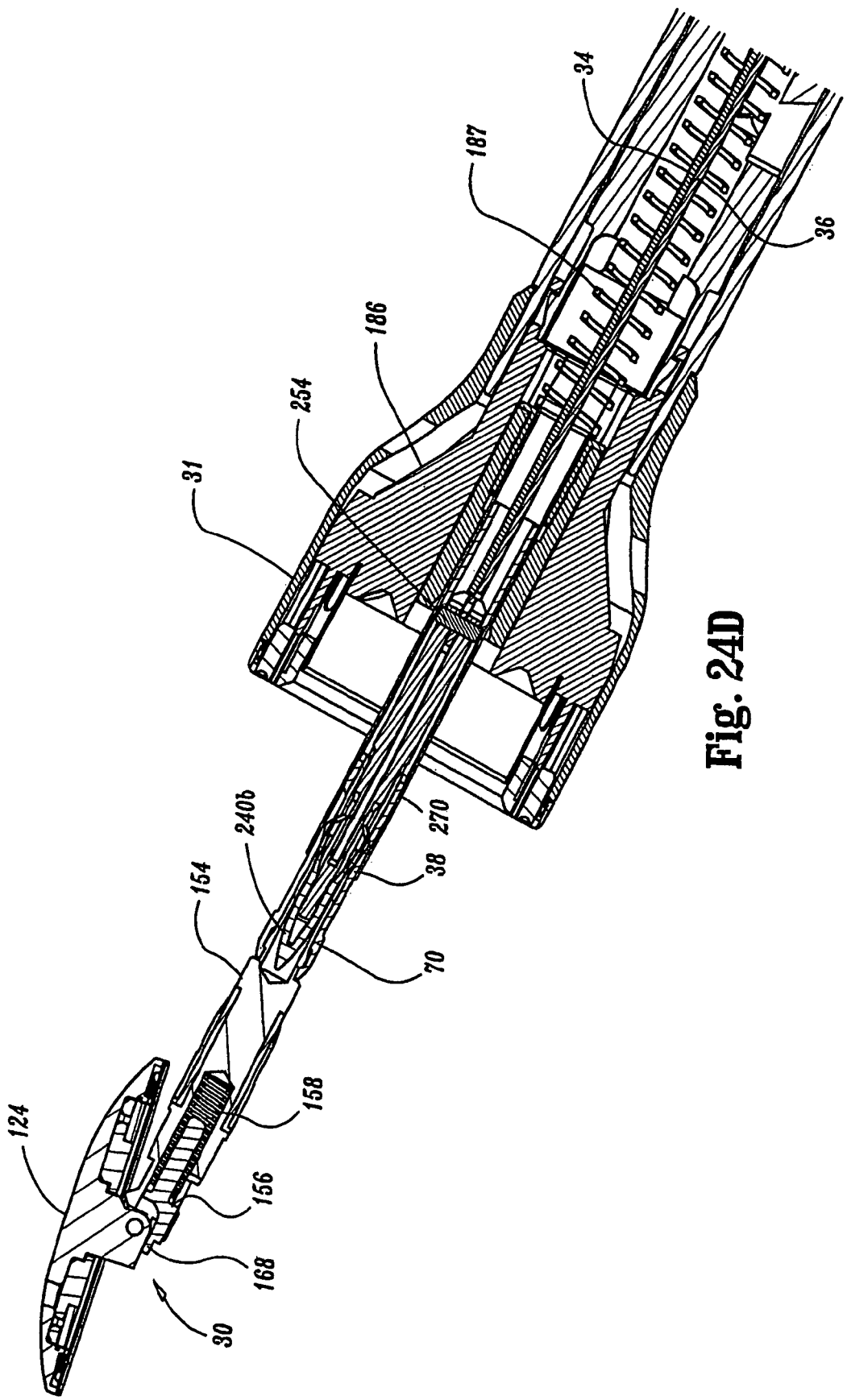
FIG. 24D is an enlarged view of the indicated area of detail shown in FIG. 24B.
Figure 24E:
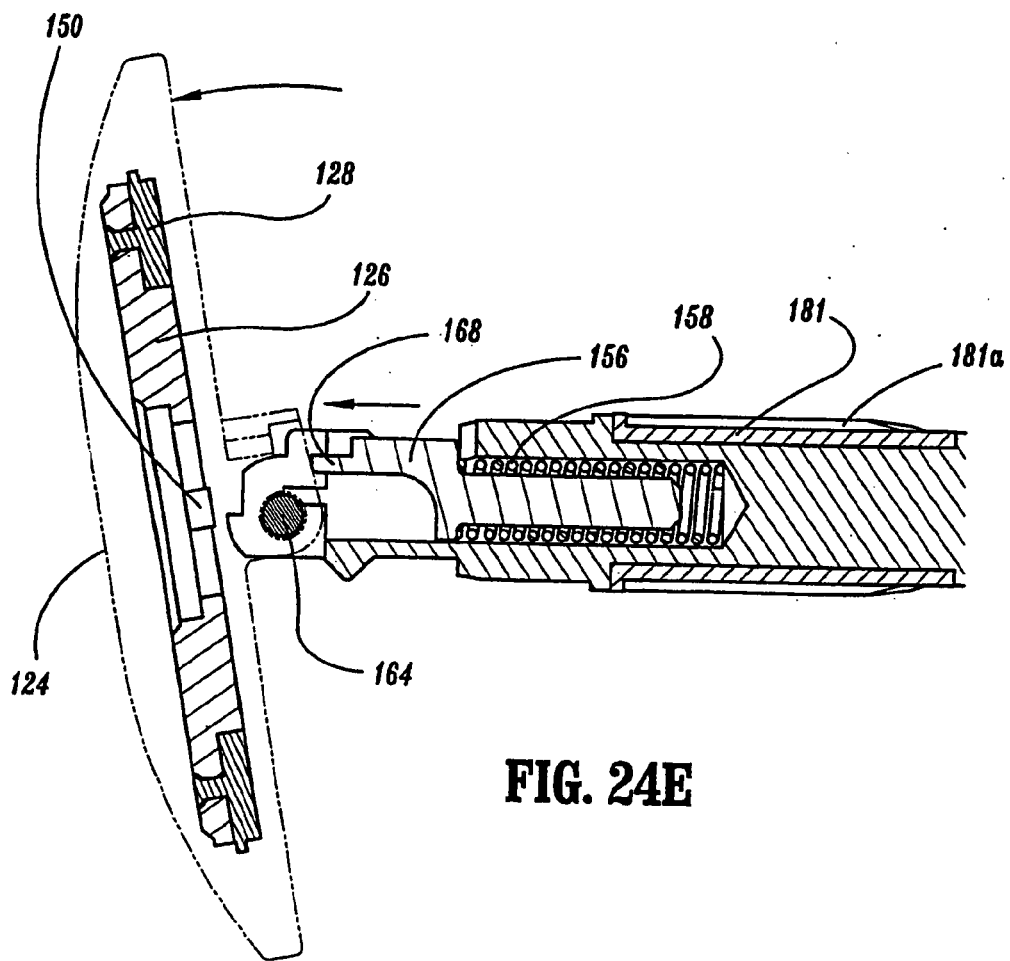
FIG. 24E is a side cross-sectional part phantom view of the distal end of the anvil assembly shown in FIG. 1 with the anvil head partially tilted.
Figure 24F:
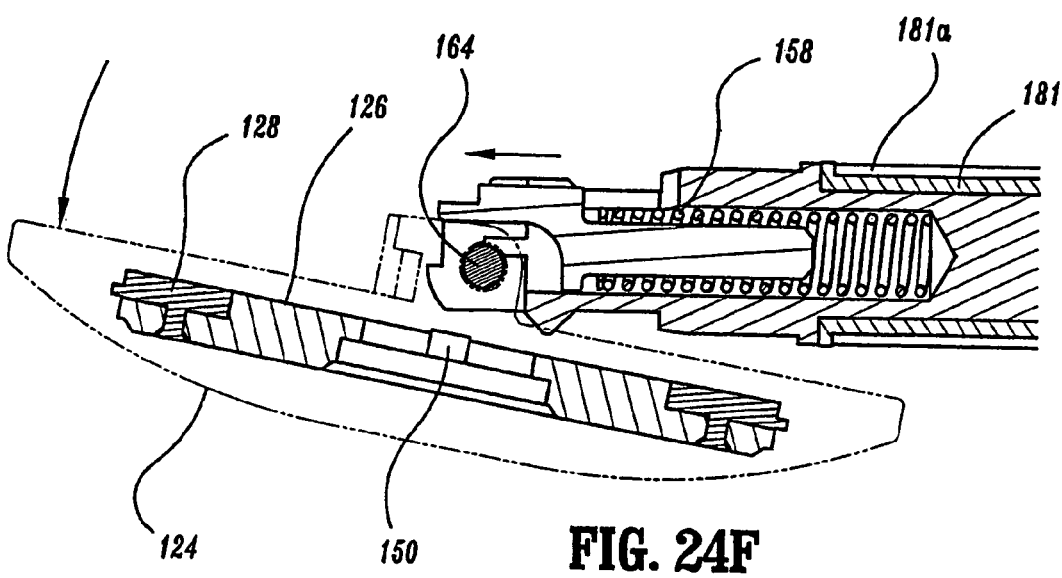
FIG. 24F is a side cross-sectional part phantom view of the distal end of the anvil assembly shown in FIG. 24E with the anvil head in a fully tilted position.

FIGS. 24-24H illustrates surgical stapling device 10 after it has been fired and unapproximated. As illustrated, anvil head 124 has been moved to the pivoted position by plunger 156 (FIGS. 24E and 24F). Screw stop 306 has been advanced from its rearward-most position adjacent safety bracket 520 to its forward-most position adjacent the proximal end of pusher link 74. Retainer slide 506, which is supported on screw stop 306, has moved with screw stop 306 to a forward position. As retainer slide 506 moves forwardly, spring 502 returns indicator plate 500 to its forward-most position and spring 536 returns safety bracket 520 to its forward-most position. As such, indicator plate 500 once again identifies the device as being in a fire not ready condition and safety bracket 520 moves to a position preventing movement of trigger lock 520.

Referring to FIGS. 24G and 24H, as screw stop 306 is moved from its rearward-most position (FIG. 23) to its forward-most position within stationary handle 18, wing 584 of screw stop 306 engages tactile indicator 580 at the point of unapproximation at which anvil head 124 pivots (FIG. 24F). This contact between screw stop 306 and tactile indicator 580 provides a tactile and/or audible indication to a surgeon that the anvil head 124 has tilted and the device can be removed from the patient. It is noted that by providing additional force to approximation knob 22, wing 584 of screw stop 306 will force tactile indicator 580 to return to its retracted position to allow device 10 to be fully unapproximated.

FIGS. 25-29 illustrate another preferred embodiment of the presently disclosed surgical stapling device shown generally as 610. Briefly, surgical stapling device 610 includes aproximal handle portion 612, an elongated central body portion 614 including a curved elongated outer tube 614a, and a distal head portion 616.

Handle portion 612 includes a stationary handle 618, a firing trigger assembly 620, a rotatable approximation knob 622 and an indicator window 624. Stationary handle 618 is preferably formed from thermoplastic handle sections, e.g., polycarbonate, which together define a housing for the internal components of handle portion 612. These internal components will be discussed in detail below. A pivotably mounted trigger lock 626 is fastened to handle portion 612 and is manually positioned to prevent inadvertent firing of stapling device 610. Indicator window 624 defines an opening or translucent surface 628 which facilitates viewing of an internally positioned indicator which identifies a multiplicity of operational positions of the stapling device.

Head portion 616 includes an anvil assembly 630 and a shell assembly 631. Each of these assemblies will be discussed in detail below. Except where otherwise noted, the components of surgical device 610 are formed from thermoplastics including polycarbonates and metals including stainless steel and aluminum. The particular material selected to form a particular component will depend upon the strength requirements of the particular component. For example, the anvil will be formed from a metal, such as stainless steel, and the stationary handle will be formed from a thermoplastic such as polycarbonate. Alternately, other materials not listed above may be used to form components of stapling device 610 provided the materials are suitable for surgical use and meet the strength requirements of the particular component.

Figure 30:
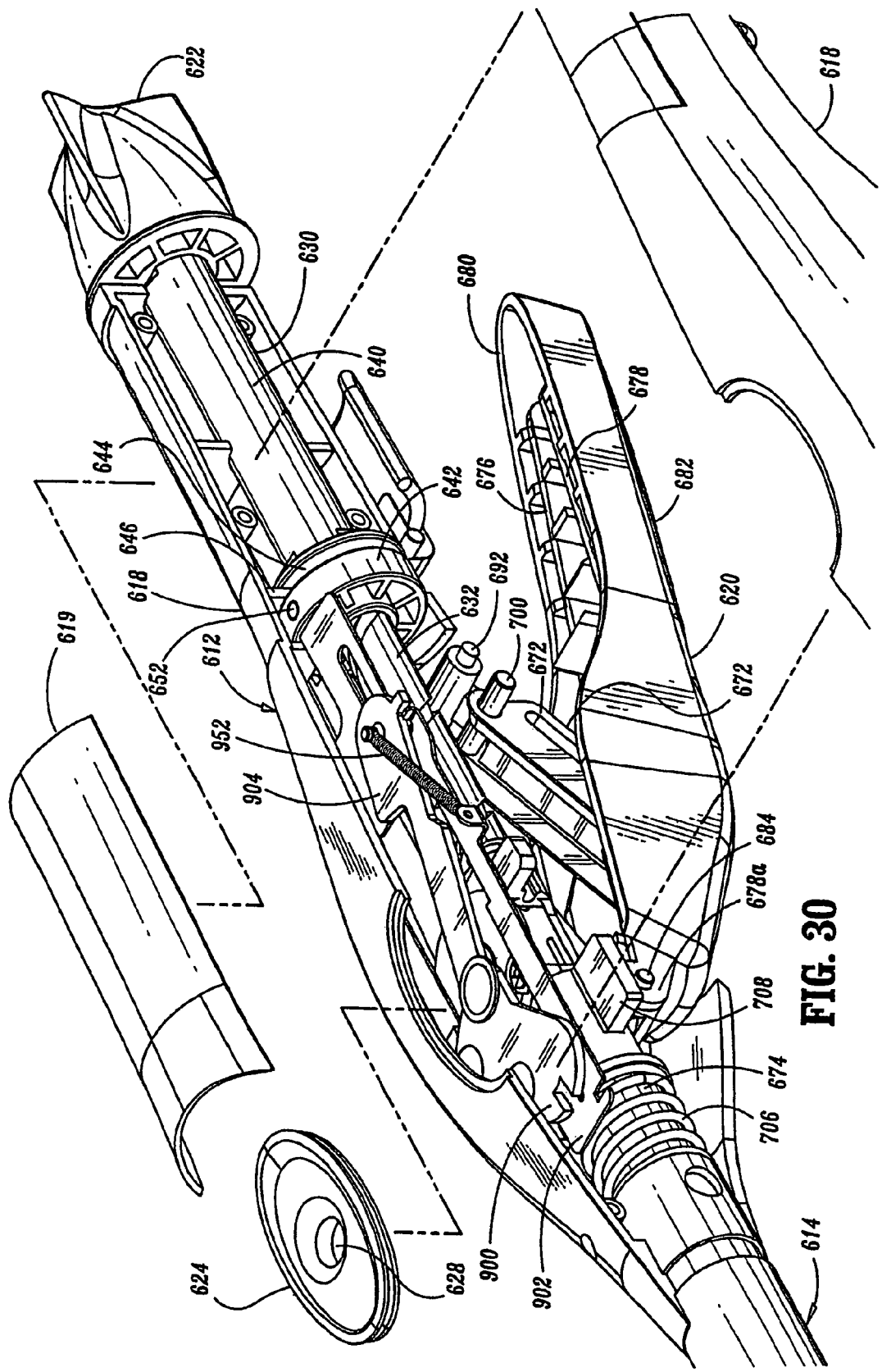
FIG. 30 is a side perspective view of the surgical stapling device shown in FIG. 25 with a section of the stationary handle removed.
Figure 31:
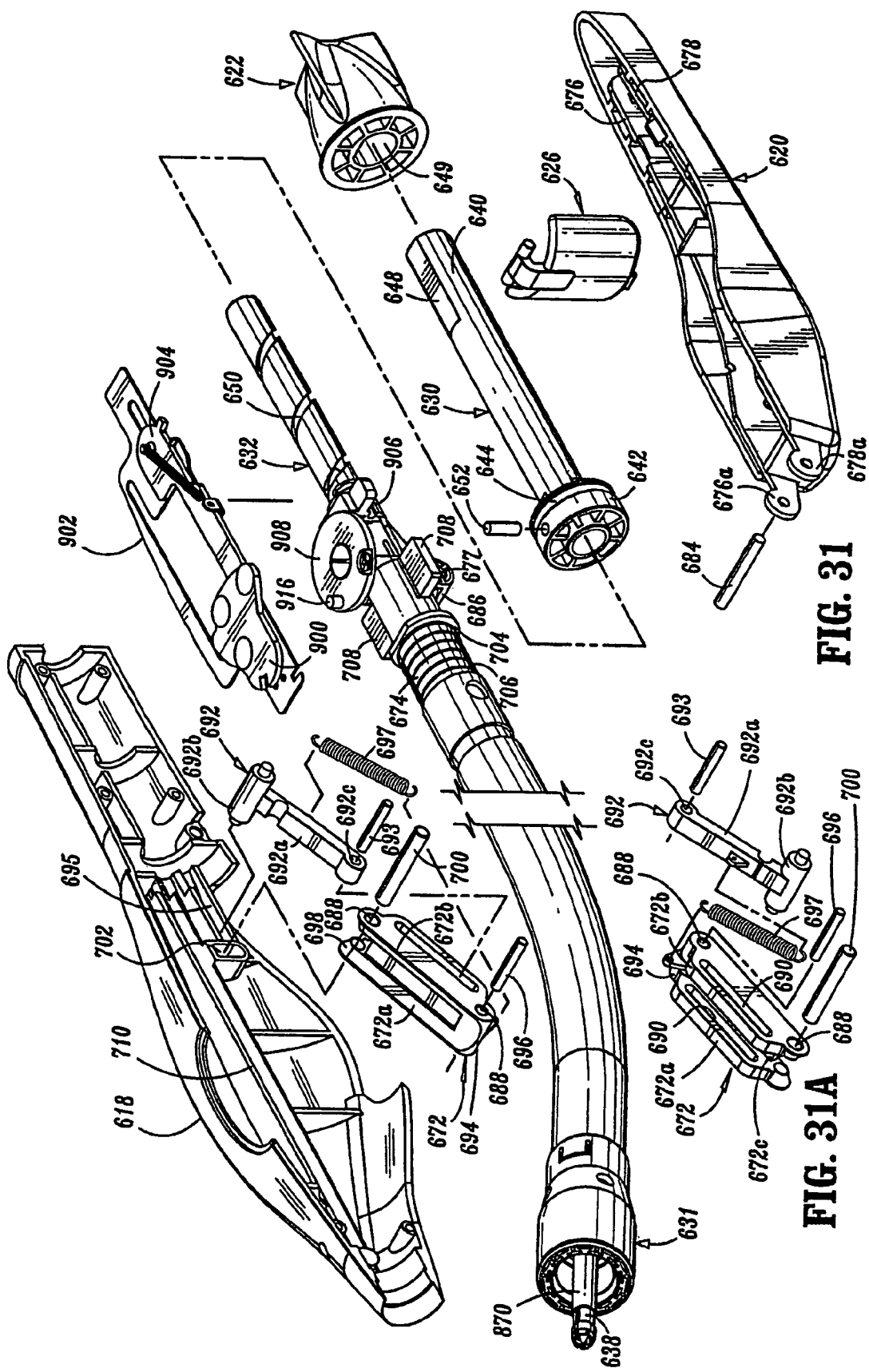
FIG. 31 is a perspective, partial cutaway view of the surgical stapling device shown in FIG. 25 excluding the anvil assembly with the parts of the handle portion separated.
Figure 32:
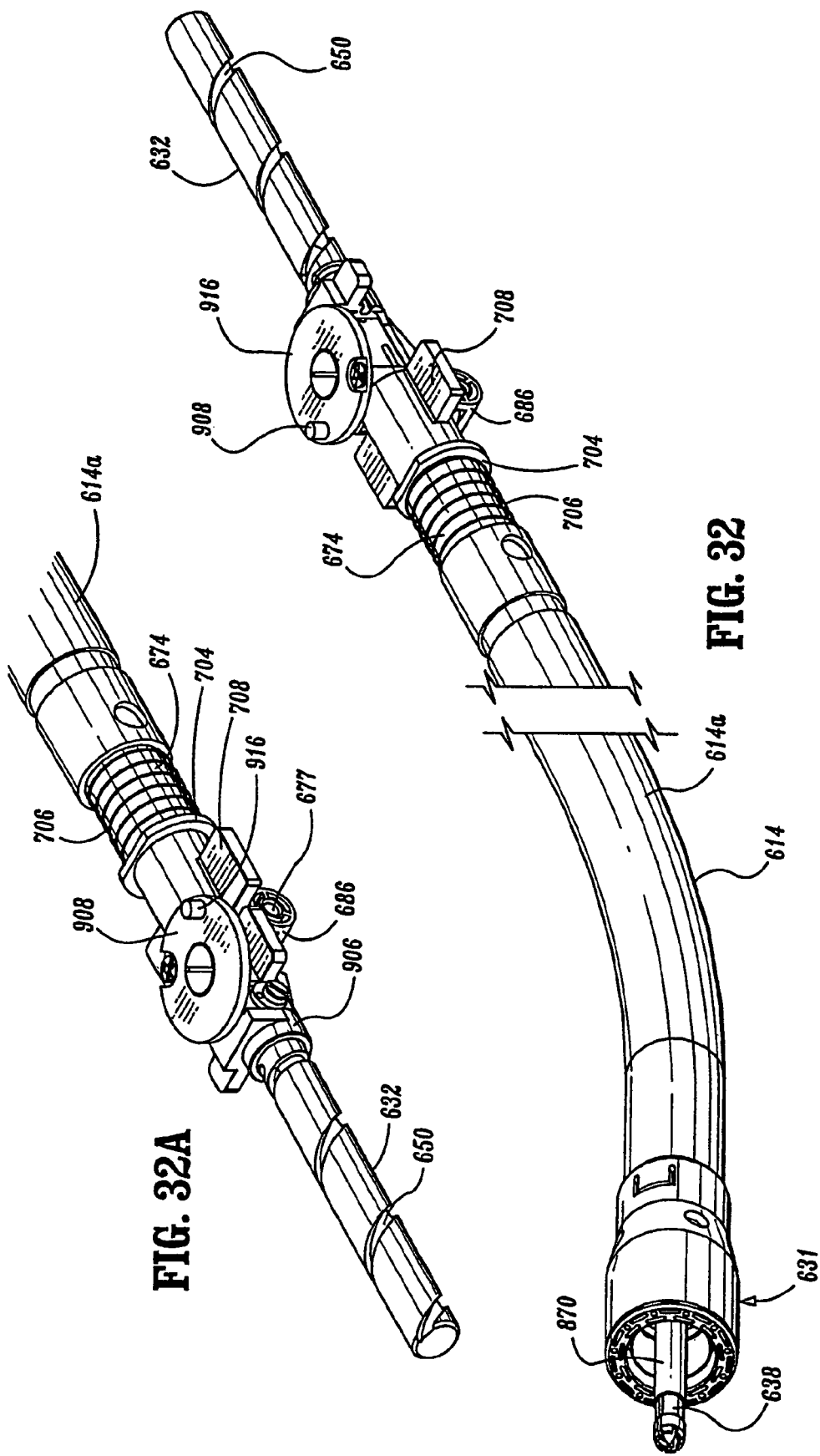
FIG. 32 is a front, perspective, partial cutaway view of the surgical stapling device shown in FIG. 25 with the stationary handle, trigger and indicator assemblies removed.
Figure 33:
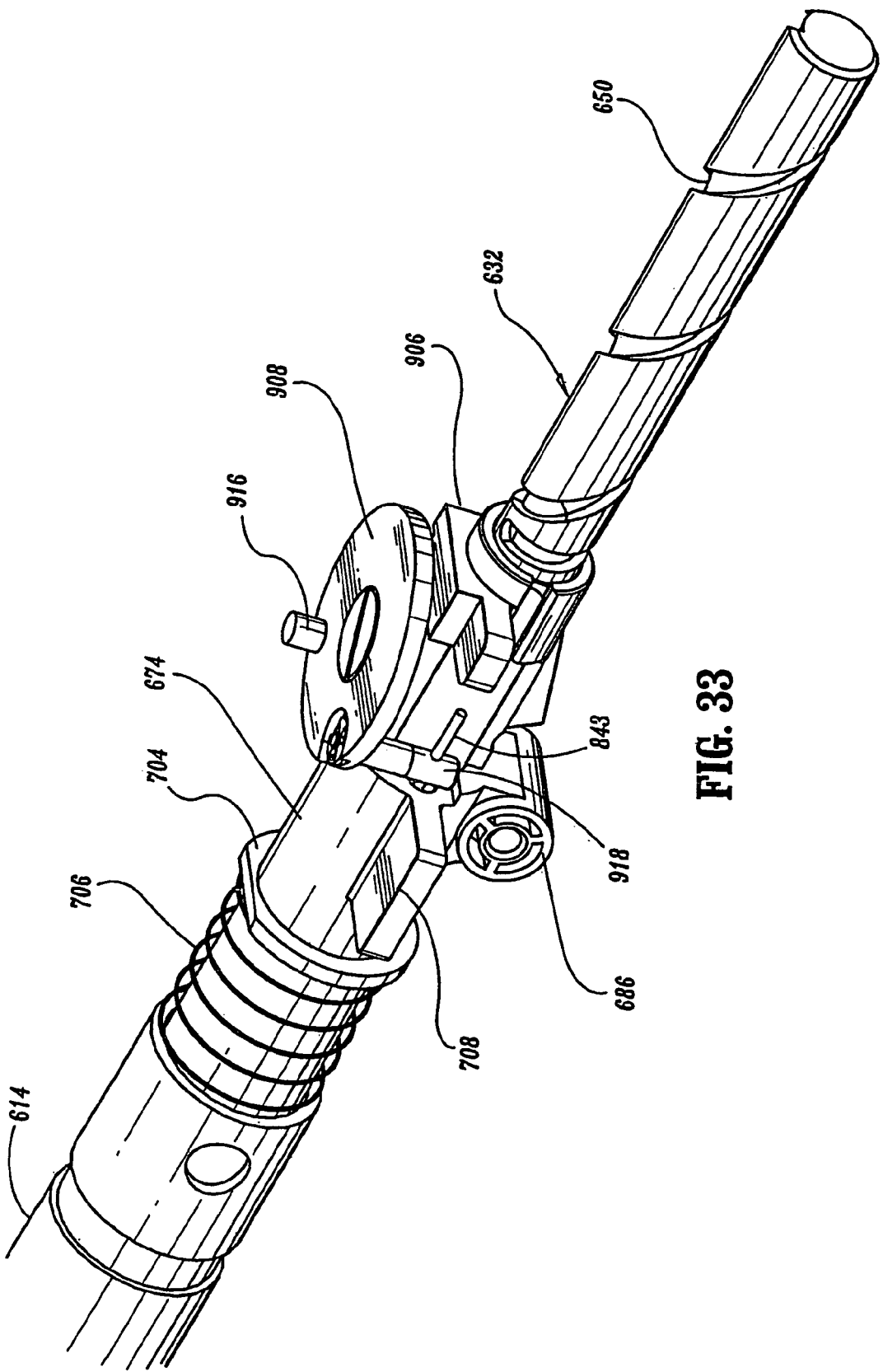
FIG. 33 is an enlarged view of the proximal portion of FIG. 32.

FIG. 30 illustrates handle portion 612 of surgical stapling device 610 with a section of stationary handle 618 removed to expose the internal components of handle portion 612. Handle portion 612 houses an indicator mechanism and the proximal components of an approximation mechanism and a firing mechanism. Each of these mechanisms will be described in detail hereinbelow. A cushion non-slip grip 619 is fastened to stationary handle 612. Grip 619 may be formed from rubber or neoprene and secured to stationary handle 18 using an overmolding process. Alternately, other materials and attachment methods not mentioned here may be used.

Figure 34:
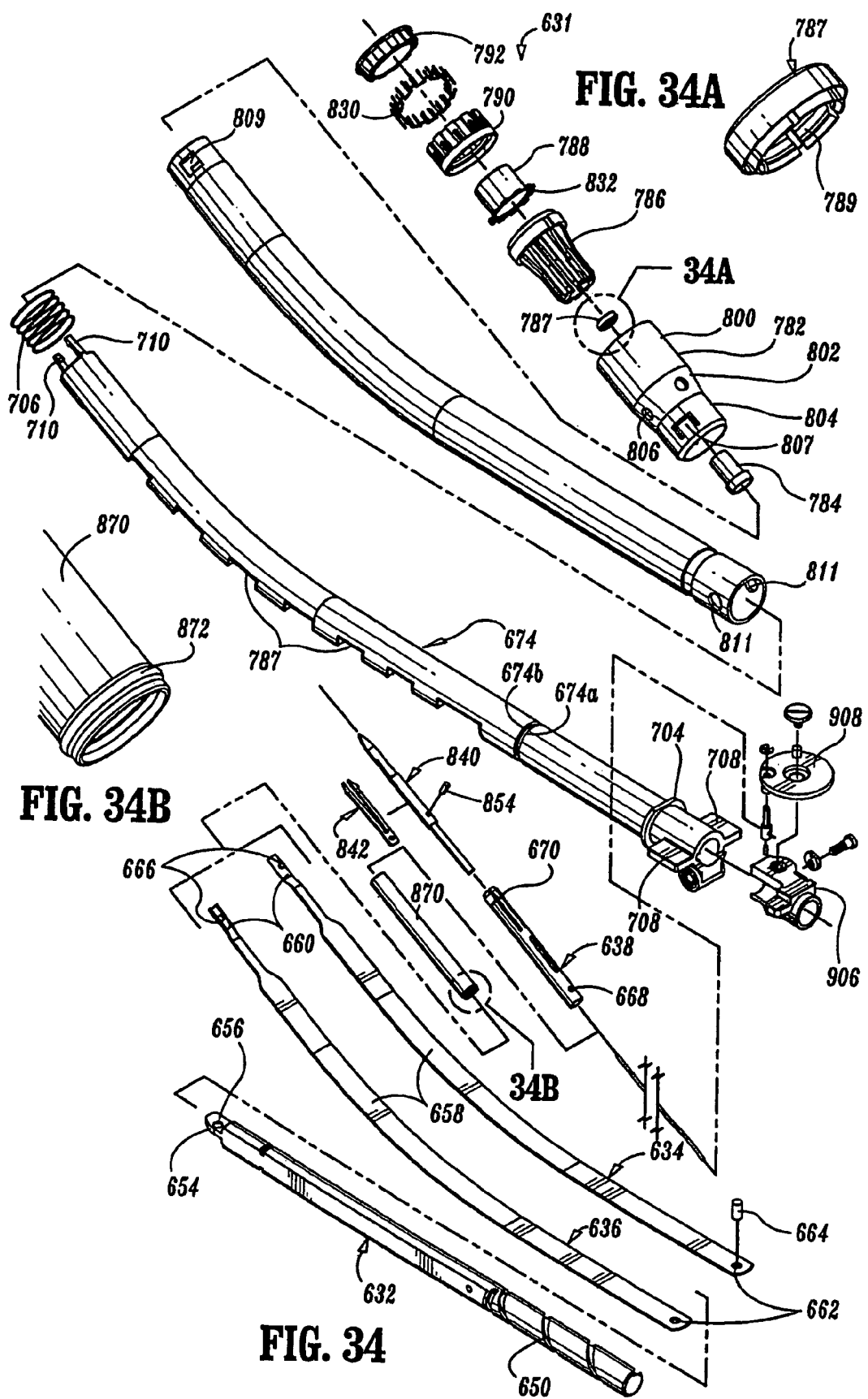
FIG. 34 is a perspective view with parts separated of the elongated body portion and the head portion, excluding the anvil, of the surgical stapling device shown in FIG. 25.
Figure 35:
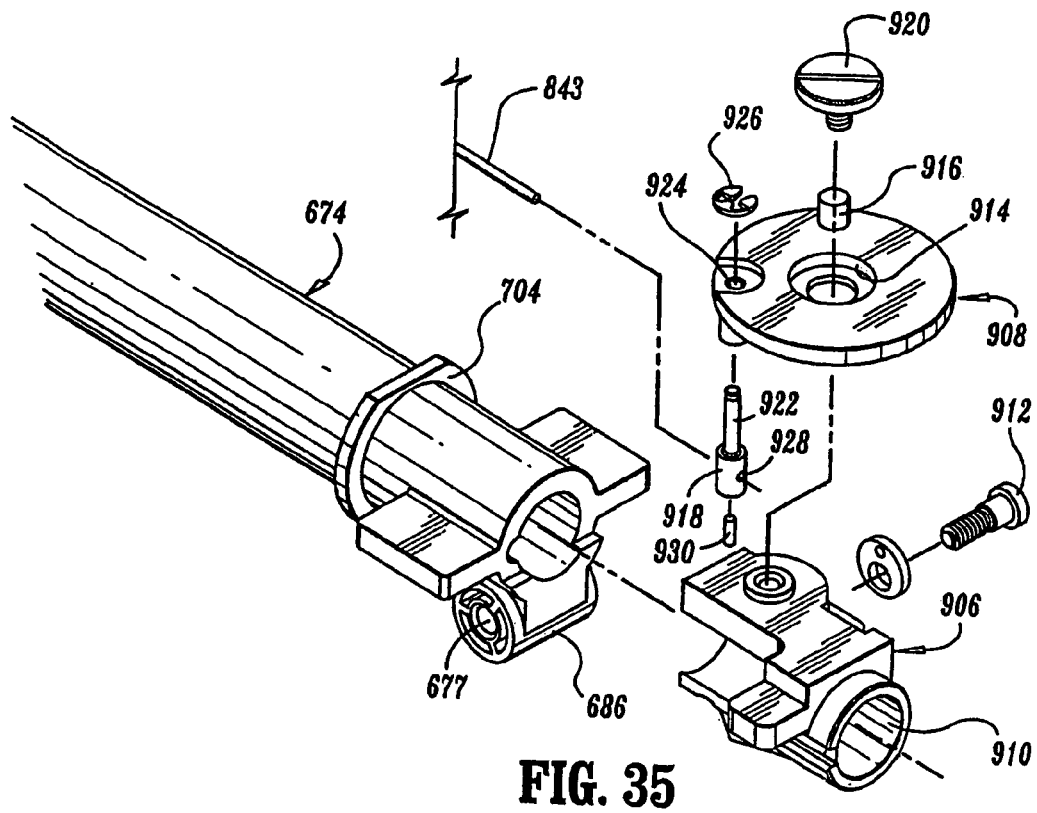
FIG. 35 is a perspective view with parts separated of the proximal end of the pusher link and the indicator connector assembly.
Figure 36:
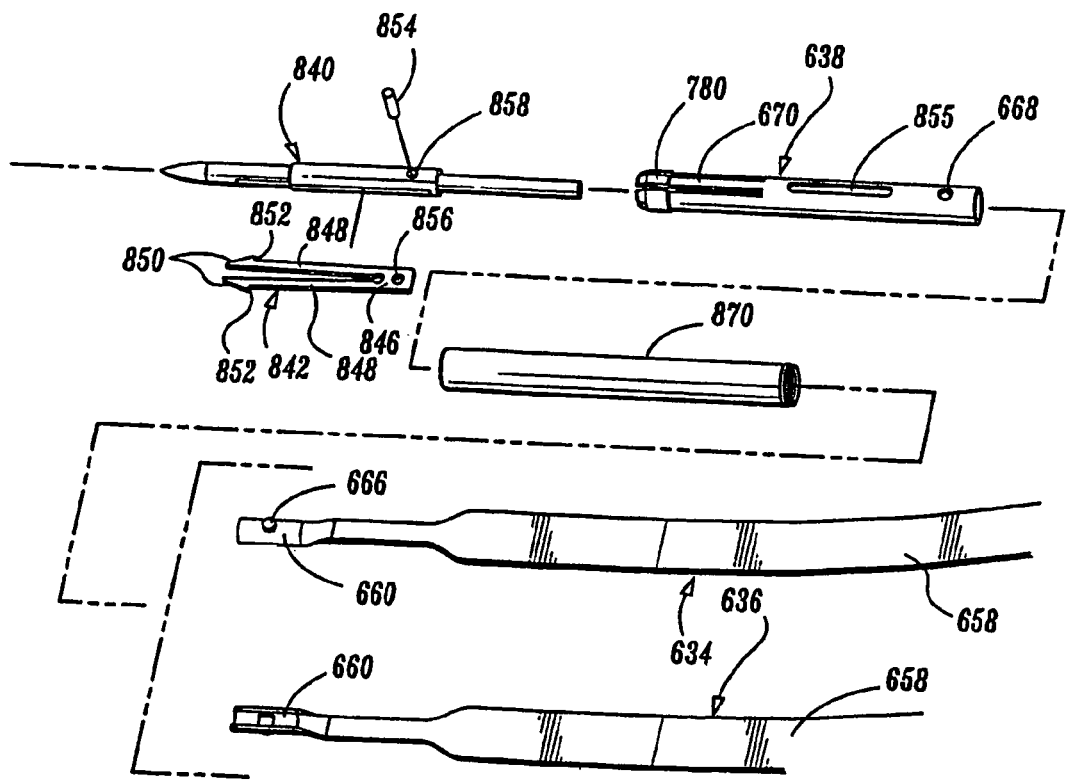
FIG. 36 is a perspective view with parts separated of the distal portion of the approximation mechanism and the retractable trocar assembly of the surgical stapling device shown in FIG. 25.
Figure 37:
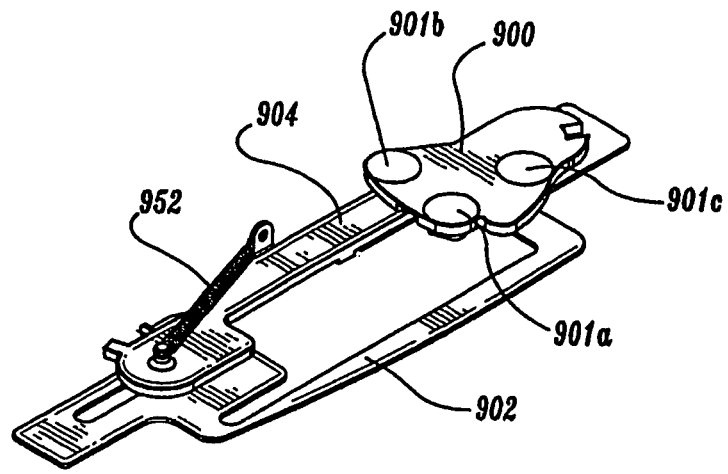
FIG. 37 is a top, perspective view of the indicator assembly of the surgical stapling device shown in FIG. 25.
Figure 38:
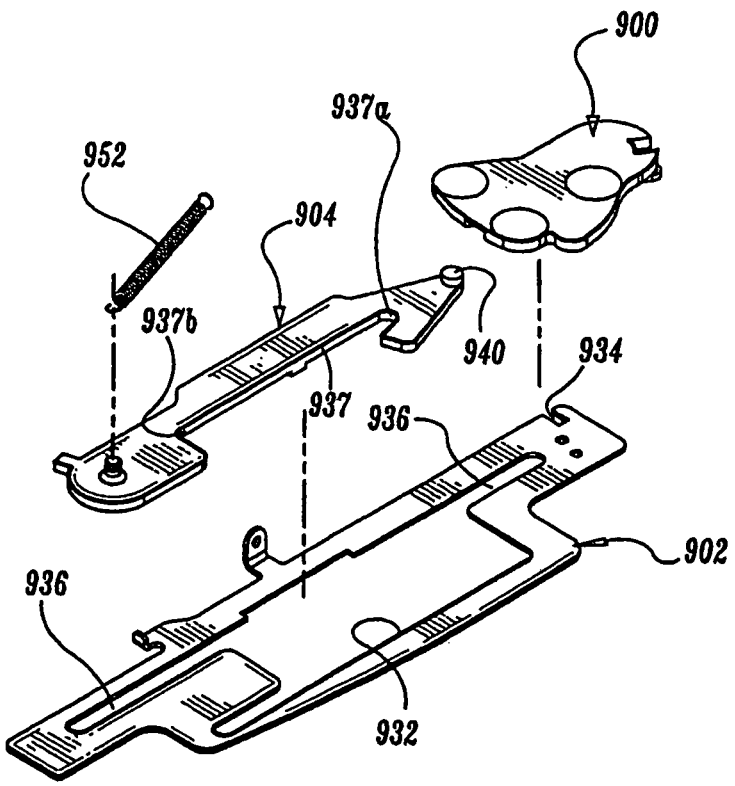
FIG. 38 is a top, perspective view with parts separated of the indicator assembly shown in FIG. 37.
Figure 38A:
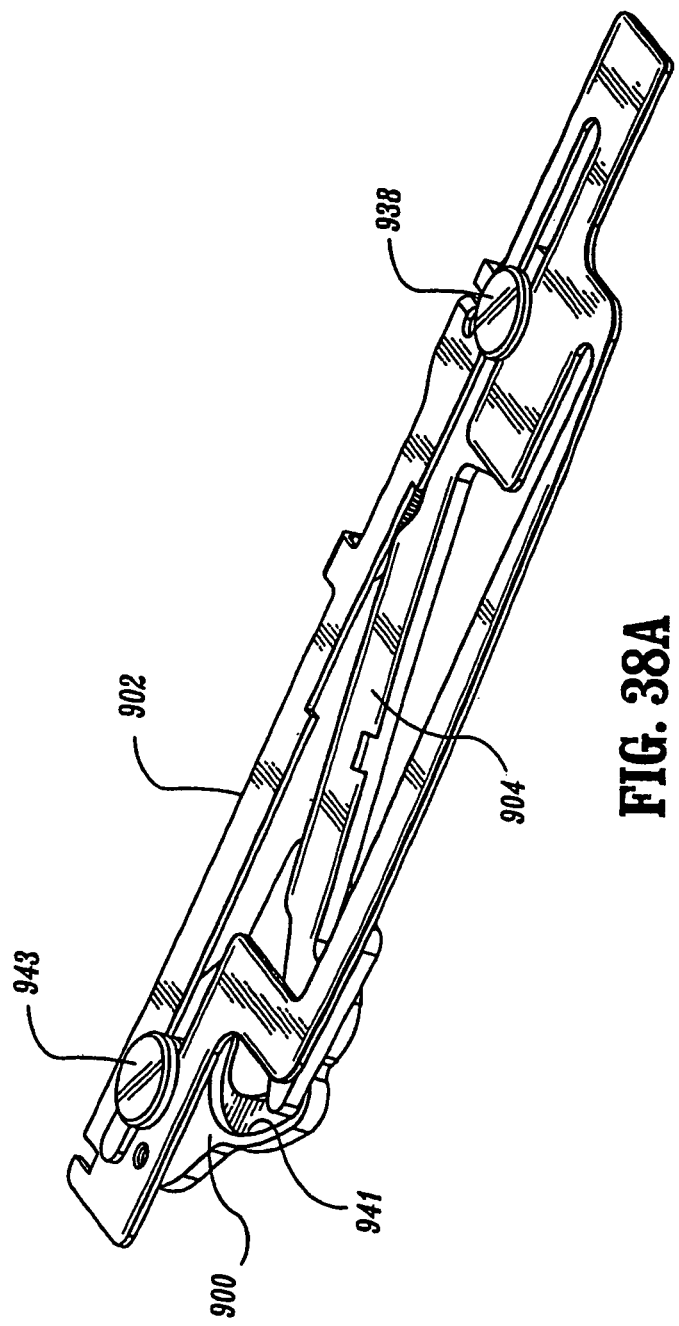
FIG. 38A is a bottom perspective view of the indicator assembly shown in FIG. 37.

Referring to FIGS. 30-36, the approximation mechanism includes approximation knob 622, a rotatable sleeve 633, a screw 632, first and second screw extensions 634 and 636, respectively, and anvil retainer 638 (FIG. 34). Rotatable sleeve 633 includes a small diameter cylindrical hollow body portion 640 and a large diameter hollow body portion 642. Body portion 642 includes an annular groove 644 dimensioned to receive an inwardly extending annular flange 646 formed on an internal wall of stationary handle 618. Engagement between groove 644 and flange 646 axially fixes sleeve 633 within stationary handle 618 while permitting relative rotation. The proximal end of body portion 640 of rotatable sleeve 633 extends through an opening formed in the proximal end of stationary handle 618 and includes a flat surface 648. Approximation knob 622 includes a bore 649 configured to receive the proximal end of sleeve 633 such that rotation of knob 622 effects concurrent rotation of sleeve 633.

Screw 632 is dimensioned to be slidably positioned within rotatable sleeve 633. A helical channel 650 is formed in the proximal end of screw 632. A pin 652 extends radially through body portion 642 of sleeve 633 into helical channel 650. Since sleeve 633 is axially fixed with respect to stationary handle 618, rotation of sleeve 633 about screw 632 causes pin 652 to move along channel 650 of screw 632 to effect axial movement of screw 632 within stationary handle 618.

The distal end of screw 632 includes an extension 654 having upper and lower flat surfaces and a throughbore 656. Top and bottom screw extensions 634 and 636 each include a flexible flat band portion 658 and a distal semi-cylindrical portion 660. The flexibility of top and bottom screw extensions 634 and 636 facilitate movement of screw extensions 634 and 636 through curved elongated body portion 614. The proximal end of each band portion 658 includes an opening 662 dimensioned to receive a pin 664 for securing the proximal end of screw extensions 634 and 636 to extension 654 of screw 632 via throughbore 656. Each semi-cylindrical portion 660 of screw extensions 634 and 636 includes an outwardly extending projection 666. When top and bottom screw extensions 634 and 636 are positioned in juxtaposed alignment, semi-cylindrical portions 660 of screw extensions 634 and 636 together define a cylindrical member which is dimensioned to be received within a proximal end of anvil retainer 638. Projections 666 are dimensioned to be received in openings 668 formed in the proximal end of anvil retainer 638 to fasten anvil retainer 638 to the distal end of screw extensions 634 and 636. The distal end of anvil retainer 638 includes a plurality of flexible legs 670 which are configured to flex outwardly to receive and engage the anvil assembly as will be discussed in further detail below.

In operation, when approximation knob 622 is manually rotated, rotatable sleeve 633 is rotated about the proximal end of screw 632 to move pin 652 along channel 650 of screw 632. Since sleeve 630 is axially fixed to stationary handle 618, as pin 652 is moved through channel 650, screw 632 is advanced or retracted within stationary handle 618. As a result, top and bottom screw extensions 634 and 636, which are fastened to the distal end of screw 632, and anvil retainer 638, which is fastened to the distal end of screw extensions 634 and 636, are moved axially within elongated body portion 614. Since anvil assembly 630 is secured to the distal end of anvil retainer 638, rotation of approximation knob 622 will effect movement of anvil assembly 630 in relation to shell assembly 631 between spaced and approximated positions.

Figure 39:
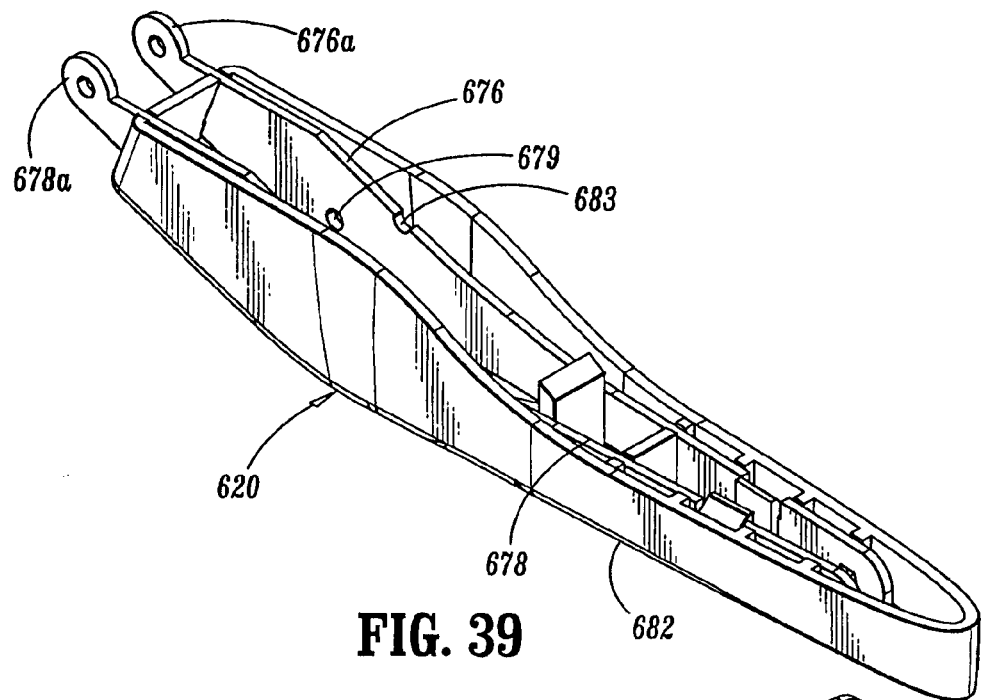
FIG. 39 is a perspective view of the trigger assembly of the surgical stapling device shown in FIG. 25.
Figure 40:
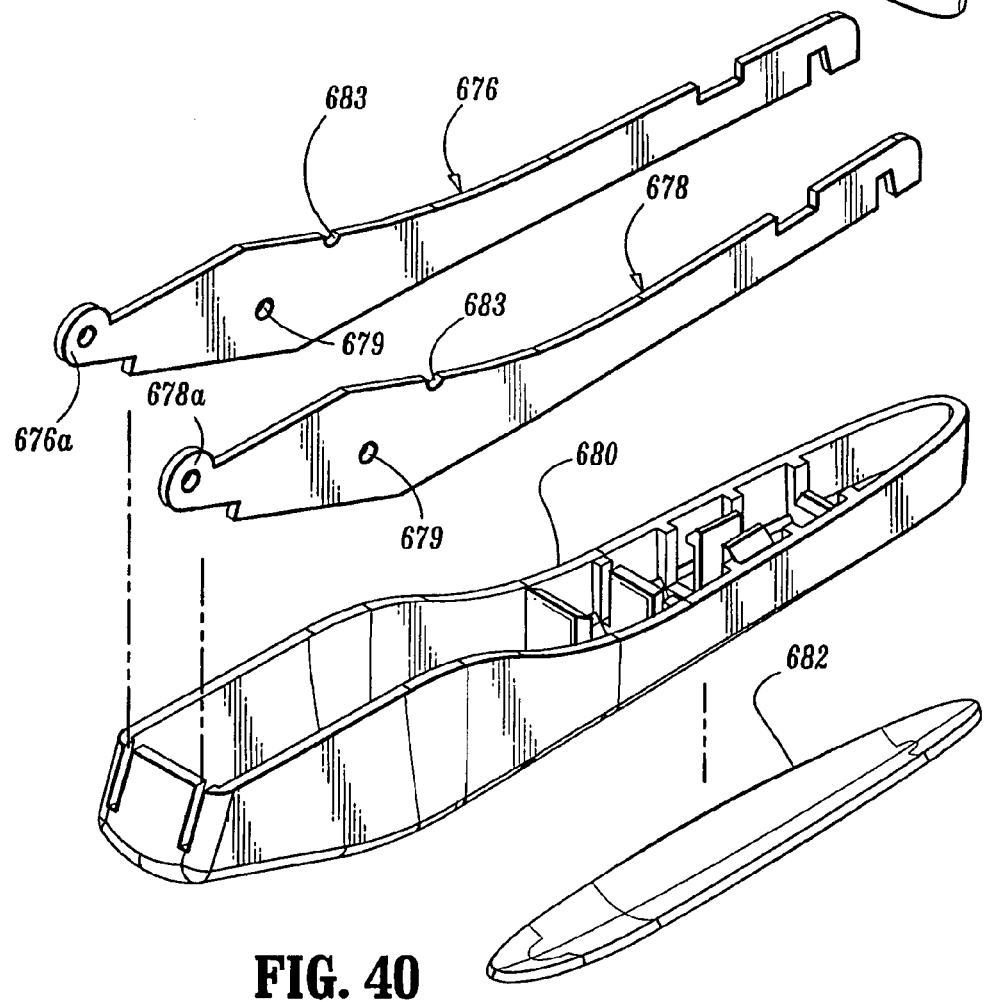
FIG. 40 is a perspective view with parts separated of the trigger assembly shown in FIG. 39.
Figure 41:
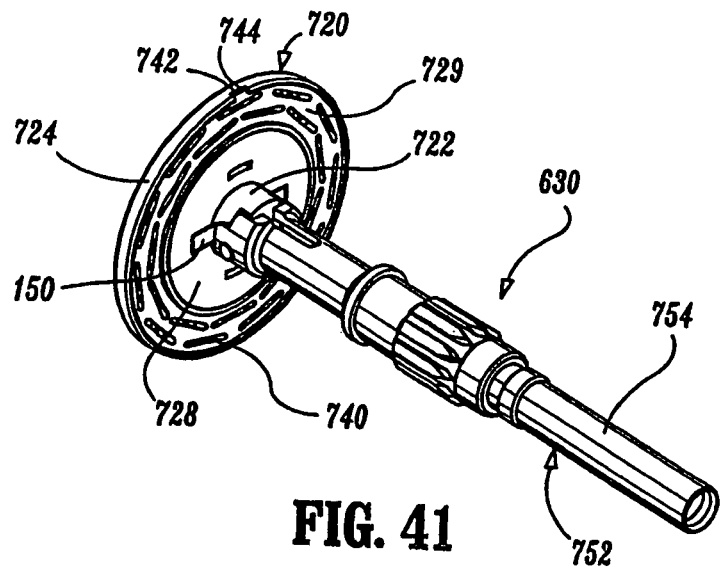
FIG. 41 is a rear, perspective view of the anvil assembly of the surgical stapling device shown in FIG. 25.
Figure 42:
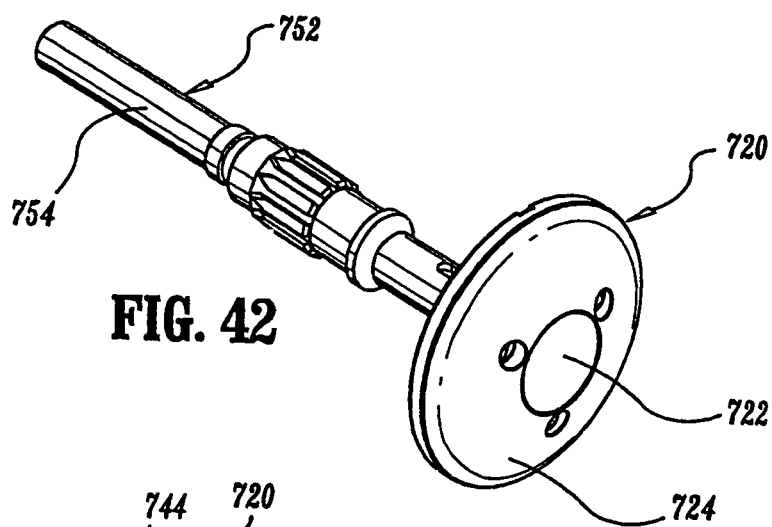
FIG. 42 is a front, perspective view of the anvil assembly shown in FIG. 41.
Figure 43:
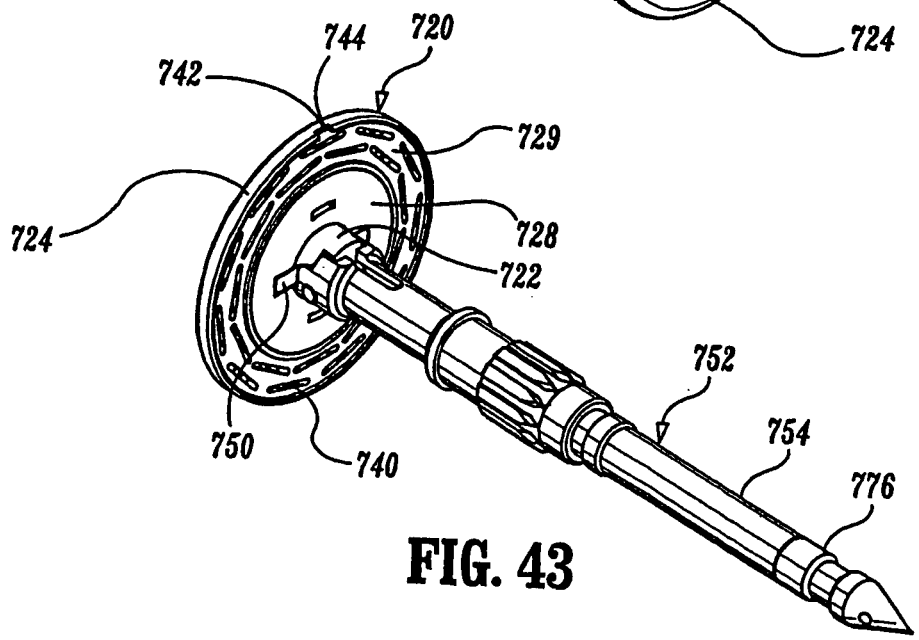
Figure 44:
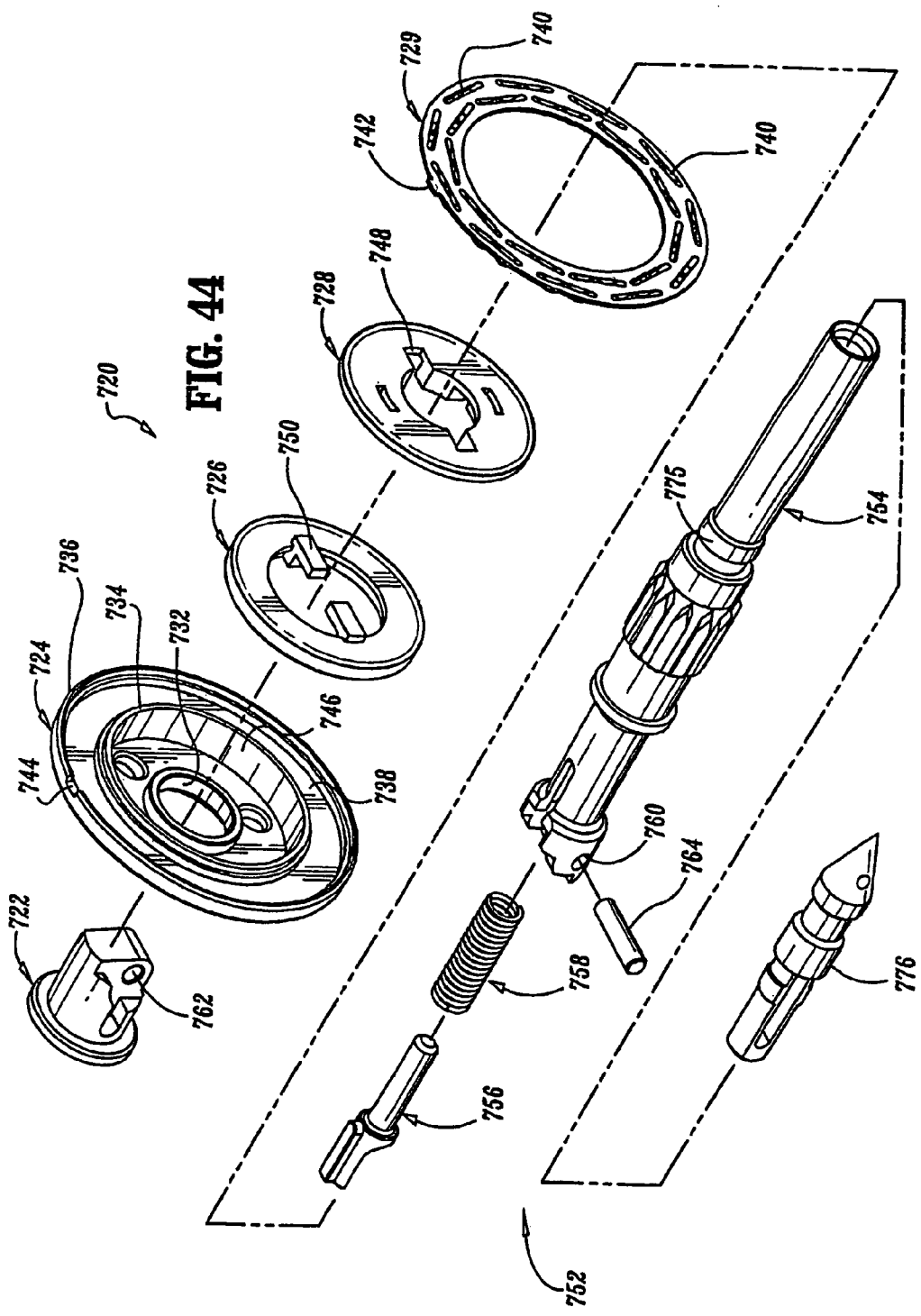

Referring again to FIGS. 30-35, the firing mechanism includes firing trigger 620, a firing link 672, and an elongated pusher link 674. Firing trigger 620 includes a pair of trigger plates 676 and 678, a trigger cover 680, and a cushioned gripping member 682. See also FIGS. 39 and 40. Gripping member 682 is preferably formed from rubber or neoprene and overmolded onto trigger cover 680. Alternately, other cushioned non-slip gripping materials may be used and fastened to trigger cover using any known technique, e.g., adhesives. The distal end of each of trigger plates 676 and 678 includes a hinge portion 676a and 678a, respectively, having a hole for receiving a pivot member 684. Pivot member 684 is dimensioned to extend between hinge portions 676a and 676b through a bore 677 formed in a connector 686 secured to the proximal end of pusher link 674 to pivotably secure the distal end of firing trigger 620 to the proximal end of pusher link 674. Alternately, connector 686 may be formed integrally with pusher link 674. The top surface of each trigger plate 676 and 678 includes a notch 683 dimensioned to receive a locking pin 693 to prevent inadvertent firing of device 610.

Firing link 672 includes a right-side link portion 672a and a left-side link portion 672b interconnected by a spacer 672c (FIG. 31A). Each link portion includes a pivot opening 688 at each end thereof and a centrally positioned elongated slot 690. The space between link portions 672a and 672b is dimensioned to receive a safety link 692. The function and operation of safety link 692 will be described in detail below. One end 694 of firing link 672 is pivotably connected between openings 679 (FIG. 40) in trigger plates 676 and 678 about pivot member 696. The other end 698 of firing link 672 is pivotably connected to stationary handle 618 about pivot member 700. Pivot member 700 is supported in a vertically oriented pocket 702 (only one is shown) formed along the internal wall of stationary handle 618. Pivot members 696 and 700 may be formed as pins, integral nubs formed on firing link 672, or any other structure which provides the desired function.

Safety link 692 includes a body portion 692a having a guide member 692b formed at one end thereof and a bore 692c formed at an opposite end thereof. Bore 692c is dimensioned to receive a locking pin 693. Safety link 692 is positioned between right-side link portion 672a and left-side link portion 672b of firing link 672. Locking pin 693 is slidably positioned in slots 690 of firing link 672 and guide member 692b is slidably positioned in a horizontal slot 695 formed along the internal wall of stationary handle 618. A biasing member, e.g., coil spring 697, is secured between end 694 of firing link 672 and a central portion of safety link 692 to bias safety link 692 towards end 694 of firing link 672. Body portion 692a of firing link includes a weakened portion 699. The purpose of weakened portion 699 will be discussed in detail below.

Elongated pusher link 674 includes a flange 704 positioned about its proximal end distally of connector 686. A spring 706, positioned between a forward end of stationary handle 618 and flange 704, biases pusher link 674 to a retracted, non-fired position. A pair of wings 708 extend radially outwardly from the proximal end of pusher link 674. Wings 708 are dimensioned to slide along slots 710 formed along the internal walls of stationary handle 618 to maintain proper alignment of pusher link 674 within stationary handle 618 during firing of device 610. The distal end of pusher link 674 includes a pair of flexible arms 710 which are dimensioned to extend through slots 820 (FIG. 50) formed in the proximal end of pusher back 786. Pusher back 786 forms part of shell assembly 631 and will be discussed in greater detail below. Pusher link 674 is preferably formed from a flexible plastic material and includes a plurality of notches 787 which allow the pusher link to bend more easily as it moves through body 614. An annular channel 674a is formed about pusher link 674 to receive an o-ring seal 674b. Operation of the firing mechanism of the device will be described in detail below.

As discussed above, head portion 616 includes anvil assembly 630 and shell assembly 631. Referring to FIGS. 41-46, anvil assembly 630 includes an anvil head assembly 720 and an anvil center rod assembly 752. Anvil head assembly 720 includes a post 722, an anvil head 724, a backup plate 726, a cutting ring 728 and an anvil 729. Anvil head 724 includes a central hole 732 dimensioned to receive post 722, an inner annular ring 734, and an outer annular ring 736. Anvil 729 is supported on anvil head 724 in an annular channel 738 defined between annular rings 734 and 736. Anvil 729 includes a plurality of pockets 740 for receiving and deforming staples. A tab 742 formed on anvil 729 is dimensioned to be received in a slot 744 formed in anvil head 724 to maintain proper alignment of anvil 729 and anvil head 724. Cutting ring 724 and backup plate 726 each include a central opening and are positioned about post 722 in stacked relation in an annular channel 746 defined between central hole 732 and annular ring 734. Preferably, cutting ring 724 is formed from polyethylene and is fixedly secured to backup plate 726 using, for example, adhesives. Cutting ring 724 includes a pair of diametrically opposed slots 748 dimensioned to receive tabs 750 formed on backup plate 726. The cutting ring 726 and backup plate 748 assembly is slidably mounted about post 722.

Figure 45:
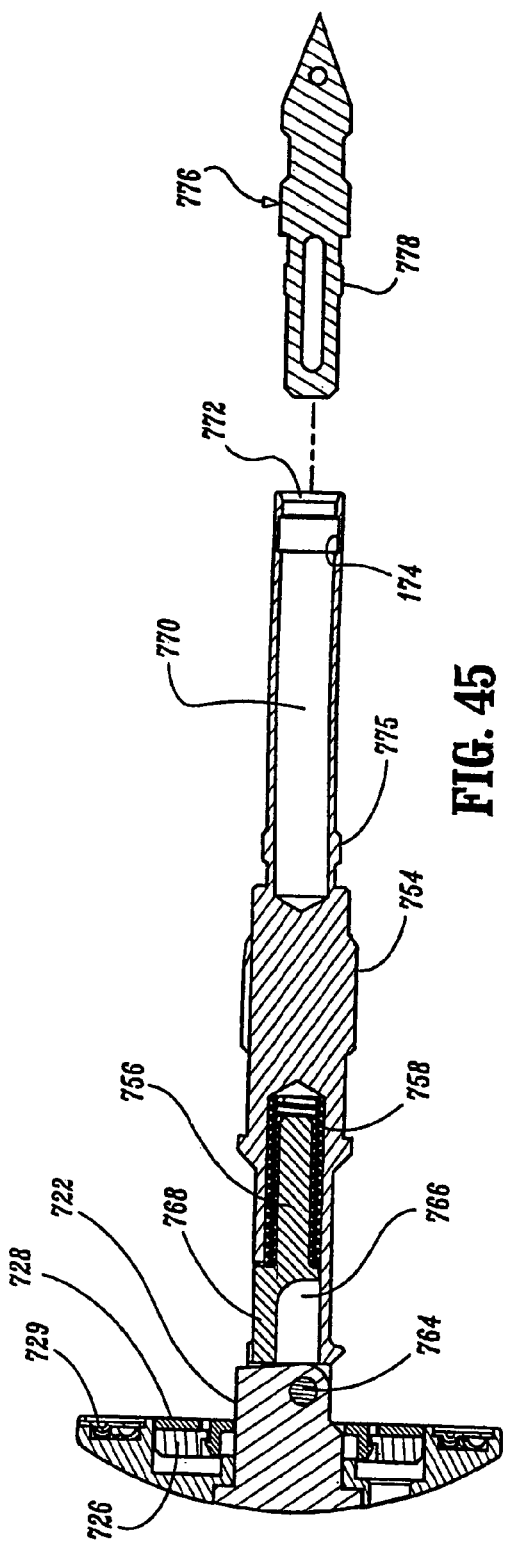
Figure 46:
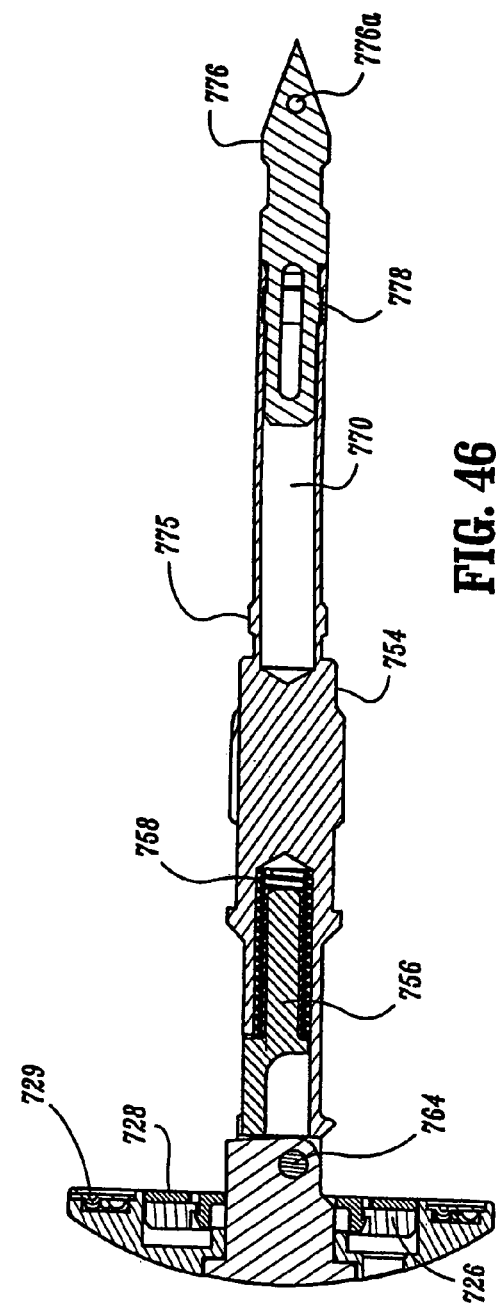

Anvil center rod assembly 752 includes anvil center rod 754, a plunger 756 and plunger spring 758. A first end of center rod 754 includes a transverse throughbore 760 (FIG. 44) which is spaced radially of a central longitudinal axis of center rod 754. Post 722 of anvil head assembly 720 also includes a transverse throughbore 762. A pivot member 764 pivotably secures post 722 to center rod 754 such that anvil head assembly 720 is pivotably mounted to anvil center rod assembly 752. As best seen in FIGS. 45 and 46, plunger 756 is slidably positioned in a bore 766 formed in the first end of center rod 754. Plunger 756 includes an engagement finger 768 which is offset from the pivot axis of anvil head assembly 720 and biased into engagement with the base of post 722 by plunger spring 758 to urge anvil head assembly 720 to a pivoted position. In a prefired position, tabs 750 formed on backup plate 726 engage a top surface 754a of center rod 754 to prevent anvil head assembly 720 from pivoting (see FIGS. 63 and 64). As device 610 is being fired, backup plate 726 and cutting ring 728 are moved deeper into anvil head 724 about post 722 by knife 788 to move tabs 750 out of engagement with top surface 754a of center rod 754 to permit plunger 756 to pivot anvil head assembly 720 about pivot member 764. See FIGS. 66-68. As illustrated in FIG. 68, the upper end of 754b of center rod 754 is angled to further accommodate a tissue specimen. It is noted that after the device has been fired, the anvil will only move to the tilted position after the anvil assembly and the shell assembly have been unapproximated a predetermined distance.

A second end of center rod 754 includes a blind bore 770 (FIGS. 45 and 46). Blind bore 770 includes an inwardly tapering opening 772 and a spaced annular recess 774. Blind bore 770 is dimensioned to receive a removable trocar 776. Annular recess 774 is positioned within blind bore 770 and dimensioned to receive annular rib 778 formed on trocar 776 to secure center rod 754 in engagement with trocar 776. The outer surface of center rod 754 also includes an annular abutment 775. Annular abutment 775 is dimensioned to be received within an annular recess 777 (FIG. 50) formed in the distal end of anvil retainer 638 to retain anvil assembly 630 within anvil retainer 638.

Figure 50:
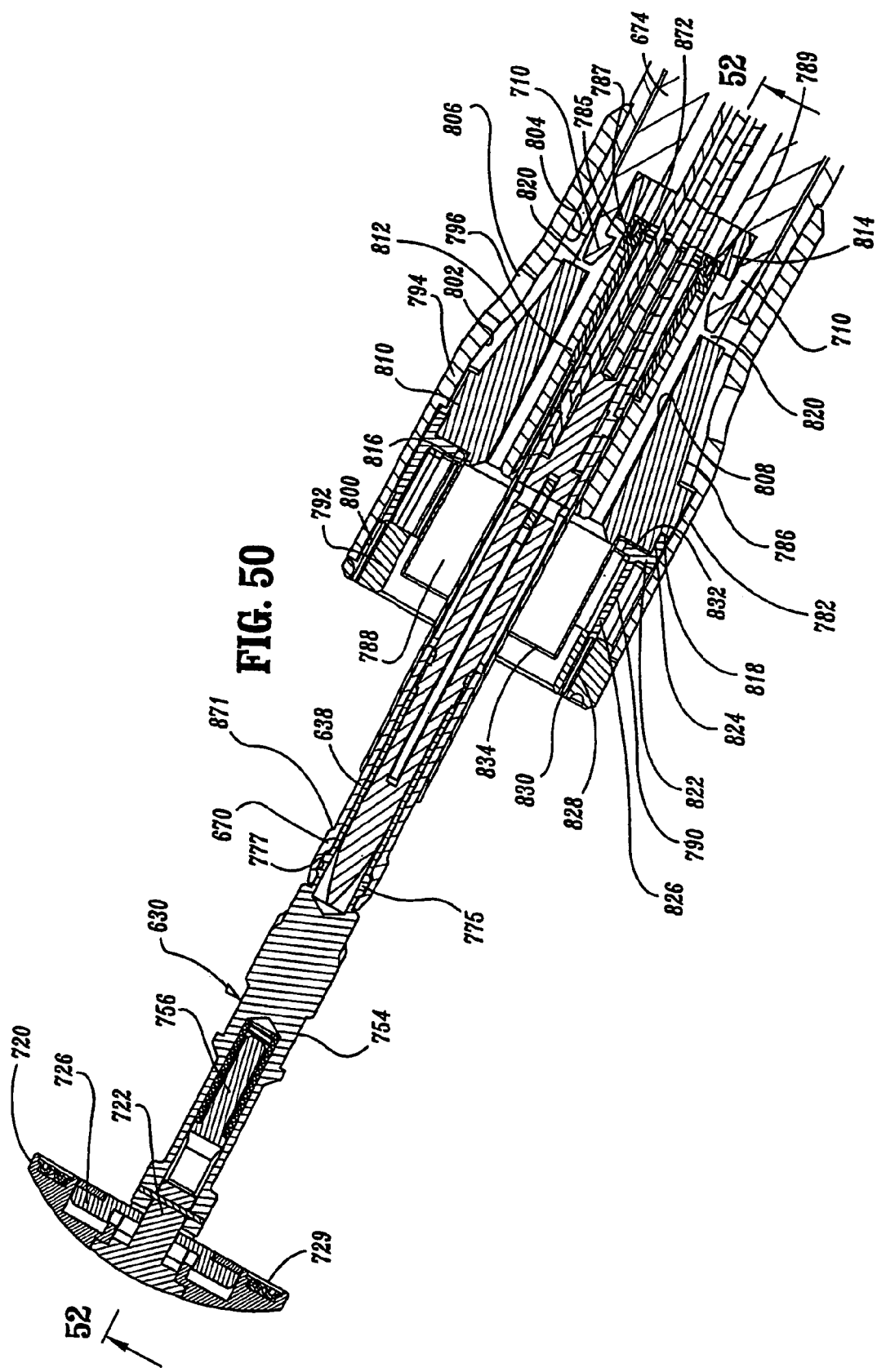

Referring to FIGS. 34 and 50, shell assembly 631 includes a shell 782, a sleeve 784, a pusher back 786, a cylindrical knife 788, a pusher 790 and a staple guide 792. Shell 782 includes an outer housing portion 794 and an inner guide portion 796. Sleeve 784 is fixedly positioned within inner guide portion 796 of shell 782 and defines a stepped bore 785. A locking member 787 having a detent 789 (FIG. 34A) is retained within the stepped bore 785. Outer housing portion 794 defines a throughbore 798 having a distal cylindrical section 800, a central conical section 802 and a proximal smaller diameter cylindrical section 804. A plurality of openings 806 are formed in conical section 802. Openings 806 are dimensioned to permit fluid and tissue passage during operation of the device. A pair of diametrically opposed flexible engagement members 807 are formed on proximal cylindrical section 804 of shell 782. Engagement members 807 are positioned to be received in openings 809 formed on the distal end of elongated body 614 to secure shell 782 to elongated body 614. A pair of openings 811 are formed in the proximal end of outer tube 614a. Openings 811 are dimensioned to receive protrusions (not shown) formed on the internal wall of stationary handle 618 to facilitate attachment of tube 614a to handle portion 612.

Pusher back 786 includes a central throughbore 808 which is slidably positioned about inner guide portion 796 of shell 782. Pusher back 786 includes a distal cylindrical section 810 which is slidably positioned within distal cylindrical section 800 of shell 782, a central conical section 812 and a proximal smaller diameter cylindrical section 814. A distal face of pusher back 786 includes an inner annular shoulder 816 and an outer annular recess 818. The proximal end of pusher back 786 includes a pair of slots 820 configured to receive flexible arms 710 of pusher link 674 to fasten pusher link 674 to pusher back 786 such that a distal face of pusher link 674 abuts a proximal face of pusher back 786 (see FIG. 53).

Pusher 790 includes a body 822 having a proximally extending ring 824 and a multiplicity of distally extending fingers 826 dimensioned to be slidably received within slots 828 formed in staple guide 792 to eject staples 830 therefrom. Ring 824 is dimensioned to be received within annular recess 818 formed in the distal face of pusher back 786 to fasten pusher 790 to pusher back 786. Cylindrical knife 788 includes a plurality of radially extending tabs 832 formed about its proximal end and is positioned within annular shoulder 816 of backing 786 with tabs 832 positioned between the distal face of pusher back 786 and body 822 of pusher 790 to fixedly secure knife 788 in relation to pusher 790. The distal end of knife 788 includes a circular cutting edge 834.

In operation, when pusher link 674 is advanced distally in response to actuation of firing trigger 620, as will be described below, pusher back 786 is advanced distally within shell 782. Advancement of pusher back 786 effects advancement of pusher 790 and knife 788. As pusher 790 is advanced, fingers 826 engage staples 830 positioned within slots 828 in staple guide 792 to eject staples 830 from staple guide 192.

Referring to FIGS. 34, 36, 51 and 52, stapling device 610 includes a retractable trocar assembly slidably positioned within anvil retainer 638. The retractable trocar assembly includes a trocar 840 and a engagement member 842. Engagement member 842 may be in the form of a spring clip, as shown. Alternately, other engagement members are envisioned, e.g., spring loaded protrusions, etc. Trocar 840 includes a slot 844 which extends through the body of trocar 840 along a portion of its length. Slot 844 is dimensioned to receive engagement member 842. Engagement member 842 includes a proximal body portion 846 and a pair of distally extending resilient legs 848. Each leg 848 includes a tapered tip 850 and a proximally facing shoulder 852. A pin 854 is positioned through openings 856 and 858 formed in body portion 846 of member 842 and trocar 840, respectively, to secure engagement member 842 within slot 844 of trocar 840. Pin 854 also extends through an elongated slot 855 formed in anvil retainer 638, such that the distal and proximal surfaces of slot 855 function as stops to define the fully advanced and fully retracted positions of the retractable anvil assembly. Legs 848 are formed of a resilient material such as spring steel. In an unbiased position, legs 848 of member 842 extend outwardly of trocar 840 and anvil retainer 638 such that in the fully advanced position of trocar 840, shoulders 852 of legs 848 engage a distal end of anvil retainer 638 to retain the trocar 840 in the advanced position. See FIG. 51.

Referring to FIG. 53, when the anvil assembly 630 is attached to anvil retainer 638, anvil center rod 754 of anvil assembly 630 is slid over tapered tips 852 of legs 848 to compress legs 848 inwardly in the direction indicated by arrow "A" such that trocar 840 and member 842 move inside blind bore 770 of center rod 754. When the tip of trocar 840 engages the bottom of bore 770, further movement of center rod 754 towards anvil retainer 638 in the direction indicated by arrow "B" causes the trocar assembly to move to the retracted position within anvil retainer 638.

Referring to FIG. 53A, when the anvil assembly is disengaged from anvil retainer 638 by pulling the anvil assembly in the direction indicated by arrow "C", legs 848 flex outwardly to move shoulders 852 of legs 848 of member 842 into annular recess 774 of center rod 754. As a result, as anvil assembly 630 is disengaged from anvil retainer 638, member 842 and thus trocar 840 are pulled distally in the direction indicated by arrow "D" with the anvil assembly to the advanced position as shown in FIG. 57.

The proximal end of trocar 840 includes a blind bore 841. A rigid flexible wire 843 has a distal end which is secured within bore 841 of trocar 840 and extends rearwardly through elongated body portion 614 and into handle portion 612 of stapling device 610. Wire 843 has a proximal end which is secured to an indicator assembly in handle portion 612 which will be discussed in detail below.

Referring again to FIGS. 34, 36, 51 and 52, a cylindrical lockout tube 870 is slidably positioned about the outer surface of anvil retainer 638 and positioned to extend through inner guide portion 796 of shell 782, sleeve 784 and locking member 787 of shell assembly 631. The proximal end of lockout tube 870 includes an annular protrusion 872 (FIG. 34B). Locking member 787, which is fixedly positioned within sleeve 784 of shell assembly 631, includes a detent 789 (FIG. 34A) dimensioned to frictionally receive annular protrusion 872 to prevent sliding movement of lockout tube 870 about anvil retainer 638 until a predetermined force has been exerted on lockout tube 870. Lockout tube 870 is positioned about flexible legs 670 of anvil retainer 638 to provide rigidity to legs 670 during approximation of the anvil to prevent anvil assembly 630 from becoming inadvertently detached from anvil retainer 638. Movement of cylindrical lockout tube 870 about anvil retainer will be discussed in more detail below.

Referring to FIGS. 33, 35, 37, 38A, and 69-72 an indicator assembly is mounted within stationary handle 618 and includes an indicator 900 with indicia 901a, 901b and 901c which provides a visual indication to a surgeon via indicator window 624 that the anvil assembly is not attached (901a), that the anvil assembly is attached (901b), or that anvil assembly is attached and approximated 901c, i.e., the device is ready to fire. The indicia 901a-c may include red, yellow, and green coloring, respectively. Alternately, other color coded, graphic, or written indicia may be used to indicate the above described device conditions.

The indicator assembly includes an indicator 900, an indicator subplate 902, an indicator arm 904, a screw stop 906 and a rotatable disk 908. Screw stop 906 includes a throughbore 910 dimensioned to be positioned about screw 632. A set screw 912 is used to fixedly secure screw stop 906 to screw 632. Disk 908 includes a central throughbore 914, an upwardly extending cam member 916 and a wire connector 918. Disk 908 is rotatably secured to the top of screw stop 906 by screw 920. Wire connector 918 includes a post 922 which extends through an opening 924 in disk 908 and is rotatably fixed therein by a D-clip 926 or the like. Wire connector 918 includes a bore 928 for receiving one end of wire 843. A pin 930 secures wire 843 to wire connector 918, such that when wire 843 is advanced or retracted in response to attachment or detachment of anvil assembly 630 onto or from anvil retainer 638, as discussed above, disk 908 will rotate about screw 920 to rotate cam member 916.

Indicator subplate 902 is fixedly secured between internal walls of stationary handle 618 via a notch 934 formed in subplate 902 and channels (not shown) formed in the internal walls of stationary handle 618. A centrally disposed cutout 932 defining on elongated channel 936 is formed in subplate 902. Indicator arm 904 also includes a cutout 937 having a first end 937a and a second end 937b. A projection 938 which is slidably and rotatably positioned in elongated channel 936 extends downward from indicator arm 900 in subplate 902. A projection 940 extends from a top surface of indicator arm 904 into a curved bore 941 formed in the bottom of indicator 900. A projection 943 extends downwardly from indicator 900 and is positioned in channel 936 of subplate 902 to rotatably secure indicator 900 to subplate 902. The bottom of indicator 900 also includes a cam slot 942 for receiving cam member 916 of disk 908.

In the assembled condition, indicator subplate 902 is fixedly secured within stationary handle 618, with indicator arm 904 and indicator 900 slidably and rotatably mounted thereon and curved bore 941 of indicator 900 positioned on projection 940 of indicator arm 904. The entire assembly is engaged and maintained in an assembled state by indicator window 624. Cam member 916 extends upwardly from disk 908 through channel 936 in subplate 902 and cutout 937 in indicator arm 904 into cam slot 942 formed in the bottom of indicator 900. A spring 952 supported between indicator subplate 902 and indicator arm 904 biases indicator arm 904 towards the end of subplate 902 supporting indicator 900. Referring also to FIGS. 73-75, prior to attaching anvil assembly 630 to anvil retainer 638, indicia 901a (e.g., red dot) is positioned beneath opening 628 of indicator window 624 (FIG. 73). When anvil assembly 630 is attached to anvil retainer 638 in the manner described above, trocar 840 is retracted, i.e., pushed proximally, within anvil retainer 638 to move wire 843 proximally. Wire 843 is secured to connector 918 which is secured to the bottom of disk 908. As wire 843 is moved proximally, disk 908 is rotated in the direction indicated by arrow "E" on screw stop 906 about screw 920 to move cam member 916 which is positioned within the cam slot 942 formed in the bottom of indicator 900 in the same direction. Movement of cam member 916 against cam slot 942 causes indicator 900 to rotate in the direction indicated by arrow "F" about protrusion 943 to move indicia 901b (e.g., yellow dot) beneath opening 628 of indicator window 624 (FIG. 25). Cam member 916 also engages cutout 937 of indicator arm 904 near first end 937a of cutout 937 to rotate arm 904 in the direction indicated by arrow "G" about protrusion 938 to the position shown in FIG. 74. As discussed above, indicia 901b indicates to a surgeon that the anvil has been attached to the anvil retainer.

Next, when the surgeon approximates the device, screw 632 is moved proximally in the manner described above. Thus, screw stop 906, which is mounted on screw 632, and disk 908, including cam member 916, are moved proximally. As cam member 916 is moved proximally, cam member 916 moves out of cam slot 942 in indicator 900 and moves from first end 937a of cutout 937 formed in indicator arm 904 to second end 937b of cutout 937. When cam member 916 reaches second end 937b of cutout 937, cam member 916 engages a wall 950 of indicator arm 904 and drags indicator arm 904 proximally, against the bias of spring 952. As indicator arm 904 is moved proximally in the direction indicated by arrow "H", indicator 900 is also moved proximally to move indicia 901c (e.g., green light) beneath opening 628 of indicator window 624. As discussed above, indicia 901c indicates to a surgeon that the anvil assembly has been attached to the anvil retainer 638 and approximated, i.e., the instrument is ready to fire.

Operation of surgical stapling device 610 will now be described in detail.

Figure 47:
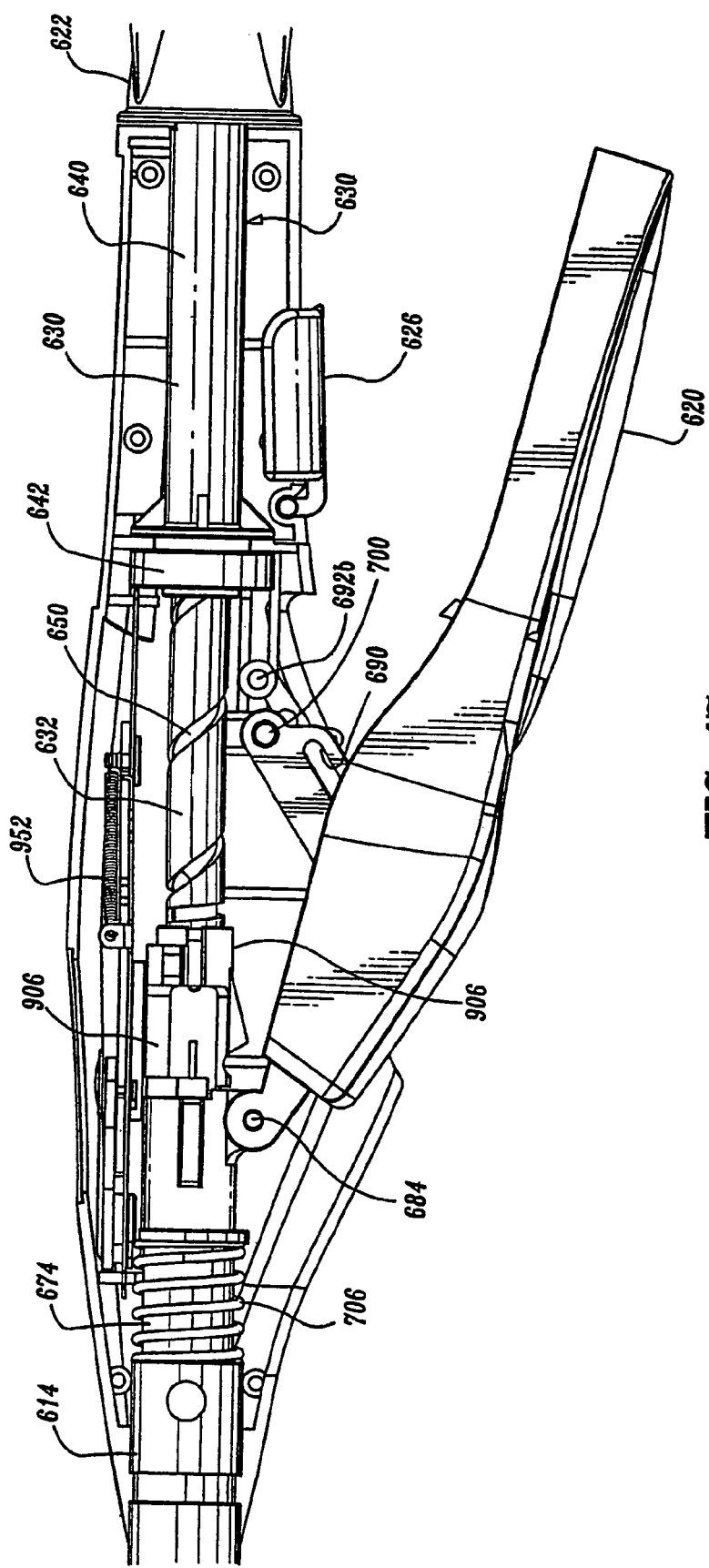
Figure 48:
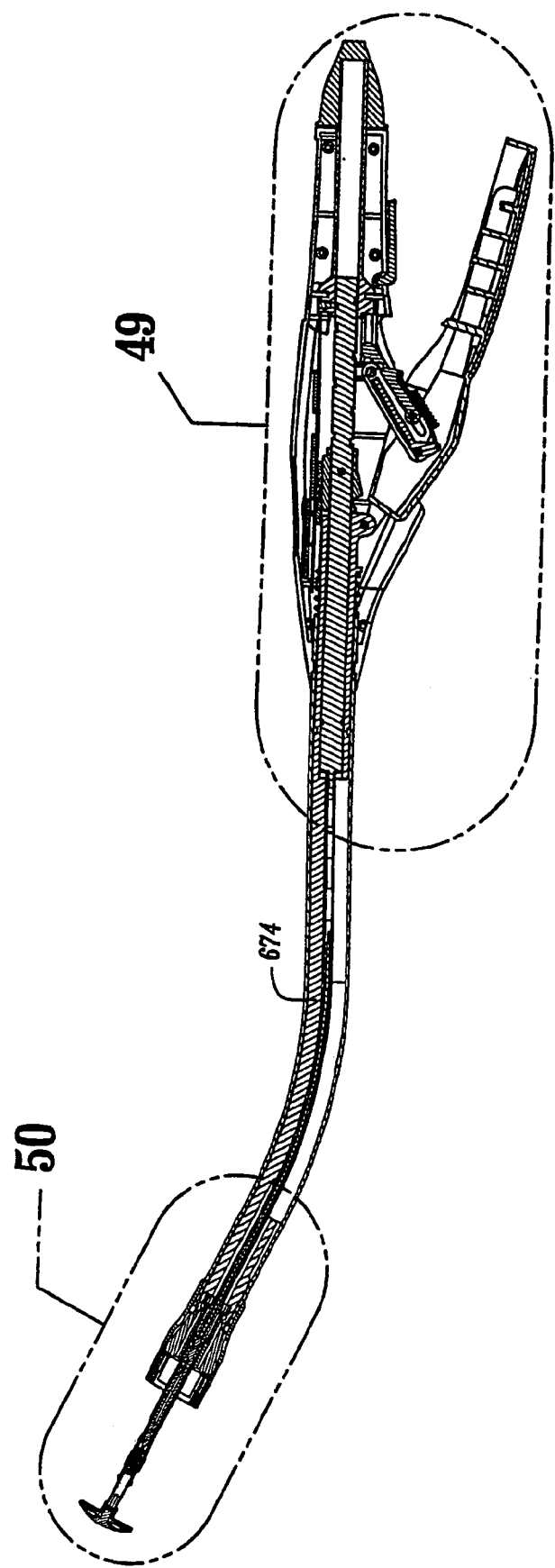

FIGS. 47-51 illustrate surgical stapling device 610 with anvil assembly 631 attached to anvil retainer 638 in the unapproximated position. As shown in FIGS. 47 and 49, screw 632 is in its distal-most position, with screw stop 906 positioned adjacent the proximal end of pusher link 674. In this position, locking pin 693, which is secured to safety link 692 (FIG. 31) is positioned in notches 683 on firing trigger plates 676 and 678 (FIG. 39) to prevent actuation of firing trigger 620. As shown in FIG. 50, legs 670 of anvil retainer 638 are positioned about center rod 754 of anvil assembly 630 such that abutment 775 of center rod 754 is positioned within annular recess 777 of anvil retainer 638. Annular protrusion 872 of lockout tube 870 is positioned within detent 789 of locking member 787 (FIG. 54A) to fix lockout tube 870 about legs 670 of anvil retainer 638 during approximation of the device. As anvil retainer 638 is retracted into lockout tube 870 during approximation, the exposed length of legs 870 of anvil retainer 638 will shorten to increase the force required to remove anvil assembly 630 from anvil retainer 638. When anvil retainer is retracted into lockout tube 870 a predetermined distance, shoulder 871 on anvil retainer 638 will engage the distal end of lockout tube 870 (FIG. 54B) to force annular protrusion 872 from detent 789 and force lockout tube 870 proximally with anvil retainer 638.

Referring to FIGS. 56 and 57, anvil assembly 630 and shell assembly 631 are approximated by rotating approximation knob 622 in the direction indicated by arrow "J" in FIG. 56. Rotation of knob 622 effects rotation of sleeve 633 to move sleeve pin 652 along channel 650 of screw 632. Since sleeve 633 is axially fixed to stationary handle 618, as pin 652 is moved through channel 650, screw 650 is moved proximally within stationary handle 618. As screw 650 is moved proximally, it pulls screw extensions 634 and 636, anvil retainer 638 and anvil assembly 630 proximally. Anvil assembly 630 is approximated into juxtaposed alignment with shell assembly 631.

As illustrated in FIG. 56, as screw 632 is moved proximally within stationary handle 618, screw stop 906, which is fixedly secured to screw 632, also moves proximally. Screw top 906 includes a downwardly extending abutment 1000 and a concavity 1002. During the final stages of approximation, abutment 1000 engages guide member 692b of safety link 692 and pulls safety link 692 proximally such that guide member 692b moves along slot 695 in internal wall of stationary handle 618 against the bias of spring 697. As safety link 692 is moved proximally, locking pin 693 moves upwardly in channel 690 of firing link 672 and locking pin 693 is moved out of engagement with notches 683 in firing trigger 620 to activate the firing trigger.

As illustrated in FIG. 57A, shoulder 871 on anvil retainer 638 has moved lockout tube 870 proximally such that annular protrusion 872 on lockout tube 870 is no longer positioned in detent 789 of locking member 787.

FIGS. 58-61 illustrate handle portion 62 of surgical stapler 610 during the firing stroke of trigger 620. After anvil 630 and shell assembly 631 have been approximated, pivot member 700 on end 698 of firing link 672 is positioned in concavity 1002 of screw stop 906 and locking pin 693 is positioned proximally of notches 683. Trigger lock 626 has also been released, i.e., manually pivoted to an unlocked position. Surgical stapling device 610 is now in a firing position.

To fire stapling device 610, firing trigger 620 is pivoted in the direction indicated by arrow "K". Since pivot member 700 is locked in concavity 1002 of screw stop 906, trigger 620 is forced to move distally. Trigger 620 is secured to the proximal end of pusher link 674 by pivot member 684. Thus, pusher link 674 is also moved distally within elongated body portion 614. Concurrently, a top surface of trigger plates 676 and 678 engages locking pin 693 to force guide member 692b of safety link 692 further proximally in the direction indicated by arrow "L" along slot 695. When firing trigger 620 reaches the end of its firing stroke, an engagement member 1010 formed on firing trigger 620 engages weakened portion 699 of safety link 692 (FIG. 60) to break safety link 692 into two parts (FIG. 61). As safety link 692 breaks, an audible and tactile indication is given to the surgeon that firing is complete. When firing trigger 620 is released (FIG. 61), spring 706 returns pusher link 674 to the retracted position. Spring 697 also returns locking pin 693 into engagement with notches 683 in firing trigger 620 to prevent further pivoting of firing trigger 620. Since safety link 692 is broken, approximation of device 610 will not remove locking member 693 from notches 683.

FIGS. 62 and 65 illustrate head portion 616 of surgical stapling device 610 immediately prior to and immediately after the firing stroke of firing trigger 620. As discussed above, as pusher link 674 is moved in the direction indicated by arrow "M" in FIG. 65, pusher back 786 and pusher 790 are advanced distally such that fingers 826 are pushed through slots 828 to force staples 830 through tissue 1040 into pockets 740 of anvil 729. Simultaneously, circular knife 788 is advanced to core the tissue. As knife 788 is advanced distally, knife 788 engages and moves cutting ring 728 and backup plate 726 further into anvil head 724 to move tabs 750 of backup plate 726 out of engagement with center rod 754. See FIGS. 66-68. By moving tabs 750 out of engagement with center rod 754, as discussed above, anvil head assembly 720 is free to pivot about pivot member 764 on center rod 754 after anvil assembly 630 and shell assembly 631 have been unapproximated.

Surgical stapling device 610 is used to perform a circular anastomoses. Typically, circular anastomoses are required during procedures for removing a portion of a diseased vessel such as the colon or the intestine. During such a procedure, the diseased portion of the vessel is removed and the remaining vessel section end portions are joined together using a surgical stapling device.

Figure 51:
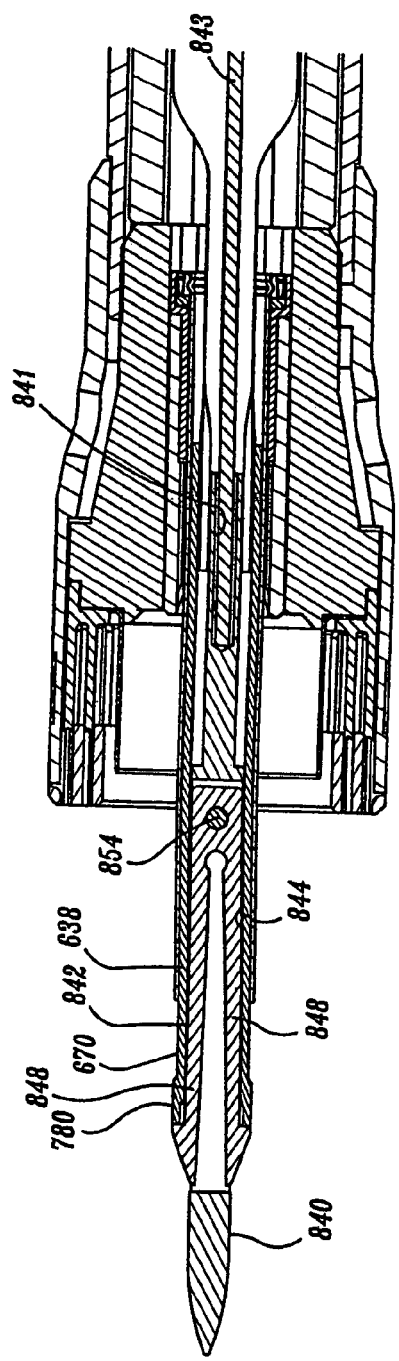
Figure 52:
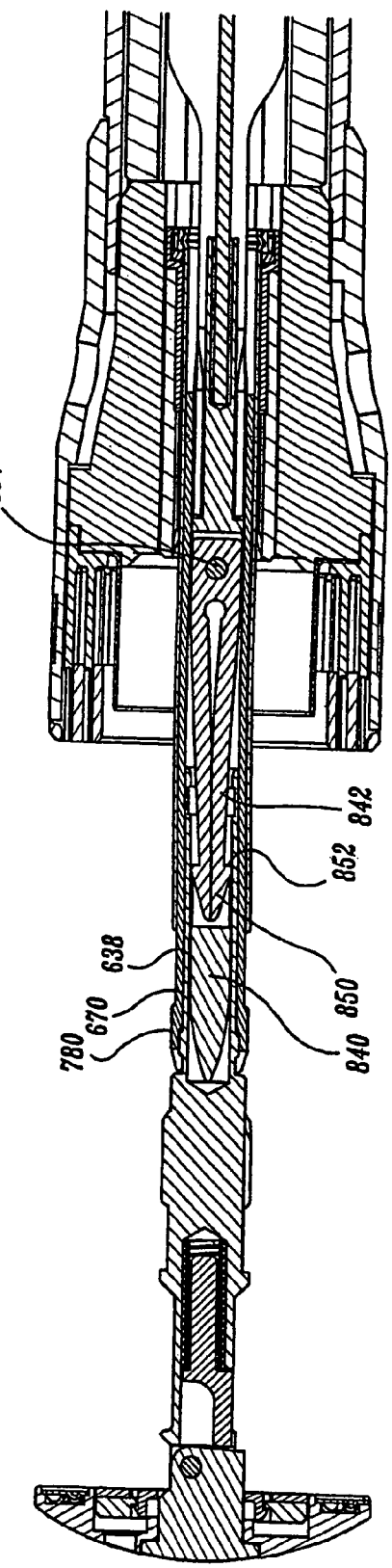

During such a procedure using surgical stapling device 610, prior to removing the diseased vessel portion, anvil assembly 630 with removable trocar 776 attached thereto (FIG. 46) is positioned in a first vessel section on a first side of the diseased vessel portion. Removable trocar 776 includes bore 776a for receiving a suture line for manipulating the anvil assembly. After the diseased vessel portion is removed and the open ends of the first and second vessel sections have been sutured, the distal end of device 610 as shown in FIG. 51 is positioned in the second vessel section on the other side of the diseased (now removed) vessel portion. At this time, trocar 776 is pushed through the suture line in the end of the first vessel section and removed from center rod 754. Next, trocar 840 is pushed through the suture line in the second vessel section. Center rod 754 is now positioned about trocar 840 and pushed into anvil retainer 638 to secure anvil assembly 630 to anvil retainer 638 (FIG. 52). Surgical stapling device 610 can now be approximated and fired in the manner discussed above, to join the ends of the first and second vessel sections and core out any tissue obstructing the vessel section lumen. After surgical stapling device is fired and unapproximated, head assembly 720 will tilt to the position shown in FIG. 68 to reduce the profile of the anvil assembly and simplify removal of the instrument from the vessel lumen. It has been contemplated providing an engagement member in handle portion 612 which would engage a component of the approximation mechanism during unapproximation of the anvil assembly to provide a tactile and/or audible indication that the anvil head assembly has been unapproximated a sufficient distance to tilt. It is envisioned that the engagement member may be moved to a position aligned with a component of the approximation mechanism by the firing trigger.

It will be understood that various modifications may be made to the embodiments disclosed herein. For example, the materials used to construct the individual components of the device may be chosen from a variety of known materials to achieve the desired result. Moreover, the particular indicia formed on the indicator may be other than that disclosed herein, i.e., other indicia is envisioned. Therefore, the above description should not be construed as limiting, but merely as exemplifications of preferred embodiments. Those skilled in the art will envision other modifications within the scope and spirit of the claims appended hereto.

What is claimed is:

1. A surgical stapling device comprising:
   a handle assembly including an approximation knob and a firing trigger assembly including a firing trigger and a firing link including an extension on the firing link, the firing trigger being movable between an unactuated position and an actuated position;
   an elongated body portion extending distally from the handle assembly;
   an anvil retainer supported adjacent a distal end of the elongated body portion;
   a shell assembly supported on a distal end of the elongated body portion and housing a plurality of staples, the anvil retainer extending through the shell assembly;
   an anvil assembly releasably mounted to the anvil retainer;
   an approximation mechanism including the approximation knob, a screw operatively associated with the anvil retainer and operable to move the anvil assembly in relation to the shell assembly and a screw stop positioned on the screw; and
   a tactile indicator positioned within the handle assembly and being positioned to engage the screw stop, the tactile indicator being movable in response to engagement with the screw stop to provide a tactile indication that the anvil assembly has moved a predetermined distance from the shell assembly after the device has been fired.

2. The surgical stapling device according to claim 1, wherein the anvil assembly includes an anvil head and an anvil center rod, the anvil head being pivotally secured to the anvil center rod about a pivot axis and being movable between an operative position and a tilted position.

3. The surgical stapling device according to claim 2, wherein the screw stop is positioned to engage and move the tactile indicator from an extended position to a retracted position to provide a tactile indication to an operator that the anvil head is in an unapproximated and pivoted position.

4. The surgical stapling device according to claim 3, further comprising an elongated pusher link defining a longitudinal axis and having a proximal end, a distal end, annular portions adjacent the proximal and distal ends, and an elongated intermediate portion between and in communication with the annular portions.

5. The surgical stapling device according to claim 4, wherein the approximation mechanism includes a pair of elongated substantially flat extension members housed in and along a diameter of the elongated body portion, wherein a portion of the elongated intermediate portion of the pusher link has a U-shaped configuration along a transverse vertical section relative to a longitudinal axis of the pusher link, the U-Shaped configuration including a substantially flat bottom wall that is parallel to, and disposed to one side of the diameter of the elongated body portion, each end of the bottom wall having an adjoining upstanding side wall that extends transversely through the diameter and along a portion of the interior surface of a bore of the elongated body portion, the bottom wall having a thickness that is less than half of the radius of the bore of the elongated body portion.

* * * * *